(12) United States Patent
Burk et al.

(10) Patent No.: US 9,562,241 B2
(45) Date of Patent: Feb. 7, 2017

(54) SEMI-SYNTHETIC TEREPHTHALIC ACID VIA MICROORGANISMS THAT PRODUCE MUCONIC ACID

(71) Applicant: GENOMATICA, INC., San Diego, CA (US)

(72) Inventors: Mark J. Burk, San Diego, CA (US); Robin E. Osterhout, San Diego, CA (US); Jun Sun, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 14/308,292

(22) Filed: Jun. 18, 2014

(65) Prior Publication Data

US 2014/0302573 A1    Oct. 9, 2014

Related U.S. Application Data

(63) Continuation of application No. 12/851,478, filed on Aug. 5, 2010, now abandoned.

(60) Provisional application No. 61/231,637, filed on Aug. 5, 2009.

(51) Int. Cl.
*C12N 1/20* (2006.01)
*C12P 7/44* (2006.01)

(52) U.S. Cl.
CPC ........................................ *C12P 7/44* (2013.01)

(58) Field of Classification Search
CPC .......................................................... C12P 7/44
USPC ......................................................... 435/142
See application file for complete search history.

(56) References Cited

U.S. PATENT DOCUMENTS

| | | |
|---|---|---|
| 3,513,209 A | 5/1970 | Clement |
| 3,912,586 A | 10/1975 | Kaneyuki et al. |
| 3,965,182 A | 6/1976 | Worrel |
| 4,048,196 A | 9/1977 | Broecker et al. |
| 4,082,788 A | 4/1978 | Mims |
| 4,190,495 A | 2/1980 | Curtiss |
| 4,301,077 A | 11/1981 | Pesa et al. |
| 4,624,920 A | 11/1986 | Inoue |
| 4,652,685 A | 3/1987 | Cawse et al. |
| 4,871,667 A | 10/1989 | Imada et al. |
| 5,079,143 A | 1/1992 | Klein et al. |
| 5,143,833 A | 9/1992 | Datta |
| 5,143,834 A | 9/1992 | Glassner et al. |
| 5,168,055 A | 12/1992 | Datta et al. |
| 5,173,429 A | 12/1992 | Gaddy et al. |
| 5,182,199 A | 1/1993 | Hartley |
| 5,192,673 A | 3/1993 | Jain et al. |
| 5,403,721 A | 4/1995 | Ward, Jr. et al. |
| 5,413,922 A | 5/1995 | Matsuyama et al. |
| 5,416,020 A | 5/1995 | Severson et al. |
| 5,457,040 A | 10/1995 | Jarry et al. |
| 5,478,952 A | 12/1995 | Schwartz |
| 5,487,987 A * | 1/1996 | Frost .................... C12N 9/0069 435/142 |
| 5,504,004 A | 4/1996 | Guettler et al. |
| 5,521,075 A | 5/1996 | Guettler et al. |
| 5,573,931 A | 11/1996 | Guettler et al. |
| 5,616,496 A | 4/1997 | Frost et al. |
| 5,686,276 A | 11/1997 | Lafend et al. |
| 5,700,934 A | 12/1997 | Wolters et al. |

(Continued)

FOREIGN PATENT DOCUMENTS

| | | |
|---|---|---|
| CN | 1 358 841 | 7/2002 |
| EP | 0 494 078 | 7/1992 |

(Continued)

OTHER PUBLICATIONS

Abadjieva et al., "The Yeast ARG7 Gene Product is Autoproteolyzed to Two Subunit Peptides, Yielding Active Ornithine Acetyltransferase," J. Biol. Chem. 275(15):11361-11367 (2000).

Abe et al., "Discovery of amide (peptide) bond synthetic activity in Acyl-CoA synthetase," J. Biol. Chem. 283(17):11312-11321 (2008).

Aberhart and Hsu, "Stereospecific hydrogen loss in the conversion of [H$_7$ $_1$isobutyrate to β—hydroxyisobutyrate in Pseudomonas putida. The stereochemistry of hydroxyisobutyrate dehydrogenase," J. Chem. Soc. rPerkin1I6:1404-1406 (1979).

(Continued)

Primary Examiner — Tekchand Saidha
(74) Attorney, Agent, or Firm — Kagan Binder, PLLC

(57) ABSTRACT

The invention provides a non-naturally occurring microbial organism having a muconate pathway having at least one exogenous nucleic acid encoding a muconate pathway enzyme expressed in a sufficient amount to produce muconate. The muconate pathway including an enzyme selected from the group consisting of a beta-ketothiolase, a beta-ketoadipyl-CoA hydrolase, a beta-ketoadipyl-CoA transferase, a beta-ketoadipyl-CoA ligase, a 2-fumarylacetate reductase, a 2-fumarylacetate dehydrogenase, a trans-3-hydroxy-4-hexendioate dehydratase, a 2-fumarylacetate aminotransferase, a 2-fumarylacetate aminating oxidoreductase, a trans-3-amino-4-hexenoate deaminase, a beta-ketoadipate enol-lactone hydrolase, a muconolactone isomerase, a muconate cycloisomerase, a beta-ketoadipyl-CoA dehydrogenase, a 3-hydroxyadipyl-CoA dehydratase, a 2,3-dehydroadipyl-CoA transferase, a 2,3-dehydroadipyl-CoA hydrolase, a 2,3-dehydroadipyl-CoA ligase, a muconate reductase, a 2-maleylacetate reductase, a 2-maleylacetate dehydrogenase, a cis-3-hydroxy-4-hexendioate dehydratase, a 2-maleylacetate aminoatransferase, a 2-maleylacetate aminating oxidoreductase, a cis-3-amino-4-hexendioate deaminase, and a muconate cis/trans isomerase. Other muconate pathway enzymes also are provided. Additionally provided are methods of producing muconate.

13 Claims, 6 Drawing Sheets

(56) References Cited

U.S. PATENT DOCUMENTS

| | | |
|---|---|---|
| 5,770,435 A | 6/1998 | Donnelly et al. |
| 5,807,722 A | 9/1998 | Gaddy et al. |
| 5,869,301 A | 2/1999 | Nghiem et al. |
| 5,908,924 A | 6/1999 | Burdette et al. |
| 5,958,745 A | 9/1999 | Gruys et al. |
| 6,117,658 A | 9/2000 | Dennis et al. |
| 6,133,014 A | 10/2000 | Mukouyama et al. |
| 6,136,577 A | 10/2000 | Gaddy et al. |
| 6,159,738 A | 12/2000 | Donnelly et al. |
| 6,194,572 B1 | 2/2001 | Buijs et al. |
| 6,214,592 B1 | 4/2001 | Crouzet et al. |
| 6,274,790 B1 | 8/2001 | Kunst et al. |
| 6,280,986 B1 | 8/2001 | Hespell et al. |
| RE37,393 E | 9/2001 | Donnelly et al. |
| 6,340,581 B1 | 1/2002 | Gaddy et al. |
| 6,353,100 B1 | 3/2002 | Guit et al. |
| 6,432,686 B1 | 8/2002 | Bulthuis et al. |
| 6,448,061 B1 | 9/2002 | Pan et al. |
| 6,455,284 B1 | 9/2002 | Gokarn et al. |
| 6,485,947 B1 | 11/2002 | Rajgarhia et al. |
| 6,562,958 B1 | 5/2003 | Breton et al. |
| 6,660,857 B2 | 12/2003 | Agterberg et al. |
| 6,686,194 B1 | 2/2004 | Mutzel et al. |
| 6,686,310 B1 | 2/2004 | Kourtakis et al. |
| 6,743,610 B2 | 6/2004 | Donnelly et al. |
| 6,852,517 B1 | 2/2005 | Suthers et al. |
| 7,127,379 B2 | 10/2006 | Palsson et al. |
| 7,186,541 B2 | 3/2007 | Gokarn et al. |
| 7,223,567 B2 | 5/2007 | Ka-Yiu et al. |
| 7,241,594 B2 | 7/2007 | Lee et al. |
| 7,244,610 B2 | 7/2007 | San et al. |
| 7,256,016 B2 | 8/2007 | San et al. |
| 7,262,046 B2 | 8/2007 | Ka-Yiu et al. |
| 7,285,402 B2 | 10/2007 | Gaddy et al. |
| 7,309,597 B2 | 12/2007 | Liao et al. |
| 7,371,558 B2 | 5/2008 | Cervin et al. |
| 7,393,676 B2 | 7/2008 | Gokarn et al. |
| 7,432,091 B2 | 10/2008 | Yukawa et al. |
| 7,491,520 B2 | 2/2009 | Raemakers-Franken et al. |
| 7,569,380 B2 | 8/2009 | San et al. |
| 2002/0012939 A1 | 1/2002 | Palsson |
| 2002/0040123 A1 | 4/2002 | Patil et al. |
| 2002/0106358 A1 | 8/2002 | Hopwood et al. |
| 2002/0168654 A1 | 11/2002 | Maranas et al. |
| 2003/0028915 A1 | 2/2003 | Tilton et al. |
| 2003/0059792 A1 | 3/2003 | Palsson et al. |
| 2003/0087381 A1 | 5/2003 | Gokarn |
| 2003/0113886 A1 | 6/2003 | Brzostowicz et al. |
| 2003/0182678 A1 | 9/2003 | Mitsky et al. |
| 2003/0224363 A1 | 12/2003 | Park et al. |
| 2003/0233218 A1 | 12/2003 | Schilling |
| 2004/0009466 A1 | 1/2004 | Maranas et al. |
| 2004/0029149 A1 | 2/2004 | Palsson et al. |
| 2004/0072723 A1 | 4/2004 | Palsson et al. |
| 2004/0096946 A1 | 5/2004 | Kealey et al. |
| 2004/0152159 A1 | 8/2004 | Causey et al. |
| 2005/0042736 A1 | 2/2005 | San et al. |
| 2005/0079482 A1 | 4/2005 | Maranas et al. |
| 2005/0250135 A1 | 11/2005 | Klaenhammer et al. |
| 2005/0287655 A1 | 12/2005 | Tabata et al. |
| 2006/0035348 A1 | 2/2006 | Gulevich et al. |
| 2006/0073577 A1 | 4/2006 | Ka-Yiu et al. |
| 2006/0099578 A1 | 5/2006 | Wallace et al. |
| 2006/0110810 A1 | 5/2006 | Rajgarhia et al. |
| 2006/0172399 A1 | 8/2006 | Nomoto et al. |
| 2006/0259998 A1 | 11/2006 | Brumbley et al. |
| 2006/0281156 A1 | 12/2006 | Aoyama et al. |
| 2007/0042476 A1 | 2/2007 | Lee et al. |
| 2007/0072279 A1 | 3/2007 | Meynial-Salles et al. |
| 2007/0087425 A1 | 4/2007 | Ohto |
| 2007/0092957 A1 | 4/2007 | Donaldson et al. |
| 2007/0111294 A1 | 5/2007 | Burgard et al. |
| 2007/0117191 A1 | 5/2007 | Kamachi et al. |
| 2007/0184539 A1 | 8/2007 | San et al. |
| 2007/0190605 A1 | 8/2007 | Bessler et al. |
| 2007/0259410 A1 | 11/2007 | Donaldson et al. |
| 2008/0138870 A1 | 6/2008 | Bramucci et al. |
| 2008/0171371 A1 | 7/2008 | Yukawa et al. |
| 2008/0182308 A1 | 7/2008 | Donaldson et al. |
| 2008/0274522 A1 | 11/2008 | Bramucci et al. |
| 2008/0293125 A1 | 11/2008 | Subbian et al. |
| 2009/0047718 A1 | 2/2009 | Blaschek et al. |
| 2009/0047719 A1 | 2/2009 | Burgard et al. |
| 2009/0068207 A1 | 3/2009 | Breitbart et al. |
| 2009/0075351 A1 | 3/2009 | Burk et al. |
| 2009/0305364 A1 | 12/2009 | Burgard et al. |
| 2010/0009419 A1 | 1/2010 | Burk et al. |
| 2010/0099925 A1 | 4/2010 | Kharas |

FOREIGN PATENT DOCUMENTS

| | | |
|---|---|---|
| EP | 1 473 368 | 11/2004 |
| EP | 2 017 344 | 1/2009 |
| GB | 1230276 | 4/1971 |
| GB | 1314126 | 4/1973 |
| GB | 1344557 | 1/1974 |
| GB | 1512751 | 6/1978 |
| JP | 50 006776 | 1/1975 |
| WO | WO 82/03854 | 11/1982 |
| WO | WO 91/13997 | 9/1991 |
| WO | WO 99/06532 | 2/1999 |
| WO | WO 99/58686 | 11/1999 |
| WO | WO 01/16346 | 3/2001 |
| WO | WO 02/42418 | 5/2002 |
| WO | WO 02/055995 | 7/2002 |
| WO | WO 02/090312 | 11/2002 |
| WO | WO 03/010322 | 2/2003 |
| WO | WO 03/106691 | 12/2003 |
| WO | WO 03/106998 | 12/2003 |
| WO | WO 2005/026338 | 3/2005 |
| WO | WO 2005/047498 | 5/2005 |
| WO | WO 2005/068643 | 7/2005 |
| WO | WO 2006/028063 | 3/2006 |
| WO | WO 2006/031424 | 3/2006 |
| WO | WO 2006/034156 | 3/2006 |
| WO | WO 2007/001982 | 1/2007 |
| WO | WO 2007/030830 | 3/2007 |
| WO | WO 2007/141208 | 12/2007 |
| WO | WO 2008/018930 | 2/2008 |
| WO | WO 2008/024023 | 2/2008 |
| WO | WO 2008/027742 | 3/2008 |
| WO | WO 2008/115840 | 3/2008 |
| WO | WO 2008/080124 | 7/2008 |
| WO | WO 2008/131286 | 10/2008 |
| WO | WO 2008/137403 | 11/2008 |
| WO | WO 2008/152016 | 12/2008 |
| WO | WO 2009/014437 | 1/2009 |
| WO | WO 2009/023493 | 2/2009 |
| WO | WO 2009/031766 | 3/2009 |
| WO | WO 2009/049274 A2 | 4/2009 |
| WO | WO 2009/094485 A1 | 7/2009 |
| WO | WO 2009/103026 | 8/2009 |
| WO | WO 2009/113853 | 9/2009 |
| WO | WO 2009/113855 | 9/2009 |
| WO | WO 2009/131040 | 10/2009 |
| WO | 2010129936 A1 | 11/2010 |

OTHER PUBLICATIONS

Abiko et al., "Localization of NAD-isocitrate dehydrogenase and glutamate dehydrogenase in rice roots: candidates for providing carbon skeletons to NADH-glutamate synthase," Plant Cell Physiol. 46:1724-1734 (2005).

Abo-Dalo et al., "A novel member of the GCN5-related N-acetyltransferase superfamily from Caenorhabditis elegans preferentially catalyses the N-acetylation of thialysine [S-(2-aminoethyl)-L-cysteine]," Biochem. J. 384:129-137 (2004).

Adams and Kletzin, "Oxidoreductase-type enzymes and redox proteins involved in fermentative metabolisms of hyperthermophilic Archaea," Adv. Protein Chem. 48:101-180 (1996).

(56) References Cited

OTHER PUBLICATIONS

Aevarsson et al., "Crystal structure of 2-oxoisovalerate and dehydrogenase and the architecture of 2-oxo acid dehydrogenase multienzyme complexes," Nat. Struct. Biol. 6:785-792 (1999).
Agnihotri and Liu, "Enoyl-CoA Hydratase: Reaction, Mechanism, and Inhibition," Bioora. Med. Chem. 11(1):9-20 (2003).
Ahmed and Lewis, "Fermentation of Biomass-Generated Synthesis Gas: Effects of Nitric Oxide," Biotechol. Bioeng. 97:1080-1086 (2007).
Ahmed et al., Effects of biomass-generated producer gas constituents on cell growth, product distribution and hydrogenase activity of Clostridium carboxidivorans P7r,. Biomass Bioenergy 30(7):665-672 (2006).
Akashi et al., "Molecular and biochemical Characterization of 2-Hydroxyisoflavanone Dehydratase. Involvement of Carboxylesterase-Like Proteins in Leguminous Isoflavone Biosynthesis," Plant. Physiol. 137:882-891 (2005).
Akatsuka et al., "The Serratia marcescens bioH gene encodes an esterase," Gene 302(1-2):185-192 (2003).
Akhtar and Jones, "Construction of a synthetic YdbK-dependent pyruvate:$H_2$ pathway in Escherichia coli BL21(DE3)," Metab. Eng. 11(3):139-147 (2009).
Alam et al., "Anaerobic Fermentation Balance of Escherichia coli as Observed by in Vivo Nuclear Magnetic Resonance Spectroscopy," J. Bacterial. 171(11):6213-6217 (1989).
Alber et al., "3-Hydroxypropionyl-Coenzyme a synthetase from Metallosphaera sedula, an enzyme involved in autotrophic $CO_2$ fixation," J. Bacteriol. 190:1383-1389 (2008).
Alber et al., "Malonyl-Coenzyme A reductase in the modified 3-hydroxypropionate cycle for autotrophic carbon fixation in archaeal Metallosphaera and Sulfolobus soo.,"*J. Bacteriol.* 188(24):8551-8559 (2006).
Alber et al., "Propionyl-Coenzyme a synthase from Chloroflexus aurantiacus, a key enzyme of the 3-hydroxypropionate cycle for autotrophic $CO_2$ fixation,"*J. Biol. Chem.* 27712137-12143 (2002).
Alber et al., "Study of an alternate glyoxylate cycle for acetate assimilation by Rhodobacter sphaeroides,"*Mol. Microbiol.* 61(2):297-309 (2006).
Alberty, Biochemical thermodynamics. *Biochim. Biophvs. Acta* 1207:1-11 (1994).
Aldor and Keasling, "Metabolic engineering of poly(3-hydroxybutyrate-co-3- hydroxyvalerate) composition in recombinant *Salmonella enterica* serovar typhimurium,"*Biotechnol. Bioeng.* 76(2):108-114 (2001).
Aldor et al., "Metabolic Engineering of a Novel Propionate-Independent Pathway for the Production of Poly(3-Hydroxybutyrate-co-3-Hydroxyvalerate) in Recombinant *Salmonella enterica* Serovar Typhimurium," Appl. Environ. Microbiol. 68(8):38483854 (2002).
Aldrich Catalog, Sigma-Aldrich Company, Milwaukee, WI, p. 481 (2002).
Aldrich et al., "Cloning and complete nucleotide sequence determination of the catB gene encoding cis,cis-muconate lactonizing enzyme,"*Gene* 52:185-195 (1987).
Alexeeva et al., "Requirement of ArcA for redox regulation in *Escherichia coli* under microaerobic but not anaerobic or aerobic conditions "*J. Bacteriol.,*185(1):204-209.
Alexson et al., "NADH-sensitive propionyl-CoA hydrolase in brown-adipose-tissue mitochondria of the rat,"*Biochim. Biophys. Acta* 1005(1):13-19 (1989).
Alhapel et al., "Molecular and functional analysis of nicotinate catabolism in Eubacterium barkeri,"*Proc. Natl. Acad. Sci. U.S.A.* 103(33):12341-12346 (2006).
Alper et al., "Construction of lycopene-overproducing *E. coli* strains by combining systematic and combinatorial gene knockout targets,"*Nat. Biotechnol.* 23(5):612-616 (2005).
Alper et al., "Identifying gene targets for the metabolic engineering of lycopene biosynthesis in *Escherichi coli,*"*Metab. Eng.* 7(3):155-164 (2005).

Alper et al., "Engineering yeast transcription machinery for improved ethanol tolerance and production,"*Science* 314(5805):1565-1568 (2006).
Altamirano et al., "Decoupling cell growth and product formation in Chinese hamster ovary cells throguh metabolic control," Biotechnol. Bioenq. 76(4):351-360 (2001).
Altmiller and Wanger, "Purification and properties of dihydroxy acid dehydratase from soluble and mitochondrial fractions of Neurospora crassa," Arch. Biochem. Biophvs. 138:160-170 (1970).
Amann et al., "Tightly regulated tac promoter vectors useful for the expression of unfused and fused proteins in *Escherichia coli*," Gene 69:301-315 (1988).
Andersen and Hansen, "Cloning of the lysA gene from Mycobacterium tuberculosis," Gene 124(1):105-109 (1993).
Andersen et al., "A gene duplication led to specialized γ-aminobutyrate and β—alanine aminotransferase in yeast," FESS J. 274:1804-1817 (2007).
Anderson and Dawes, "Occurrence, metabolism, metabolic role, and industrial uses of bacterial polyhydroxyalkanoates," Microbiol. Rev. 54(4):450-472 (1990).
Anderson et al., "Evaluation of 5-enolpyruvoylshikimate-3-phosphate synthase substrate and inhibitor binding by stopped-flow and equilibrium fluorescence measurements," Biochemistry 27:1604-1610 (1988).
Andersson et al., "Effect of different carbon sources on the production of succinic acid using metabolically engineered *Escherichia coli*," Biotechnol. Prog. 23(2):381388 (2007).
Andreesen and Ljungdahl, "Formate Dehydrogenase of Clostridium thermoaceticum: Incorporation of Selenium-75, and the Effects of Selenite, Molybate, and Tungstate on the Enzyme," J. Bacterial. 116(2):867-873 (1973).
Aneja and Charles, "Poly-3-hydroxybutyrate degradation in Rhizobium (Sinorhizobium) meliloti: isolation and characterization of a gene encoding 3-hydroxybutryate dehydrogenase," J. Bacterial. 181(3):849-857 (1999).
Angrand et al., "Simplified generation of targeting constructs using ET recombination," Nucleic Acids Res. 27(17):e16 (1999).
Ansorge and Kula, "Production of Recombinant L-Leucine Dehydrogenase from Bacillus cereus in Pilot Scale Using the Runaway Replication System *E. coli*[plET981]," Biotechnol. Bioeng. 68:557-562 (2000).
Aoshima and Igarashi, "A novel biotin protein required for reductive carboxylation of 2-oxoglutarate by isocitrate dehydrogenase in Hydrogenobacter thermophilus TK-6," Mal. Microbial. 51(3):791-798 (2004).
Aoshima and Igarshi, "Nondecarboxylating and decarboxylating isocitrate dehydrogenases: oxalosuccinate reductase as an ancestral form of isocitrate dehydrogenase," J. Bacteriol. 190(6):2050-2055 (2008).
Aoshima et al., "A novel enzyme, citryl-CoA lyase, catalysing the second step of the citrate cleavage reaction in Hydrogenobacter thermophilus TK-6," Mol. Microbiol. 52(3):763-770 (2004).
Aoshima et al., "A novel enzyme, citryl-CoA synthetase, catalysing the first step of the citrate cleavage reaction in Hydrogenobacter thermophilus TK-6," Mol. Microbiol. 52(3):751-761 (2004).
Aoshima et al., "A novel oxalosuccinate-forming enzyme involved in the reductive carboxylation of 2-oxoglutarate in Hydrogenobacter thermophilus TK-6," Mol. Microbiol. 62(3):748-759 (2006).
Aoshima, "Novel enzyme reactions related to the tricarboxylic acid cycle: phylogenetic/functional implications and biotechnological applications,"*Appl. Microbiol. Biotechnol.* 75(2):249-255 (2007).
Aragon and Lowenstein, "A survey of Enzymes Which Generate or Use Acetoacetyl Thioesters in Rat Liver," J. Biol. Chem. 258(8):4725-4733 (1983).
Arendsen et al., "Nitrate-Dependent Regulation of Acetate Biosynthesis and Nitrate Respiration by Clostridium thermoaceticum," J. Bacteriol. 181:1489-1495 (1999).
Argyrou and Blanchard, "Kinetic and chemical mechanism of Mycobacterium tuberculosis 1-deoxy-D-xylulose-5-phosphate isomeroreductase," Biochemistry 43:4375-4384 (2004).
Arikawa et al., "Soluble fumarate reductase isoenzymes from *Saccharomyces cerevisiae* are required for anaerobic growth," FEMS Microbiol. Lett. 165:111-116 (1998).

(56) References Cited

OTHER PUBLICATIONS

Aristidou et al., "Metabolic Engineering of *Escherichia coli* to Enhance Recombinant Protein Production through Acetate Reduction," Biotechnol. Prog. 11(4):475-478 (1995).
Aristidou et al., "Metabolic flux analysis of *Escherichia coli* expressing the *Bacillus subtilis* Acetolactate Synthase in Batch and Continuous Cultures," Biotechnol. Bioena. 63(6):737-749 (1999).
Armstrong et al., "Steroselectivity and sterospecificity of the a, 13-dihydroxyacid dehydratase from *Salmonella typhimurium*," Biochim. Biophys. Acta 498:282-293 (1977).
Arps et al., "Genetics of serine pathway enzymes in Methylobacterium extorquens AM1: phosphoenolpyruvate carboxylase and malyl Coenzyme a lyase,"*J. Bacteriol.* 175:3776-3783 (1993).
Asano and Kato, "Crystalline 3-methylaspartase from a facultative anaerobe, Escherichia coli strain YG1002,"*FEMS Microbiol. Lett.* 118(3):255-258 (1994).
Asano et al., "Alteration of substrate specificity of aspartase by directed evolution,"*Biomol. Eng.* 22(1-3):95-101 (2005).
Asanuma et al., "Characterization and transcription of the genes encoding enzymes involved in butyrate production in Butyrivibrio fibrisolvens,"*Curr. Microbial.* 45:203-207 (2003).
Asuncion et al., "Overexpression, purification, crystallization and data collection of 3-methylaspartase from Clostridium tetanomorphum,"*Acta. Crystalloqr. D. Biol. Crystallogr.* 57(Pt 5):731-733 (2001).
Asuncion et al., "The structure of 3-methylaspartase from Clostridium tetanomorphum functions via the common enolase chemical step,"*J. Biol. Chem.* 277(10):8306-8311 (2002).
Atsumi et al., "Metabolic engineering of *Escherichia coli* for 1-butanol production," Metab. Ena. 10(6):305-311 (2007).
Atsumi et al., "Non-fermentative pathways for synthesis of branched-chain higher alcohols as biofuels," Nature 451(7174):86-89 (2008).
Atteia et al., "Pyruvate formate-lyase and a novel route of eukaryotic ATP synthesis in Chlamydomonas mitochondria,"*J. Biol. Chem.* 281:9909-9918 (2006).
Auerbach et al., "Lactate dehydrogenase from the hyperthermophilic bacterium thermotoga maritima: the crystal structure at 2.1 A resolution reveals strategies for intrinsic protein stabilization,"*Structure* 6:769-781 (1998).
Baba et al., "Construction of *Escherichia coli* K-12 in-frame, single-gene knockout mutants: the Keio collection," Mol. Syst. Biol. 2:2006.0008 (2006).
Bachmann and Townsend, "-Lactam synthetase: a new biosynthetic enzyme," Proc. Natl. Acad. Sci. U.S.A. 95(16):9082-9086 (1998).
Bai et al., "Lewis-acid assisted cross metathesis of acrylonitrile with functionalized olefins catalyzed by phosphine-free ruthenium carbene complex,"*Org. Biomol. Chem.* 3:4139-4142 (2005).
Bailey et al., "Identification, cloning, purification, and enzymatic characterization of Mycobacterium tuberculosis 1-deoxy-o-xylulose 5-phosphate synthase,"*Glycobiology* 12:813-820 (2002).
Baird et al., "Enzymes involved in acetoacetate formation in various bovine tissues,"*Biochem. J.* 117(4):703-709 (1970).
Baker and van der Drift, "Purification and properties of L-erythro-3,5-diaminohexanoate dehydrogenase from Clostridium sticklandii,"*Biochemistry* 13(2):292-299(1974).
Baker et al., "Purification and properties of L-erythro-3,5-diaminohexanoate dehydrogenase from a lysine-fermenting Clostridium,"*J. Biol. Chem.* 247:7724-7734.
Bakker et al., "Stoichiometry and compartmentation of NADH metabolism in Saccharomvces cerevisiae,"*FEMS Microbiol. Rev.* 25:15-37 (2001).
Banerji et al., "The cloning and characterization of the arom gene of Pneumocystis carinii,"*J. Gen. Microbiol.* 139:2901-2914 (1993).
Barber et al., "Structure and regulation of acetyl-CoA carboxylase genes of metazoa,"*Biochimica. Bioohysica.* Acta 1733:1-28 (2005).
Barker and Frost, "Microbial synthesis of p-hydroxybenzoic acid from glucose,"*Biotechnol. Bioeng.* 76:376-390 (2001).

Barker et al., "Butyryl-CoA:Acetoacetate CoA-transferase from Lysine-fermenting clostridium,"*J. Biol. Chem.* 253(4):1219-1225 (1978).
Barker et al., "Pathway of Lysine Degradation in Fusobacterium nucleatum,"*J. Bacteriol.* 152(1):201-207 (1982).
Barrick et al., "Quantitative analysis of ribosome binding sites in E.coli,"*Nucleic. Acids Res.* 22(7):1287-1295 (1994).
Barrowman et al., "Immunological comparison of microbial TPP-dependent non-oxidative a-keto acid decarboxvlase,"*FEMS Microbiol. Lett.* 34:57-60 (1986).
Barthelmebs et al., "Expression of *Escherichia coli* of Native and chimeric Phenolic Acid Decarboxylases with Modified Enzymatic Activities and Method for Screening Recombinant *E. coli* Strains Expressing These Enzymes,"*Appl. Environ. Microbiol.* 67:1063-1069 (2001).
Barthelmebs et al., "Inducible metabolism of phenolic acids in Pedicoccus pentosaecus is encoded by an autoregulated operon which involves a new class of negative transcriptional regulator,"*J. Bacteriol.* 182:6724-6731 (2000).
Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD),"*J. Bacterial.* 172(12):7035-7042 (1990).
Basset et al., "Folate synthesis in plants: the p-aminobenzoate branch is initiated by a bifunctional PabA-PabB protein that is targeted to plastids,"*Proc. Natl. Acad. Sci. U.S.A* 101:1496-1501 (2004)
Battaile et al., "Structures of isobutyryl-CoA dehydrogenase and enzyme-product complex: Comparison with isovaleryl- and short-chain acyl-CoA dehydrogenases,"*J. Biol. Chem.* 279:16526-16534 (2004).
Baudin et al., "A simple and efficient method for direct gene deletion in Saccharomyces cerevisiae,"*Nucleic Acids Res.* 21(14):3329-3330 (1993).
Bauer et al., "Improved Expression of Human Interleukin-2 in High-Cell-Density Fermentor Cultures of *Escherichia coli* K-12 by a Phosphotransacetylase Mutant,"*Appl. Environ. Microbiol.* 56:1296-1302 (1990).
Beatrix et al., "The biotin-dependent sodium ion pump glutaconyl-CoA decarboxylase from Fusobactevium nucleatum (subsp. Nucleatum). Comparison with the glutaconyl-CoA decarboxylases from gram-positive bacteria,"*Arch. Microbial.* 154(4):362-369 (1990).
Beckers et al., "Large-scale mutational analysis for the annotation of the mouse genome,"*Curr. Ooin. Chem. Biol.* 6:17-23 (2001).
Benner et al., "Stereospecificity and sterochemical infidelity of acetoacetate decarboxvlase (AAD),"*J. Am. Chem. So.* 103:993-994 (1981).
Benning et al., "New reactions in the crotonase superfamily: Structure of methylmalonyl CoA decarboxylase from *Escherichia coli*,"*Biochemistry* 39:4630-4639 (2000).
Berg et al., "A 3-Hydroxypropionate/4-Hydroxybutyrate Autotrophic Carbon Dioxide Assimilation Pathway in Archaea,"*Science* 318(5857) 1782-1786 (2007).
Bergquist and Gibbs, "Degenerate oligonucleotide gene shuffling,"*Meth. Mol. Biol.* 352:191-204 (2007).
Bergquist et al., "Degenerate oligonucleotide gene shuffling (DOGS) and random drift mutagenesis (RNDM): Two complementary techniques for enzyme evolution,"*Biomol. Eng.* 22:63-72 (2005).
Berkovitch et al., "A locking mechanism preventing radical damage in the absence of substrate, as revealed by the x-ray structure of lysine 5,6-aminomutase,"*Proc. Natl. Acad. Sci. U.S.A.* 101:15870-15875 (2004).
Berman and Magasanik, "The pathway of myo-inositol degradation in Aerobacter aerogenes,"*J. Biol. Chem.* 241(4):800-806 (1966).
Bermejo et al., "Expression of C*lostridium acetobutylicum* ATCC 824 Genes in *Escherichia coli* for Acetone Production and Acetate Detoxification,"*Appl. Environ. Microbiol.* 64(3):1079-1085 (1998).

(56) References Cited

OTHER PUBLICATIONS

Berrios-Rivera et al., "Metabolic Engineering of *Escherichia coli*: Increase of NADH Availability by Overexpressing an NAD+-Dependent Formate Dehydrogenase,"*Metab Eng.* 4(3):217-229 (2002).

Berthold et al., "Structure of the branched-chain keto acid decarboxylase (KdcA) from Lactococcus lacti prvides insights into structural basis for the chemoselective enantioselective carboligation reaction,"*Acta. Crystallogr. D. Biol. Crystallogr.* 63(Pt12):1217-1224 (2007).

Biellmann et al., "Aspartate-β-semialdehyde dehydrogenase from *Escherichia coli*. Purification and general properties,"*Eur. J. Biochem.* 104(1):53-58 (1980).

Binieda et al., "Purification, characterization, DNA sequence and cloning of a pimeloyl-CoA synthetase from Pseudomonas mendocina 35,"*Biochem. J.* 340:793-801 (1999).

Binstock and Schulz, "Fatty acid oxidation complex from *Escherichia coli*,"*Methods Enzymol.* 71(Pt C):403-411 (1981).

Birch et al., "Cloning, sequencing, and expression of the gene encoding methylmalonyl-Coenzyme a mutase from Streptomyces cinnamonensis,"*J. Bacteriol.* 175(11):3511-3519 (1993).

Birrer et al., "Electro-transformation of C*lostridium beijerinckii* NRRL B-592 with shuttle plasmid pHR106 and recombinant derivatives,"*Appl. Microbial. Biotechnol.* 41(1):32-38 (1994).

Bisswanger, "Substrate specificity of the Pyruvate Dehydrogenase Complex from *Escherichia coli*,"*J. Biol. Chem.* 256(2):815-822 (1981).

Blanco et al., "Critical catalytic functional groups in the mechanism of aspartate-β-semialdehyde dehydrogenase,"*Acta. Crystallogr. D. Biol. Crystallogr.* 60(Pt 10):1808-1815 (2004).

Blanco et al., "The role of substrate-binding groups in the mechanism of aspartate-β-semialdehyde dehydrogenase,"*Acta. Crystallogr. D. Biol. Crystallogr.* 60(Pt 8):1388-1395 (2004).

Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase,"*Eur. J. Biochem.* 123(3):563-569 (1982).

Blazquez et al., "Identification and analysis of a glutaryl-CoA dehydrogenase-encoding gene and its cognate transcriptional regulator from Azoarcus sp. CIB,"*Environ. Microbial.* 10(2):474-482 (2008).

Blombach et al., "Corynebacterium glutamicum tailored for high-yield L-valine production,"*Appl. Microbiol. Biotechnol.* 79(3):471-479 (2008).

Blomqvist et al., "Characterization of the genes of the 2,3-butanediol operons from Klebsiella terrigena and Enterobacter aerogenes,"*J. Bacteriol.* 175:1392-1404 (1993).

Bobik and Rasche, "HPLC assay for methylmalonyl-CoA epimerase,"*Anal. Bioanal. Chem.* 375(3):344-349 (2003).

Bobik and Rasche, "Identification of the human methylmalonyl-CoA racemase gene based on the analysis of prokaryotic gene arrangements. Implications for decoding the human genome,"*J. Biol. Chem.* 276(40):37194-37198 (2001).

Bobik et al., "Propanediol Utilization Genes (pdu) of Salmonella typhimurium: Three Genes for the Propanediol Dehydratase,"*J. Bacteriol.* 179(21):6633-6639 (1997).

Bock et al., "Purification and characterization of two extremely thermostable enzymes, phosphate acetyltransferase and acetate kinase, from the hyperthermophilic eubacterium Thermotoga maritima,"*J. Bacteriol.* 181:1861-1867 (1999).

Boiangiu et al., "Sodium Ion Pumps and Hydrogen Production in Glutamate Fermenting Anaerobic Bacteria,"*J. Mol. Microbial. Biotechnol.* 10:105-119 (2005).

Boles et al., "Characterization of a glucose-repressed pyruvate kinase (Pyk2p) in Saccharomyces cerevisiae that is catalytically insensitive to fructose-1, 6-bisphosohate,"*J. Bacteriol.* 179:2987-2993 (1997).

Bonnarme et al., "Itaconate biosynthesis in Aspergillus terreus,"*J. Bacteriol.* 177(12):3573-3578 (1995).

Bonner and Bloch, "Purification and properties of fatty acyl thioesterase l from *Escherichia coli*,"*J. Biol. Chem.* 247(10):3123-3133 (1972).

Boronin et al., "Plasmids specifying £-caprolactam degradation in Pseudomonas strains,"*FEMS Microbial Lett.* 22(3): 167-170 (1984).

Bose et al., "Genetic analysis of the methanol- and methylamine-specific methyltransferase 2 genes of Methanosarcina acetivorans C2A,"*J. Bacterial.* 190(11):4017-4026 (2008).

Bott et al., "Methylmalonyl-CoA decarboxylase from Propionigenium modestum. Cloning and sequencing of the structural genes and purification of the enzyme complex,"*Eur. J. Biochem.* 250:590-599 (1997).

Botting et al., "Substrate Specificity of the 3-Methylaspartate Ammonia-Lyase Reactin: Observation of Differential relative Reaction Rates for Substrate-Product Pairs,"*Biochemistry* 27:2953-2955 (1988).

Bottomley et al., "Cloning, sequencing, expression, purification and preliminary characterization of type II dehydroquinase from Helicobacter pylori,"*Biochem. J.* 319:559-565 (1996).

Bower et al., "Cloning, sequencing, and characterization of the Bacillus subtilis biotin biosynthetic operon,"*J. Bacterial.* 178(14):4122-4130 (1996).

Boylan and Dekker, "L-Threonine Dehydrogenase of *Escherichia Coli* K-12,"*Biochem. Biophys. Res. Commun.* 85(1):190-197 (1978).

Boynton et al., "Cloning, sequencing, and expression of clustered genes encoding β-hydroxybutyryl-Coenzyme A (CoA) dehydrogenase, crotonase, and butyryl-CoA dehydrogenase from Clostridium acetobutylicum ATCC 824,"*J. Bacterial.* 178(11):3015-3024 (1996).

Brachmann et al., "Designer deletion strains derived from Saccharomyces cerevisiae S288C: a useful set of strains and plasmids for PCR-mediated gene disruption and other applications,"*Yeast* 14(2):115-132 (1998).

Bradford, "A rapid and sensitive method for the quantitation of microgram quantities of protein utilizing the principle of protein-dye binding,"*Anal. Biochem.* 72:248-254 (1976).

Branlant, "Nucleotide sequence of *Escherichia coli* gap gene. Different evolutionary behavior of the NAD+-binding domain and of the catalytic domain of D-glyceraldehyde-3-phosphate dehydrogenase,"*Eur. J. Biochem.* 150:61-66 (1985).

Brasen and Schonheit, "Unusual ADP-forming acetyl-Coenzyme a synthetases from the mesophilic halophilic euryarchaeon Haloarcula marismortui and from the hyperthermophilic crenarchaeon Pyrobaculum aerophilum ,"*Arch. Microbial.* 182(4):277-287 (2004).

Braune et al., "The sodium ion translocating glutaconyl-CoA decarboxylase from Acidaminococcus fermentans: cloning and function on the genes forming a second operon,"*Mol. Microbial.* 31(2):473-487 (1999).

Bravo et al., "Reliable, sensitive, rapid and quantitative enzyme-based assay for gamma-hydroxybutyric acid (GHB),"*J. Forensic Sci.* 49:379-387 (2004).

Bredwell et al., "Reactor Design Issues for Synthesis-Gas Fermentations,"*Biotechnol. Prog.* 15(5):834-844 (1999).

Breese et al., "Genes coding for the benzoyl-CoA pathway of anaerobic aromatic metabolism in the bacterium Thauera aromatica,"*Eur. J. Biochem.* 256(1):148-154 (1998).

Breitkruez et al., "A novel y-hydroxybutyrate dehydrogenase: Identification and expression of an Arabidopsis cDNA and potential role under oxygen deficiency,"*J. Biol. Chem.* 278:41552-41556 (2003).

Bremer, "Pyruvate Dehydrogenase, Substrate Specificity and Product Inhibition,"*Eur. J. Biochem.* 8:535-540 (1969).

Brey et al., "Cloning of multiple genes involved with cobalamin {Vitamin $B_{12}$ ) biosynthesis in Bacillus megaterium,"*J. Bacterial.* 167:623-630 (1986).

Bro et al., "In silico aided metabloic engineering of Saccharomyces cerevisiae for improved bioethanol production,"*Metab. Eng.* 8(2):102-111 (2006).

Brooke et al., "GAMS: A User's Guide. GAMS Development Corporation," (1998).

(56) References Cited

OTHER PUBLICATIONS

Broun et al., "Catalytic plasticity of fatty acid modification enzymes underlying chemical diversity of plant lipids," Science 282:1315-1317 (1998).
Brown et al., "A role for pabAB, a p-aminobenzoate synthase gene of *Streptomyces venezuelae* ISP5230, in chloramphenicol biosynthesis,"*Microbiol.* 142 { Pt 6):1345-1355 (1996).
Brown et al., "Comparative structural analysis and kinetic properties of lactate dehydrogenases from the four species of human malarial parasites,"*Biochemistry* 43:6219-6229 (2004).
Browner et al., "Sequence analysis, biogenesis, and mitochondrial import of the a-subunit of rat liver propionyl-CoA carboxylase,"*J. Biol. Chem.* 264:12680-12685. (1989).
Bu and Tobin, "The exon-intron organization of the genes (GAD1 and GAD2) encoding two human glutamate decarboxylases ($GAD_{67}$ and $GAD_{65}$) suggests that they derive from a common ancestral GAD,"*Genomics* 21:222-228 (1994).
Bu et al., "Two human glutamate decarboxylases, 65-kDa GAD and 67-kDa GAD, are each encoded by a single gene,"*Proc. Natl. Acad. Sci. U.S.A.* 89:2115-2119 (1992).
Buchanan et al., "An extremely thermostable aldolase from Sulfolobus solfataricus with specificity for non-phosphorylated substrates,"*Biochem. J.* 343:563-570 (1999).
Buck et al., "Primary structure of the succinyl-CoA synthetase of *Escherichia coli*,"*Biochem.* 24(22):6245-6252 (1985).
Buckel and Barker, "Two pathways of glutamate fermentation by anaerobic bacteria,"*J. Bacterial.* 117(3):1248-1260 (1974).
Buckel and Golding, "Radical enzymes in anaerobes,"*Annu. Rev. Microbiol.* 60:27-49 (2006).
Buckel and Golding, "Radical species in the catalytic pathways of enzymes from anaerobes,"*FEMS Microbiol. Rev.* 22(5):523-541 (1999).
Buckel et al., "ATP-Driven electron transfer in enzymatic radical reactions,"*Curr. Opin. Chem. Biol.* 8:462-467 (2004).
Buckel et al., "Glutaconate CoA-Transferase from Acidaminococcus fermentans,"*Eur. J. Biochem.* 118:315-321 (1981).
Buckel et al., "Radical-mediated dehydration reactions in anaerobic bacteria,"*Biol. Chem.* 386:951-959 (2005).
Buckel, "Sodium ion-translocating decarboxylases,"*Biochimica. Biophvsica. Acta* 1505:15-27 (2001).
Bueding and Yale, "Production of a-methylbutyric acid by bacteria-free Ascaris lumbricoides,"*J. Biol. Chem.* 193:411-423 (1951).
Buhler and Simon, "On the kinetics and mechanism of enoate reductase,"*Hoppe Sevlers Z. Phvsiol. Chem.* 363(6):609-625 (1982).
Bunch et al., "The ldhA gene encoding the fermentative lactate dehydrogenase of *Escherichia coli*,"*Microbiol.* 143:187-195 (1997).
Burgard and Maranas, "Probing the performance limits of the *Escherichia coli* metabolic network subject to gene additions or deletions,"*Biotechnol. Bioend.* 74:364-375 (2001).
Burgard et al., "Minimal Reaction Sets for *Escherichia coli* Metabolism under Different Growth Requirements and Uptake Environments,"*Biotechnol. Prod.* 17:791-797 (2001).
Burgard et al., "Optknock: a bilevel programming framework for identifying gene knockout strategies for microbial strain optimization,"*Biotechnol. Bioeng.* 84(6):647-.657 (2003).
Burke et al., "The Isolation, Characterization, and Sequence of the Pyruvate Kinase Gene of Saccharomyces cerevisiae,"*J. Biol. Chem.* 258(4):2193-2201 (1983).
Burks et al., "Stereochemical and Isotopic Labeling Studies of 2-0xo-hept-4-ene-1, 7-dioate Hydratase: Evidence for an Enzyme-Catalyzed Ketonization Step in the Hydration Reaction," J. Am. Chem. Soc. 120(31):7665-7675 (1998).
Buu et al., "Functional characterization and localization of acetyl-CoA hydrolase, Ach1p, in Saccharomyces cerevisiae,"*J. Biol. Chem.* 278:17203-17209 (2003).
Buzenet et al., "Purification and properties of 4-Aminobutyrate 2-Ketoglutarate Aminotransferase From Pig Liver,"*Biochimica. Biophysica. Acta* 522:400-411.

Byrnes et al., "Thermodynamics of reactions catalyzed by anthranilate synthase,"*Biophys. Chem.* 84:45-64 (2000).
Cahyanto et al., "Regulation of aspartokinase, asparate semialdehyde dehydrogenase, dihydrodipicolinate synthease and dihydropdipicolinate reductase in Lactobacillus plantarum," *Microbiology.* 152 (Pt 1): 105-112 (2006).
Caldovic and Tuchman, "N-Acetylglutamate and its changing role through evolution,"*Biochem. J.* 372:279-290 (2003).
Calhoun et al., "Threonine deaminase from *Eschericiha coli*. I. Purification and properties,"*J. Biol. Chem.* 248(10):3511-3516 (1973).
Camara et al., "Characterization of a Gene Cluster Involved in 4-Chlorocatechol Degradation by *Pseudomonas reinekei* MT1,"*J. Bacteriol.* 191(15):4905-4915 (2009).
Campbell and Cronan, Jr., "The enigmatic *Escherichia coli* fadE gene is yafH,"*J.Bacteriol.* 184(13):3759-3764 (2002).
Campbell et al., "A complete shikimate pathway in Toxoplasma gondii: an ancient eukaryotic innovation,"*Int. J. Parasitol.* 34:5-13 (2004).
Campbell et al., "A new *Escherichia coli* metabolic competency: growth on fatty acids by a novel anaerobic β-oxidation pathway,"*Mol. Microbiol.* 47(3):793-805. (2003).
Canovas et al., "Characterization of the genes for the biosynthesis of the compatible solute ecotine in the moderately haliphilic bacterium Halomonas elongata DSM 3043,"*Syst. Appl. Microbiol.* 21:487-497 (1998).
Cao et al., "Simultaneous Production and recovery of Fumaric Acid from Immobilized Rhizopus oryzae with a Rotary biofilm Contactor and an Adsorption col.,"*Appl. Environ. Microbiol.* 62(8):2926-2931 (1996).
Carlini et al., "Guerbet condensation of methanol with n-propanol to isobutyl alcohol over heterogeneous copper chromite/Mg-Al mixed oxides catalysts,"*J. Mol. Catal. A. Chem.* 220:215-220 (2004).
Carlini et al., "Selective synthesis of isobutanol by means of the Guerbet reaction Part 3: Methanol/n-propanol condensation by using bifunctional catalytic systems based on nickel, rhodium and ruthenium species with basic components,"*J. Mol. Catal. A. Chem.* 206:409-418 (2003).
Carlini et al., "Selective synthesis of isobutanol by means of the Guebet reaction Part 1. Methanol/n-propanol condensation by using copper based catalytic systems,"*J. Mol. Catal. A. Chem.* 184:273-280 (2002).
Carlini et al., "Selective synthesis of isobutanol by means of the Guerbet reaction Part 2. Reaction of methanol/ethanol and methanol/ethanol/n-propanol mixtures over copper based MeONa catalytic systems,"*J. Mol. Catal. A. Chem.* 200:137-146.
Carpenter et al., "Structure of dehydroquinate synthase reveals an active site capable of multisteo catalysis,"*Nature* 394:299-302 (1998).
Carretero-Paulet et al., "Expression and molecular analysis of the Arabidopsis DXR gene encoding1-deoxy-o-xylulose 5-phosphate reductoisomerase, the firszt committed enzyme of the 2-C-methyl-D-erythritiol 4-phosphate pathway,"*Plant Physiol.* 129:1581-1591 (2002).
Carta et al., "Production of fumaric acid by fermentation of enzymatic hydrolysates derived from *Cassava bagasse*,"*Biores. Tech.* 68:23-28 (1999).
Cary et al., "Cloning and Expression of Clostridium acetobutylicum ATCC 824 Acetoacetyl-Coenzyme A:Acetate/Butyrate:Coenzyme A-Transferase in *Escherichia coli*,"*App. Environ. Microbiol.* 56(6):1576-1583 (1990).
Cary et al., "Cloning and expression of Clostridium acetobutylicum phosphotransbutyrylase and butyrate kinase genes in *Escherichia coli*,"*J. Bacteriol.* 170(10):4613-4618 (1988).
Casero and Pegg, "Spermidine/spermine N'-acetyltransferase-the turning point in polyamine metabolism,"*Faseb J.* 7:653-661 (1993).
Caspi et al., "MetaCyc: a multiorganism database of metabolic pathways and enzymes,"*Nucleic Acids Res.* 34(Database issue):D511-D516 (2006).
Cavin et al., "Gene cloning, transcriptional analysis, purification, and characterization of phenolic acid decarboxylase from bacillus subtilis,"*Appl. Environ. Microbiol.* 64(4):1466-1471 (1998).

(56) References Cited

OTHER PUBLICATIONS

Cha and Bruce, "Stereo- and regiospecific cis,cis-muconate cycloisomerization by Rhodococcus rhodochrous N75,"*FEMS Microbiol. Lett.* 224:29-34 (2003).
Cha and Parks, Jr., "Succinic Thiokinase. I. Purification of the Enzyme from Pig Heart,"*J. Biol. Chem.* 239:1961-1967 (1964).
Chandra et al. "Pyruvate decarboxylase: a key enzyme for the oxidative metabolism of lactic acid by Acetobacter pasteurianus,"*Arch. Microbiol.* 176:443-451 (2001).
Chang et al., "p-Aminobenzoic acid and chloramphenicol biosynthesis in *Streptomyces venezue/ae* : gene sets for a key enzyme, 4-amino-4-deoxychorismate synthase,"*Microbiology* 147:2113-2126 (2001).
Chang et al., "Effects of deletions at the carboxyl terminus of Zymomonas mobills pyruvate decarboxylase on the kinetic properties and substrate specificity,"*Biochemistry* 39(31):9430-9437 (2000).
Chao and Ramsdell, "The effects of wall populations on coexistence of bacteria in the liquid ohase of chemostat cultures,"*J. Gen. Microbiol.* 131(5):1229-1236 (1985).
Chaparro-Riggers et al., "Comparison of Three Enoate Reductases and their Potential Use for Biotransformations,"*Adv. Synth. Catal.* 349:1521-1531 (2007).
Charles et al., "The isolation and nucleotide sequence of the complex AROM locus of Aspergillus nidulans,"*Nucleic Acids Res.* 14:2201-2213 (1986).
Charrier et al., "A novel class of CoA-transferase involved in short-chain fatty acid metabolism in butyrate-producing human colonic bacteria,"*Microbiology* 152:179-185 (2006).
Chatterjee et al., "A general model for selectively in olefin cross methathesis,"*J. Am. Chem. Soc.* 125(37):11360-11370 (2003).
Chatterjee et al., "Mutation of the ptsG Gene Results in Increased Production of Succinate in Fermentation of Glucose by *Escherichia coli*,"*Appl. Env. Microbial.* 67:148-154 (2001).
Chaudhuri et al., "Identification of the active-site lysine residues of two biosynthetic 3-dehydroquinases,"*Biochem. J.* 275:1-6 (1991).
Chen and Hiu, "Acetone-Butanol-Isopropanol Production by Clostridium beijerinckii (Synonym, Clostridium Butylicum),"*Biotechnology Letters* 8(5):371-376 (1986).
Chen et al., "A novel lysine 2,3-aminomutase encoded by the yodO gene of Bacillus subtilis: characterization and the observation of organic radical intermediates,"*Biochem. J.* 348:539-549 (2000).
Chen et al., "Cloning, Sequencing, Heterologous Expression, Purification, and Characterization of Adenosylcobalamin-dependent D-Ornithine Aminomutase from *Clostridium sticklandii*,"*J. Biol. Chem.* 276:44744-44750 (2001).
Chen et al., "The control region of the pdu/cob regulon in *Salmonella typhimurium*,"*J. Bacterial.* 176:5474-5482 (1994).
Cheng et al., "Genetic Analysis of a Gene Cluser for Cyclohexanol Oxidation in Acinetobacter sp. Strain SE19 by in Vitro Transportation,"*J. Bacterial.* 182(17):4744-4751 (2000).
Cheng et al., "Mammalian Wax Biosynthesis. I. Identification of two fatty acyl-Coenzyme a reductases with different substrate specificities and tissue distributions,"*J. Biol. Chem.* 279(36):37789-37797 (2004).
Cheng et al., "Mammalian Wax Biosynthesis. II. Expression cloning of wax synthase cDNAs encoding a member of the acyltransferase enzyme family,"*J. Biol. Chem.* 279(36):37798-37807 (2004).
Cheng et al., "Structural basis for shikimate-binding specificity of Helicobacter pylori shikimate kinase,"*J. Bacterial.* 187:8156-8163 (2005).
Chicco et al., "Regulation of Gene Expression of Branched-chain Keto Acid Dehydrogenase Complex in Primary Cultured Hepatocytes by Dexamethasone and a cAMP Analog,"*J. Biol. Chem.* 269(30):19427-19434 (1994).
Chirpich et al., "Lysine 2,3-Aminomutase. Purification and Properties of Pyridoxal Phosphate and S-Adenosylmethionine-Activated Enzyme,"*J. Biol. Chem.* 245(7):1778-1789 (1970).

Cho et al., "Critical residues for the Coenzyme specificity of NAO+ -dependent 15-hydroxyprostaglandin dehydrogenase,"*Arch. Biochem. Biophys.* 419:139-146 (2003).
Choi et al, "Olefin Metathesis Involving Ruthenium Enoic Carbene Complexes,"*Am. Chem. Soc.* 123(42):10417-10418 (2001).
Choi et al., "Enhanced production of cis, cis-muconate in a cell-recycle bioreactor,"*J. Ferment. Bioeng.* 84:70-76 (1997).
Choi-Rhee and Cronan, "The biotin carboxylase-biotin carboxyl carrier protein complex of *Escherichia coli* acetyl-CoA carboxylase,"*J. Biol. Chem.* 278:30806-30812 (2003).
Chopra et al., "Expression, purification, and biochemical characterization of *Mycobacterium tuberculosis* aspartate decarboxylase, PanD,"*Protein Expr. Purif.* 25:533-540 (2002).
Chou et al., "Effect of Modulated Glucose Uptake on High-Level Recombinant Protein Production in a Dense *Escherichia coli* Culture,"*Biotechnol. Prog.* 10:644-647 (1994).
Chowdhury et al., "3-Hydroxyisobutyrate dehydrogenase from Pseudomonas putida E23: purification and characterization,"*Biosci. Biotechnol. Biochem.* 60(12):2043-2047 (1996).
Chowdhury et al., "Cloning and overexpression of the 3-hydroxyisobutyrate dehydrogenase gene from pseudomonas putida E23,"*Biosci. Biotechnol. Biochem.* 67(2):438-441 (2003).
Christenson et al., "Kinetic analysis of the 4-methylideneimidazole-5-one-containing tyrosine aminomutase in enediyne antitumor antibiotic C-1027 biosynthesis,"*Biochemistry* 42:12708-12718 (2003).
Chuakrut et al., "Characterization of a bifunctional archael acyl Coenzyme a carboxylase,"*J. Bacteriol.* 185:938-947 (2003).
Clark and Ljungdahl, "Purification and properties of 5,10-methylenetetrahydrofolate reductase from Clostridium formicoaceticum,"*Methods Enzymol.* 122:392-399.(1986).
Clark and Ljungdahl, "Purification and Properties of 5,10-Methylenetetrahydrofolate Reductase, an Iron-sulfur Flavoprotein from Clostridium formicoaceticum,"*J. Biol.Chem.* 259(17)10845-10849 (1984).
Clark et al., "Mutants of *Escherichia coli* defective in acid fermentation,"*Appl. Biochem. Biotechnol.* 17:163-173 (1988).
Clark, Progress Report for Department of Energy Grant DE-FG02-88ER13941, "Regulation of Alcohol Fermentation in *Escherichia coli*," pp. 1-7 for the period: Jul. 1991-Jun. 1994.
Clarke et al., "Rational construction of a 2-Hydroxyacid Dehydrogenase With New Substrate Specificity,"*Biochem. Biophys. Res. Commun.* 148:15-23 (1987).
Clausen et al., "PAD1 encodes phenylarcrylic acid decarboxylase which confers resistance to cinnamic acid in *Saccharomyces cerevisiae*,"*Gene* 142:107-112 (1994).
Coco et al., "DNA shuffling method for generating highly recombined genes and evolved enzymes,"*Nat. Biotechnol.* 19:354-359 (2001).
Coggins et al., "The arom multifunctional enzyme from *Neurospora crassa*,"*Methods Enzymol.* 142:325-341 (1987).
Colby and Chen, "Purification and properties of 3-hydroxybutyryl-Coenzyme A dehydrogenase from *Clostridium beijerinckii* ("*Clostridium butylicum*") NRRL 8593,"*Appl. Environ. Microbiol.* 58:3297-3302 (1992).
Coleman, "Expression of a glutamate decarboxylase homologue is required for normal oxidative stress tolerance in *Saccharomyces cerevisiae*,"*J. Biol. Chem.* 276:244-250 (2001).
Conrad et al., "D- and L-Isoleucine Metabolism and Regulation of Their Pathways in *Pseudomonas Putida*,"*J. Bacteriol.* 118(1):103-111 (1974).
Cooper, "Glutamate-y-aminobutyrate transaminase,"*Methods Enzymol.* 113:80-82 (1985).
Corthesy-Theulaz et al., "Cloning and Characterization of Helicobacter pylori Succinyl CoA:Acetoacetate CoA-transferase, a Novel Prokaryotic Member of the CoA-transferase Family,"*J. Biol. Chem.* 272(41):25659-25667 (1997).
Couturier et al., "A Cyclometalated Aryloxy (chloro)neopentylidenetungsten Complex: A Highly Active and Stereoselective Catalyst for the Metathesis of cis- and trans-2-Pentene, Norbornene, 1-Methyl-norbornene, and Ethyl Oleate,"*Angew. Chem Int. Ed. Enal.* 31(5):628-631 (1992).

(56) References Cited

OTHER PUBLICATIONS

Cox et al., "Development of a metabolic network design and optimization framework incorporating implementation constraints: A succinate production case study,"*Metab. Ena.* 8(1):46-57 (2006).
Craney et al., "A synthetic luxCDABE gene cluster optimized for expression in high-GC bacteria,"*Nucleic Acids Res.* 35(6):e46 (2007).
Cukalovic et al., "Feasibility of production method for succinic acid derivatives: a marriage of renewable resources and chemical technology,"*Biofuels Bioprod. Bioref.* 2:505-529 (2008).
Cunningham et al., "Transcriptional regulation of the aconitase genes (acnA and acnB) of *Escherichia coli*,"*Microbiology* 143(Pt 12):3795-3805 (1997).
Dai et al., "Highly Selective Diels-Alder Reactions of directly Connected Enzyme Dienphiles,"*J. Am. Chem. Soc.* 129:645-657 (2007).
Dakoji et al., "Studies on the inactivation of bovine liver enoyl-CoA hydratase by (methylenecyclopropyl)formyl-CoA: elucidation of the inactivation mechanism and identification of cysteine-114 as the entrapped nucleophile,"*J. Am. Chem. Soc.* 123(4):9749-9759 (2001).
Dal et al., "Transcriptional Organization of Genes for Protocatechuate and quinate Degradation from Acinetobacter sp. Strain ADP1,"*Appl. Environ. Microbiol.* 71(2):1025-1034 (2005).
Dangel et al., "Anaerobic metabolism of cyclohexanol by denitrifying bacteria,"*Arch. Microbiol.* 150(4):358-362 (1988).
Dangel et al., "Enzyme reactions involved in anaerobic cyclohexanol metabolism by a dentitrifying Psedomonas species,"*Arch. Microbiol.* 152:273-279 (1989).
D'Ari and Rabinowitz, "Purification Characterization, cloning, and Amino Acid Sequence of the Bifunctional Enzyme 5,10-Methylenetetrahydrofolate Dehydrogenase/5,10-Methenyltetrahydrofolate Cyclohydrolase from *Escherichia coli*,"*J. Biol. Chem.* 266(35):23953-23958 (1991).
Das et al., "Characterization of a corrinoid protein involved in the C1 metabolism of strict anaerobic bacterium *Moorella thermoacetica*,"*Proteins* 67(1):167-176 (2007).
Datar et al., "Fermentation of biomass-generated producer gas to ethanol,"*Biotechnol. Bioeng.* 86(5):587-594 (2004).
Datsenko et al., "One-step inactivation of chromosomal genes in *Escherichia coli* K-12 using PCR products,"*Proc. Natl. Acad. Sci. U.S.A.* 97:6640-6645 (2000).
Datta et al., "Covalent structure of biodegradative threonine dehydratase of *Escherichi coli*: homology with other dehydratases,"*Proc. Natl. Acad. Sci. U.S.A.* 84(2):393-397 (1987).
Davey and Trudgill, "The metabolism of trans-cyclohexan-1,2-diol by an Acinetobacter species,"*Eur. J. Biochem.* 74(1):115-127 (1977).
Davids et al, "Characterization of the N-acetyltransferases respectively responsible for arylalkylamine and diamine acetylation in Ascaris suum,"*Mol. Biochem. Parasitol.* 64(2):341-344 (1994).
Davie et al., "Expression and assembly of a functional E1 component ($a_2$ $B_2$) of mammalian branched-chain a-ketoacid dehydrogenase complex in *Escherichia coli*,"*J. Biol. Chem.* 267:16601-16606 (1992).
De Biase et al., "Isolation, overexpression, and biochemical characterization of the two isoforms of glutamic acid decarboxylase from *Escherichia coli*," Protein Expr. Purif. 8:430-438 (1996).
de Bok et al., "Two W-containing formate dehydrogenases (CO2-reductases) involving syntrophic propionate oxidation by *Syntrophobacter fumaroxidans*,"*Eur. J. Biochem.* 270:2476-2485 (2003).
de Crecy et al., "Development of a novel continuous culture device for experimental evolution of bacterial populations,"*Appl. Microbiol. Biotechnol.* 77(2): 489-496 (2007).
de la Torre et al., "Identification and functional analysis of a prokaryotic-type aspartate aminotransferase: implications for plant amino acid metabolism,"*Plant. J.* 46(3):414-425 (2006).
de Mata and Rabinowitz, "Formyl-methenyl-methylenetetrahydrofolate synthetase (combined) from yeast. Bio-chemical characterization of the protein from an ADE3 mutant lacking the formyltetrahydrofolate synthetase function,"*J. Biol Chem.* 255:2569-2577 (1980).
de Mendonca et al., "Functional characterization by genetic complementation of aroB-encoded dehydroquinate synthase from Mycobacterium tuberculosis H37Rv and its heterologous expression and purification,"*J. Bacteriol.* 189:6246-6252 (2007).
de Smidt et al., "The alcohol dehydrogenases of Saccharomyces cerevisiae: a comprehensive review,"*FEMS Yeast Rev.* 7:967-978 (2008).
Deana, "Substrate specificity of a dicarboxyl-CoA: dicarboxylic acid Coenzyme A transferase from rat liver mitochondria,"*Biochem. Int.* 26(4):767-773 (1992).
DeFeyter and Pittard, "Purification and properties of shikimate kinase II from *Escherichia coli* K-12,"*J. Bacteriol.* 165:331-333 (1986).
Del Campillo-Campbell et al., "Biotin-requiring Mutants of *Escherichia coli* K-12,"*J. Bacteriol.* 94(6):2065-2066 (1967).
Deno, "The Diels-Alder Reaction with a, p, y, 8-Unsaturated Acids,"*J. Am. Chem. Soc.* 72:4057-4059 (1950).
Department of Energy, "Top value added chemicals from biomass. Volume I—Results of Screening for Potential Candidates from Sugars and Synthesis Gas,"*Biomass.* Aug. 2004.
Desvaux, "Clostridium cellulolyticum: model organism of mesophilic cellulolytic clostridia."*FEMS Microbiol. Rev.* 29(4):741-764 (2005).
Devos et al., "Practical limits of function prediction,"*Proteins* 41:98-107 (2000).
Di Gennaro, "Styrene lower catabolic pathway in Pseudomonas fluorescens ST: identification and characterization of genes for phenylacetic acid degradation,"*Arch. Microbiol.* 188(2):117-125 (2007).
Diao et al., "Crystal structure of butyrate kinase 2 from *Thermotoga maritima*, a member of the ASKHA superfamily of phosphotransferases,"*J. Bacteriol.* 191:2521-2529 (2009).
Diao et al., "Crystallization of the butyrate kinase 2 from *Thermotoga maritima* mediated by vapor diffusion of acetic acid,"*Acta. Crystallogr D. Biol. Crystallogr.* 59(Pt 6):1100-1102 (2003).
Dias et al., "Well-Defined Ruthenium Olefin Metathesis Catalyst: Mechanism and Activity,"*J. Am. Chem. Soc.* 119(17):3887-3897 (1997).
Diaz et al., "Gene cloning, heterologous overexpression and optimized refolding of the NAD-glutamate dehydrogenase from *Haloferax mediterranei*,"*Extremophiles* 10:105-115 (2006).
Diderichsen et al., "Cloning of aldB, Which Encodes a-Acetolactate Decarboxylase, an Exoenzyme from bacillus brevis,"*J Bacterial.* 172(8):4315-4321 (1990).
Dittrich et al., "Redistribution of Metabolic Fluxes in the Central Aerobic Metabolic Pathway of *E.coli* Mutant Strains with Deletion of the *ackA-pta and poxB* Pathways for the Synthesis of Isoamyl Acetate,"*Biotechnol Prog.* 21(2).:627-631 (2005).
Do et al., "Engineering *Escherichia coli* for fermentative dihydrogen production: potential role of NADH-ferredoxin oxidoreductase from the hydrogenosome of anaerobic protozoa,"*Appl. Biochem. Biotechnol.* 153(1-3):21-33 (2009).
Do et al., "Growth of *rhodospirillum rubrum*on synthesis gas: conversion of CO to $H_2$ and Poly-β-hydroxyalkanoate,"*Biotechnol. Bioeng.* 97(2):279-286 (2007).
Dobbek et al., "Crystal structure of a carbon monoxide dehydrogenase reveals a [Ni-4Fe-5S] cluster,"*Science* 293(5533):1281-1285 (2001).
Dombek and Ingram, "Ethanol production during batch fermentation with *Saccharomyces cerevisiae*: Changes in glycolytic enzymes and internal pH,"*Appl. Environ. Microbiol.* 53:1286-1291 (1987).
Donnelly and Cooper, "Succinic semialdehyde dehydrogenases of *Escherichia coli*: Their role in the degradation of p-hydroxyphenylacetate and y-aminobutyrate "*Eur. J. Biochem.* 113:555-561 (1981).
Donnelly and Cooper, "Two succinic semialdehyde dehydrogenases are induced when *Escherichia coli* K-12 Is grown on y-aminobutyrate,"*J. Bacteriol.* 145:1425-1427 (1981).

(56) References Cited

OTHER PUBLICATIONS

Donnelly et al., "A novel fermentation pathway in an *Escherichia coli* mutant producing succinic acid, acetic acid, and ethanol," *App. Biochem. Biotech.* 70-72:187-198 (1998).

Doten et al., "Cloning and Genetic Organization of the pca Gene cluster from *Acinetobacter calcoaceticus*," *J. Bacteriol.* 169(7):3168-3174 (1987).

Doyle et al., "Structural Basis for a Change in substrate Specificity: Crystal Structure of S113E Isocitrate Dehydrogenase in a Complex with Isopropylmalate, $Mg^2$ and NAPD," *Biochemistry* 40:4234-4241 (2001).

Drake and Daniel, "Physiology of the thermophilic acetogen *Moorella thermoacetica*," *Res. Microbiol.* 155(10):869-883 (2004).

Drake, "*Acetogenesis*, acetogenic bacteria, and the acetyl-CoA "Wood/Ljungdahl" pathway: past and current perspectives," in *Acetogenesis*, H. L. Drake, (ed.), Chapman & Hall, New York, p. 3-60 (1994).

Drake, "Demonstration of hydrogenase in extracts of the homoacetate-fermenting bacterium *Clostridium thermoaceticum*," *J. Bacteriol.* 150(2):702-709 (1982).

Draths and Frost, "Environmentally compatible synthesis of adipic acid from D-glucose," *J. Am. Chem. Soc.* 116:399-400 (1994).

Drevland et al., "Enzymology and Evolution of the Pyruvate Pathway to 2-Oxobutyrate in *Methanocaldococcus jannachii*," *J. Bacteriol.* 189(12):4391-4400 (2007).

Drewke et al., "4-0-Phosphoryl-L-threonine, a substrate of the pdxC(serC) gene product involved in vitamin $B_6$ biosynthesis," *FEBS Lett.* 390:179-182 (1996).

Drewke et al., "Ethanol formation in adh) mutants reveals the existence of a novel acetaldehyde-reducing activity in *Saccharomyces cerevisiae*," *J. Bacteriol.* 172:3909-3917 (1990).

Driscoll and Taber, "Sequence Organization and Regulation of the *bacillus subtilis* menBE Qperon," *J. Bacteriol.* 174(15):5063-5071 (1992).

Drummond and Stern, "Enzymes of ketone body metabolism. II. Properties of an acetoacetate-synthesizing enzyme prepared from ox liver," *J. Biol. Chem.* 235:318-325 (1960).

Du et al., "Succinic acid production from wheat using a biorefining strategy," Appl. Microbiol. Biotechnol. 76:1263-1270 (2007).

Duarte et al., "Reconstruction and validation of *Saccharomyces cerevisiae* iND750, a fully compartmentalized genome-scale metabolic model," *Genome Res.* 14(7):1298-1309 (2004).

Duckworth et al., "The Binding of Reduced Nicotinamide Adenine Dinucleotide to Citrate Synthase of *Escherichia coli* K12," *Biochemistry* 15(1):108-114 (1976).

Duncan et al., "The pentafunctional arom enzyme of *Saccharomyces cerevisiae* is a mosaic of monofunctional domains," *Biochem. J.* 246:375-386 (1987).

Duncan et al., "Acetate utilization and butyryl Coenzyme A (CoA):acetate-CoA transferase in butyrate-producing bacteria from the human large intestine," *Appl. Environ. Microbiol.* 68(10):5186-5190 (2002).

Duncombe and Frerman, "Molecular and catalytic properties of the acetoacetyl-Coenzyme a thiolase of *Escherichia coli*," *Arch. Biochem. Biophys.* 176(1):159-170 (1976).

Duran et al., "Characterization of cDNA clones for the 2-methyl branched-chain enoyl-CoA reductase. An enzyme involved in branched-chain fatty acid synthesis in anerobic mitochondria of the parasitic nematode *Ascaris suum*," *J. Biol. Chem.* 268(30):22391-22396 (1993).

Durner et al., "Accumulation of Poly[(R)-3-Hydroxyalkanoates] Pseudomonas oleovorans during Growth with Octanoate in continuous culture at Different Dilution Rates," *Appl. Environ. Microbiol.* 66(8):3408-3414 (2000).

Durre and Bahl, "Microbial Production of Acetone/Butanol/Isopropanol," In Biotechnology vol. 6: "Products of Primary Metabolism", Second edition pp. 229-268, M. Roehr, ed. Published jointly by: VCH Verlagsgesellschaft mbH, Weinheim, Federal Republic of Germany and VCH Publishers Inc., New York, NY (1996).

Durre et al., "Solventogenic enzymes of *Clostridium acetobutylicum*: catalytic properties, genetic organization, and transcriptional regulation," *FEMS Microbiol. Rev.* 17:251-262 (1995).

Durre, "Biobutanol: an attractive biofuel," *Biotechnol. J.* 2(12):1525-1534 (2007).

Durre, "New insights and novel developments in clostridial acetone/butanol/isopropanol fermentation," *Appl. Microbiol. Biotechnol.* 49:639-648 (1998).

Dusch et al., "Expression of the *Corynebacterium glutamicum* panD gene encoding L-aspartate-a-decarboxylase leads to pantothenate overproduction in *Escherichia coli*," *Appl. Environ. Microbiol.* 65(4)1530-1539 (1999).

Dutscho et al., "Cloning and sequencing of the genes of 2-hydoxyglutaryl-CoA dehydratase from *Acidaminococcus fermentans*," *Eur. J. Biochem.* 181(3):741-746 (1989).

Dwiarti et al., "Purification and characterization of cis-aconitic acid decarboxylase from *Aspergillus terreus* TN484-M1, "*J. Biosci Bioena.* 94(1):29-33 (2002).

Dwyer et al., "Proton Abstraction reaction, Steady-State kinetics, and Oxidation-Reduction Potential of Human Glutaryl-CoA Dehydrogenase," *Biochemistry.* 39:11488-11499 (2000).

Dykhuizen, "Chemostats used for studying natural selection and adaptive evolution," *Methods. Enzymol.* 224:613-631 (1993).

Eberhard and Gerlt, "Evolution of Function in the Crotonase Superfamily: The Stereochemical course of the Reaction catalyzed by 2-Ketocyclohexanecarboxyl-CoA Hydrolase," *J. Am. Chem. Soc.* 126:7188-7189 (2004).

Edegger et al., "Biocatalytic deuterium- and hydrogen-transfer using over-expressed ADH-'A': enhanced steroselectivity and $^2$H-labeled chiral alcohols," *Chem. Commun.* 22:2402-2404 (2006).

Eden et al., "Involvement of branched-chain amino acid aminotransferases in the production of fusel alcohols during fermentation in yeast," *Appl. Microbiol. Biotechnol.* 55:296-300 (2001).

Edwards and Palsson, "Metabolic flux balance analysis and the in silico analysis of *Escherichia coli* K-12 aene deletions," *BMC Bioinform.* 1:1 (2000).

Edwards and Palsson, "Systems properties of the *Haemophilus influenzae* Rd metabolic genotype," *J. Biol. Chem.* 274(25):17410-17416 (1999).

Edwards and Palsson, "The *Escherichia coli* MG1655 in silico Metabolic Genotype: Its Definition, Characteristics, and Capabilities," *Proc. Natl. Acad. Sci. U.S.A.* 97(10):5528-5533 (2000).

Edwards et al., "Metabolic modelling of microbes: the flux-balance approach," *Environ. Microbiol.* 4(3):133-140 (2002).

Edwards et al., "In Silica Predictions of *Escherichia coli* metabolic capabilities are Consistent with Experimental Data," *Nat. Biotechnol.* 19(2):125-130 (2001).

Efe et al., "Options for biochemical production of 4-hydroxybutyrate and its lactone as a substitute for petrochemical production," *Biotechnol. Bioeng.* 99:1392-1406 (2008).

Egland et al., "A cluster of bacterial genes for anaerobic benzene ring biodegradation," *Proc. Natl. Acad. Sci. U.S.A.* 94:6484-6489 (1997).

Eikmanns et al., "The phosphoenolpyruvate carboxylase gene of *Corynebacterium glutamicum*: Molecular cloning, nucleotide sequence, and expression." *Mol. Gen. Genet.* 218:330-339 (1989).

Elshahed et al., "Metabolism of Benzoate, Cyclohex-1-ene Carboxylate, and Cyclohexane Carboxylate by "*Syntrophus aciditrophicus*" Strain SB in Syntrophic Association with H2-Using Microorganisms," *Appl. Environ. Microbiol.* 67(4):1728-1738 (2001)

Engel, "Butyryl-CoA Dehydrogenase from *Megasphaera e/sdenii*, "*Methods Enzymol.* 71:359-366 (1981).

Enomoto et al., "Cloning and sequencing of the gene encoding the soluble fumarate reductase from *Saccharomyces cerevisiae*," *DNA Res.* 3:263-267 (1996).

Ensign and Ludden, "Characterization of the Co Oxidation/H2 Evolution System of *Rhodospirillum rubrum*. Role of a 22-kDa iron-sulfur protein in mediating electron transfer between carbon monoxide dehydrogenase and hydrogenase," *J. Biol. Chem.* 266(27)18395-18403 (1991).

(56) References Cited

OTHER PUBLICATIONS

Estevez et al., "X-ray crystallographic and kinetic correlation of a clinically observed human fumarase mutation,"*Protein Sci.* 11(6):1552-1557 (2002).
Eulberg et al., "Characterization of a protocatechuate catabolic gene cluster from *Rhodococcus opacus* 1CP: evidence for a merged enzyme with 4-carboxymuconolactone-cecarboxylating and 3-oxoadipate enol-lactone-hydrolyzing activity,"*J. Bacteriol.* 180:1072-1081 (1998).
Evans et al., "[13C]propionate oxidatin in wild-type and citrate synthase mutant *Escherichia coli*: evidence for multiple pathways of propionate utilization,"*Biochem. J.* 291(Pt 3):927-932 (1993).
Ezeji et al., "Butanol fermentation research: upstream and downstream manipulations,"*Chem. Rec.* 4(5):305-314 (2004).
Faehnle et al., "A New Branch in the Family: Structure of Aspartate-β-semialdehyde Dehydrogenase from *Methanococcus jannaschii*,"*J. Mol. Biol.* 353:1055-1068. (2005).
Feist et al., "The growing scope of applications of genome-scale metabolic reconstructions using *Escherichia coli*,"*Nat. Biotechnol.* 26(6):659-667 (2008).
Feldberg and Datta, "L-threonine deaminase of Rhodospirillum rubrum. Purification and characterization"*Eur. J. Biochem.* 21(3):438-446 (1971).
Fell and Small, "Fat Synthesis in Adipose Tissue. An Examination of Stoichiometric Constraints,"*Biochem. J.* 238(3):781-786 (1986).
Fernandez-Canon and Penalva, "Characterization of a fungal maleylacetoacetate isomerase gene and indentification of its human homologue,"*J. Biol. Chem.* 273:329-337 (1998).
Fernandez-Valverde et al., "Purification of *Pseudomonas putida* Acyl Coenzyme A Ligase Active with a Range of aliphatic and Aromatic substrates,"*Appl. Environ. Microbiol.* 59(4):1149-1154 (1993).
Fischer and Sauer, "Metabolic flux profiling of *Escherichi coli* mutants in central carbon metabolism using GC-MS,"*Eur. J. Biochem.* 270(5):880-891 (2003).
Fish and Blumenthal, "2-Keto-3-deoxy-o-glucarate aldolase,"*Methods Enzymol.* 9:529-534 (1966).
Fishbein and Bessman, "Purification and properties of an enzyme in human blood and rat liver microsomes catalyzing the formation and hydrolysis of y-lactones. I. Tissue localization, stoichiometry, specificity, distinction from esterase,"*J. Biol. Chem.* 241:4835-4841 (1966).
Fishbein and Bessman, "Purification and properties of an enzyme in human blood and rat liver microsomes catalyzing the formation and hydrolysis of y-lactones. Ii. Metal ion effects, kinetics, and equilibria "*J. Biol. Chem.* 241:4842-4847 (1966).
Fitzgerald and Flanagan, "Characterization and sequence analysis of the human ornithine decarboxylase gene,"*DNA* 8:(9):623-634 (1989).
Flint et al., "The role and properties of the iron-sulfur cluster in *Escherichia coli* dihydroxy-acid dehydratase,"*J. Biol. Chem.* 268:14732-14742 (1993).
Flint, "Initial kinetic and mechanistic characterization of *Escherichia coli* fumarase A,"*Arch. Biochem. Biophys.* 311(2):509-516 (1994).
Fochi, "Selective catalytic dehydrogenation of 1, 4-cyclohexadiene to benzene. 1. Radical anions derived from stransition-metal arene complexes as promoters,"*Organometallics* 7:2255-2256 (1988).
Fomine and Tlenkopatchey, "Cross-methathesis of dimethyl maleate and ethylene catalyzed by second generation ruthenium carbene compleses: B3LYP and MPW1K comparison study,"*J. Org. Chem.* 691:5189-5196 (2006).
Fong and Palsson, "Metabolic gene-deletion strains of *Escherichia coli* evolve to computationally predicted growth phenotypes,"*Nat. Genet.* 36(10):1056-1058. (2004).
Fong et al., "Description and Interpretation of Adaptive Evolution of *Escherichia coli* K-12 MG1655 by Using a Genome-Scale in Silico Metabolic Model,"*J. Bacteriol.* 185(21):6400-6408 (2003).
Fong et al., "In Silico design and adaptive evolution of *Escherichia coli* for production of lactic acid,"*Biotechnol. Bioend.* 91(5):643-648 (2005).
Fonknechten et al., "A conserved gene cluster rules anaerobic oxidative degradation of L-ornithine,"*J. Bacteriol.* 191(9):3162-3167 (2009).
Fontaine et al., "Molecular charcterization and transcriptional analysis of adhE2, the gene encoding the NADH-dependent aldehyde/alcohol dehydrogenase responsible for butanol production in alcohologenic cultures of *Clostridium acetobutylicum* ATCC 824,"*J. Bacteriol.* 184:821-830 (2002).
Fontaine et al., "A New Type of Glucose Fermentation by *Clostridium thermoaceticum* N.Sp.,"*J. Bacteriol.* 43(6):701-715 (1942).
Ford et al., "Molecular properties of the lyst1+gene and the regulation of a-aminoadipate reductase in *Schizosaccharomyces pombe*,"*Curr. Genet.* 28:131-137. (1995).
Forouhar et al., "Structural and Functional Evidence for *Bacillus subtilis* PaiA as a Novel $N^1$-Spermidine/spermine Acetyltransferase,"*J. Biol. Chem.* 280(48):40328-40336 (2005).
Forster et al., "Genome-scale reconstruction of the *Saccharomyces cerevisiae* metabolic network,"*Genome Res.* 13(2):244-253 (2003).
Fox et al., "Characterization of the region encoding the CO-induced hydrogenase of *Rhodospirillum rubrum*,"*J. Bacteriol.* 178(21):6200-6208 (1996).
Freiberg et al., "Identification and characterization of the first class of potent bacterial acetyl-CoA carboxylase inhibitors with antibacterial activity,"*J. Biol. Chem.* 279:26066-26073 (2004).
Freidrich et al., "The complete stereochemistry of the enzymatic dehydration of 4-hydroxybutyryl Coenzyme A to crontonyl Coenzyme A,"*Angew. Chem. Int. Ed.* 47:3254-3257 (2008).
Frerman and Duncombe, "Studies on the subunits of *Escherichia coli* Coenzyme A transferase. Reconstitution of an active enzyme,"*Biochim. Biophys. Acta.* 580(2):289-297 (1979).
Fries et al., "Reaction Mechanism of the heterotetrameric ($a_{2\ 2}$) E1 Component of 2-Oxo Acid Dehydrogenase Multienzyme Complexes,"*Biochemistry* 42:6996-7002. (2003).
Frost and Draths, "Synthesis of adipic acid from biomass-derived carbon sources,"*Biotechnol Adv.* 15(1):294 (1997).
Frost et al., "Dehydroquinate synthase from *Escherichia coli*: purification, cloning, and construction of overproducers of the enzyme,"*Biochemistry* 23:4470-4475 (1984).
Frost, "Redefining chemical manufacture. Replacing petroleum with plant-derived feedstocks,"*Ind. Biotechnol.* 1(1):23-24 (2005).
Fu et al., "Crystal structures of human glutaryl-CoA dehydrogenase with and without an alternate substrate: structural bases of dehydrogenation and decarboxylation reactions,"*Biochemistry* 43(30):9674-9684 (2004).
Fujii et al., "Characterization of L-lysine 6-aminotransferase and its structural gene from *Flavobacterium lutescens* IF03084,"*J. Biochem.* 128:391-397 (2000).
Fujii et al., "Error-prone rolling circle amplification: the simplest random mutagenesis protocol,"*Nat. Protoc.* 1:2493-2497 (2006).
Fujii et al., "One-step random mutagenesis by error-prone rolling circle amplification,"*Nucleic Acids Res.* 32:e145 (2004).
Fujii, T. et al. "Molecular Cloning, Sequence Analysis, and Expression of the Yeast Alcohol Acetyltransferase Gene," Appl. Environ. Microbial. 60:2786-2792 (1994).
Fujishiro et al., "Crystallization and Some Properties of Acetylpolyamine Amidohydrolase From *Mycoplana Bullata*,"*Biochem. Biophys. Res. Commun.* 157(3):1169-1174 (1988).
Fujita et al., "Novel Substrate Specificity of Designer 3-Isopropylmalate Dehydrogenase Derived from *Therm us thermophilus* HB8,"*Biosci. Biotechnol. Biochem.* 65(12):2695-2700 (2001).
Fukao et al., "Succinyl-CoA:3-ketoacid CoA transferase (SCOT): cloning of the human SCOT gene, tertiary structural modeling of the human Scot monomer, and characterization of three pathogenic mutations,"*Genomics* 68:144-151 (2000).
Fukuda and Wakagi, "Substrate recognition by 2-oxoacid:ferredoxin oxidoreductase from *Sulfolobus sp.* Strain 7,"*Biochim. Biophys. Acta* 1597:74-80 (2002).

(56) References Cited

OTHER PUBLICATIONS

Fukuda et al., "Role of a highly conserved YPITP motif in 2-oxoacid:ferredoxin oxidoreductase Heterologous expression of the gene from *Sulfolobus sp.* Strain 7, and characterization of the recombinant and variant enzymes,"*Eur. J. Biochem.* 268:5639-5646 (2001).

Fukui et al., "Engineering of Ralstonia eutropha .for production of poly(3-hydroxybutyrate-co-3-hydroxyhexanoate) from fructose and solid-state properties of the copolymer,"*Biomacromolecules* 3(3):618-624 (2002).

Fukumura et al, "Hydrolysis of cyclic and linear oligomers of 6-aminocaproic acid by a bacterial cell extract,"*J. Biochem.* 59(6):531-536 (1966).

Fukumura et al., "Purification and properties of a novel enzyme, L-a-amino-E-caprolactamase from *Cryptococcus laurentii*,"*FEBS Lett.* 89(2):298-300 (1978).

Fuller and Leadlay, "Proton transfer in methylmalonyl-CoA epimerase from *Propionibacterium shermanii*. The reaction of (2R)-methylmalonyl-CoA in tritiated water,"*Biochem. J.* 213(3):643-650 (1983).

Furdui and Ragsdale, "The role of pyruvate ferredoxin oxidoreductase in pyruvate synthesis during autotrophic growth by the Wood-Ljungdahl pathway "*J. Biol. Chem.* 275(37):28494-28499 (2000).

Furukawa et al., "Increased alcohol acetyltransferase activity by inositol limitation in *Saccharomyces cerevisiae* in sake mash "*J. Biosci. Bioena.* 96(4):380-386 (2003).

Galagan et al., "The genome of M. acetivorans reveals extensive metabolic and physiological diversity "*Genome Res.* 12(4):532-542 (2002).

Gallagher et al., "The crystal structure of chorismate lyase shows a new fold and a tightly retained product,"*Proteins* 44:304-311 (2001).

Gangloff et al., "Molecular cloning of the Yeast Mitochondrial Aconitase Gene (AC01) and Evidence of a Synergistic Regulation of Expression by Glucose plus Glutamate," Mol. Cell. Biol. 10(7):3551-3561 (1990).

Garras et al., "Subcellular localisation and induction of NADH-sensitive acetyl-CoA hydrolase and propionyl-CoA hydrolase activities in rat liver under lipogenic conditions after treatment with sulfur-substituted fatty acids," Biochim. *Biophys* Acta 1255(2):154-160 (1995).

Garvie, "Bacterial lactate dehydroqenases," Microbiol. Rev. 44:106-139 (1980).

Gay et al., "Cloning Structural Gene sacB, Which Codes for Exoenzyme Levansucrase of *Bacillus subtilis*: Expression of the Gene in *Escherichia coli*,"*J. Bacteriol.* 153(3):1424-1431 (1983).

Genda et al., "Purification and characterization of fumarase from *Corynebacterium glutamicum*,"*Biosci. Biotechnol. Biochem.* 70:1102-1109 (2006).

Gerhardt et al. "Fermentation of 4-aminobutyrate by *Clostridium aminobutyricum*: cloning of two genes involved in the formation dehydration of 4-hydroxybutyrl-CoA,"*Arch. Microbiol.* 174:189-199 (2000).

Gerischer and Durre, "mRNA Analysis of the adc Gene Region of *Clostridium acetobutylicum* during the Shift to Solventogenesis,"*J. Bacteriol.* 174(2):426-433 (1992).

Gescher et al., "Genes coding for a new pathway of aerobic benzoate metabolism in *Azoarcus evansii*,"*J Bacteriol.* 184(22):6301-6315 (2002).

Giaever et al., "Functional profiling of the *Saccharomyces cerevisiae* genome," Nature 418(6896):387-391 (2002).

Gibbs et al., "Degenerate olignucleotide gene shuffling (DOGS): a method for enhancing the frequence of recombination with family shuffling,"*Gene* 271:13-20. (2001).

Gibson (nee Thomas) et al., "Cross metathesis of the amino acid homoallylglycine,"*Chem. Commun.* 1107-1108 (1997).

Gibson and McAlister-Henn, "Physical and genetic interactions of cytosolic malate dehydrogenase with other gluconeogenic enzymes,"*J. Biol. Chem.* 278:25628-25636 (2003).

Giesel and Simon, "On the occurrence of enoate reductase and 2-oxo-carboxylate reductase in clostridia and some observations on the amino acid fermentation by *Peptostreptococcus anaerobius*,"*Arch. Microbiol.* 135(1):51-57 (1983).

Gillyon et al., "Putrescine Breakdown in the Yeast *Candida boidinii*: Subcellular Location of Some of the Enzymes Involved and Properties of Two Acetamidoaldehyde Dehydrogenases,"*J. Of Gen. Microbiol.* 133:2477-2485 (1987).

Glasemacher et al., "Purification and properties of acetyl-CoA synthetase (ADP-forming), an archaeal enzyme of acetate formation and ATP synthesis, from the hyperthermophile *Pyrococcus furiosus*,"*Eur. J. Biochem.* 244:561-567 (1997).

Gobel et al., "Degradation of Aromatics and Chloroaromatics by *Pseudomonas* sp. Strain B13: Cloning, Characterization, and analysis of Sequences Encoding 3-Oxoadipate:Succinyl-Coenzyme A (CoA) Transferase and 3-oxoaipyl-CoA Thiolase,"*J. Bacteriol.* 184(1):216-223 (2002).

Goda et al., "Cloning, sequencing, and expression in *Escherichia coli* of the Clostridium tetanomorphum gene encoding β-methylaspartase and characterization of the recombinant protein,"*Biochemistry* 31(44):10747-10756 (1992).

Gokarn et al., "Expression of pyruvate carboxylase enhances succinate production in *Escherichia coli* without affecting glucose uptake,"*Biotechnol. Lett.* 20:795-798 (1998).

Gokarn et al., "Metabolic Analysis of *Escherichia coli* in the Presence and Absence of the Carboxylating Enzymes Phosphoenolpyruvate Carboxylase and Pyruvate Carboxylase,"*Appl. Environ. Microbiol.* 66:1844-1850 (2000).

Gokarn, et al., "The physiological effects and metabolic alterations caused by the expression of Rhizobium etli pyruvate carboxylase in *Escherichia coli*,"*Appl. Microbiol. Biotechnol.* 56(1-2):188-195 (2001)

Gokulan et al., "Crystal structure of Mycobacterium tuberculosis diaminipimelate decarboxylase, an essential enzyme in bacterial lysine biosynthesis,"*J. Biol. Chem.* 278(20):18588-18596 (2003).

Goldberg et al., "Improved Conversion of Fumarate to Succinate by *Escherichia coli* Strains Amplified for Fumarate Reductase,"*Appl. Environ. Microbiol.* 45:1838-1847 (1983).

Gong et al., "Specificity Determinants for the Pyruvate Dehydrogenase Component Reaction Mapped with Mutated and Prosthetic Group Modified Lipoyl Domains,"*J. Biol. Chem.* 275(18):13645-13653 (2000).

Gonzalez and Robb, "Genetic analysis of Carboxydothermus hydrogenoformans carbon monoxide dehydrogenase genes cooF and cooS,"*FEMS Microbiol. Lett.* 191(2):243-247 (2000).

Gonzalez et al., "Characterization of a (2R,3R)-2,3-Butanediol Dehydrogenase as the *Saccharomyces cerevisiae* YAL060W Gene Product,"*J. Biol. Chem.* 275(46):35876-35885 (2000).

Gonzalez-Pajuelo et al., "Metabolic engineering of *Clostridium acetobutylicum* for the industrial production of 1, 3-propanediol from glycerol,"*Met. Eng.* 7:329-336 (2005).

Gordon and Doelle, "Purification, properties and immunological relationship of L(+)-lactate dehydrogenase from *Lactobacillus casei*,"*Eur. J. Biochem.* 67:543-555.(1976).

Goupil et al., "Imbalance of Leucine Flux in *Lactococcus lactis* and Its Use for the Isolation of Diacetyl-Overproducing Strains,"*Appl. Environ. Microbiol.* 62(7):2636-2640 (1996).

Goupil-Feuillerat et al., "Transcriptional and Translational Regulation of a-Acetolactate Decarboxylase of *Lactococcus lactis* subsp. *Lactis*,"*J. Bacteriol.* 182(19):5399-5408 (2000).

Gourley et al., "The two types of 3-dehydroquinase have distinct structures but catalyze the same overall reaction,"*Nat. Struct. Biol.* 6:521-525 (1999).

Grant and Patel. "The non-oxidative decarboxylation of p-hydroxybenzoic acid, gentisic acid, protocatechuic acid and gallic acid by *Klebsieha aerogenes* (*Aerobacter aerogenes*),"*Antonie Van Leeuwenhoek* 35:325-343 (1969).

Green and Bennett, "Genetic manipulation of acid and solvent formation in clostridium acetobutvlicum ATCC 824," Biotechnol. Bioena. 58(2-3):215-221 (1998).

Green and Nichols, "p-Aminobenzoate biosynthesis in *Escherichia coli*. Purification of aminodeoxychorismate lyase and cloning of pabC,"*J. Biol. Chem.* 266:12971-12975 (1991).

(56) References Cited

OTHER PUBLICATIONS

Green et al., "Catabolism of a-ketoglutarate by a sucA mutant of *Bradyrhizobium japonicum*: evidence for an alternative tricarboxylic acid cycle,"*J. Bacteriol.* 182:2838-2844 (2000).
Green et al., "Characterization and sequence of *Escherichia coli* pabC, the gene encoding aminodeoxychorismate lyase, a pyridoxal phosphate-containing enzyme,"*J. Bacteriol.* 174:5317-5323 (1992).
Grethlein and Jain, "Bioprocessing of coal-derived synthesis gases by anaerobic bacteria,"*Trends Biotech.* 10:418-423 (1992).
Grolle et al., "Isolation of the dxr gene of *Zymomonas mobilis* and characterization of the 1-deoxy-D-xylulose 5-phosphate reductoisomerase,"*FEMS Microbiol. Lett.* 191:131-137 (2000).
Grubbs, "Olefin Meethathesis,"*Tetrahedron* 60:7117-7140 (2004).
Gu et al., "Crystal structure of shikimate kinase from Mycobacterium tuberculosis reveals the dynamic role of the LID domain in catalysis,"*J. Mol. Biol.* 319:779-789 (2002).
Gueldener et al., "A second set of loxP marker cassettes for Cre-mediated multiple gene knockouts in budding yeast,"*Nucleic Acids Res.* 30(6):e23 (2002).
Guerra et al., "Role of transmembrane segment M8 in the biogenesis and function of yeast plasma-membrane H+-ATPase,"*Biochim. Biophys. Acta* 1768:2383-2392 (2007).
Guest et al., "The fumarase genes of *Escherichia coli*: location of the fumB gene and discovery of a new gene (fumC),"*J. Gen. Microbiol.* 131(11):2971-2984 (1985).
Guettler et al., "*Actinobacillus succinogenes* sp. nov., a novel succinic-acid-producing strain from the bovine rumen,"*Int. J. SYst. Bacteriol.* 49:207-216 (1999).
Guirard and Snell, "Purification and properties of ornithine decarboxylase from *Lactobacillus* sp. 30a,"*J. Biol. Chem.* 255:5960-5964 (1980).
Guo and Bhattacharjee, "Posttranslational activation, site-directed mutation and phylogenetic analyses of the lysine biosynthesis enzymes a-aminoadipate reductase Lys1p (AAR) and the phosphopantetheinyl transferase Lys7p (PPTase) from *Schizosaccharomyces pombe*,"*Yeast* 21:1279-1288 (2004).
Guo and Bhattacharjee, "Site-directed mutational analysis of the novel catalytic domains of a-aminoadipate reductase (Lys2p) from *candida albicans*,"*Mol. Gen. Gemonics* 269:271-279 (2003).
Guterman et al., "Generation of phenylpropanoid pathway-derived volatiles in transgenic plants: rose alcohol acetyltransferase produces phenylethyl acetate and benzyl acetate in petunia flowers,"*Plant Mol. Biol.* 60(4):555-563 (2006).
Gutierrez et al., "A mutant D-amino acid aminotransferase with broad substrate specificity: construction by replacement of the interdoman loop Pro119-Arg120-Pro121 by Gly-Gly-Gly,"*Protein Eng.* 11:53-58 (1998).
Gutknecht et al., "The dihydroxyacetone kinase of *Escherichia coli* utilizes a phosphoprotein instead of ATP as phosphoryl donor,"*Embo J.* 20(10):2480-2486 (2001).
Guyer et al., "Identification of a sex-factor-affinity site in E. coli as Yσ," Cold Spring Harbor Symp. Quant. Biol. 45:135-140 (1981).
Guzman et al., "Tight regulation, modulation, and high-level expression by vectors containing the arabinose $P_{bad}$ promoter,"*J. Bacteriol.* 177:4121-4130 (1995).
Haarasilta and Oura, "On the activity and regulation of anaplerotic and gluconeogenetic enzymes during the growth process of baker's yeast. The biphasic growth,"*Eur. J. Biochem.* 52:1-7 (1975).
Hadfield et al., "Active Site Analysis of the Potential Antimicrobial Target Aspartate Semialdehyde Dehydrogenase,"*Biochemistry* 40:14475-14483 (2001).
Hadfield et al., "Structure of Aspartate-β-semialdehyde Dehydrogenase from *Escherichia coli*, A Key Enzyme in the Aspartate Family of Amino Acid Biosynthesis,"*J. Mol. Biol.* 289:991-1002 (1999).
Hagemeier et al., "Insight into the mechanism of biological methanol activation based on the crystal structure of the methanol-cobalamin methyltransferase complex,"*Proc. Natl. Acad. Sci. U.S. A.* 103(50):18917-18922 (2006).

Hahm et al., "Characterization and evaluation of a pta (phosphotransacetylase) negative mutant of *Escherichia coli* HB101 as a production host of foreign lipase,"*Appl. Microbiol. Biotechnol.* 42:100-107 (1994).
Haller et al., "Discovering new enzymes and metabolic pathways: conversion of succinate to propionate by *Escherichia coli*,"*Biochem.* 39(16):4622-4629 (2000).
Hambraeus and Nyberg, "Enzymatic Hydrogenation of trans-2-Nonenal in Barley,"*J. Aeric. Food Chem.* 53:8714-8721 (2005).
Hamilton-Kemp et al., "Production of the long-chain alcohols octanol, decanol, and dodecanol by *Escherichia coli*,"*Curr. Microbiol.* 51:82-:-86 (2005).
Hammer and Bode, "Purification and characterization of an inducible L-lysine:2-oxoglutarate 6-aminotransferase from *Candida utilis*,"*J. Basic Microbiol.* 32:21-27 (1992).
Han et al., "Biochemical characterization and inhibitor discovery of shikimate dehydroaenase from *Helicobacter pylori*,"*FEBS J.* 273:4682-4692 (2006).
Hanai et al., "Engineered synthetic pathway for isopropanol production in *Escherichia coli*,"*Appl. Environ. Microbiol.* 73(24):7814-7818 (2007).
Hansford, "Control of mitochondrial substrate oxidation,"*Curr. Top Bioenergy.* 10:217-278 (1980).
Harder, "Anaerobic degradation of cyclohexane-1,2-diol by a new Azoarcus species,"*Arch. Microbiol.* 168:199-204 (1997).
Hardison et al., "Globin Gene Server: A prototype E-Mail Database Server Featuring Extensive Multiple Alignments and Data Compilation for Electronic Genetic Analysis,"*Genomics* 21:344-353 (1994).
Harker and Bramley, "Expression of prokaryotic 1-deoxy-D-xylulose-5-phosphatases in *Escherichia coli* increases carotenoid and ubiquinone biosynthesis,"*FEBS Lett.* 448:115-119 (1999).
Harms and Thauer, "Methylcobalamin: Coenzyme M methyltransferase isoenzymes MtaA and MtbA from *Methanosarcina barkeri*. Cloning, sequencing and differential transcription of the encoding genes, and functional overexpression of the mtaA gene in *Escherichia coli*,"*Eur. J. Biochem.* 235(3):653-659 (1996).
Harrison and Harwood, The pimFABCDE operon from *Rhodopseudomonas palustris* mediates dicarboxylic acid degradation and participates in anaerobic benzoate degradation, *Microbiology* 151:727-736 (2005).
Hartel et al., "Purification of glutaryl-CoA dehydrogenase from *Pseudomonas* sp., an enzyme involved in the anaerobic degradation of benzoate,"*Arch. Mirobiol.* 159:174181 (1993).
Harwood and Parales, "The β-ketoadipate pathway and the biology of self-identity,"*Annu. Rev. Microbiol.* 50:553-590 (1996).
Harwood et al., "Anaerobic metabolism of aromatic compounds via the benzoyl-CoA pathway,"*FEMS Microbiol. Rev.* 22:439-458 (1999).
Harwood et al., "Identification of the pcaRKF Gene cluster from *Pseudomonas putida*: Involvement in Chemotaxis, Biodegradation, and Transport of 4-Hydroxybenzoate"*J. Bacteriol.* 176(21):6479-6488 (1994).
Hasan and Nester, "Dehydroquinate synthase in *Bacillus subtilis*. An enzyme associated with chorismate synthase and flavin reductase,"*J. Biol. Chem.* 253:49995004 (1978).
Hasegawa et al., "Transcriptional regulation of ketone body-utilizing enzyme, acetoacetyl-CoA synthetase, by C/EBPa during adipocyte differentiation,"*Biochim.Biophys. Acta.* 1779(6-7):414-419 (2008).
Haselbeck and McAlister-Henn, "Isolation, nucleotide sequence, and disruption of the *Saccharomyces cerevisiae* gene encoding mitochondrial NADP(H)-specific isocitrate dehydrogenase,"*J. Biol. Chem.* 266(4):2339-2345 (1991).
Hashidoko et al., "Cloning of a DNA fragment carrying the 4-hydroxycinnamate decarboxylase (pofK) gene from *Klebsielss oxytoca* and its constitutive expression in *Escherichia coli* JM109 cells,"*Biosci. Biotech. Biochem.* 58(1):217-218 (1994).
Hashimoto et al., "Activation of L-Lysine $_E$-Dehydrogenase from Agrobacterium tumefaciens by Several Amino Acids and Monocarboxylates,"*J. Biochem.* 106:76-80 {1989}.

(56) References Cited

OTHER PUBLICATIONS

Hasson et al., "The crystal structure of benzoylfomate decarboxylase at 1.6A resolution: diversity of catalytic residues in thiamin diphosphate-dependent enzymes,"*Biochemistry* 37:9918-9930 (1998).

Hatakeyama et al., "Analysis of oxidation sensitivity of maleate cis-trans isomerase from *Serratia marcescens*,"*Biosci. Biotechnol. Biochem.* 64:1477-1485 (2000).

Hatakeyama et al., "Gene Cloning and Characterization of Maleate cis-trans Isomerase from *Alcaligenes faecalis*,"*Biochem. Biophys. Res. Comm.* 239:74-79 (1997).

Hawes et al., "Primary structure and tissue-specific expression of human β- hydroxyisobutyryl-Coenzyme A hydrolase,"*J. Biol. Chem.* 271 :26430-26434 (1996).

Hawes et al., "Mammalian 3-hydroxyisobutyrate dehydrogenase,"*Methods Enzymol.* 324:218-228 (2000).

Hayashi et al., "Properties of 2-hydroxyglutarate dehydrogenase from *Fusobacterium*,"*J. Nihon. Univ. Sch. Dent.* 28(1):12-21 (1986).

Hayden et al., "Glutamate dehydrogenase of *Halobacterium salinarum*: evidence that the gene sequence currently assigned to the NADP+-dependent enzyme is in fact that of the NAD+-dependent glutamate dehydrogenase,"*FEMS Microbiol. Lett.* 211:37-41 (2002).

Hayes et al., "Combining computational and experimental screening for rapid optimization of protein properties,"*Proc. Natl. Acad. Sci. U.S.A.* 99(25):15926-15931 (2002).

Hayes et al., "The Biofine Process: Production of Levulinic Acid, Furfural and Formic Acid from Lignocellulosic Feedstocks," In Biorefineries: *Industrial Proceses and Products.* Wiley, Weinheim, Germany, 139-164. (2006).

Haywood and Large, "4-Acetamidobutyrate Deacetylase in the Yeast *Candida boidinii* Grown on Putrescine or Spermidine as Sole Nitrogen, Source and Its Probable Role in Polyamine Catabolism,"*J. Gen. Microbiol.* 132:7-14 (1986).

Haywood et al., "Characterization of two 3-ketothiolases possessing differing substrate specificities in the polyhydroxyalkanoate synthesizing organism *Alcaliqenes eutrophus*,"*FEMS Microbiol. Lett.* 52:91-96 (1988).

He and Wiegel. "Purification and characterization of an oxygen-sensitive reversible 4-hydroxybenzoate decarboxylase from *Clostridium hydroxybenzoicum*,"*Eur. J. Biochem.* 229:77-82 (1995).

Heidlas and Tressl, "Purification and Properties of two oxidoreductases catalyzing the enantioselective reduction of diacetyl and other diketones from baker's yeast,"*Eur. J. Biochem.* 188:165-174 (1990).

Heipieper and Isken, "Ethanol tolerance and membrane fatty acid adaptation in adh multiple and null mutants of *Kluyveromyces lactis*,"*Res. Microbiol.* 151:(9):777-784.(2000).

Helin et al., "The refined x-ray structure of muconate lactonizing enzyme from Pseudomonas putida PRS2000 at 1.85 A resolution,"*J. Mol. Biol.* 254:918-941 (1995).

Heller et al., "Cloning and expression of the gene for the vitamin $B_{12}$ receptor protein in the outer membrane of *Escherichia coli*,"*J. Bacteriol.* 161:896-903 (1985).

Hemschemeier et al., "Biochemical and physiological characterization of the pyruvate formate-lyase Pfl1 of *Chlamydomonas reinhardtii*, a typically bacterial enzyme in eukarvotic alga,"*Eukarvot. Cell* 7:518-526 (2008).

Henne et al., "Construction of environmental DNA libraries in *Escherichia coli* and screening for the presence of genes conferring utilization of 4-hydroxybutyrate,"*Appl. Environ. Microbiol.* 65(9):3901-3907 (1999).

Hennessy et al., "The reactivity of gamma-hydroxybutyric acid (GHB) and gamma-butyrolactone (GBL) in alcoholic solutions,"*J. Forensic. Sci.* 49(6):1220-1229 (2004). (provided electronically by publisher as pp. 1-10).

Henning et al., "Identification of novel benzoylformate decarboxylases by growth selection,"*Appl. Environ. Microbiol.* 72:7510-7517 (2006).

Henriksson et al., "The 1.9 A resolution structure of Mycobacterium tuberculosis 1-deoxy-$_D$-xylulose 5-phosphate reductoisomerase, a potential drug target,"*Acta. Crystallogr. D. Biol. Crystallogr.* 62(Pt 7):807-813 (2006).

Henstra et al., "Microbiology of synthesis gas fermentation for biofuel production,"*Curr. Opin. Biotechnol.* 18:200-206 (2007).

Hermes et al., "Searching sequence space by definably random mutagenesis: Improving the catalytic potency of an enzyme,"*Proc. Natl. Acad. Sci U.S.A.* 87:696-700 (1990).

Herrmann et al., "Energy Conservation via Electron-Transferring Flavoprotein in Anaerobic Bacteria,"*J. Bacteriol.* 190(3):784-791 (2008).

Herrmann et al., "Two β-alanyl-CoA:ammonia lyases in Clostridium propionicum,"*FEBS J.* 272:813-821 (2005).

Hespell et al., "Stabilization of *pet* Operon Plasmids and Ethanol Production in *Escherichia coli* Strains Lacking Lactate Dehydrogenase and Pyruvate Formate-Lyase Activities,"*Appl. Environ. Microbiol.* 62:4594-4597 (Dec. 1996).

Hesslinger et al., "Novel keto acid formate-lyase and propionate kinase enzymes are components of an anaerobic pathway in *Escherichia coli* that degrades L-threonine to propionate,"*Mol. Microbiol.* 27(2):477-492 (1998).

Hester et al., "Purification of active $E1a_2\beta_2$ of *Pseudomonas putida* branched-chainoxoacid dehydrogenase,"*Eur. J. Biochem.* 233:828-836 (1995).

Hetzel et al., "Acryloyl-CoA reductase from *clostridium propionicum*. An enzyme complex of pripionyl-CoA dehydrogenase and electron-transferring flavoprotein,"*Eur. J. Biochem.* 270:902-910 (2003).

Heydari et al., "Highly Stable L-Lysine 6-Dehydrogenase from the thermophile *Geobacillus stearothermophilus* Isolated from a Japanese Hot Spring: characterization, Gene Cloning and sequencing, and Expression,"*Appl. Environ. Microbiol.* 70(2):937-942 (2004).

Hibbert et al., "Directed evolution of biocatalytic processes,"*Biomol. Eng.* 22:11-19 (2005).

Highbarger et al., "Mechanism of the reaction catalyzed by acetoacetate decarboxylase. Importance of lysine 116 in determining the pKa of active-site lysine 115,"*Biochemistry* 35(1):41-46 (1996).

Hijarrubia et al., "Domain Structure Characterization of the Multifunctional a-Aminoadipate Reductase from *Penicillium chrysogenum* by Limited Proteolysis,"*J. Biol. Chem.* 278(10):8250-8256 (2003).

Hill et al., "PCR based gene engineering of the Vibrio harveyi lux operon and the *Escherichia coli* trp operon provides for biochemically functional native and fused gene products"*Mol. Gen. Genet.* 226:41-48 (1991).

Hillmer and Gottschalk, "Particulate Nature of Enzymes Involved in the Fermentation of Ethanol and Acetate by *Clostridium Kluyveri*,"*FEBS Lett.* 21(3):351-354 (1974).

Hillmer and Gottschalk, "Solubilization and partial characterization of particulate dehydrogenases from *Clostridium kluyveri*,"*Biochim. Biophys. Acta* 334:12-23 (1974).

Hirano et al., "Purification and characerization of the Alcohol Dehydrogenase with a Broad Substrate Specificy Originated from 2-Phenylethanol-Assimilating *Brevibacterium* sp. KU 1309,"*J. Biosci. Bioeng.* 100(3): 318-322 (2005).

Hirata et al., "Stereochemistry of reduction of the endocyclic double bond of (-)-carvone with the enzyme preparation from cultured cells of *Nicotiana tabacum*," Phytochemistry 28(12):3331-3333 (1989).

Hiser et al., "ERG10 from *Saccharomyces cerevisiae* encodes acetoacetyl-CoA thiolase,"*J. Biol. Chem.* 269:31383-31389 (1994).

Ho et al., "Regulation of serine biosynthesis in Arabidopsis. Crucial role of plastidic 3-phosphoglycerate dehydrogenase in non-photosynthetic tissues,"*J. Biol. Chem.* 274:397-402 (1999).

Hoang et al., "A broad-host-range Flp-FRT recombination system for site-specific excision of chromosomally-located DNA sequences: application for isolation of unmarked *Pseudomonas aeruginosa* mutants," Gene 212(1):77-86 (1998).

(56) References Cited

OTHER PUBLICATIONS

Hoffmann and Dimroth, "Sterochemistry of the methylmalonyl-CoA decarboxylation reaction,"*FEBS Lett.* 220:121-125 (1987).

Hoffmeister et al., "Mitochondrial trans-2-enoyl-CoA reductase of wax ester fermentation from *Euglena gracilis* defines a new family of enzymes involved in lipid synthesis,"*Biol. Chem.* 280(6):4329-4338 (2005).

Hofmeister and Buckel, "(R)-lactyl-CoA dehydratase from *Clostridium propionicum*. Stereochemistry of the dehydration of (R)-2-hydroxybutyryl-CoA to crotonly-CoA,"*Eur. J. Biochem.* 206(2):547-552 (1992).

Hofmeister et al., "Cloning and expression of the two genes coding for L-serine dehydratase from *Peptostreptococcus asaccharolyticus*: relationship of the iron-sulfur protein to both L-serine dehydratases from *Escherichia coli*,"*J. Bacteriol.* 179(15):4937-4941 (1997).

Hogan et al., "Improved Specificity toward Substrates with Positively Charged Side chains by Site-Directed Mutagenesis of the L-Lactate Dehydrogenase of *Bacillus stearothermophilus*,"*Biochemistry* 34:4225-4230 (1995).

Holloway and Marsh, "Adenosylcobalamin-dependent glutamate mutase from *Clostridium tetanomorphum*. Overexpression in *Escherichia coli*, purification, and characterization of the recombinant enzyme,"*J. Biol. Chem.* 269(32):20425-20430 (1994).

Holms, "The central metabolic pathways in *Escherichia coli*: relationship between flux and control at a branch point, efficiency of conversion to biomass, and excretion of acetate,"*Curr. Top Cell. Redul.* 28:69-105 (1986).

Hong and Lee, "Metabolic flux analysis for succinic acid production by recombinant *Escherichia coli* with amplified malic enzyme activity,"*Biotechnol. Bioeng.* 74(2):89-95 (2001).

Hong and Lee, "Enhanced Production of Succinic Acid by Metabolically Engineered *Escherichia coli* with Amplified Activities of Malic Enzyme and Fumarase,"*Biotechnol. Bioprocess. Eng.* 9:4:252-255 (2004).

Hong et al., "The genome sequence of the capnophilic rumen bacterium *Mannheimia succiniciproducens*."*Nat. Biotechnol.* 22(10):1275-1281 (2004).

Hong et al., "Importance of redox balance on the production of succinic acid by metabolically engineered *Escherichia coli*,"*Appl. Microbiol. Biotechnol.* 58:286-290 (2002).

Horswill and Escalante-Semerena, "In vitro conversion of propionate to pyruvate by *Salmonella enterica* enzymes: 2-methylcitrate dehydratase (PrpD) and aconitas Enzymes catalyze the conversion of 2-methylcitrate to 2-methylisocitrate,"*Biochemistry* 40(15):4703-4713 (2001).

Horton et al., "Heterologous expression of the *Saccharomyces cerevisiae* alcohol acetyltransferase genes in *Clostridium acetobutylicum* and *Escherichia coli* for the production of isoamyl acetate,"*J. Ind. Microbiol. Biotechnol.* 30(7):427-432 (2003).

Howard et al., "Titanium Metallacarbene-Metallacylobutane Reactions: Stepwise Metathesis,"*J. Am. Chem. Soc.* 102:6876-6878 (1980).

Hsu et al., "Expression of an aromatic-dependent decarboxylase which provides growth-essential $CO_2$ equivalents for the acetogenic (Wood) pathway of *Clostridium thermoaceticum*,"*J. Bacteriol.* 172:5901-5907 (1990).

Hu et al., "The catalytic intermediate stabilized by a "down" active site loop for diaminopimelate decarboxylase from *Helicobacter pylori*. Enzymatic characterization with crystal structure analysis,"*J. Biol. Chem.* 283(30):21284-21293 (2008).

Huang et al., "Genetic characterization of the resorcinol catabolic pathway in *Corynebacterium alutamicum*,"*Appl. Environ. Microbiol.* 72:7238-7245 (2006).

Huang et al., "Purification and characterization of a ferulic acid decarboxylase from *Pseudomonas fluorescens*,"*J. Bacteriol.* 176:5912-5918 (1994).

Huang et al., "Identification and characterization of a second butyrate kinase from *Clostridium acetobutylicum* ATCC 824,"*J. Mol. Microbiol. Biotechnol.* 2(1):33-38 (2000).

Hubner et al., "The mechanism of substrate activation of pyruvate decarboxylase: A first approach,"*Eur. J. Biochem.* 92:175-181 (1978).

Huder and Dimroth, "Sequence of the sodium ion pump methylmalonyl-CoA decarboxylase from *Veillonella parvula*,"*J. Biol. Chem.* 268:24564-24571 (1993).

Hughes et al., "Cloning and expression of pca genes from *Pseudomonas putida* in *Escherichia coli*,"*J. Gen. Microbiol.* 134:2877-2887 (1988).

Hughes et al., "Evidence for isofunctional enzymes in the degradation of phenol, m-and p-toluate, and p-cresol via catechol meta-cleavage pathways in *Alcaligenes eutrophus*,"*J. Bacteriol.* 158(1):79-83 (1984).

Hugler et al., "Malonyl-Coenzyme a Reductase from *Chloroflexus aurantiacus*, a Key Enzyme of the 3-Hydroxypropionate Cycle for Autotrophic CO2 Fixation,"*J. Bacteriol.* 184(9):2404-2410 (2002).

Huh et al., "Global analysis of protein localization in budding yeast,"*Nature* 425:686-691 (2003).

Huisman and Lalonde, "Enzyme evolution for chemical process applications," in R.N. Patel (ed.), *Biocatalysis in the pharmaceutical and biotechnology industries.* CRC Press, pp. 717-742 (2007).

Huo and Viola, "Substrate Specificity and Identification of Functional Groups of Homoserine Kinase from *Escherichia coli*,"*Biochemistry* 35:16180-16185 (1996).

Husain and Steenkamp, "Partial purification and characterization of glutaryl-Coenzyme a dehydrogenase, electron transfer flavoprotein-Q oxidoreductase from *Paracoccus denitrificans*,"*J. Bacteriol.* 163:709-715 (1985).

Hustede et al., "Cloning of poly(3-hydroxybutyric acid) synthase genes of *Rhodobacter sphaeroides* and *Rhodospirillum rubum* and heterologous expression in *Alcaligenes eutrophys*,"*FEMS Microbiol. Lett.* 93:285-290 (1992).

Ibarra et al., "*Escherichia coli* K-12 undergoes adaptive evolution to achieve in silico predicted optimal growth,"*Nature* 420(6912):186-189 (2002).

Ichikawa et al., "Catalytic reaction of 1, 3-butanediol over solid acids,"*J. Mol. Catalysis A Chem.* 256:106-112 (2006).

Ichikawa et al., "PIO study on 1, 3-butanediol dehydration over $CeO_2$ (1 1 1) surface,"*J. Mol. Catalysis A Chem.* 231:181-189 (2005).

Iffland et al., "Directed Molecular Evolution of Cytochrome c Peroxidase,"*Biochemistry* 39:10790-10798 (2000).

Ikai and Yamamoto, "Identification and analysis of a gene encoding L-2,4- 4-diaminobutyrate:2-ketoglutarate aminotransferase involved in the 1,3-diaminopropane production pathway in *Acinetobacter baummanni*,"*J. Bacteriol.* 179:5118-5125 (1997).

Imai and Ohno, "Measurement of yeast intracellular pH by image processing and the change it undergoes during growth phase,"*J. Biotechnol.* 38:165-172 (1995).

Ingoldsby et al., "The discovery of four distinct glutamate dehydrogenase genes in a strain of *Halobacterium salinarum*,"*Gene* 349:237-244 (2005).

Ingram and Vreeland, "Differential-Effects of Ethanol and Hexanol on the *Escherichia-coli* Cell-Envelope,"*J. Bacteriol.* 144:481-488 (1980).

Inui et al., "Occurrence of Oxygen-Sensitive, NADP+-Dependent Pyruvate-Dehydrogenase in Mitochondria of *Euglena-Gracilis*,"*J. Biochem.* 96:931-934 (1984).

Inui et al., "Pyruvate-NADP+ Oxidoreductase from *Euglena-Gracilis* the Kinetic-Properties of the Enzyme,"*Arch. Biochem Bipophys.* 274:434-442 (1989).

Inui et al., Wax Ester Fermentation in *euglena-Gracilis*, *FESS Lett.* 150:89-93. (1982).

Inui et al., "Fatty acid synthesis in mitochondria of *Euglena gracilis*,"*Euro. J. Biochem.* 142(1):121-126 (1984).

Inui et al., "Production and Composition of Wax Esters by Fermentation of *Euglena gracilis*,"*Agr. Biol. Chem.* 47(11):2669-2671 (1983).

Inui et al., "Purification and characterization of pyruvate:NADP+ oxidoreductase in *Euglena gracilis*,"*J. Biol. Chem.* 262(19):9130-9135 (1987).

(56) References Cited

OTHER PUBLICATIONS

Inui et al., "Pyruvate:NADP+ oxidoreductase from *Euglena gracilis*: mechanism of $O_2$-nactivation of the enzyme and its stability in the aerobe,"*Arch. Biochem. Biophys.* 280:292-298 (1990).

Inui et al., "The physiological role of oxygen-sensitive pyruvate dehydrogenase in mitochondrial fatty acid synthesis in *Euglena gracilis*,"*Arch. Biochem. Biophys.* 237(2):423-429 (1985).

Ishida et al., "Efficient production of $_L$-lactic acid by metabolically engineered *Saccharomyces cerevisiae* with a genome-integrated L-lactate dehydrogenase gene,"*Appl. Environ. Microbiol.* 71:1964-1970 (2005).

Ishige et al, "Long-chain aldehyde dehydrogenase that participates in n-alkane utilization and wax ester synthesis in *Acinetobacter* sp. strain M-1,"*Appl. Environ. Microbiol.* 66:3481-3486 (2000).

Ishige et al., "Wax ester production from n-alkanes by *Acinetobacter* sp. strain M-1:ultrastructure of cellular inclusions and role of acyl Coenzyme A reductase,"*Appl. Environ. Microbiol.* 68(3):1192-1195 (2002).

Ismaiel et al., "Purification and Characterization of a Primary-Secondary Alcohol Dehydrogenase from Two Strains of *Clostridium beijerinckii*,"*J. Bacteriol.* 175(16)5097-5105 (1993).

Ismail et al., "Functional genomics by NMR spectroscopy. Phenylacetate catabolism in *Escherichia coli*,"*Eur. J. Biochem.* 270(14):3047-3054 (2005).

Ito and Yanofsky, "Anthranilate synthetase, an enzyme specified by the tryptophan operon of *Escherichia coli*: Comparative studies on the complex and the subunits,"*J. Bacteriol.* 97:734-742 (1969).

Ito et al., "Colistin nephrotoxicity: report of a case with light and electron microscopic studies,"*Acta. Pathol. Jpn.* 19:55-67 (1969).

Ito et al.. "$_D$-3-hydroxybutyrate dehydrogenase from *Pseudomonas fragi*: molecular cloning of the enzyme gene and crystal structure of the enzyme,"*J. Mol. Biol.* 355(4):722-733 (2006).

Iverson et al., "Structure of the *Escherichia coli* fumarate reductase respiratory complex,"*Science* 284(5422):1961-1966 (1999).

Iwakura et al., "Studies on regulatory functions of malic enzymes. VI. Purification and molecular properties of NADP-linked malic enzyme from *Escherichia coli* W,"*J. Biochem.* 85:1355-1365 (1979).

Izard and Blackwell, "Crystal structures of the metal-dependent 2-dehydro-3-deoxy-galacarate aldolase suggest a novel reaction mechanism,"*EMBO J.* 19:3849-3856 (2000).

Izumi et al., "Structure and Mechanism of HpcG, a Hydratase in the Homoprotocatechuate Degradation Pathway of *Escherichia coli*,"*J. Mol. Biol.* 370:899-911 (2007).

Jacobi et al., "The hyp operon gene products are required for the maturation of catalytically active hydrogenase isoenzymes in *Escherichia coli*,"*Arch. Microbiol.* 158(6):444-451 (1992).

Jacques et al., "Characterization of yeast homoserine dehydrogenase, an antifungal target: the invariant histidine 309 is important for enzyme integrity,"*Biochem. Biophys. Acta* 1544:28-41 (2001).

Jager and Farber, "Die Alanatreduktion von β-Carbonyl-oxalylsaure-estern,"*Chem. Ber.* 92:2492-2499 (1959).

James and Cronan, "Expression of two *Escherichia coli* acetyl-CoA carboxylase subunits is autoregulated,"*J. Biol. Chem.* 279:2520-2527 (2004).

James and Viola, "Production and characterization of bifunctional enzymes. Domain swapping to produce new bifunctional enzymes in the aspartate pathway,"*Biochemistry* 41(11) 3720-3725 (2002).

Jansen and Wanders, "$_L$-2-hydroxyglutarate dehydrogenase: identification of a novel enzyme activity in rat and human liver. Implications for $_L$-2-hydroxyglutaric academia,"*Biochim. Biophys. Acta* 1225(1):53-56 (1993).

Janssen, "Propanol as an end product of theonine fermentation,"*Arch. Microbiol.* 182:482-486 (2004).

Jantama et al., "Combining metabolic engineering and metabolic evolution to develop nonrecombinant strains of *Escherichia coli* C that produce succinate and malate,"*Biotechnol. Bioeng.* 99(5):1140-1153 (2008).

Jantama et al., "Eliminating Side Products and Increasing succinate Yields in Engineered Strains of *Escherichia coli* C,"*Biotechnol. Bioeng.* 101(5) 881-893 (2008).

Javid-Majd and Blanchard, "Mechanistic Analysis of the argE-Encoded N-Acetylornithine Deacetylase,"*Biochemistry* 39:1285-1293 (2000).

Jeng et al., "Ornithine degradation in *Clostridium sticklandii*; pyridoxial phosphate and Coenzyme A dependent thiolytic cleavage of 2-amino-4-ketopentanoate to alanine and acetyl Coenzyme A,"*Biochemistry* 13(14):2898-2903 (1974).

Jenkins and Nunn, "Genetic and molecular characterization of the genes involved in short-chain fatty acid degradation in *Escherichia coli*: the ato system,"*J. Bacteriol.* 169(1):42-52 (1987).

Jennert et al., "Gene transfer to *Clostridium cellulolyticum* ATCC 35319,"*Microbiol.* 146:3071-3080 (2000).

Jenssen et al., "A literature network of human genes for high-throughput analysis of gene expression,"*Nat. Gene.* 28:21-28 (2001).

Jeon et al., "Heterologous expression of the alcohol dehydrogenase (adhl) gene from *Geobacillius thermoglucosidasius* strain M10EXG,"*J. Biotechnol.* 135:127-133 (2008).

Jewell et al., "Bioconversion of propionic, valeric and 4-hydroxybutyric acids into the corresponding alcohols by *Clostridium acetobutylicum* NRRL 527,"*Curr. Microbiol.* 13(4):215-219 (1986).

Jiang et al., "De Novo Computational Design of Retro-Aldol Enzymes,"*Science* 319:1387-1391 (2008).

Jin and Sonenshein, "Characterization of the major citrate synthase of *Bacillus subtilis*,"*J. Bacteriol.* 178(12):3658-3660 (1996).

Johanson et al., "Strain engineering for steroselective bioreduction of dicarbonyl comoounds by yeast reductases,"*FEMS Yeast Res.* 5:513-525 (2005).

Johnson et al., "Alteration of a single amino acid changes the substrate specificity of dihydroflavonol 4-reductase,"*Plant J.* 25(3):325-333 (2001).

Johnston et al., "Structure of naphthoate synthase (MenB) from *Mycobacterium tuberculosis* in both native and product-bound forms,"*Acta. Crvstallogr. D. Biol. Crvstallogr.* 61(Pt 9):1199-1206 (2005).

Jojima et al., "Production of isopropanol by metabolically engineered *Escherichia coli*,"*Appl. Microbiol. Biotechnol.* 77:1219-1224 (2008).

Jones and Woods, "Acetone-butanol fermentation revisited,"*Microbiol. Rev.* 50(4):484-524 (1986).

Junker and Ramos, "Involvement of the cis/trans isomerase Cti in solvent resistance of *Pseudomonas outida* DOT-T1E,"*J. Bacteriol.* 181:5693-5700 (1999).

Kaclikova et al., "Fumaric acid overproduction in yeast mutants deficient in fumarase,"*FEMS Microbiol. Lett.* 91(2):101-106 (1992).

Kahng et al., "Characterization of strain HY99, a novel microorganism capable of aerobic and anaerobic degradation of aniline,"*FEMS Microbiol. Lett.* 190:215-221. (2000).

Kai et al., "Phosphoeno/pyruvate carboxylase: three-dimensional structure and molecular mechanisms,"*Arch. Biochem. Biophys.* 414:170-179 (2003).

Kakimoto et al., "β-aminoisobutyrate-a-ketoglutarate transaminase in relation to βaminoisobutyric aciduria,"*Biochim. Biophys. Acta* 156(2):374-380 (1968).

Kalousek et al., "Isolation and characterization of propionyl-CoA carboxylase from normal human liver. Evidence for a protomeric tetramer of nonidentical subunits,"*J. Biol. Chem.* 255:60-65 (1980).

Kalpos, "On the mammalian acetone metabolism: from chemistry to clinical implications,"*Biochim. Biophys. Acta* 1621(2):122-139 (2003).

Kalscheuer and Steinbuchel, "A novel bifunctional wax ester synthase/acyl-CoA:diacylglycerol acyltransferase mediates wax ester and triacylglycerol biosynthesis in *Acinetobacter calcoaceticus* ADP1,"*J. Biol. Chem.* 278(10):8075-8082 (2003).

Kalscheuer et al., "Analysis of storage lipid accumulation in *Alcanivorax borkumensis*: Evidence for alternative triacylglycerol biosynthesis routes in bacteria,"*J. Bacteriol.* 189(3):918-928 (2007).

(56) References Cited

OTHER PUBLICATIONS

Kanagawa et al., "Characterization of the 6-aminohexanoate-dimer hydrolase from *Pseudomonas* sp. NK87,"*J. Gen. Microbiol.* 139(4):787-795 (1993).
Kanamasa et al., "Cloning and functional characterization of the cis-aconitic acid decarboxylase (CAD) gene from *Aspergillus terreus*,"*Appl. Microbiol. Biotechnol.* 80(2):223-229 (2008).
Kanao et al., "Characterization of isocitrate dehydrogenase from the green sulfur bacterium *Chlorbium limicola*. A carbon dioxide-fixing enzyme in the reductive tricarboxylic acid cycle,"*Eur. J. Biochem.* 269(7):1926-1931 (2002).
Kanaujia et al., "Cloning, expression, purification, crystallization and preliminary X-ray crystallographic study Crystallogr. Sect. F. Struct. of DHNA synthetase from *Geobacillus kaustophilus*,"*Acta. Crystallogr. Sect. F. Struct. Biol. Cryst. Commun.* 63(Pt 2):103-105 (2007).
Kanehisa and Goto, "KEGG: Kyoto Encyclopedia of Genes and Genomes database,"*Nucleic Acids Res.* 28(1):27-30 (2000).
Kapatral et al., "Genome Sequence and Analysis of the Oral Bacterium *Fusobacterium nucleatum* Strain ATCC 25586,"*J. Bacteriol.* 184(7):2005-2018. (2002).
Karyakin et al., "Kinetic properties of $_L$-lysine-2-monooxygenase from *Pseufomonas putida* and its application to biosensors for $_L$-lysine,"*Prikladnaya Biokhimiya I Mikrobioloqiya* 27:825-832 (1991).
Kasberg et al., "Cloning, characterization, and sequence analysis of the cicE gene encoding the maleylacetate reductase of *Pseufomonas* sp. Strain B13,"*J. Bacteriol.* 179:3801-3803 (1997).
Kaschabek and Reineke, "Degradation of chloroaromatics: purification and characterization of maleylacetate reductase from *Pseudomonas* sp. Strain B13,"*J. Bacteriol.* 175:6075-6081 (1993).
Kaschabek and Reineke, "Maleylacetate reductase of *Pseufomonas* sp. Strain B13: specificity of substrate conversion and halide elimination,"*J. Bacteriol.* 177:320-325 (1995).
Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase,"*J. Bacteriol.* 184(1):207-215 (2002).
Kashket and Cao, "Isolation of a Degeneration-Resistant Mutant of *clostridium acetobutylicum* NCIMB 8052,"*Appl.. Environ. Microbiol.* 59:4198-4202 (1993).
Kato and Asano, "3-Methylaspartate ammonia-lyase as a marker enzyme of the mesaconate pathway for (S)-glutamate fermentation in *Enterobacteriaceae*,"*Arch.Microbiol.* 168(6):457-463 (1997).
Katti et al., "Crystal structure of muconolactone isomerase at 3.3 A resolution,"*J. Mol. Biol.* 205:557-571 (1989).
Katz et al., "Screening of two complementary collections of *Saccharomyces cerevisiae* to identify enzymes involved in stereoselective reductions of specific carbonyl compounds: an alternative to protein purification,"*Enzyme Microb. Technol.* 33:163-172 (2003).
Kawabata et al., "The Effect of Growth Temperature on Wax Ester Content and Composition of *Euglena qraci/is*,"*J. Gen. Microbiol.* 135: 1461-1467 (1989).
Kazahaya et al, "Aerobic Dissimilation of Glucose by *Heterolactic Bacteria III*. Aldehyde dehydrogenase and alcohol dehydrogenase of luconostoc mesenteroids,"*J. Gen. Appl. Microbiol.* 18(1):43-55 (1972).
Kefala et al., "Cloning, expression, purification, crystallization and preliminary x-ray diffraction analysis of LysA (Rv1293) from *Mycobacterium tuberculosis*," Acta. *Crystallogr. Sect. F. Struct. Biol. Cryst. Commun.* 61(Pt 8):782-784 (2005).
Kellum and Drake, "Effects of cultivation gas phase on hydrogenase of the acetogen *Clostridium thermoaceticum* "*J. Bacteriol.* 160(1):466-469 (1984).
Kenealy et al., "Biochemical Aspects of Fumaric Acid Accumulation by *Rhizopus arrhizus*,"*Appl. Environ. Microbiol.* 52:128-133 (1986).

Keng and Viola, "Specificity of Aspartokinase III from *Escherichia coli* and Examination of Important Catalytic Residues,"*Arch. Biochem. Biophys.* 335(1):73-81. (1996).
Kenklies et al., "Praline biosynthesis from $_L$-ornithine in *Clostridium sticklandii*: purification of $\Delta^1$-pyrroline-5-carboxylate reductase, and sequence and expression of encoding gene, proC,"*Microbiology* 145(Pt 4):819-826 (1999).
Kerby et al., "Carbon Monoxide-Dependent Growth of *Rhodospirillum rubrum*,"*J. Bacteriol.* 177:2241-2244 (1995).
Kerby et al., "Genetic and physiological characterization of the *Rhodospirillum rubrum* carbon monoxide dehydrogenase system,"*J. Bacteriol.* 174(16):5284-5294 (1992).
Kern et al., "Isoamyl alcohol-induced morphological change in *Saccharomyces cerevisiae* involves increases in mitochondria and cell wall chitin content,"*FEMS Yeast Res.* 5:43-49 (2004).
Kessler et al., "Pyruvate-formate-lyase-deactivase and acetyl-CoA reductase activities of *Escherichia coli* reside on a polymeric protein particle encoded by adhE,"*FEBS Lett.* 281(1-2):59-63 (1991).
Khan et al., "Molecular Properties and Enhancement of Thermostability by Random Mutagenesis of Glutamate Dehydrogenase from *Bacillus subtilis*,"*Biosci. Biotechnol. Biochem.* 69(10):1861-1870 (2005).
Killenberg-Jabs et al., "Active oligomeric states of pyruvate decarboxylase and their functional characterization,"*Eur. J. Biochem.* 268:1698-1704 (2001).
Kim et al, "Effect of Overexpression of *Actinobacillus succinogenes* Phosphoenolpyruvate Carboxykinase on Succinate Production in *Escherichia coli*,"*Appl. Env. Microbiol.* 70(2) 1238-1241 (2004).
Kim et al., "2-Hydroxyisocaproyl-CoA dehydratase and its activator from *Clostridium difficile*,"*FEBS J.* 272:550-561 (2005).
Kim et al., "Construction of an *Escherichia coli* K-12 Mutant for Homoethanologenic Fermentation of Glucose or Xylose without Foreign Genes,"*Appl. Environ. Microbiol.* 73(6):1766-1771 (2007).
Kim et al., "Dehydration of (R)-2-hydroxyacyl-CoA to enoyl-CoA in the fermentation of a-amino acids by anaerobic bacteria,"*FEMS Microbiol. Rev.* 28:455-468 (2004).
Kim et al., "Dihydrolipoamide dehydrogenase mutation alters the NADH sensitivity of pyruvate dehydrogenase complex of *Escherichia coli* K-12,"*J. Bacteriol.* 190:3851-.3858 (2008).
Kim et al., "Studies of the hyperthermophile *Thermotoga maritima* by random sequencing of cDNA and genomic libraries. Identification and sequencing of the trpEG (D) operon,"*J. Mol. Biol.* 231:960-981 (1993).
Kim, "Purification and Properties of a diamine α-Ketoglutarate Transminase from *Escherichia coli*,"*J. Biol. Chem.* 239(3):783-786 (1964).
Kino et al. Synthesis of DL-tryptophan by modified broad specificity amino acid racemase from *Pseudomonas putida* IFO 12996, *Appl. Microbiol. Biotechnol.* 73:1299-1305 (2007).
Kinoshita et al., "Purification and characterization of 6-aminohexanoic-acid-oligomer hydrolase of *Flavobacterium* so. K172,"*Eur. J. Biochem.* 116(3):547-551 (1981).
Kinoshita, "Purification of two alcohol dehydrogenases from *Zymomonas mobilis* and their properties,"*Appl. Microbiol. Biotechnol.* 22:249-254 (1985).
Kisselev L., "Polypeptide release factors in prokaryotes and eukaryotes: same function. different structure,"*Structure* 10:8-9 (2002).
Klassen, et al., "Biological conversion of coal and coal-derived synthesis gas,"*Fuel.* 72(12):1673-1678 (1993).
Klatt et al., "Comparative genomics provides evidence for the 3-hydroxypropionate autotrophic pathway in filamentous anoxygenic phototrophic bacteria and in hot spring microbial mats,"*Environ. Microbiol.* 9:2067-2078 (2007).
Kleanthous et al., "A comparison of the enzymological and biophysical properties of two distinct classes of dehydroquinase enzymes,"*Biochem. J.* 282(Pt3):687-695 (1992).
Klyosov, "Kinetics and specificity of human liver aldehyde dehydrogenases toward aliphatic, aromatic, and fused polycyclic aldehydes,"*Biochemistry* 35(14):4457-4467 (1996).

(56) References Cited

OTHER PUBLICATIONS

Knapp et al., "Crystal Structure of the Truncated Cubic Core component of the *Escherichia coli* 2-Oxoglutarate Dehydrogenase Multienzyme Complex,"*J. Mol. Biol.* 280:655-668 (1998).
Knappe and Sawers, "A radical-chemical route to acetyl-CoA: the anaerobically induced pyruvate formate-lyase system of *Escherichia coli*,"*FEMS. Microbiol. Rev.* 75:383-398 (1990).
Knappe et al., "Post-translational activation introduces a free radical into pyruvate formate-lyase,"*Proc. Natl. Acad. Sci. U.S.A.* 81:1332-1335 (1984).
Knothe, "'Designer' Biodiesel: Optimizing Fatty Ester Composition to Improve Fuel Properties,"*Energy Fuels* 22:1358-1364 (2008).
Kobayashi et al., "Physicochemical, catalytic, and immunochemical properties of fumarases crystallized separately from mitochondrial and cytosolic fractions of rat liver,"*J. Biochem.* 89(6):1923-1931 (1981).
Koch and Fuchs, "Enzymatic reduction of benzoyl-CoA to alicyclic compounds, a key reaction in anaerobic aromatic metabolism,"*Eur. J. Biochem.* 205:195-202 (1992).
Koch et al., "Products of enzymatic reduction of benzoyl-CoA, a key reaction in anaerobic aromatic metabolism,"*Eur. J. Biochem.* 211:649-661 (1993).
Koland and Gennis, "Proximity of Reactive Cysteine Residue and Flavin in *Escherichia coli* Pyruvate Oxidase As Estimated by Flourescence Energy Transfer,"*Biochemistry* 21:4438-4442 (1982).
Kollmann-Koch et al.,"Nicotinic acid metabolism. Dimethylmaleate hydratase,"*Hodge Seylers Z Physiol Chem.* 365:s. 847-857 (1984).
Koo et al., "Cloning and characterization of the bifunctional alcohol/acetaldehyde dehydrogenase gene (adhE) in *Leuconostoc mesenteroides* isolated from kimchi,"*Biotechnol. Lett.* 27(7):505-510 (2005).
Korbert et al., "Crystallization of the NAPD+-dependent Glutamate Dehydrogenase from *Escherichia coli*,"*J. Mol. Biol.* 234:1270-1273 (1993).
Kornberg, "The role and control of the glyoxylate cycle in *Escherichia coli*,"*Biochem. J.* 99:1-11 (1966).
Korolev et al., "Autotracing of *Escherichia coli* acetate CoA-transferase a-subunit structure using 3.4 A MAD and 1.9 A native data,"*Acta. Crystallogr. D. Biol. Crystalloar.* 58(Pt 12):2116-2121 (2002).
Korotkova and Lidstrom, "Connection between poly-β-hydroxybutyrate biosynthesis and growth on $C_1$ and $O_2$ compounds in the methylotroph *Methylobacterium extorquens* AM1,"*J. Bacteriol.* 183(3):1038-1046 (2001).
Korotkova and Lidstrom, "MeaB is a component of the methylmalonyl-CoA mutase complex required for protection of the enzyme from inactivation,"*J. Biol. Chem.* 279(14):13652-13658 (2004).
Kort et al., "Glutamate dehydrogenase from the hyperthermophilic bacterium *Thermotoga maritima*: molecular characterization and phylogenetic implications,"*Extremophiles* 1:52-60 (1997).
Kosaka et al., "Characterization of the sol operon in butanol-hyperproducing *Clostridium saccharoperbutylacetonicum* strain N1-4 and its degeneration mechanism,"*Biosci. Biotechnol. Biochem.* 71:58-68 (2007).
Kosjek et al., "Purification and characterization of a chemotolerant alcohol dehydrogenase applicable to coupled redox reactions,"*Biotechnol. Bioena.* 86(1):55-62 (2004).
Kouzarides, "Acetylation: a regulatory modification to rival phosphorylation?"*EMBO J.* 19(6):1176-1179 (2000).
Kovachy et al., "Recognition, Isolation, and Characterization of Rat Liver D-Methylmalonyl Coenzyme A Hydrolase,"*J. Biol. Chem.* 258(18):11415-11421 (1983).
Kowalchuk et al., "Contrasting patterns of evolutionary divergence within the *Acinetobacter calcoaceticus* pca operon,"*Gene* 146:23-30 (1994).
Kraus et al., "Biosynthesis and mitochondrial processing of the β subunit of propionyl Coenzyme A carboxylase from rat liver,"*J. Biol. Chem.* 258:7245-7248 (1983).

Kreimeyer.et al., "Identification of the Last Unknown Genes in the Fermentation Pathway of Lysine,"*J. Biol. Chem.* 282(10):7191-7197 (2007).
Kress et al., "First direct observation of the simultaneous presence and of the interconversion of chain-propagating metal-carbene and metallacyclobutane complexes in a catalytic olefin metathesis reaction: the ring-opening polymerization of norbornene,"*J. Am. Chem. Soc.* 109(3):899-901 (1987).
Kress et al., "Tungsten(VI) and molybdenum(VI) oxo-alkyl species. Their role in the metathesis of olefins,"*J. Chem. Soc. Chem. Commun.* 431-432 (1980).
Kretz et al., "Gene site saturation mutagenesis: a comprehensive mutagenesis approach,"*Methods Enzmol.* 388:3-11 (2004).
Krieger et al., "Pyruvate decarboxylase from Kluyveromyces lactis an enzyme with an extraordinary substrate activation behaviour,"*Eur. J. Biochem.* 269:3256-3263 (2002).
Krishna et al., "Enzymatic synthesis of isoamyl acetate using immobilized lipase from *Rhizomucor miehei*,"*J. Biotechnol.* 87:193-201 (2001).
Kuchta and Abeles, "Lactate Reduction in *Clostridium propionicum* Purification and properties of lactyl-CoA dehydratase,"*J. Biol. Chem.* 260(24):13181-13189 (1985).
Kuhnt et al., "Functional analysis of the methylmalonyl-CoA epimerase from *Caenorhabditis elegans*,"*FEBS J.* 272(6):1465-1477 (2005).
Kulkarni and Kanekar, "Bioremediation of ε:-caprolactum from nylon-6 waste water by use of *Pseudomonas aeruginosa* MCM B-407,"*Curr. Microbiol.* 37(3):191-194 (1998).
Kumamaru et al., "Enhanced degradation of polychlorinated biphenyls by directed evolution of biphenyl dioxygenase,"*Nat. Biotechnol.* 16:663-666 (1998).
Kumari et al., "Cloning, Characterization, and Functional Expression of acs, the Gene Which Encodes Acetyl Coenzyme A Synthetase in *Escherichia coli*,"*J.Bacteriol.* 177(10): 2878-2886 (1995).
Kuntze et al., "6-0xocyclohex-1-ene-1-carbonyl-Coenzyme A hydrolases from obligately anaerobic bacteria: characterization and indentification of its gene as a functional marker for aromatic compounds degrading anaerobes,"*Environ. Microbiol.* 10(6):1547-1556 (2008).
Kurihara et al., "γ-Glutamyputrescine synthetase in the putrescine utilization pathway of *Escherichia coli* K-12,"*J. Biol. Chem.* 283(29)19981-19990 (2008).
Kurihara et al., "A Novel Putrescine Utilization Pathway Involves y-Glutamylated Intermediates of *Escherichia coli* K-12,"*J. Biol. Chem.* 280(6):4602-4608 (2005).
Kuznetsova et al., "Enzyme genomics: Application of general enzymatic screens to discover new enzymes,"*FEMS Microbiol. Rev.* 29(2):263-279 (2005).
Kwok and Hanson, "GFP-labelled Rubisco and aspartate aminotransferase are present in plastid stromules and traffic between plastids,"*J. Exp. Bot.* 55(397):595-604 (2004).
Kwon et al., "Influence of gluconegoenic phosphoenolpyruvate carbosykinase (PCK) expression on succinic acid fermentation in *Escherichi coli* under high bicarbonate condition,"*J. Microbiol. Biotechnol.* 16(9):1448-1452 (2006).
Laempe et al., "6-Hydroxycyclohex-1-ene-1-carbonyl-CoA dehydrogenase and 6- oxocyclohex-1-ene-1-carbonyl-CoA hydrolase, enzymes of the benzoyl-CoA pathway of anaerobic aromatic metabolism in the denitrifying bacterium *Thauera aromatica*,"*Eur. J. Biochem.* 263(2):420-429 (1999).
Laivenieks et al., "Cloning sequencing, and overexpression of the *Anaerobiospirillum succinicproducens* phosphoenolpyruvate carboxykinase (pckA) gene,"*Appl. Environ. Microbiol.* 63:2273-2280 (1997).
Lam and Winkler, "Metabolic Relationships between Pyridoxine (Vitamin $B_6$) and Serine Biosynthesis in *Escherichia coli* K-12,"*J. Bacteriol.* 171(11):6518-6528 (1990).
Lamas-Maceiras et al., "Amplification and disruption of the phenylacetyl-CoA ligase gene of *Penicillium chrysogenum* encoding an aryl-capping enzyme that supplies phenylacetic acid to the isopenicillin N-acyltransferase,"*Biochem. J.* 395(1):147-155. (2006).

(56) References Cited

OTHER PUBLICATIONS

Lamed and Zeikus, "Novel NADP-linked alcohol-aldehyde/ketone oxidoreductase in thermophilic ethanologenic bacteria,"*Biochem. J.* 195:183-190 (1981).

Lardizabal et al., "Purification of a jojoba embryo wax synthase, cloning of its cDNA, and production of high levels of wax in seeds of transgenic arabidopsis,"*Plant. Physiol.* 122(3):645-655 (2000).

Lawrence and Roth, "Evolution of Coenzyme $B_{12}$ synthesis among enteric bacteria: evidence for loss and reacquisition of a multigene complex,"*Genetics* 142(1):11-24 (1996).

Lawrence and Roth, "The cobalamin (Coenzyme $B_{12}$) biosynthetic genes of *Escherichia coli*,"*J. Bacteriol.* 177(22):6371-6380 (1995).

Lebbink et al., "Engineering activity and stability of Thermotoga maritima glutamate dehydrogenase I. Introduction of a six-residue ion-pair network in the hinge region,"*J. Mol. Biol.* 280:287-296 (1998).

Lebbink et al., "Engineering Activity and Stability of Thermotoga maritima glutamate Dehydrogenase. II: construction of a 16-Residue Ion-pair Network at the Subunit Interface,"*J. Mol. Biol.* 289:357-369 (1999).

Leduc et al., "The hotdog thioesterase EntH (YbdB) plays a role in vivo in optimal enterobactin biosynthesis by interacting with the ArCP domain of EntB,"*J. Bacteriol.* 189(19):7112-7126 (2007).

Lee and Cho, "Identification of essential active-site residues in ornithine decarboxylase of Nicotiana glutinosa decarboxylating both L-ornithine and L-lysine,"*Biochem. J.* 360:657-665 (2001).

Lee et al., "A new approach to directed gene evolution by recombined extension on truncated templates (RETT),"*J. Molec. Catalysis* 26:119-129 (2003).

Lee et al., "Batch and continuous cultivation of *Anaerobiospirillum succiniciproducens* for the production of succinic acid from whey,"*Appl. Microbiol. Biotechnol.* 54(1):23-27 (2000).

Lee et al., "Biological conversion of wood hydrolysate to succinic acid by *Anaerobiospirillum succiniciproducens*,"*Biotechnol. Lett.* 25(2): 111-114 (2003).

Lee et al., "Biosynthesis of enantiopure (S)-3-hydroxybutyric acid in metabolically engineered *Escherichia coli*,"*App. Microbiol. Biotechnol.* 79:633-641 (2008).

Lee et al., "Chaperonin GroESL mediates the protein folding of human liver mitochondrial aldehyde dehydrogenase in *Escherichia coli*,"*Biochem. Biophys. Res.Commun.* 298(2):216-224 (2002).

Lee et al., "Cloning and Characterization of Mannheimia succiniciproducens MBEL55E Phosphoenolpyruvate Carboxykinase (pckA) Gene,"*Biotechnol. Bioprocess Eng.* 7:95-99 (2002).

Lee et al., "Fermentative production of chemicals that can be used for polymer synthesis,"*Macromol. Biosci.* 4:157-164 (2004).

Lee et al., "Genome-based metabolic engineering of *Mannheimia succiniciproducens* for succinic acid productiion,"*Appl. Environ. Microbiol.* 72(3):1939-1948 (2006).

Lee et al., "Isolation and characterization of a new succinic acid-producing bacterium, *Mannheimia succiniciproducens* MBEL55E, from bovine rumen,"*Appl. Microbio. Biotechnol.* 58(5):663-668 (2002).

Lee et al., "Phylogenetic diversity and the structural basis of substrate specificity in the β/a-barrel fold basic amino acid decarboxylases,"*J. Biol. Chem.* 282:27115-27125 (2007).

Lee et al., "Metabolic engineering of *Escherichia coli* for enhanced production of succinic acid, based on genome comparison and in silica gene knockout simulation,"*Appl. Environ Microbiol.* 71(12):7880-7887 (2005).

Lehtio and Goldman, "The pyruvate format lyase family: sequences, structures and activation,"*Protein Eng. Des.Sel.* 17:545-552 (2004).

Lehtio et al., "Crystal structure of glycyl radical enzyme from *Archaeoglobus fulgidus*,"*J. Mol. Biol.* 357(1):221-235 (2006).

Lei et al., "A shared binding site for NAD+ and Coenzyme A in an acetaldehyde dehydrogenase involved in bacterial degradation of aromatic compounds,"*Biochemistry* 47:6870-6882 (2008).

Lemoine et al., "Microcorrespondence: Monofunctional biosynthetic peptidoglycan transglycosylases,"*Mol. Microbiol.* 19(3):639-647 (1996).

Lemonnier and Lane, "Expression of the second lysine decarboxylase gene of *Escherichia coli*,"*Microbiology* 144(Pt 3):751-760 (1998).

Lenski and Travisano, "Dynamics of adaptation and diversification: a 10,000-generation experiment with bacterial populations,"*Proc. Natl. Acad. Sci. U.S.A.* 91(15):6608-6814 (1994).

Leonardo et al., "Anaerobic Regulation of the adhE gene, Encoding the Fermentative Alcohol Dehydrogenase of *Escherichia coli*,"*J. Bacteriol.* 175(3):870-878 (1993).

Lepore et al., "The x-ray crystal structure of lysine-2,3-aminomutase from *Clostridium subterminale*,"*Proc. Natl. Acad. Sci U.S.A.* 102:13819-13824 (2005).

Leppanen et al., "Pyruvate formate lyase is structurally homologous to type I ribonucleotide reductase,"*Structure* 7:733-744 (1999).

Lessner et al., "An unconventional pathway for reduction of $CO_2$ to methane in CO-grown Mehanosarcina acetivorans revealed by proteomics,"*Proc. Natl. Acad. Sci. U.S.A.* 103(47):17921-17926 (2006).

Leutwein and Heider, "Succinyl-CoA(R)-benzylsuccinate CoA-Transferase: an enzyme of the anaerobic toluene catabolic pathway in denitrifying bacteria,"*J. Bacteriol.* 183(14):4288-4295 (2001).

Levanon et al., "Effect of Oxygen on the *Escherichia coli* ArcA and FNR Regulation Systems and Metabolic Responses,"*Biotechnol. Bioeng.* 89(5):556-564 (2005).

Li and Jordan, "Effects of substitution of tryptophan 412 in the substrate activation pathway of yeast pyruvate decarboxylase,"*Biochemistry* 38:10004-10012.

Li et al., "Properties of Nicotinamide Adenine Dinucleotide Phosphate-Dependent Formate Dehydrogenase from *Clostridium thermoaceticum*,"*J. Bacteriol.* 92(2):405-412 (1966).

Li et al., "Purification, crystallization and preliminary crystallographic studies on 2 dehydro-3-deoxygalactarate aldolase from *Leptospira* interrogans,"*Acta. Crystallodr. Sect. F. Struct. Biol. Cryst. Commun.* 62(Pt 12):1269-1270 (2006).

Li, Guang-Shan, "Development of a reporter system for the study of gene expression for solvent production in *Clostridium beijerinckii* NRRL B592 and Clostridium acetobutylicum ATCC 824," Dissertation, Department of Biochemistry, Virginia Polytechnic Institute and State University (Sep. 1998).

Lian et al., "Stereochemical and Isotopic Labeling Studies of 4-Oxalocrotonate Decarboxylase and Vinylpyruvate hydratase: Analysis and Mechanistic Implications,"*J. Am. Chem Soc.* 116:10403-10411 (1994).

Lin et al., "Chemostat culture characterization of *Escherichia coli* mutant strains metabolically engineered for aerobic succinate production: A study of the modified metabolic network based on metabolite profile, enzyme activity, and gene expression profile,"*Metab. Eng.* 7(5-6):337-352 (2005).

Lin et al., "Functional Expression of Horseradish Peroxidase in *E. coli* by Directed Evolution,"*Biotechnol. Prod.* 15:467-471 (1999).

Lin et al., "Effect of carbon sources differing in oxidation state and transport route on succinate production in metabolically engineered *Escherichia coli*,"*J. Ind. Microbiol. Biotechnol.* 32:87-93 (2005).

Lin et al., "Fed-batch culture of a metabolically engineered *Escherichia coli* strain designed for high-level succinate production and yield under aerobic conditions,"*Biotechnol. Bioeng.* 90:775-779 (2005).

Lin et al., "Genetic Reconstruction of the Aerobic Central Metabolism in *Escherichia coli* for the Absolute Aerobic Production of Succinate,"*Biotechnol. Bioeng.* 89(2):148-156 (2005).

Lin et al., "Increasing the Acetyl-CoA pool in the Presence of Overexpressed Phosphoenolpyruvate Carboxylase or Pyruvate Carboxylase Enhances Succinate Production in *Escherichia coli*,"*Biotechnol. Prog.* 20(5):1599-1604 (2004).

Lin et al., "Metabolic engineering of aerobic succinate production systems in *Escherichia coli* to improve process productivity and achieve the maximum theoretical succinate yield,"*Metab. Eng.* 7(2):116-127 (2005).

Lin, Metabolic Network Design and Engineering in *Escherichia coli* Ph.D. Thesis, Rice University, Dept. of Bioengineering (2005).

(56) References Cited

OTHER PUBLICATIONS

Lin, H et al., "Effect of *Sorghum vulgare* phosphoenolpyruvate carboxylase and *Lactococcus lactis* pyruvate carboxylase coexpression on succinate production in mutant strains of *Escherichia coli*,"*Appl. Microbiol. Biotechnol.* 67(4): 515-523 (2005).
Lingen et al., "Alteration of the substrate specificity of benzoylformate decarboxylase from Pseudomonas putida by directed evolution,"*Chembiochem.* 4:721-726 (2003).
Lingen et al., "Improving the carboligase activity of benzoylformate decarboxylase from Pseudomonas putida by a combination of directed evolution and site-directed mutagenesis,"*Protein Eng.* 15:585-593 (2002).
Link et al., "Methods for generating precise deletions and insertions in the genome of wild-type *Eshcerichia coli*: application to open reading frame characterization,"*J. Bacteriol.* 179:6228-6237 (1997).
Liou et al., "*Clostridium carboxidivorans* sp. nov., a solvent-producing clostridium isolated from an agricultural settling lagoon, and reclassification of the acetogen *Clostridium scatologenes* strain SL1 as *Clostridium drakei* sp. nov,"*Int. J. Syst. Evol. Microbiol.* 55(Pt 5):2085-2091 (2005).
Liu et al., "Kinetic and crystallographic analysis of active site mutants of *Escherichia coli* y-aminobutyrate aminotransferase,"*Biochemistry* 44:(8):2982-2992 (2005).
Liu et al., "Microbial production of R-3-hydroxybutyric acid by recombinant *E. coli* harboring genes of phbA, phbB, and tesB,"*Appl. Microbiol. Biotechnol.* 76:811-818 (2007).
Liu et al., "Purification and characterization of ornithine acetyltransferase from *Saccharomvces cerevisiae*,"*Eur. J. Biochem.* 228:291-296 (1995).
Liu et al., "Crystal structures of unbound and aminooxyacetate-bound *Escherichia coli* y-aminobutyrate aminotransferase,"*Biochemistry* 43(34):10896-10905 (2004).
Liu et al., "Economical succinic acid production from cane molasses by *Actinobacillus succinogenes*,"*Bioresour Technol* 99(6):1736-1742 (2008).
Ljungdahl and Andreesen, "Formate dehydrogenase, a selenium-tungsten enzyme from *Clostridium thermoaceticum*,"*Methods Enzmol.* 53:360-372 (1978).
Ljungdahl and Andreesen, "Tungsten, a component of active formate dehydrogenase from *Clostridium thermoacetium*,"*FEBS Lett.* 54:279-282 (1975).
Ljungdahl, "The Autotrophic Pathway of Acetate Synthesis in Acetogenic Bacteria,"*Ann. Rev. Microbiol.* 40:415-450 (1986).
Lloyd-Jones et al., "Rate Enhancement by Ethylene in the Ru-Catalyzed Ring-Closing Metathesis of Enynes: Evidence for an "Ene-then-Yne" Pathway that Diverts through a Second Catalytic Cycle,"*Anew Chem Int Ed.* 44(45):7442-7447 (2005).
Lokanath et al., "Crystal structure of novel NADP-dependent 3-hydroxyisobutyrate dehydrogenase from *Thermus thermophilus* HB8,"*J. Mol. Biol.* 352(4):905-917 (2005).
Lake et al., "Active acetyl-CoA synthase from *Clostridium thermoaceticum* obtained by cloning and heterologous expression of acsAB in *Escherichia coli*,"*Proc. Natl. Acad. Sci. U.S.A.* 97:12503-12535 (2000).
Longtine et al., "Additional modules for versatile and economical PCR-based gene deletion and modification in *Saccharomyces cerevisiae*,"*Yeast* 14(10): 953-961 (1998).
Lopez-Barragan et al., "The *bzd* gene cluster, coding for anaerobic benzoate catabolism, in *Azoarcus* sp. Strain CIB,"*J. Bacteriol.* 186(17):5762-5774 (2004).
Louie and Chan, "Cloning and characterization of the gamma-glutamyl phosphate reductase gene of *Campylobacter jejuni*,"*Mol. Gen. Genet.* 240:29-35 (1993).
Louis et al., "Restricted distribution of the butyrate kinase pathway among butyrate-producing bacteria from the human colon,"*J. Bacteriol.* 186:2099-2106 (2004).

Lovell et al., "Cloning and expression in *escherichia coli* of the *Clostridium thermoaceticum* gene encoding thermostable formyltetrahydrofolate synthetase,"*Arch. Microbiol.* 149(4):280-285 (1988).
Lovell et al., "Primary structure of the thermostable formyltetrahydrofolate synthetase from *Clostridium thermoaceticum*,"*Biochemistry* 20(29):5687-5694 (1990).
Low et al., "Mimicking somatic hypermutation: Affinity maturation of antibodies displayed on baceriophage using a bacterial mutator strain,"*J. Mol. Biol.* 260(3):359-368 (1996).
Lu et al., "Controlled Poetntial Enzymology of Methyl Transfer Reactions Involved in Acetyl-CoA Synthesis by CO Dehydrogenase and the Corrinoid/Iron-Sulfur Protein from *Clostridium thermoaceticum*,"*J. Biol. Chem.* 265(6):3124-3133 (1990).
Lu et al., "Functional Analysis and Regulation of the Divergent spuABCDEFGH-spuI Operons for Polyamine Uptake and Utilization in *Pseudomonas aeruginosa* PA01,"*J. Bacteriol.* 184(14):3765-3773 (2002).
Lu et al., "Sequence and expression of the gene encoding the corrinoid/iron-sulfur protein from *Clostridium thermoaceticum* and reconstitution of the recombinant protein to full activity,"*J. Biol. Chem.* 268(8):5605-5614 (1993).
Luersen, "Leishmania major thialsine Nϵ-acetyltransferase: Identification of amino acid residues crucial for substrate binding,"*FEBS Lett.* 579:5347-5352 (2005).
Luli and Stroh!, "Comparison of Growth, Acetate Production, and Acetate Inhibition of *Escherichia coli* Strains in Batch and Fed-Batch Fermentations,"*Appl. Environ. Microbiol.* 56:1004-1011 (1990).
Lupa et al., "Distribution of genes encoding the microbial non-oxidative reversible hydroxyarylic acid decarboxylases/phenol carboxylases,"*Genomics* 86:342-351 (2005).
Lupa et al., "Properties of the reversible nonoxidative vanillate/4-hydroxybenzoate decarboxylase from *Bacillus subtilis*,"*Can. J. Microbiol* 54:75-81 (2008).
Lutke-Eversloh and Steinbuchel, "Biochemical and molecular characterization of a succinate semialdehyde dehydrogenase involved in the catabolism of 4-hydroxybutyric acid in *Ralstonia eutropha*,"*FEMS Microbiol. Lett.* 181(1):63-71 (1999).
Lutz and Bujard, "Independent and tight regulation of transcriptional units in *Escherichia coli* via the LacR/O, the TetR/0 and AraC/$1_1$-$1_2$ regulatory elements,"*Nucleic Acids Res.* 25(6):1203-1210 (1997).
Lutz et al., "Creating multiple-crossover DNA libraries independent of sequence identity,"*Proc. Natl. Acad. Sci U.S.A.* 98:11248-11253 (2001).
Lutz et al., "Dissecting the functional program of *Escherichia coli* promoters: the combined mode of action of Lac repressor and AraC activator,"*Nucleic Acids Res.* 29(18):3873-3881 (2001).
Lutz et al., "Rapid generation of incremental truncation libraries for protein enginering using a-phosphothioate nucleotides,"*Nucleic Acids Res.* 29:E16 (2001).
Lynch et al., "SCALEs: multiscale analysis of library enrichment,"*Nat. Methods.* 4(1):87-93 (2007).
Lynd et al., "Microbial Cellulose Utilization: Fundamentals and Biotechnology,"*Microbial. Mol. Biol. Rev.* 66:506-577 (2002).
Lynn et al., "Living Ring-Opening Metathesis Polymerization in Aqueous Media Catalyzed by Well-Defined Ruthenium Carbene Complexes,"*J. Am. Chem. Soc.* 118(4):784-790 (1996).
Lynn et al., "Living Ring-Opening Metathesis Polymerization in Water,"*J. Am. Chem.Soc.* 120(7):1627-1628 (1998).
Ma et al., "Induced rebuilding of aspartase conformation,"*Ann. NY Acad. Sci.* 672:60-65 (1992).
Macis et al., "Properties and sequence of the Coenzyme $B_{12}$-dependent glycerol dehydratase of *Clostridium pasteruianum*,"*FEMS Microbiol. Lett.* 164:21-28 (1998).
Mack and Buckel, "Conversion of glutaconate CoA-transferase from *Acidaminococcus fermentans* into an acyl-CoA hydrolase by site-directed mutaaenesis"*FEBS Lett.* 405(2):209-212 (1997).
Mack et al., "Location of the two genes encoding glutaconate Coenzyme A-transferase at the beginning of the hydroxyglutarate operon in *Acidaminococcus fermentans*,"*Eur. J. Biochem.* 226:41-51 (1994).

(56) References Cited

OTHER PUBLICATIONS

Maeda et al., "Enhanced hydrogen production from glucose by metabolically engineered *Escherichia coli*,"*Appl. Microbiol. Biotechnol.* 77:879-890 (2007).
Maeder et al., "The *Methanosarcina barkeri* genome: comparative analysis with *Methanosarcina acetivorans* and *Methanosarcina mazei* reveals extensive rearrangement within *methanosarcinal* genomes,"*J. Bacteriol.* 188(22):7922-7931 (2006).
Maes et al., "Crystallization of ornithine acetyltransferase from yeast by counter-diffusion and preliminary x-ray study,"*Acta. Crystallogr. Sect. F. Struct. Biol. Cryst.Commun.* 62(Pt 12):1294-1297 (2006).
Mahadevan and Schilling, "The effects of alternate optimal solutions in constraint-based genome-scale metabolic models,"*Metab. Eng.* 5(4):264-276 (2003).
Mahan and Csonka, "Genetic analysis of the proBA genes of *Salmonella typhimurium*: physical and genetic analyses of the cloned proB+A+ genes of *Escherichia coli* and of a mutant allele that confers praline overproduction and enhanced osmotolerance,"*J. Bacteriol.* 156:1249-1262 (1983).
Mai and Adams, "Purification and characterization of two reversible and ADP-dependent acetyl Coenzyme A synthetases from the hyperthermophilic archaeon *Pyrococcus furiosus*,"*J. Bacteriol.* 178:5897-5903 (1996).
Maicas, S. et al., "NAD(P)H regeneration is the key for heterolactic fermentation of hexoses in *Oenococcus oeni*,"*Microbiology* 148:325-332 (2002).
Maitra and Sprinson, "5-Dehydro-3-deoxy-o-arabino-heptulosonic acid 7-phosphate. An intermediate in the 3-dehydroquinate synthase reaction,"*J Biol. Chem.* 253:5426-5430 (1978).
Majewski and Domach, "Simple Constrained-Optimization View of Acete Overflow in *E. Coli*,"*Biotechnol. Bioeng.* 35(7):732-738 (1990).
Maklashina et al., "Anaerobic expression of *Escherichia coli* succinate dehydrogenase: functional replacement of fumarate reductase in the respiratory chain during anaerobic growth,"*J. Bacteriol.* 180(22):5989-5996 (1998).
Manjasetty et al., "Crystallization and preliminary X-ray analysis of dmpFG-encoded 4-hydroxy-2-ketovalerate aldolase-aldehyde dehydrogenase (acylating) from *Pseudomonas* sp strain CF600,"*Acta. Crystallogr. D. Biol. Crystallogr.* 57(Pt 4):582-585 (2001).
Manning and Pollitt, "Tracer studies of the interconversion of R– and S– methylmalonic semialdehydes in man,"*Biochem. J.* 231(2):481-484 (1985).
Marco-Mann et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase,"*J. Mol. Biol.* 334:459-476 (2003).
Marek and Henson, "Cloning and expression of the *Escherichia coli* K-12 sad gene,"*J. Bacteriol.* 170:991-994 (1988).
Marks et al., "Molecular cloning and characterization of (R)-3-hydroxybutyrate dehydrogenase from human heart,"*J. Biol. Chem.* 267(22):15459-15463 (1992).
Martin et al., "Engineering a mevalonate pathway in *Escherichia coli* for production of terpenoids,"*Nat. Biotechnol.* 21:796-802 (2003).
Martin et al., "Nematode.net update 2008: improvements enabling more efficient data mining and comparative nematode genomics,"*Nucleic Acids Res.* 37:0571-0578 (2009).
Martinez-Blanco et al., "Purification and biochemical characterization of phenylacetyl-CoA ligase from *Pseudomonas putida*. A specific enzyme for the catabolism of phenylacetic acid,"*J. Biol. Chem.* 265(12):7084-7090 (1990).
Martinez-Carrion and Jenkins, "D-Alanine-D-glutamate transaminase. I. Purification and characterization,"*J. Biol. Chem.* 240(9):3538-3546 (1965).

Martins et al., "Crystal structure of 4-hydroxybutyryl-CoA dehydratase: radical catalysis involving a [4Fe-4S] cluster and flavin,"*Proc. Natl. Acad. Sci. U.S.A.* 101(44):15645-15649 (2004).
Mason and Dufour, "Alcohol acetyltransferases and the significance of ester synthesis in yeast,"*Yeast* 16(14):1287-1298 (2000).
Matiasek et al., "Volatile ketone formation in bacteria: release of 3-oxopentanoate by soil pseudomonads during growth on heptanoate "*Curr. Microbiol.* 42:276-281 (2001).
Mat Jan et al., "Mutants of *Escherichia coli* Deficient in the Fermentative Lactate Dehydrogenase,"*J. Bacteriol.* 171(1):342-348 (1989).
Matsumura et al., "Constitutive expression of catABC genes in the aniline-assimilating bacterium *Rhodococcus* species AN-22: production, purification, characterization and gene analysis of CatA, Cats and CatC,"*Biochem. J.* 393:219-226 (2006).
Matsushima et al., "An enone reductase from *Nicotiana tabacum*: cDNA cloning, expression in *Escherichia coli*, and reduction of enones with the recombinant proteins,"*Bioorg. Chem.* 36:23-28 (2008).
Matta et al., "Interactions of the antizyme Atoe with regulatory elements of the *Escherichia coli* atoDAEB operon,"*J. Bacteriol.* 189(17):6324-6332 (2007).
Mattevi et al., "Atomic structure of the cubic core of the pyruvate dehydrogenase multienzyme complex,"*Science* 255(5051):1544-1550 (1992).
Matthies and Schink, "Reciprocal Isomerization of Butyrate and Isobutyrate by the Strictly Anaerobic Bacterium Strain WoG13 and Methanogenic Isobutyrate Degradation by a Defined Triculture,"*Appl. Environ. Microbiol.* 58(5):1435-1439 (1992).
Maurus et al., "Insights into the Evolution of Allosteric Properties. The NADH Binding Site of Hexameric Type II Citrate Synthases,"*Biochemistry* 42:5555-5565 (2003).
Mavrovouniotis, Estimation of standard Gibbs energy changes of biotransformations, *J. Biol. Chem.* 266:14440-14445 (1991).
Maynard et al., "Autocatalytic activation of acetyl-CoA synthase,"*J. Biol. Inorg. Chem.* 9:316-322 (2004).
Mazur et al., "Cis, cis-muconate lactonizing enzyme from *Trichosporon cutaneum*: evidence for a novel class of *cycloisomerases* in eucaryotes,"*Biochemistry* 33:1961-1970 (1994).
McAlister-Henn and Thompson, "Isolation and expression of the gene encoding yeast mitochondrial malate dehydrogenase,"*J. Bacteriol.* 169:5157-5166 (1987).
McCarthy et al., "Crystal structure of methylmalonyl-Coenzyme A epimerase from P. *shermanii*: a novel enzymatic function on an ancient metal binding scaffold,"*Structure* 9(7):637-646 (2001).
McCullough et al., "Enzymatic decarboxylation of the aminobenzoates,"*J. Am. Chem. Soc.* 79:628-630 (1957).
McGregor et al., "argE-Encoded N-Acetyl-L-Ornithine Deacetylase from *Escherchia coli* Contains a Dinuclear Metalloactive Site,"*J. Am. Chem. Soc.* 127:14100-14107 (2005).
Mcinerney et al., "The genome of *Syntrophus aciditrophicus*: Life at the thermodynamic limit of microbial growth,"*Proc. Natl. Acad. Sci U.S.A.* 104:7600-7605 (2007).
McKinlay et al., "Prospects for a bio-based succinate industry,"*Appl. Microbiol. Biotechnol.* 76(4):727-740 (2007).
McPherson and Wootton, "Complete nucleotide sequence of the *Escherichia coli* gdhA gene,"*Nucleic Acids Res.* 11:5257-5266 (1983).
McPherson et al., "Multiple interactions of lysine-128 of *Escherichia coli* glutamate dehydrogenase revealed by site-directed mutagenesis studies,"*Protein Eng.* 2(2):147-152 (1988).
Meagher, "Purification and partial amino acid sequence of the cyanogen bromide fragments of muconolactone isomerase from *Pseudomonas putida*,"*Biochim. Biophys. Acta* 494:33-47 (1977).
Mechichi et al., "*Alicycliphilus denitrificans* gen. nov., sp. nov., a cyclohexanol-degrading, nitrate-reducing β-proteobacterium,"*Int. J. Syst. Evol. Microbiol.* 53:147-152 (2003).
Megraw et al., "Formation of lactyl-Coenzyme A and pyruvyl-Coenzyme A from lactic acid by *Escherichia coli*,"*J. Bacteriol.* 90(4):984-988 (1965).
Meinnel et al., "Structural and Biochemical Characterization of the *Escherichia coli* argE Gene Product,"*J. Bacteriol.* 174(7):2323-2331 (1992).

(56) References Cited

OTHER PUBLICATIONS

Melchiorsen et al., "The level of pyruvate-formate lyase controls the shift from homolactic to mixed-acid product formation in *Lactococcus lactis*,"*Appl. Microbiol. Biotechnol.* 58:338-344 (2002).
Meng and Chuang, "Site-directed Mutagenesis and Functional Analysis of the Active-Site Residues of the E2 Component of Bovine Branched-Chain a-Kto Acid Dehydrogenase Complex,"*Biochemistry* 33:12879-12885 (1994).
Meng and Li, "Cloning, expression and characterization of a thiolase gene from *Clostridium pasteurianum*,"*Biotechnol. Lett.* 28(16):1227-1232 (2006).
Menon and Ragsdale, "Mechanism of the *Clostridium thermoaceticum* pyruvate:ferredoxin oxidoreductase: evidence for the common catalytic intermediacy of the hydroxyethylthiamine pyropyrophosphate radical,"*Biochemistry* 36(28):8484-8494 (1997).
Menzel et al., "Enzymatic evidence for an involvement of pyruvate dehydrogenase in the anaerobic glycerol metabolism of *Klebsiella pneumoniae*,"*J. Biotech.* 56:135-142 (1997).
Menzel et al., "Kinetic, dynamic, and pathway studies of glycerol metabolism by *Klebsiella pneumoniae* in anaerobic continuous culsutre: IV. Enzymes and fluxes of pyruvate metabolism,"*Botechnol. Bioeng.* 60(5):617-626 (1998).
Merkel and Nichols, "Characterization and sequence of the *Escherichia coli* panBCD gene cluster,"*FEMS Microbiol. Lett.* 143(2-3):247-252 (1996).
Mermelstein et al., "Metabolic Engineering of *Clostridium acetobutylicum* ATCC 824 for Increased Solvent Production by Enhancement of Acetone Formation Enzyme Activities Using a Synthetic Acetone Operon,"*Biotechnol. Bioeng.* 42(9):1053-1060 (1993).
Metz et al., "Purification of a jojoba embryo fatty acyl-Coenzyme A reductase and expression of its cDNA in high erucic acid rapeseed,"*Plant Phys.* 122:635-644 (2000).
Meynial-Salles, I., et al., "A new process for the continuous production of succinic acid from glucose at high yield, titer and productivity,"*Biotechnol. Bioeng.* 99(1):129-135 (2008).
Millard et al., "Enhanced production of succinic acid by overexpression of phosphoenolpyruvate carboxylase in *Escherichia coli*,"*Appl. Environ. Microbiol.* 62(5):1808-1810 (1996).
Miller and Jenesel, "Enzymology of butyrate Formation by *Butyrivibrio-Fibrisolvens*,"*J. Bacteriol.* 138:99-104 (1979).
Miller et al., "Structure of β-lactam synthetase reveals how to synthesize antibiotics instead of asparagine,"*Nat. Struct. Biol.* 8(8):684-689 (2001).
Miller et al., "The catalytic cycle of β-lactam synthetase observed by x-ray crystallographic snapshots,"*Proc. Natl. Acad. Sci. U.S.A.* 99(23):14752-14757 (2002).
Minard and McAlister-Henn, "Isolation, nucleotide sequence analysis, and disruption of the MDH2 gene from *Saccharomyces cerevisiae*: evidence for three isozymes of yeast malate dehydrogenase,"*Mol. Cell. Biol.* 11:370-380 (1991).
Misono and Nagasaki, "Occurrence of L -Lysine ε-Dehydrogenase in *Agrobacterium tumefaciens*,"*J. Bacteriol.* 150(1):398-401 (1982).
Misono et al., "Properties of L-lysine epsilon-dehydrogenase from *Agrobacterium tumefaciens*,"*J. Biochem.* 105(6):1002-1008 (1989).
Miura et al., "Molecular Cloning of the *nemA* Gene Encoding *N*-Ethylmaleimide Reductase from *Escherichia Coli*,"*Biol. Pharm. Bull.* 20(1):110-112 (1997).
Miyazaki et al., "a-Aminoadipate aminotransferase from an extremely thermophilic bacterium, *Thermus thermophilus*,"*Microbiology* 150:2327-2334 (2004).
Mizobata et al., "Purification and characterization of a thermostable class II fumarase from *Thermus thermophilus*,"*Arch. Biochem. Biophys.* 355(1):49-55 (1998).
Mizugaki et al. "Studies on the metabolism of unsaturated fatty acids. IX. Stereochemical studies of the reaction catalyzed by trans-2-enoyl-Coenzyme A reductase of *Escherichia coli*,"*J. Biochem.* 92(5):1649-1654 (1982).

Mizugaki et al., "Studies on the Metabolism of Unsaturated Fatty Acids. V. Isomerization of Thiol Esters of cis-2-Alkenoic Acids during Their Preparation and Alkaline Hydrolysis,"*Chem. Pharm. Bull.* 30(1):206-213 (1982).
Momany et al., "Crystallization of diaminopimelate decarboxylase from *Escherichia coli*, a stereo specific o-amino-acid decarboxylase,"*Acta. Crystallogr. D. Biol. Crystallogr.* 58(Pt 3):549-552 (2002).
Momany et al., "Crystallographic Structure of PLP-Dependent Ornithine Decarboxylase from *Lactobacillus* 30a to 3.0 A Resolution,"*J. Maol. Biol.* 252:643-655 (1995).
Monnet et al., "Regulation of branched-chain amino acid biosynthesis by a-acetolactate decarboxylase in *Streptococcus thermophilus*,"*Lett. Appl. Microbiol.* 36(6):399-405 (2003).
Moon et al., "Metabolic engineering of *Escherichia coli* for the production of malic acid,"*Biochem. Eng. J.* 40(2):312-320 (2008).
Moore et al., "Expression and Purification of Aspartate β-Semialdehyde Dehydrogenase from Infectious Microorganisms,"*Protein Expr. Purif.* 25:189-194 (2002).
Moresi et al., "Fumaric acid production from hydrolysates of starch-based substrates,"*J. Chem. Technol. Biotechnol.* 54(3):283-290 (1992).
Mori et al., "Characterization, Sequencing, and Expression of the Genes Encoding a Reactivating Factor for Glycerol-inactivated Adenosylcobalamin-dependent Diol Dehydratase,"*J. Biol. Chem.* 272(51):32034-32041 (1997).
Morris and Jinks-Robertson, "Nucleotide sequence of the LYS2 gene of *Saccharomyces cerevisiae*: homology to *Bacillus* brevis tyrocidine synthetase 1,"*Gene* 98:141-145 (1991).
Morsomme et al., "Single point mutations in various domains of a plant plasma membrane H+-ATPase expressed in *Saccharomyces cerevisiae* increase H+-pumping and permit yeast growth at low pH,"*Embo. J.* 15(20):5513-5526 (1996).
Morton et al., "Cloning, sequencing, and expressions of genes encoding enzymes of the autotrophic acetyl-CoA pathway in the acetogen *Clostridium thermoaceticum*," in M. Sebald (ed.), *Genetics and molecular biology of anaerobic bacteria*, Springer Verlag, New York, 389-406 (1992).
Morton et al., "The primary structure of the subunits of carbon monoxide dehydrogenase/acetyl-CoA synthase from *Clostridium thermoaceticum*,"*J. Biol. Chem.* 266(35):23824-23828 (1991).
Moskowitz et al., "Metabolism of poly-β-hydroxybutyrate. II. Enzymatic synthesis of D-(−)-β-hydroxybutyryl Coenzyme A by an enoyl hydrase from *rhodospirillum rubrum*," Biochemistry 8:2748-2755 (1969).
Moszer, "The complete genome of *Bacillus subtilis*: from sequence annotation to data management and analysis,"*FEBS Lett.* 430:28-36 (1998).
Mouttaki et al.. "Cyclohexane Carboxylate and Benzoate Formation from Crotonate in *Syntrophus aciditrophicus*,"*Appl. Environl. Microbiol.* 73(3):930-938 (2007).
Muh et al., "4-Hydroxybutyryl-CoA dehydratase from *Clostridium aminobutyricum*: characterization of FAD and iron-sulfur clusters involved in an overall non-redox reaction,"*Biochemistry* 35:11710-11718 (1996).
Muh et al., "Mossbauer study of 4-hydroxybutyryl-CoA dehydratase probing the role of an iron-sulfur cluster in an overall non-redox reaction,"*Eur. J. Biochem.* 248:380-384 (1997).
Mukhopadhyay and Purwantini, "Pyruvate carboxylase from *Mycobacterium smegmatis*: stabilization, rapid purification, moleculare and biochemical characterization and regulation of the cellular level,"*Biochim. Biophys. Acta.* 1475(3):191-206 (2000).
Muller and Buckel, "Activation of (R)-2-hydroxyglutaryl-CoA dehydratase from *Acidaminococcus fermentans*,"*Eur. J. Biochem.* 230(2):698-704 (1995).
Muller et al., "Nucleotide exchange and excisiion technology (NExT) DNA shuffling; a robust method for DNA fragmentation and directed evolution,"*Nucleic Acids Res.* 33:e117 (2005).
Muller, "Energy Conservation in *Acetogenic Bacteria*,"*Appl. Environ. Microbiol.* 69:6345-6353 (2003).
Murakami et al., "Purification and characterization of two muconate cycloisomerase isozymes from aniline-assimilating *Frateuria* species ANA-18,"*Biosci. Biotechnol.Biochem.* 62:1129-1133 (1998).

(56) References Cited

OTHER PUBLICATIONS

Muratsubaki and Enomoto, "One of the fumarate reductase isoenzymes from *Saccharomyces cerevisiae* is encoded by the OSM1 gene,"*Arch. Biochem. Biophys.* 352:175-181 (1998).

Musfeldt and Schonheit, "Novel type of ADP-forming acetyl Coenzyme A synthetase in hyperthermophilic archaea: heterologous expression and characterization of isoenzymes from the sulfate reducer *Archaeoglobus fulgidus* and the methanogen *Methanococcus jannaschii*,"*J. Bacteriol.* 184(3):636-644 (2002).

Muyrers et al., "Rapid modification of bacterial artificial chromosomes by ET-recombination,"*Nucleic Acids Res.* 27:1555-1557 (1999).

Nagasawa et al., "Cloning and Nucleotide Sequence of the Alcohol Acetyltransferase II gene (ATF2) from *Saccharomyces cerevisiae* Kyokai No. 7,"*Biosci. Biotechnol. Biochem.* 62:1852-1857 (1998).

Nagata et al., "Gene cloning, purification, and characterization of thermostable and halophilic leucine dehydrogenase from a halophilic thermophile, *Bacillus licheniformis* TSN9,"*Appl. Microbiol. Biotechnol.* 44:432-438 (1995).

Naggert et al., "Cloning, sequencing, and characterization of *Escherichia coli* thioesterase II,"*J. Biol. Chem.* 266(17):11044-11050 (1991).

Nahvi et al., "Genetic Control by a Metabolite Binding mRNA,"*Chem. Biol.* 9:1043-1049 (2002).

Naidu and Ragsdale, "Characterization of a three-component vanillate 0-demethylase from *Moorella thermoacetica*,"*J. Bacteriol.* 183(11):3276-3281 (2001).

Najafpour and Younesi, "Ethanol and acetate synthesis from waste gas using batch culture of *Clostridium ljungdahlii*,"*Enzyme Microb. Technol.* 38:223-228 (2006).

Najmudin et al., "Purification, crystallization and preliminary X-ray crystallographic studies on acetolactate decarboxylase,"*Acta. Crystallogr. D. Biol. Crystalloar.* 59(Pt 6):1073-1075 (2003).

Nakahigashi and Inokuchi, "Nucleotide sequence of the fadA and fadB genes from *Escherichia coli*,"*Nucleic Acids Res.* 18(16):4937 (1990).

Nakano et al., "Characterization of Anaerobic Fermentative Growth of Bacillus subtilis: Identification of Fermentation End Products and Genes Required for Growth,"*J. Bacteriol.* 179(21):6749-6755 (1997).

Nakazawa et al., "Studies on monooxygenases. V. Manifestation of amino acid oxidase activity by L-lysine monooxygenase," J. Biol. Chem. 247:3439-3444 (1972).

Namba et al., "Coenzyme A- and Nicotinamide Adenine Dinucleotide-dependent Branched Chain a-Keto Acid Dehydrogenase,"*J. Biol. Chem.* 244(16):4437-4447 (1969).

Neidhart et al., "Mandelate racemase and muconate lactonizing enzyme are mechanistically distinct and structurally homologous,"*Nature* 347:692-694 (1990).

Ness et al., "Synthetic shuffling expands functional protein diversity by allowing amino acids to recombine independently,"*Nat. Biotechnol.* 20:1251-1255 (2002).

Nicolaou et al., "The Diels-Alder Reaction in Total Synthesis,"*Angew Chemie Int Ed.* 41:1668-1698 (2002).

Niegemann et al., "Molecular organization of the *Escherichia coli* gab cluster: nucleotide sequence of the structural genes gabD and gabP and expression of the GABA permease gene,"*Arch.Microbiol* 160:454-460 (1993).

Nimmo, "Kinetic mechanism of *Escherichia coli* isocitrate dehydrogenase and its inhibition by glyoxylate and oxaloacetate,"*Biochem. J.* 234(2):317-323 (1986).

Nishimaki et al., "Studies on the Metabolism of Unsaturated Fatty Acids. XIV. Purification and Properties of NADPH-Dependent trans-2-Enoyl-CoA Reductase of *Escherichia coli* K-12,"*J. Biochem.* 95(5):1315-1321 (1984).

Nishizawa et al., "Gene expression and characterization of two 2-oxoacid:ferredoxin oxidoreductases from *Aeropyrum pernix* K1,"*FEBS Lett.* 579:2319-2322 (2005).

Nissen et al., "Expression of a cytoplasmic transhydrogenase in *Saccharomyces cerevisiae* results in formation of 2-oxoglutarate due to depletion of the NADPH pool,"*Yeast* 18:19-32 (2001).

Nogales et al., "Characterization of the last step of the aerobic phenylacetic acid degradation pathway,"*Microbiology* 153(Pt 2):357-365 (2007).

Noichinda et al., "Subcellular Localization of Alcohol Acetyltransferase in Strawberry Fruit,"*Food Sci. Technol. Res.* 5(3):239-242 (1999).

Noiling et al., "Genome sequence and comparative analysis of the solvent-producing bacterium *Clostridium acetobutylicum*,"*J. Bacteriol.* 183(16):4823-4838 (2001).

Norton, "The Diels-Alder Diene Synthesis,"*Chem. Rev.* 31:319-523 (1942).

Nowicki et al., "Recombinant tyrosine aminotransferase from *Trypanosoma cruzi*: structural characterization and site directed mutagenesis of a broad substrate specificity enzyme,"*Biochim. Biophysica Acta* 1546:268-281 (2001).

O'Brien and Gennis, "Studies of the Thiamin Pyrophosphate Binding Site of *Escherichia coli* Pyruvate Oxidase,"*J. Biol. Chem.* 255(8):3302-3307 (1980).

O'Brien et al, "Regulation by Lipids of Cofactor Binding to a Peripheral Membrane Enzyme: Binding of Thiamin Pyrophosphate to Pyruvate Oxidase,"*Biochemistry.* 16(14):3105-3109 (1977).

O'Brien et al., "Chemical, physical and enzymatic comparisons of formyltetrahydrofolate synthetases from thermo- and *mesophilic clostridia*,"*Experientia. Suppl.* 26:249-262 (1976).

O'Brien et al., "Insight into the Mechanism of the $B_{12}$Independent Glycerol Dehydratase from *Clostridium butyricum*: Preliminary Biochemical and Structural Characterization,"*Biochemistry* 43:4635-4645 (2004).

Ofman et al., "2-Methyl-3-hydroxybutyryl-CoA dehydrogenase deficiency is caused by mutations in the HADH2 gene,"*Am. J. Hum. Genet.* 72:1300-1307 (2003).

Ohgami et al., "Expression of acetoacetyl-CoA synthetase, a novel cytosolic ketone body-utilizing enzyme, in human brain,"*Biochem. Pharmacol.* 65:989-994 (2003).

Ohsugi et al., "Metabolism of L-β-Lysine by Pseudomonas. Purification and Properties of a Deacetylase-Thiolestrerase Utilizing 4-Acetamidobutyryl CoA and Related Compounds,"*J. Biol. Chem.* 256(14):7642-7651 (1981).

Okino et al., "An effeicient succinic acid production process in a metabolically engineered *Corynebacterium glutamicum* strain,"*Appl. Microbiol. Biotechnol.* 81(3):459-464 (2008).

Oku and Kaneda, "Biosynthesis of branched-chain fatty acids in *bacillus subtilis*. A decarboxylase is essental for branched-chain fatty acid synthetase,"*J. Biol. Chem.* 263:18386-18396 (1988).

Okuno et al., "2-Aminoadipate-2-oxoglutarate aminotransferase isoenzymes in human liver: a plausible physiological role in lysine and tryptophan metabolism,"*Enzyme Protein* 47:136-148 (1993).

Olivera et al., "Molecular characterization of the phenylacetic acid catabolic pathway in *Pseudomonas putida* U: the phenylacetyl-CoA catabolon,"*Proc. Natl. Acad. Sci. U.S.A.* 95(11):6419-6424 (1998).

Onuffer and Kirsch, "Redesign of the substrate specificity of *Escherichia coli* aspartate aminotransferase to that of *Escherichia coli* tyrosine aminotransferase by homology modeling and site-directed mutagenesis,"*Protein Sci.* 4:1750-1757 (1995).

O'Reilly and Devine, "Sequence and analysis of the citrulline biosynthetic operon argC-F from *Bacillus subtilis*,"*Microbiology.* 140:1023-1025 (1994).

Orencio-Trejo et al., "Metabolic regluation analysis of an ethanologenic *Escherichia coli* strain based on RT-PCR and enzymatic activities,"*Biotechnol. Biofuels* 1:8.(2008). (orovided electronically by publisher as pp. 1-13).

Ostermeier et al., "A Combinatorial approach to hybrid enzymes independent of DNA homology"*Nat. Biotechnol.* 17:1205-1209 (1999).

Ostermeier et al., "Combinatorial protein engineering by incremental truncation,"*Proc. Natl. Acad. Sci. U.S.A.* 96:3562-3567 (1999).

O'Sullivan et al., "Purification and characterisation of acetolactate decarboxylase from *Leuconostoc lactis* NCW1,"*FEMS Microbiol. Lett* 194(2):245-249 (2001).

(56) References Cited

OTHER PUBLICATIONS

Otten and Quax, "Directed evolution:selecting today's biocatalysts,"*Biomol. Eng.* 22:1-9 (2005).
Overkamp et al., "Functional analysis of structural genes for NAD+-dependent formate dehydrogenase in *Saccharomyces cerevisiae*,"*Yeast* 19:509-520 (2002).
Overkamp et al., "In vivo analysis of the mechanism for oxidation of cytosolic NADH by *Saccharomyces cerevisiae mitochondria*," J. Bacterial. 182:2823-2830 (2000).
Padovani and Banerjee, "Assembly and protection of the radical enzyme, methylmalonyl-CoA mutase, by its chaperone."*Biochem* 45(30):9300-9306 (2006).
Paik and Kim, "Enzymic syntehsis of e-N-Acetyl-L-Lysine,"*Arch. Biochem. Biophys.* 108:221-229 (1964).
Palosaari and Rogers, "Purification and Properties of the Inducible Coenzyme A-Linked Butyraldehyde Dehydrogenase from *Clostridium acetobutylicum*,"*J. Bacteriol.* 17Q(7):2971-2976 (1988).
Parales and Harwood, "Characterization of the Genes Encoding -Ketoadipate: Succinyl-Coenzyme A Transferase in *Pseudomonas putida*,"*J. Bacteriol.* 174(14):4657-4666 (1992).
Park and Lee, "Biosynthesis of poly(3-hydroxybutyrate- co-3-hydroxyalkanoates) by metabolically engineered *Escherichia coli* strains,"*Appl. Biochem. Biotechnol.* 113-116:335-346 (2004).
Park and Lee, "Identification and characterization of a new enoyl Coenzyme A hydratase involved in biosynthesis of medium-chain-length polyhydroxyalkanoates in recombinant *Escherichia coli*,"*J. Bacteriol.* 185(18):5391-5397 (2003).
Park and Lee, "New FadB homologous enzymes and their use in enhanced biosynthesis of medium-chain-length polyhydroxyalkanoates in FadB mutant *Escherichia coli*,"*Biotechnol. Bioeng.* 86(6):681-686 (2004).
Park et al., "Metabolic engineering of *Escherichia coli* for the production of L-valine based on transcriptome analysis and in silico gene knockout simulation,"*Proc. Natl. Acad. Sci. U.S.A.* 104(19):7797-7802 (2007).
Park et al., "Regulation of succinate dehydrogenase (sdhCDAB) operon expression in *Escherichia coli* in response to carbon supply and anaerobiosis: role of ArcA and Fnr"*Mol. Microbiol.* 15(3):473-482 (1995).
Park et al., "Utilization of Electrically Reduced Neutral Red by *Actinobacillus succinogenes*: Physiological Function of Neutral Red in Membrane-Driven Fumarate Reduction and Enerav Conservation,"*J. Bacteriol* 181(8):2403-2410 (1999).
Parkin et al., "Rapid and efficient electrocatalytic $CO_2/CO$ interconversions by *Carboxydothermus hydrogenoformans* CO dehydrogenase I on an electrode,"*J. Am.Chem. Soc.* 129(34):10328-10329 (2007).
Parsot et al., "Nucleotide sequence of *Escherichia coli* argB and argC genes: comparison of N-acetylglutamate kinase and N-acetylglutamate-y-semialdehyde dehydrogenase with homologous and analogous enzymes,"*Gene* 68:275-283 (1988).
Patel and Clark, "Acetoacetate metabolism in rat brain. Development of acetoacetyl-Coenzyme A deacylase and 3-hydroxy-3-methylglutaryl-Coenzyme a synthase,"*Biochem. J.* 176(3):951-958 (1978).
Patel et al., "(3-ketoadipate enol-lactone hydrolases I and II from *Acinetobacter calcoaceticus*,"*J. Biol. Chem.* 250:6567-6577 (1975).
Patil et al., "Use of genome-scale microbial models for metabolic engineering,"*Curr. Opin. Biotechnol.* 15(1):64-69 (2004).
Patnaik et al., "Genome shuffling of *Lactobacillus* for improved acid tolerance,"*Nat.Biotechnol.* 20:707-712 (2002).
Pauli and Overath, "ato Operon: a Highly Inducible System for Acetoacetate and Butyrate Degradation in *Escherichia coli*"*Eur. J. Biochem.* 29:553-562 (1972).
Pauwels et al., "The N-acetylglutamate synthase/N-acetylgltamate kinase metabolon of *Saccharomyces cerevisiae* allows co-ordinated feedback regulation of the first two steps in arginine biosynthesis,"*Eur. J. Biochem.* 270:1014-1024 (2003).

Paxton et al., "Role of branched-chain 2-oxo acid dehydrogenase and pyruvate dehydrogenase in 2-oxobutyrate metabolism,"*Biochem. J.* 234:295-303 (1986).
Peisach et al., "Crystallographic study of steps along the reaction pathway of D-amino acid aminotransferase,"*Biochemistry* 37(14)4958-4967 (1998).
Pelletier and Harwood, "2-Ketocyclohexanecarboxyl Coenzyme A Hydrolase, the Ring cleavage Enzyme Required for Anaerobic Benzoate Degradation of *Rhodopseudomonas palustris*,"*J. Bacteriol.* 180(9):2330-2336 (1998).
Peoples and Sinskey, "Fine structural analysis of the Zoogloea ramigera phbA-phbB locus encoding β-ketothiolase and acetoacetyl-CoA reductase: nucleotide sequence of phbB,"*Mol. Microbiol.* 3:349-357 (1989).
Pereira et al., "Active site mutants of *Escherichia coli* citrate synthase. Effects of mutations on catalytic and allosteric properties,"*J. Biol. Chem.* 269:412-417 (1994).
Peretz and Burstein, "Amino acid sequence of alcohol dehydrogenase from the thermophilic bacterium *Thermoanaerobium brockii*,"*Biochemistry* 28(16):6549-6555 (1989).
Peretz et al., "Molecular cloning, nucleotide sequencing, and expression of genes encoding alcohol dehydrogenases from the thermophile *Thermoanaerobacter brockii* and the mesophile *Clostridium beiierinckii*,"*Anaerobe.* 3:259-270 (1997).
Perez et al., "*Escherichia coli* YqhD exhibits aldehyde reductase activity and protects from the harmful effect of lipid peroxidation-derived aldehydes,"*J. Biol. Chem.* 283(12):7346-7353 (2008).
Perez-Prior et al., "Reactivity of lactones and GHB formation,"*J. Orq. Chem.* 70:420-426 (2005).
Petersen and Bennett, "Purification of acetoacetate decarboxylase from clostridium acetobutylicum ATCC 824 and cloning of the acetoacetate decarboxylase gene in *Escherichia coli*,"*Appl. Environ. Microbiol.* 56:3491-3498 (1990).
Petitdemange et al., "Regulation of the NADH and NADPH-ferredoxin oxidoreductases in *clostridia* of the butyric group,"*Biochim. Biophys. Acta* 421(2):334-347 (1976).
Pfanner and Geissler, "Versatility of the mitochondrial protein import machinery,"*Nat. Rev. Mol. Cell. Biol.* 2(5):339-349 (2001).
Pfluger et al., "Lysine-2, 3-Aminomutase and β-Lysine Acetyltransferase Genes of Methanogenic Archaea Are Salt Induced and Are Essential for the Biosynthesis of Nε-Acetyl-β-Lysine and Growth at High Salinity,"*Appl. Environ. Microbiol.* 69(10):6047-6055 (2003).
Phalip et al., "Purification and properties of the a-acetolactate decarboxylase from *lactococcus lactis* subsp. Lactis NCDO 2118,"*FEBS Lett.* 351(1):95-99 (1994).
Pharkya et al., "OptiStrain: A computational Framework for redesign of microbial production systems,"*Genome Res.* 14(11):2367-2376 (2004).
Pharkya et al., "Exploring the overproduction of amino acids using the bilevel optimization framework OptKnock,"*Biotechnol. Bioeng.* 84(7):887-899 (2003).
Phillips et al., "High Copy Number Plasmids Compatible with Commonly Used Cloning Vectors,"*Biotechniques* 28:400, 402, 404, 406, 408 (2000).
Pierce et al., "The Complete Genome Sequence of *Moorella thermoacetia* (f. *Clostridum thermoaceticum*),"*Environ. Microbiol.* 10(10):2550-2573 (2008).
Pieulle et al., "Isolation and analysis of the gene encoding the pyruvate-ferredoxin oxidoreductase of *Desulfovibrio africanus*, production of the recombinant enzyme in *Escherichia coli*, and effect of carboxy-terminal deletions on its stability,"*J. Bacteriol.* 179(18):5684-5692 (1997).
Pine et al., "Titanium-Mediated Methylene-Transfer Reactions. Direct Conversion of Esters into Vinyl Ethers,"*J. Am. Chem. Soc.* 102:3270-3272 (1980).
Ploux et al., "Investigation of the first step of biotin biosynthesis in *Bacillus sphericus*,"*Biochem. J.* 287:685-690 (1992).
Ploux et al., "The NADPH-linked acetoacetyl-CoA reductase from *Zoogloea ramigera*, Characterization and mechanistic studies of the cloned enzyme over-produced in *Escherichia coli*,"*Eur. J. Biochem.* 174:177-182 (1988).

(56) References Cited

OTHER PUBLICATIONS

Pohl et al., "Remarkably broad Sutstrate Tolerance of Malonyl-CoA Synthetase, an Enzyme Capable of Intracellular Synthesis of Polyketide Precursors,"*J. Am. Chem. Soc.* 123:5822-5823 (2001).
Pohlmann et al., "Genome sequence of the bioplastic-producing "Knallgas" bacterium *Ralstonia eutropha* H16,"*Nat. Biotechnol.* 24(10):1257-1262 (2006).
Pollard et al., "Purification, characterisation and reaction mechanisms of monofunctional 2-hydroxypentadienoic acid hydratase from *Escherichia coli*,"*Eur. J.Biochem.* FEBS 251:98-106 (1998).
Pollard et al., "Substrate Selectivity and biochemical Properties of 4-Hydroxy-2-Keto-Pentanoic Acid Aldolase from *Escherichia coli*,"*Appl. Environ. Microbiol.* 64(10):4093-4094 (1998).
Polovnikova et al., "Structural and kinetic analysis of catalysis by a thiamine diphosphate-deptendent enzyme, benzoylformate decarboxylase,"*Biochemistry* 42:1820-1830 (2003).
Ponce, E., et al., "Cloning of the two pyruvate kinase isoenzyme structural genes from *Escherichia coli*: the relative roles of these enzymes in pyruvate biosynthesis,"*J. Bacteriol.* 177(19):5719-5722 (1995).
Postma et al., "Phosphoenolpyruvate Carbohydrate Phosphotransferase Systems of Bacteria,"*Microbiol Rev.* 57(3):543-594 (1993).
Poston, "Assay of leucine 2, 3-aminomutase,"*Methods Enzymol.* 166:130-135 (1988).
Pawlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600,"*J. Bacteriol.* 175(2):377-385 (1993).
Price et al., "Genome-scale microbial in silica models: the constraints-based approach,"*Trends Biotechnol.* 21(4):162-169 (2003).
Price et al., "Genome-scale models of microbial cells: evaluating the consequences of constraints,"*Nat. Rev. Microbiol.* 2(11):886-897 (2004).
Prieto et al., "Molecular Characterization of the 4-Hydroxyphenylacetate Catabolic Pathway of *Escherichia coli* W: Engineering a Mobile Aromatic Degradative Cluster,"*J. Bacteriol.* 178(1):111-120 (1996).
Pritchard et al., "A general model of error-prone PCR,"*J. Theor. Biol.* 234:497-509. (2005).
Pritchett and Metcalf, "Genetic, physiological and biochemical characterization of multiple methanol methyltransferase isozymes in *Methanosarcina acetivorans* C2A,"*Mol. Microbiol.* 56(5):1183-1194 (2005).
Pronk et al., "Pyruvate metabolism in *Saccharomyces cerevisiae*,"*Yeast* 12:1607-1633 (1996).
Pucci et al., "*Staphylococcus haemolyticus* contains two D-glutamic acid biosynthetic activities, a glutamate racemase and a D-amino acid transminase,"*J. Bacteriol.* 177(2):336-342 (1995).
Purnell et al., "Modulation of higher-plant NAD(H)-dependent glutamate dehydrogenase activity in transgenic tobacco via alteration of β subunit levels," Planta 222:167-180 (2005).
Qi et al., "Functional expression of prokaryotic and eukaryotic genes in *Escherichia coli* for conversion of glucose to p-hydroxystyrene,"*Metab. Eng.* 9:268-276 (2007).
Qian et al., "Metabolic engineering of *Escherichia coli* for the production of putrescine: a four carbon diamine,"*Biotechnol. Bioeng.* 104(4)651-662 (2009).
Qiu et al., "Metabolic engineering of *Aeromonas hydrophila* for the enhanced production of poly(3-hydroxybutyrate-co-3-hydroxyhexanoate),"*Appl. Microbiol. Biotechnol.* 69(5):537-542 (2006).
Qu et al., "Inhibition of human ornthine decarboxylase activity by enantiomers of difluoromethylornithine,"*Biochem. J.* 375:465-470 (2003).
Quail and Guest, "Purification, characterization and mode of action of pdhR, the transcriptional repressor of the PdhR-aceEF-Ipd operon of *Escherichia coli*,"*Mol.Microbiol.* 15(3):519-529 (1995).

Rado and Hoch, "Phosphotransacetylase from *Bacillus subtilis*: purification and physioloQical studies,"*Biochim. Biophys. Acta* 321 :114-125 (1973).
Ragsdale et al., "Acetogenesis and the Wood-Ljungdahl pathway of $CO_2$ fixation,"*Biochimica. Biophysica. Acta* 1784(12):1873-1898 (2008).
Ragsdale, "Enzymology of the wood-$_L$-jungdahl pathway of acetogenesis,"*Ann. NY Acad Sci.* 1125:129-136 (2008).
Ragsdale, "Life with carbon monoxide,"*Crit. Rev. Biochem. Mol. Biol.* 39(3):165-195 (2004).
Ragsdale, "Pyruvate ferredoxin oxidoreductase and its radical intermediate,"*Chem.Rev.* 103(6):2333-2346 (2003).
Rajpal et al., "A general method for greatly improving the affinity of antibodies by using combinatorial libraries,"*Proc. Natl. Acad. Sci. U.S.A.* 102:8466-8471 (2005).
Ramjee et al., "*Escherichia coli* L-aspartate-a-decarboxylase: preprotein processing and observation of reaction intermediates by electrospray mass spectrometry,"*Biochem. J.* 323(Pt 3):661-669 (1997).
Ramon-Maiques et al., "Structure of Acetylglutamate Kinase, a Key Enzyme for Arginine Biosynthesis and Prototype for the Amino Acid Kinase Enzyme Family, during Catalysis,"*Structure* 10:329-342 (2002).
Ramos et al., "Mutations affecting the enzymes involved in the utilization of 4-aminobutyric acid as nitrogen source by the yeast *Saccharomyces cerevisiae*,"*Eur.J.Biochem.* 149:401-404 (1985).
Rangarajan et al., "Structure of [NiFe] hydrogenase maturation protein HypE from *Escherichia coli* and its interaction with HypF,"*J. Bacteriol.* 190(4):1447-1458 (2008).
Rasmussen, L.J., et al. "Carbon Metabolism Regulates Expression of the pf/(Pyruvate-Formate-Lyase) Gene in *Escherichia coli*,"*J. Bacteriol.* 173(20):6390-6397 (1991).
Rathinasabapathi, "Propionate, a source of β-alanine, is an inhibitor of 13-alanine methylation in *Limonium latifoilium Plunbaginaces*,"*J. Plant Physiol.* 159:671-674 (2002).
Ratnatilleke et al., "Cloning and sequencing of the Coenzyme $B_{12}$-binding domain of isobutyryl-CoA mutase from *Streptomyces cinnamonensis*, reconstitution of mutase activity, and characterization of the recombinant enzyme produced in *Escherichia coli*,"*J. Biol. Chem.* 274(44):31679-31685 (1999).
Raux et al., "The role of *Saccharomyces cerevisiae* Met1p and Met8p in sirohaem and cobalamin biosynthesis,"*Biochem. J.* 338 (pt. 3):701-708 (1999).
Raux et al., "*Salmonella typhimurium* cobalamin (vitamin $B_{12}$ biosynthetic genes: functional studies in S. *typhimurium* and *Escherichia coli*,"*J. Bacteriol.* 178(3):753-767 (1996).
Ravagnani et al., "SpoOA directly controls the switch from acid to solvent production in solvent-forming clostridia,"*Mol. Microbiol.* 37(5):1172-1185 (2000).
Raybuck et al., "Kinetic characterization of the carbon monoxide-acetyl-CoA (carbonyl group) exchange activity of the acetyl-CoA synthesizing CO dehydrogenase from *Clostridium thermoaceticum*,"*Biochemistry* 27(20):7698-7702 (1988).
Raynaud et al., "Molecular characterization of the 1, 3-propanediol (1, 3-PD) operon of *clostridium butyricum*,"*Proc. Natl. Acad. Sci. U.S.A.* 100:5010-5015.
Rea et al., "Structure and Mechanism of HpcH: A Metal Ion Dependent Class II Aldolase from the Homoprotocatechuate Degradation Pathway of *Escherichia coli*,"*J. Mol. Biol.* 373:866-876 (2007).
Recasens et al., "Cystein Sulfinate Aminotransferase and Aspartate Aminotransferase Isoenzymes of Rat Brain. Purification, Characterization, and Further Evidence of Identity,"*Biochemistry* 19:4583-4589 (1980).
Reda et al., "Reversible interconversion of carbon dioxide and formate by an electroactive enzyme,"*Proc. Natl. Acad. Sci. U.S.A.* 105:10654-10658 (2008).
Reetz and Carballeira, "Iterative saturation mutagenesis (ISM) for rapid directed evolution of functional enzymes,"*Nat. Protoc.* 2:891-903 (2007).
Reetz et al., "Creation of Enantioselective Biocatalysts for Organic Chemistry by in Vitro Evolution,"*Angew. Chem. Int. Ed. Engl.* 36:2830-2832 (1997).

(56) References Cited

OTHER PUBLICATIONS

Reetz et al., "Directed Evolution of an Enantioselective Enzyme through Combinatorial Multiple-Cassette Mutagenesis,"*Angew. Chem. Int. Ed. Engl.* 40:3589-3591 (2001).
Reetz et al., "Expanding the Range of Substrate Acceptance Enzymes: Cominatorial Active-Site Saturation Test,"*Angew. Chem. Int. Ed.* 117:4264-4268 (2005).
Reetz et al., "Iterative saturation mutagenesis on the basis of B factors as a strategy for incresing protein thermostability,"*Angew. Chem. Int. Ed.* 45:7745-7751 (2006).
Regev-Rudzki et al., "Yeast Aconitase in Two Locations and Two Metabolic Pathways: Seeing Small Amounts is Believing,"*Mol. Biol. Cell* 16:4163-4171 (2005).
Reidhaar-Olson and Sauer, "Combinatorial cassette mutagenesis as a probe of the informational content of protein sequences,"*Science* 241:53-57 (1988).
Reidhaar-Olson et al., "Random mutagenesis of protein sequences using oligonucleotide cassettes,"*Methods Enzymmol.* 208:564-586 (1991).
Reiser and Somerville, "Isolation of mutants of Acinetobacter calcoaceticus deficient in wax ester synthesis and complementation of one mutation with a gene encoding a fatty acyl Coenzyme A reductase,"*J. Bacteriol.* 179(9):2969-2975 (1997).
Reitzer et al., "Crystallization and preliminary X-ray analysis of recombinant glutamate mutase and of the isolated component S from *Clostridium cochlearium*,"*Acta. Crystallogr. D. Biol. Crystalloagr.* 54(Pt 5):1039-1042 (1998).
Repetto and Tzagoloff, "Structure and Regulation of KGD1, the Structural Gene for Yeast a-Ketoglutarate Dehydrogenase,"*Mol. Cell. Biol.* 9(6):2695-2705 (1989).
Reshetnikov, et al., "Characterization of the ectoine biosynthesis genes of haloalkalotolerant obligate methanotroph '*Methylomicrobium alcaliphilum* 20Z',"*Arch. Microbiol.* 184:286-297 (2006).
Resnekov et al., "Organization and regulation of the *Bacillus subtilis* odhAB operon, which encodes two of the subenzymes of the 2-oxoglutarate dehydrogenase complex,"*Mol. Gen. Genet.* 234:285-296 (1992).
Rhodes et al., "Production of fumaric acid by *Rhizopus arrhuzus*,"*Appl. Microbiol.* 7:74-80 (1959).
Rhodes et al., "Production of Fumaric Acid in 20-Liter Fermentors,"*Appl. Microbiol.* 10(1)9-15 (1962).
Rigden et al., "A cofactor-dependent phosphoglycerate mutase homolog from *Bacillus stearothermophilus* is actually a broad specificity phosphatase,"*Protein Sci.* 10:1835-1846 (2001).
Ringer et al., "Monoterpene double-bond reductases of the (−)-menthol biosynthetic pathway: isolation and characterization of cDNAs encoding (−)-isopiperitenone reductase and (+)-pulegone reductase of peppermint,"*Arch. Biochem. Biophys.* 418(1):80-92 (2003).
Ringquist et al., "Translation initiation in *Escherichia coli*: sequences within the ribosome-binding site,"*Mol. Microbiol.* 6(9):1219-1229 (1992).
Riondet et al., "Measurement of the intracellular pH in *Escherichia coli* with the internally conjugated fluorescent probe 5- (and 6-)carboxyfluorescei n. succinimidyl ester."*Biotechnol. Tech.* 11:735-738 (1997).
Rioux et al., "Two outer membrane transport systems for vitamin B12 in *Salmonella typhimurium*,"*J. Bacteriol.* 171:2986-2993 (1989).
Rioux et al.,"Vitamin $B_{12}$ transport in *Escherichia coli* K12 does not require the btuE gene of the btuCED operon,"*Mol. Gen. Genet.* 217:301-308 (1989).
Riviere et al., "Acetyl:succinate CoA-transferase in procyclic *Trypanosoma brucei*. Gene identification and role in carbohydrate metabolism."*J. Biol. Chem.* 279:45337-45346 (2004).
Roa Engel et al., "Fumaric acid production by fermentation,"*Appl. Microbiol. Biotechnol.* 78(3):379-389 (2008).

Roberts et al, "The Role of Enoyl-CoA Hydratase in the Metabolism of Isoleucine by *Pseudomonas putida*,"*Arch Microbiol* 117:99-108 (1978).
Roberts et al., "Acetyl-Coenzyme A synthesis from methyltetrahydrofolate, CO, and Coenzyme A by enzymes purified from *Clostridium thermoaceticum*: attainment of in vivo rates and identification of rate-limiting steps,"*J. Bacteriol.* 174(14):4667-4676 (1992).
Roberts et al., "Cloning and expression of the gene cluster encoding key proteins involved in acetyl-CoA synthesis in *Clostridium thermoaceticum*: CO dehydrogenase, the corrinoid/Fe-S protein, and methyltransferase,"*Proc. Natl. Acad. Sci. U.S.A.* 86(1):32-36 (1989).
Robinson et al., "Studies on Rat Brain Acyl-Coenzyme A Hydrolase (Short Chain),"*Biochem Biophys. Res. Commun.* 71.(4):959-965 (1976).
Roca et al., "Metabolic engineering of ammonium assimilation in xylose-fermenting *Saccharomyces cerevisiae* improves ethanol production,"*Appl. Environ. Microbiol.* 69:4732-4736 (2003).
Rodriguez et al., "Characterization of the ρ-Coumaric Acid Decarboxylase from *Lactobacillus plantarium* CECT 748,"*J. Aeric. Food Chem.* 56:3068-3072 (2008).
Roffia et al., "Byproduct Identification in the Terepthalic Acid Production Process and Possible Mechanisms of their Formation,"*Ind. Eng. Chem. Prod. Res. Dev.* 23:629-634 (1984).
Rohdich et al., "Enoate reductases of *Clostridia*. Cloning, sequencing, and expression,"*J. Biol. Chem.* 276(8):5779-5787 (2001).
Rohwerder et al., "The alkyl tert-butyl ether intermediate 2-hydroxyisobutyrate is degraded via a novel cobalamin-dependent mutase pathway,"*Appl. Environ. Microbiol.* 72(6):4128-4135 (2006).
Romero et al., "Partial purification and characterization and nitrogen regulation of the lysine ε-aminotransferase of Streptomyces clavuligers,"*J. Ind. Microbiol. Biotechnol.* 18:241-246 (1997).
Roper et al., "Sequence of the hpcC and hpcG genes of the meta-fission homoprotocatechuic acid pathway of *Escherichia coli* C: nearly 40% amino-acid identity with the analogues enzymes of the catechol pathway,"*Gene* 156:47-51 (1995).
Rose and Weaver, "The role of the allosteric B site in the fumarase reaction,"*Proc. Natl. Acad. Sci. U.S.A.* 101(10):3393-3397 (2004).
Rose et al., "Enzymatic phosphorylation of acetate,"*J. Biol. Chem.* 211(2):737-756 (1954).
Rosenberg, "A Comparison of Lipid Patterns in Photosynthesizing and Nonphotosynthesizing Cells of *Euglena Gracilis*," Biochem. 2:1148-1154 (1963).
Roszak et al., "The Structure and Mechanism of the Type II Dehydroquinase from Streptomyces coelicolor,"*Structure* 10493-503 (2002).
Roth et al., "Characterization of the cobalamin (vitamin Bd biosynthetic genes of *Salmonella typhimurium*,"*J. Bacteriol.* 175:3303-3316 (1993).
Rother and Metcalf, "Anaerobic growth of *Methanosarcina acetivorans* C2A on carbon monoxide: an unusual way of life for a methanogenic archaeon,"*Proc. Natl. Acad. Sci. U.S.A.* 101(48):16929-16934 (2004).
Rother et al., "Genetic and proteomic analyses of CO utilization by *Methanosarcina acetivorans*,"*Arch. Microbiol.* 188(5):463-472 (2007).
Rous, "On the occurrence of enzymes of ketone-body metabolism in human adipose tissue,"*Biochem. Biophys. Res. Commun.* 69(1):74-78 (1976).
Roux and Walsh, "p-aminobenzoate synthesis in *Escherichia coil*: kinetic and mechanistic characterization of the amidotransferase PabA,"*Biochemistry* 31:6904-6910 (1992).
Roux and Walsh, "p-Aminobenzoate synthesis in *Escherichia coli*: mutational analysis of three conserved amino acid residues of the amidotransferase PabA,"*Biochemistry* 32:3763-3768 (1993).
Roy and Dawes, "Cloning and Characterization of the gene Encoding Lipoamide Dehydrogenase in *Saccharomyces cerevisiae*,"*J. Gen. Microbiol.* 133:925-933 (1987).
Roymoulik et al., "Rearrangement of L-2-hydroxyglutarate to L-threo-3-methylmalate catalyzed by adenosylcobalamin-dependent glutamate mutase,"*Biochem.* 39(33):10340-10346 (2000).

(56) References Cited

OTHER PUBLICATIONS

Rozell and Benner, "Stereochemical Imperative in Enzymic Decarboxylations. Stereochemical Course of Decarboxylation Catalyzed by Acetoacetate Decarboxylase,"*J. Am. Chem. Soc.* 106:4937-4941 (1984).
Rudman and Meister, "Transamination in *Escherichia coli*,"*J. Biol. Chem.* 200(2):591-604 (1953).
Ruldeekulthamrong et al., "Molecular characterization of lysine 6-dehydrogenase from Achromobacter denitrificans,"*BMB Reports* 790-795 (2008).
Sabo et al., "Purification and physical properties of inducible *Escherichia coli* lysine decarboxylase,"*Biochemistry* 13:622-670 (1974).
Sadowski, "The Flp recombinase of the 2-μm plasmid of *Saccharomyces cerevisiae*,"*Prog. Nucleic Acid Res. Mol. Biol.* 51:53-91 (1995).
Saegesser et al., "Stability of broad host range cloning vectors in the phototrophic bacterium *Rhodospirillum rubrum*,"*FEMS Microbiol. Lett.* 95:7-11 (1992).
Saito and Doi, "Microbial synthesis and properties of poly(3-hydroxybutyrate-co-4-hydroxybutyrate) in *Comamonas acidovorans* "*Int. J Biol Macromol.* 16:99-104 (1994).
Sakai et al, "Acetate and Ethanol Production from $H_2$ and $CO_2$ by Morrella sp. Using a Repeated Batch Culture,"*J. Biosci. Bioeng.* 99:252-258 (2005).
Sakanyan et al., "A re-examination of the pathway for ornithine biosynthesis in a thermophilic and two mesophilic *Bacillus* species,"*J. Gen. Microbiol.* 138:125-130 (1992).
Sakurada et al., "Acetylpolyamine Amidohydrolase from *Mycoplana ramosa*: Gene Cloning and Characterization of the Metal-Substituted Enzyme,"*J. Bacteriol.* 178(19):5781-5786 (1996).
Salmon et al., "Global gene expression profiling in *Escherichia coli* K12. Effects of oxygen availability and ArcA,"*J. Biol. Chem.* 280(15):15084-15096 (2005).
Saltzgaber-Muller et al., "Nuclear genes coding the yeast mitochondrial adenosine triphosphatase complex. Isolation of ATP2 coding the $F_1$-ATPase β subunit,"*J. Bio. Chem.* 258(19):11465-11470 (1983).
Samanta and Harwood, "Use of *Rhodopseudomonas palustris* genome sequence to identify a single amino acid that contributes to the activity of Coenzyme A ligase with chlorinated substrates,"*Mol. Microbiol.* 55(4):1151-1159 (2005).
Samsonova et al., "Molecular cloning and characterization of *Escherichia coli* K12 ygjG gene,"*BMC Microbiol.* 3:2 (2003)
Samuelov et al., "Whey fermentation by *anaerobiospirillum succiniciproducens* for production of a succinate-based animal feed additive,"*Appl. Environ. Microbiol.* 65(5):2260-2263 (1999).
San et al., "Metabolic Engineering through Cofactor Manipulation and its Effects on Metabolic Flux Redistribution in *Escherichia coli*,"*Metab Eng.* 4(2):182-192 (2002).
Sanchez et al., "Efficient succinic acid production from glucose through overexpression of pyruvate carboxylase in an *Escherichia coli* alcohol dehydrogenase and lactate dehydrogenase mutant,"*Biotechnol. Prog.* 21(2):358-365 (2005).
Sanchez et al., "Novel pathway engineering design of the anaerobic central metabolic pathway in *Escherichia coli* to increase succinate yield and productivity,"*Metab. Eng.* 7(3): 229-239 (2005).
Sanchez et al., "Batch culture characterization and metabolic flux analysis of succinate-producing *Escherichia coli* strains,"*Metab Eng.* 8(3):209-226 (2006).
Sanchez et al., "Effect of different levels of NADH availability on metabolic fluxes of *Escherichia coli* chemostat cultures in defined medium,"*J. Biotechnol.* 117(4):395-405 (2005).
Sankaranarayanan et al., "Preliminary x-ray crystallographic analysis of ornithine acetyltransferase (Rv1653) from *Mycobacterium tuberculosis*,"*Acta. Crystallogr. Sect. F. Struct. Biol. Cryst. Commun.* 65(Pt 2):173-176 (2009).
Sanyal et al., "Biosyntehsis of pimeloyl-CoA, a biotin precursor in *Escherichia coli*, follows a modified fatty acid synthesis pathway: $^{13}$C-labeling studies,"*J. Am. Chem.Soc.* 116:2637-2638 (1994).
Sariaslani, "Development of a Combined biological and Chemical Process for Production of Industrial aromatics from Renewable Resources,"*Annu. Rev.Microbiol.* 61:51-69 (2007).
Sass et al., "Folding of fumarase during mitochondrial import determines its dual targeting in yeast,"*J. Biol. Chem.* 278(46):45109-45116 (2003).
Sato et al., "Poly[(R)-3-hydroxybutyrate] formation in *Escherichia coli* from glucose through an enoyl-CoA hydratase-mediated pathway,"*J. Biosci. Bioeng.* 103(1):38-44 (2007).
Sauer and Thauer, "Methanol:Coenzyme M methyltransferase from *Methanosarcina barkeri*. Identification of the active-site histidine in the corrinoid-harboring subunit MtaC by site-directed mutagenesis,"*Eur. J. Biochem.* 253(3):698-705 (1998).
Sauer et al., "Methanol:Coenzyme M methyltransferase from *Methanosarcina barkeri*. Purification, properties and encoding genes of the corrinoid protein MT1,"*Eur. J. Biochem.* 243(3):670-677 (1997).
Sauer, "Diels-Alder Reactions II: The Reaction Mechanism,"*Angew. Chem. Int. Ed.* 6:16-33 (1967).
Sauvageot et al., "Characterisation of the diol dehydratase pdu operon of *Lactobacillus collinoides*,"*FEMS Microbiol. Lett.* 209:69-74 (2002).
Sawers and Boxer, "Purification and properties of membrane-bound hydrogenase isoenzyme 1 from anaerobically grown *Escherichia coli* K12,"*Eur. J. Biochem.* 156(2):265-275 (1986).
Sawers et al., "Characterization and physiological roles of membrane-bound hydrogenase isoenzymes from *Salmonella typhimurium*,"*J. Bacteriol.* 168(1):398-404 (1986).
Sawers et al., "Differential expression of hydrogenase isoenzymes in *Escherichia coli* K-12: evidence for a third isoenzyme,"*J. Bacteriol.* 164(3):1324-1331 (1985).
Sawers, "The hydrogenases and formate dehydrogenases of *Escherichia coli*,"*Antonie Van Leeuwenhoek* 66(1-3):57-88 (1994).
Saz and Weil, "The mechanism of the formation of a-methyl butyrate from carbohydrate by Ascaris lumbricoides muscle,"*J. Biol. Chem.* 235:914-918 (1960).
Schadt et al., "2-Amino-2-deoxyisochorismate is a key intermediate in *Bacillus subtilis* p-aminobenzoic acid biosynthesis,"*J. Am. Chem. Soc.* 131:3481-3483 (2009).
Scher and Jakoby, "Maleate isomerase,"*J. Biol. Chem.* 244:1878-1882 (1969).
Scherf and Buckel, "Purification and properties of 4-hydroxybutyrate Coenzyme A transferase from *Clostridium aminobutyricum*,"*Appl. Environ. Microbiol.* 57(9):2699-2702 (1991).
Scherf and Buckel, "Purification and properties of an iron-sulfur and FAD-containing 4-hydroxybutyryl-CoA dehadratase/vinylacetyl-CoA $\Delta^3$ $\Delta^2$-isomerase from *Clostridium aminobutricum*,"*Eur. J. Biochem.* 215:421-429 (1993).
Scherf et al, "Succinate-ethanol fermentation in clostridium kluyveri: purification and characterisation of 4-hydroxybutyryl-CoA dehydratase/vinylacetyl-CoA $\Delta^3$ $\Delta^2$-isomerase,"*Arch. Microbial.* 161(3):239-245 (1994).
Schilling et al., "Genome-Scale Metabolic Model of Helicobacter pylori 26695,"*J. Bacteriol.* 184:4582-4593 (2002).
Schilling et al., "Combining Pathway Analysis with Flux Balance Analysis for the Comprehensive Study of Metabolic Systems,"*Biotechnol. Bioeng.* 71(4):286-306 (2000/2001).
Schilling et al., "Theory for the Systematic Definition of Metabolic Pathways and Their Use in Interpreting Metabolic Function from a Pathway-Oriented Perspective,"*J. Theor. Biol.* 203(3):229-248 (2000).
Schilling et al., "Toward Metabolic Phenomics: Analysis of Genomic Data Using Flux Balances,"*Biotechnol. Prog.* 15(3):288-295 (1999).
Schmid et al., "Plasmid-mediated uptake and metabolism of sucrose by *Escherichia coli* K-12,"*J. Bacteriol.* 151(1):68-76 (1982).
Schmitzberger et al., "Structural constraints on protein self-processing in L-aspartate-a-decarboxylase,"*EMBO J.* 22:6193-6204 (2003).

(56) References Cited

OTHER PUBLICATIONS

Schneider and Betz, "Waxmonoester Fermentation in *Euglena-Gracilis* T Factors Favoring the Synthesis of Odd-Numbered Fatty-Acids and Alcohols,"*Planta.* 166:67-73 (1985).
Schneider et al., "The *Escherichia coli* gabDTPC operon: specific y-aminobutyrate catabolism and nonspecific induction,"*J Bacteriol.* 184:6976-6986 (2002).
Schnell et al., "Anaerobic degradation of aniline and dihydroxybenzenes by newly isolated sulfate-reducing bacteria and description of *Desulfobacterium anilini,*"*Arch. Microbiol.* 152:556-563 (1989).
Schousboe et al., "Purification and Characterization of the 4-Aminobutyrate-2-Ketoglurate Transminase from Mouse Brain,"*Biochem.* 2(15):2868-2873 (1973).
Schrock et al., "Preparation and Reactivity of Several Alkylidene Complexes of the Type W(CHR')(N-2, 6-$C_6H_3$-i-$Pr_2$)($OR$)$_2$ and Related Tungstacyclobutane complexes. Controlling Metathesis Activity through the Choice of Alkoxide Ligand,"*J. Am. Chem. Soc.* 110:1423-1435 (1988).
Schulz et al., "Stereospecific production of the herbicide phosphinothricin (glufosinate) by transamination: isolation and characterization of a phosphinothricinspecific transaminase from *Escherichia coli,*" Appl. Environ. Microbial. 56(1):1-6 (1990).
Schurmann and Sprenger, "Fructose-6-phosphate aldolase is a novel class I aldolase from *Escherichia coli* and is related to a novel group of bacterial transaldolases,"*J. Biol. Chem.* 276(14): p. 11055-11061 (2001).
Schwarzer et al., "Nonribosomal peptides: from genes to products," Nat. Prod. Rep. 20:275-287 (2003).
Schweiger and Buckel, "On the dehydration of (R)-lactate in the fermentation of alanine to propionat by *Clostridium propionicum,*"*FEBS Lett.* 171:79-84 (1984).
Schweiger et al., "Purification of 2-hydroxyglutaryl-CoA dehydratase from *Acidaminococcus fermentans*. An iron-sulfur protein,"*Eur. J. Biochem.* 169(2):441-448 (1987).
Scott and Jakoby, "Soluble y-Aminobutyric-Glutamic Transaminase from *Pseudomonas f/uorescens,*"*J. Biol. Chem.* 234:932-936 (1959).
Scott, A.I., "Discovering nature's diverse pathways to vitamin $B_{12}$: a 35-year odyssey,"*J. Org. Chem.* 68:2529-2539 (2003).
Seedorf et al., "The genome of *Clostridium kluyveri*, a strict anaerobe with unique metabolic features,"*Proc. Natl. Acad. Sci. U.S.A.* 105(6):2128-2133 (2008).
Seffernick et al., "Melamine deaminase and Atrazine chlorohydrolase: 98 percent identical but functionally different,"*J. Bacteriol.* 183 (8):2405-2410 (2001).
Segre et al., "Analysis of optimality in natural and perturbed metabolic networks,"*Proc. Natl. Acad. Sci. U.S.A.* 99:15112-15117 (2002).
Seibert et al., "Characterization of a gene cluster encoding the maleylacetate reductase from *Ralstonia eutropha* 335T, and enzyme recruited for growth with 4-fluorobenzoate,"*Microbiology* 150:463-472 (2004).
Seibert et al., "Characterization of the maleylacteate reductase MacA of *Rhodococcus opacus* 1CP and evidence for the presence of an isofunctional enzyme,"*J. Bacteriol.* 180:3503-3508 (1998).
Seibert et al., "Purification and characterization of maleylacetate reductase from *Alcaligenes eutrophys* JMP134(pJP4),"*J. Bacteriol.* 175:6745-6754 (1993).
Selifonova et al., "Rapid evolution of novel traits in microorganisms,"*Appl Environ. Microbiol.* 67:3645-3649 (2001).
Selmer et al., "Propionate CoA-transferase from *Clostridium propionicum*. Cloning of gene identification of glutamate 324 at the active site,"*Eur. J. Biochem.* 269:372-380 (2002).
Seltzer, "Purification and properties of maleylacetone cis-trans isomerase from *Vibrio* 01,"*J. Biol. Chem.* 248:215-222 (1973).
Sen et al., "Developments in directed evolution for improving enzyme functions,"*Appl. Biochem. Biotechnol.* 143:212-223 (2007).

Sennett et al., "Transmembrane transport of cobalamin in prokaryotic and eukaryotic cells,"*Ann. Rev. Biochem.* 50:1053-1086 (1981).
Seravalli et al., "Evidence that NiNi acetyl-CoA synthase is active and that the CuNi enzyme is not,"*Biochemistry* 43(13):3944-3955 (2004).
Seravalli et al., "Mechanism of transfer of the methyl group from (6S)- methyltetrahydrofolate to the corrinoid/iron-sulfur protein catalyzed by the methyltransferase from *clostridium thermoaceticum*: a key step in the Wood-Ljungdahl pathway of acetyl-CoA synthesis,"*Biochemistry* 38(18):5728-5735 (1999).
Seyfried et al., "Cloning, Sequencing, and Overexpression of the Genes Encoding Coenzyme $B_{12}$Dependent Glycerol Dehydratase of *Citrobacter freundii,*"*J. Bacteriol.* 178(19):5793-5796 (1996).
Shafiani et al., "Cloning and characterization of aspartate-β-semialdehyde dehydrogenase from Mycobacterium tuberculosis H37 Rv,"*J. Appl. Microbiol.* 98:832-838 (2005).
Shalel-Levanon et al., "Effect of ArcA and FNR on the expression of genes related to the oxygen regulation and the glycolysis pathway in *Escherichia coli* under microaerobic growth conditions,"*Biotechnol. Bioeng.* 92(2):147-159 (2005).
Shames et al., "Interaction of Aspartate and Aspartate-derived Antimetabolites with the Enzymes of the Threonine Biosynthetic Pathway of *Escherichia coli,*"*J. Biol. Chem.* 258(24):15331-15339 (1984).
Shanley et al., "Cloning and expression of Acinetobacter calcoaceticus catBCDE genes in *Pseudomonas putida* and *Escherichia coli,*"*J. Bacteriol.* 165:557-563 (1986).
Shao et al., "Random-priming *in vitro* recombination: an effective tool for directed evolution,"*Nucleic Acids Res.* 26:681-683 (1998).
Sharma et al., "Menaquinone (Vitamin $K_2$) Biosynthesis: Nucleotide Sequence and Expression of themenB Gene from *Escherichia coli,*"*J. Bacteriol.* 174(15): 5057-5062 (1992).
Sheppard et al., "Purification and Properties of NADH-Dependent 5,10-Methylenetetrahydrofolate Reductase (MetF) from *Escherichia coli,*"*J. Bacteriol.* 181(3):718-725 (1999).
Shi et al., "The Structure of 1-Aspartate Ammonia-Lyase from *Escherichia coli,*"*Biochemistry* 36:9136-9144 (1997).
Shiba et al., "Engineering of the pyruate dehydrogenase bypass in *Saccharomyces cerevisiae* for high-level production of isoprenoids,"*Metab. Eng.* 9:160-168 (2007).
Shibata et al., "Purification, characterization, and immunological properties of fumarase from *Euglena gracilis* var. *bacillaris*,"*J. Bacteriol.* 164(2):762-768 (1985).
Shigeoka and Nakano, "Characterization and molecular properties of 2-oxoglutarate decarboxylase from *Euglena gracilis,*"*Arch. Biochem. Biophys.* 288:22-28 (1991).
Shigeoka and Nakano, "The effect of thiamin on the activation of thiamin pyrophosphate-dependent 2-oxoglutarate decarboxylase in *Euglena gracilis,*"*Biochem. J.* 292 (Pt 2):463-467 (1993).
Shigeoka et al., "Effect of L-glutamate on 2-oxoglutarate decarboxylase in *Euglena gracilis,*"*Biochem. J.* 282 ( Pt 2):319-323 (1992).
Shimaoka et al, "Effects of edd and pgi Disruptions on Inosine Accumulation in *Escherichia coli,*"*Biosci. Boitechnol. Biochem.* 69(7):1248-1255 (2005).
Shimada et al., "Asymmetric Transformation of Enones with *Synechococcus* sp. PCC 7943,"*Bulletin of the Chemical Society of Japan* 77(12):2269-2272 (2004).
Shimomura et al., "3-hydroxyisobutyryl-CoA hydrolase,"*Methods Enzymol.* 324:229-240 (2000).
Shimomura et al., "Purification and partial characterization of 3-hydroxyisobutyryl-Coenzyme A hydrolase of rat liver,"*J. Biol. Chem.* 269(19):14248-14253 (1994).
Shimoyama et al., "MmcBC in Pelotomaculum thermopropionicum represents a novel group of prokaryotic fumarases,"*FEMS Microbiol Lett.* 270(2):207-213 (2007).
Shingler et al., "Nucleotide sequence and functional analysis of the complete phenol/3, 4-dimethylphenol catabolic pathway of *Pseudomonas* sp. strain CF600,"*J. Bacteriol.* 174(3):711-724 (1992).

(56) References Cited

OTHER PUBLICATIONS

Shlomi et al., "Regulatory on/off minimization of metabolic flux changes after genetic perturbations," *Proc. Natl. Acad. Sci. U.S.A.* 102:7695-7700 (2005).

Shukla et al., "Production of D(-)-lactate from sucrose and molasses," *Biotechnol. Lett.* 26(9):689-693 (2004).

Shuler and Kargi, Operating Considerations for Bioreactors for Suspension and Immobilized Cultures, in *Bioprocess Engineering: Basic Concepts*, Prentice Hall, Inc., Upper Saddle River, NJ., pp. 245-247 (2007).

Sibilli et al., "Two regions of the bifunctional protein aspartokinase I-homoserine dehydrogenase I are connected by a short hing," *J. Biol. Chem.* 256 (20):10228-10230 (1981).

Sieber et al., "Libraries of hybrid proteins from distantly related sequences," *Nat. Biotechnol.* 19:456-460 (2001).

Siegert et al., "Exchanging the substrate specificities of pyruvate decarboxylase from Zymomonas mobilis and benzoylformate decarboxylase from *Pseudomonas putida*," *Protein. Eng. Des. Sel.* 18:345-357 (2005).

Siew et al., "Localization and characteristics of rat liver mitochondrial aldehyde dehydrogenases," *Arch. Biochem. Biophys.* 176(2):638-649 (1976).

Sikorski and Heiter, "A system of shuttle vectors and yeast host strains designed for efficient manipulation of DNA in *Saccharomyces cerevisiae*," *Genetics* 122(1):19-27 (1989).

Simanshu et al., "Structure and function of enzymes involved in the anaerobic degradation of L-threonine to propionate," *J. Biosci.* 32(6):1195-1206 (2007).

Siminov et al., "Application of Gas Chromatography and Gas Chromatography-Mass Spectrometry to the Detection of y-Hydroxybutyric Acid and Its Precursors in Various Materials," *J. Anal. Chem.* 59:965-971 (2004).

Simon et al., "Chiral Compounds Synthesized by Biocatalytic Reductions," *Angew. Chem. Int. Ed. Engl.* 24:539-553

Sinclair et al., "Purification and characterization of the branched chain a-ketoacid dehydrogenase complex from *Saccharomyces cerevisiae*," *Biochem. Mol. Bio. Int.* 31(5):911-922 (1993).

Sipma et al., "Microbial CO conversions with applications in synthesis gas purification and bio-desulfurization," *Crit. Rev. Biotechnol.* 26:41-65 (2006).

Sivaraman et al., "Codon choice in genes depends on flanking sequence information—implications for theoretical reverse translation," *Nucleic Acids Res.* 36(3):e16 (2008).

Sjostrom et al., "Purification and characterisation of a plasminogen-binding protein from *Haemophilus influenzae*. Sequence determination reveals identity with asoartase," *Biochim. Biophys. Acta* 1324(2):182-190 (1997).

Skarstedt and Silverstein, "*Escherichia coli* acetate kinase mechanism studied by net initial rate, equilibrium, and independent isotopic exchange kinetics," *J. Biol. Chem.* 251:6775-6783 (1976).

Slater et al., "Multiple Bketothiolases mediate poly(β-hydroxyalkanoate) copolymer synthesis in *Ralstonia eutropha*," *J. Bacterial.* 180(8):1979-1987 (1998).

Sloane et al., "Studies on the metabolism of p-aminobenzoic acid by *Mycobacterium smegmatis*," *J Biol. Chem.* 193:453-458 (1951).

Slock et al., "An apparent *Bacillus subtilis* folic acid biosynthetic operon containing pab, an amphibolic *trpG* gene, a third gene required for synthesis of para-aminobenzoic acid, and the dihydropteroate synthase gene," *J. Bacteriol.* 172:7211-7226 (1990).

Smit et al., "Identification, cloning and characterization of *Lactococcus lactis* branched-chain a-keto acid decarboxylase involved in flavor formation," *Appl. Environ. Microbiol.* 71:303-311 (2005).

Smith and Gray, "Catalysis of the oxidation of 1,4-cyclohexadiene to benzene by electroactive binuclear rhodium complexes," *Catalysis Lett.* 6:195-199 (1990).

Smith and Kaplan, "Purification, properties and kinetic mechanism of Coenzyme A-linked aldehyde dehydrogenase from *Clostridium kluyveri*," *Arch. Biochem. Biophys.* 203:663-675 (1980).

Smith et al., "Purification and characteristics of a y-glutamyl kinase involved in *Escherichia coli* praline biosynthesis," *J. Bacteriol.* 157:545-551 (1984).

Smith et al., "Fumarate metabolism and the microaerophily of *Campylobacter* species," *Int. J. Biochem. Cell Biol.* 31(9):961-975 (1999).

Smith et al., "Structural and functional organization of the animal fatty acid synthase," *Prog. Lipid. Res.* 42(4):289-317 (2003).

Sobue et al., "Actin polymerization induced by calspectin, a calmodulin-binding spectrin-like protein," *FEBS Lett* 148(2):221-225 (1982).

Soda and Misono,"L-Lysine:a-ketoglutarate aminotransferase. II. Purification, crystallization, and properties," *J. Bacteriol.* 7:4110-4119 (1968).

Sohling and Gottschalk, "Molecular analysis of the anaerobic succinate degradation pathway in *Clostridium kluyveri*," *J. Bacteriol.* 178:871-880 (1996).

Sohling and Gottschalk, "Purification and characterization of a Coenzyme-A-dependent succinate-semialdehyde dehydrogenase from *Clostridium kluyveri*," *Eur.J. Biochem.* 212:121-127 (1993).

Soini et al., "High cell density media for *Escherichia coli* are generally designed for aerobic cultivations—consequences for large-scale bioprocesses and shake flask cultures," *Microb. Cell. Fact.* 7:26 (2008).

Sokatch et al., "Purification of a Branched-Chain Keto Acid Dehydrogenase from *Pseudomonas putida*," *J. Bacteriol.* 148(2):647-652 (1981).

Somerville, "The Billion-Ton Biofuels Vision," *Science* 312(5778):1277 (2006).

Sone et al., "Nucleotide sequence and expression of the Enterobacter aerogenes a-acetolactate decarboxylase gene in brewers yeast," *Appl. Environ. Microbiol.* 54:38-42 (1988).

Song et al, "Effects of dissolved $CO_2$ levels on the growth of *Mannheimia succinicproducens* and succinic acid production," *Biotechnol. Bioeng.* 98(6):1296-1304 (2007).

Song et al., "Construction of recombinant *Escherichia coli* strains producing poly (4hydroxybutyric acid) homopolyester from glucose," *Wei Shen Wu Xue. Bao.* 45:382-386 (2005).

Song et al., "Ultrasound-mediated DNA transfer for bacteria," *Nucl. Acids Res.* 35:e129 (2007).

Song et al., "Recovery of succinic acid produced by fermentation of a metabolically engineered *Mannheimia succiniciproducens* strain," *J. Biotechnol.* 132:445-452 (2007).

Song et al., "Structure, function, and mechanism of the phenylacetate pathway hot dog-fold thioesterase Paal," *J. Biol. Chem.* 281(16):11028-11038 (2006).

Soucaille et al., "Butanol tolerance and autobacteriocin production by *Clostridium acetobutylicum*," *Curr. Microbiol.* 14:295-299 (1987).

Sovik, "Mitochondrial 2-methylacetoacetyl-CoA thiolase deficiency: an inborn error of isoleucine and ketone body metabolism," *J. Inherit. Metab. Dis.* 16:46-54 (1993).

Sramek and Frerman, "Purification and properties of *Escherichia coli* Coenzyme A-transferase," *Arch. Biochem. Biopyhs.* 171(1):14-26 (1975).

St. Maurice et al., "Flavodoxin:quinone reductase (FqrB): a redox partner of pyruvate:ferredoxi oxidoreductase that reversibly couples pyruvate oxidation to NADPH production in Helicobacter pylori and Campylobacter jejuni," *J. Bacteriol.* 189:4764-4773 (2007).

Stadtman, "The enzyme synthesis of β-alanyl Coenzyme A," *J. Plant Chem. Soc.* 77:5765-5766 (1955).

Stanley et al., "Expression and stereochemical and isotope effect studies of active 4-oxalocrotonate decarboxylase," *Biochemistry* 39:718-726 (2000).

Starai et al., "Acetate excretion during growth of *salmonella enerica* on ethanolamine requires phosphotransacetylase (EutD) activity, and acetate recapture requires acetyl-CoA synthetase (Acs) and phosphotransacetylase (Pta) activities," *Microbiology* 151:3793-3801 {2005).

Starai et al., "Residue Leu-641 of Acetyl-CoA synthetase is critical for the acetylation of residue Lys-609 by the Protein acetyltransferase enzyme of *Salmonella enterica*," *J. Biol. Chem.* 280(28):26200-26205 (2005).

(56) References Cited

OTHER PUBLICATIONS

Starnes et al., "Threonine-sensitive aspartokinase-homoserine dehydrogenase complex, amino acid composition, molecular weight, and subunit composition of the complex,"*Biochemistry* 11:677-687 (1973).
Steen et al., "Metabolic engineering of *Saccharomyces cerevisiae* for the production of n-butanol,"*Microb. Cell Fact.* 7:36 (provided electronically by publisher as pp. 1-8) (2008).
Steffan and McAlister-Henn, "Isolation and characterization of the yeast gene encoding the MDH3 isozyme of malate dehydrogenase,"*J. Biol. Chem.* 267:24708-24715 (1992).
Steinbacher et al., "Enoate reductase family," in Flavins and Flavoproteins, Proceedings of the Fourteenth International Symposium, St. John's College, University of Cambridge, UK, Jul. 14-18, 2002, Chapman et al., pp. 941-949, Rudolf Weber, Agency for Scientific Publications Berlin.
Steinbuchel and Schlegel, "NAD-linked L(+)-lactate dehydrogenase from the strict aerobe *alcaligenes eutrophus*. 2. Kinetic properties and inhibition by oxaloacetate,"*Eur. J. Biochem.* 130(2):329-334 (1983).
Steinbuchel and Schlegel, "A multifunctional fermentative alcohol dehydrogenase from the strict aerobe *Alcaligenes eutrophus*: purification and properties,"*Eur. J. Biochem.* 141:555-564 (1984).
Steiner and Sauer, "Long-term continuous evolution of acetate resistant *Acetobacter aceti*,"*Biotechnol. Bioeng.* 84:40-44 (2003).
Stemmer, "DNA shuffling by random fragmentation and reassembly: in vitro recombination for molecular evolution,"*Proc. Natl. Acad. Sci. U.S.A.* 91:10747-10751 (1994).
Stemmer, "Rapid evolution of a protein in vitro by DNA shuffling,"*Nature* 370:389-391 (1994).
Stim-Herndon et al., "Characterization of an acetyl-CoA C-acetyltransferase (thiolase) gene from *Clostridium acetobutylicum* ATCC 824,"*Gene* 154(1):81-85 (1995).
Stirling and Perry, "Purification and Properties of a Nicotinamide Adenine Dinucleotide-Linked Cyclohexanol Dehydrogenase from a *cocardia* Species,"*Curr. Microbiol.* 4:37-40 (1980).
Stokell et al., "Probing the roles of key residues in the unique regulatory NADH binding site of type II citrate synthase of *Escherichia coli*,"*J. Biol. Chem.* 278:35435-35443 (2003).
Stols and Donnelly, "Production of succinic acid through overexpression of NAD+-dependent malic enzyme in an *Escherichia coli* mutant,"*Appl. Environ. Microbiol.* 63(7):2695-2701 (1997).
Stols et al., "Expression of Ascaris suum malic enzyme in a mutant *Escherichia coli* allows production of succinic acid from glucose,"*Appl. Biochem. Biotechnol.* 63-65: 153-158 (1997).
Stols et al., "New vectors for co-expression of proteins: Structure of *Bacillus subtilis* ScoAB obtained by High-throughput protocols,"*Protein Expr. Purif.* 53:396-403 (2007).
Stoyan et al., "Cloning, sequencing and overexpression of the leucine dehydrogenase gene from *Bacillus cereus*,"*J. Biotechnol.* 54:77-80 (1997).
Straathof et al., "Feasibility of acrylic acid production by fermentation,"*Microbiol. Biotechnol.* 67:727-734 (2005).
Strauss and Fuchs, "Enzymes of a novel autotrophic $CO_2$ fixation pathway in the phototrophic bacterium *Chloroflexus aurantiacus*, the 3-hydroxypropionate cycle,"*Eur. J. Biochem.* 215:633-643 (1993).
Streit and Entcheva, "Biotin in microbes, the genes involved in its biosynthesis, its biochemical role and perspectives for biotechnological production,"*Appl. Microbiol. Biotechnol.* 61:21-31 (2003).
Stringfellow et al., "Sequence of the *Escherichia coli* C homoprotocatechuic acid degradative operon completed with that of the 2,4-dihydroxyhept-2-ene-1, 7-dioicic acide aldolase-encodinq gene (hpdH),"*Gene* 166:73-76 (1995).
Stryer, *Biochemistry.* 3rd Ed. New York: W.H. Freeman and Company, pp. 374-376 (1988).

Suarez de Mata et al., "Propionyl-CoA condensing enzyme from Ascaris muscle mitochondria. I. Isolation and characterization of multiple forms,"*Arch. Biochem. Biophys.* 285(1):158-165 (1991).
Suarez de Mata et al., "Propionyl-CoA condensing enzyme from Ascaris muscle mitochondria. II. Coenzyme A modulation,"*Arch. Biochem. Biophys.* 285:166-171 (1991).
Suda et al., "Purification and properties of a-ketoadipate reductase, a newly discovered enzyme from human placenta,"*Arch. Biochem. Biophys.* 176(2):610-620 (1976).
Suda et al., "Subcellular localization and tissue distribution of a-ketoadipate reduction and oxidation in the rat,"*Biochem. Biophys. Res. Commun.* 77(2):586-591 (1977).
Suematsu et al., "Molecular cloning and functional expression of rat liver cytosolic acetyl-CoA hydrolase,"*Eur. J. Biochem.* 268(9):2700-2709 (2001).
Sulzenbacher et al., "Crystal structure of *E.coli* alcohol dehydrogenase YqhD: evidence of a covalently modified NADP Coenzyme,"*J. Mol. Biol.* 342(2):489-502 (2004).
Suthers et al., "Metabolic flux elucidation for large-scale models using C labeled isotopes,"*Metab. Eng.* 9:387-405 (2007).
Suzuki et al., "Acetylputrescine deacetylase from *Micrococcus luteus* K-11,"*Biochim. Biophys. Acta* 882:140-142 (1986).
Suzuki et al., "GriC and GriD Constitute a carboxylic acid reductase involved in grixazone biosynthesis in *streptomyces griseus*,"*J. Antibiot.* 60(6):380-387 (2007).
Suzuki et al., "Properties and metabolic role of mesaconate hydratase of an aerobic bacterium,"*J. Biochem.* 81:1917-1925 (1977).
Suzuki, "Phospotransacetylase of *Escherichia coli* B., activation by pyruvate and inhibition by NADH and certain nucleotides,"*Biochem. Biophys. Acta* 191:559-569.
Svensson et al., "Characterization and isolation of enzymes that hydrolyze short-chain acyl-CoA in rat-liver mitochondria,"*Eur. J. Biochem.* 238(2):526-531 (1996).
Svetlitchnyi et al., "A functional Ni—Ni—[4Fe-4S] cluster in the monomeric acetyl-CoA synthase from *Carboxydothermus hydrogenoformans*,"*Proc. Natl. Acad. Sci. U.S.A.* 101(2):446-451 (2004).
Svetlitchnyi et al., "Two membrane-associated NiFeS-carbon monoxide dehydrogenases from the anaerobic carbon-monoxide-utilizing eubacterium *Carboxydothermus hydrogenoformans*,"*J. Bacteriol.* 183(17):51345144 (2001).
Switzer, "Glutamate mutase," in Dolphin,.D. ed., *Vitamin $B_{12}$* (vol. 2: Biochemistry and Medicine), Wiley-Interscience: New York, p. 289-305 (1982).
Tae-Kang et al., "Purification and characterization of a cyclohexanol dehydrogenase from *Rhodococcus* sp. TK6,"*J. Microbiol. Biotechnol.* 12:39-45 (2002).
Tahlan et al., "Two sets of paralogous genes encode the enzymes involved in the early stages of clavulanic acid and clavam metabolite biosynthesis in *Streptomyces clavuliqerus*,"*Antimicrob. Agents Chemother.* 48(3):930-939 (2004).
Takacs et al., "Formate hydrogenlyase in the hyperthermophilic archaeon, *Thermococcus litoralis*,"*BMC Microbiol.* 8:88 (2008).
Takagi et al, "Purification, crystallization, and molecular properties of aspartase from *Pseudomonas fluorescens*,"*J. Biochem.* 96(2):545-552 (1984).
Takagi et al., "Isolation of a versatile Serratia marcescens mutant as a host and molecular cloning of the aspartase gene,"*J. Bacteriol.* 161:1-6 (1985).
Takagi et al., "Cloning and nucleotide sequence of the aspartase gene of Pseudomonas fluorescens,"*J. Biochem.* 100(3):697-705 (1986).
Takahashi and Yamada, "Metabolic pathways for cytoxic and end product formation from glutamate—and aspartate—containing peptides by *Porphyromonas gingivalis*,"*J. Bacteriol.* 182:4704-4710 (2000).
Takahashi-Abbe et al., "Biochemical and functional properties of a pyruvate formate-lyase (PFL)-activating system in *Streptococcus mutans*,"*Oral Microbiol. Immunol.* 18:293-297 (2003).
Takanashi et al., "Characterization of a novel 3-hydroxybutyrate dehydrogenase from *Ralstonia pickettii* T1,"*Antonie van Leeuwnhoek* 95(3):249-262 (2009).

(56) References Cited

OTHER PUBLICATIONS

Takatsuka et al., "Gene cloning and molecular characterization of lysine decarboxylase from *Selenomonas ruminantium* delineate its evolutionary relationship to ornithine decarboxylases from eukaryotes,"*J. Bacteriol.* 182:6732-6741 (2000).
Takatsuka et al., "Identification of the amino acid residues conferring substrate specificity upon *Selenomonas ruminantium* lysine decarboxylase,"*Bioxci. Biotechnol. Biochem.* 63:1843-1846 (1999).
Takeo, "Existence and Properties of Two Malic Enzymes in *Escherichia coli* Especially of NAO-linked Enzyme,"*J. Biochem.* 66:379-387 (1969).
Takigawa et al., "Probabilistic path ranking based on adjacent pairwise coexpression for metabolic transcripts analysis,"*Bioinform.* 24(2):250-257 (2008).
Tallant and Krzycki, "Coenzyme M methylase activity of the 480-kilodalton corrinoid protein from *Methanosarcina barkeri*,"*J. Bacteriol.* 178(5):1295-1301 (1996).
Tallant and Krzycki, "Methylthiol:Coenzyme M Methyltransferase from *Methanosarcina barkeri*, an enzyme of methanogenesis from dimethylsulfide and methvlmercaptoorooionate,"*J. Bacteriol.* 179(22):6902-6911 (1997).
Tallant et al., "The MtsA subunit of the methylthiol:Coenzyme M methyltransferase of *Methanosarcina barkeri* catalyses both half-reactions of corrinoid-dependent dimethylsulfide: Coenzyme M methyl transfer,"*J. Biol. Chem.* 276(6):4485-4493 (2001).
Tamaki et al., "Purification, properties, and sequencing of aminoisobutyrate aminotransferases from rat liver,"*Methods Enzymol.* 324:376-389 (2000).
Tanaka et al., "Cloning and characterization of a human orthologue of testis-specific succinyl CoA: 3-oxo acid CoA transferase (Scot-t) cDNA,"*Mol. Hum. Reprod.* 8:16-23 (2002).
Tanaka et al., "Lysine decarboxylase of *Vibrio parahaemolyticus*: kinetics of transcription and role in acid resistance,"*J. Appl. Microbiol.* 104:1283-1293 (2008).
Tang et al., "Identification of a novel pyridoxal 5'-phosphaste binding site in adenosylcobalamin-dependent lysine 5,6-aminomutase from *Porphyromonas gingivalis*,"*Biochem istry* 41(27):8767-8776 (2002).
Tani et al., "Thermostable NADP+-dependent medium-chain alcohol dehydrogenase from *Acinetobacter* sp. strain M-1: purification and characterization and gene expression in *Escherichia coli*,"*Appl. Environ. Microbiol.* 66(12):5231-5235 (2000).
Tanizawa et al., "The primary structure of thermostable D-amino acid aminotransferase from a *thermophilic Bacillus* species and is correlation with L-amino acid aminotransferases,"*J. Biol. Chem.* 264(5):2450-2454 (1989).
Tanous et al., "Glutamate dehydrogenase activity can be transmitted naturally to *Lactococcus lactis* strains to stimulate amino acid conversion to aroma compounds,"*Appl. Environ. Microbiol.* 72(2):1402-1409 (2006).
Tardif et al., "Electrotransformation studies in *Clostridium cellulolyticum*,"*J. Ind. Microbiol. Biotechnol.* 27(5):271-274 (2001).
Taylor and Fotheringham, "Nucleotide sequence of the *Bacillus licheniformis* ATCC 10716 dat gene and comparison of the predicted amino acid sequence with those of other bacterial species,"*Biochim. Biophys. Acta* 1350(1):38-40 (1997).
Tebbe et al., "Titanium-Catalyzed Olefin Metathesis,"*J. Am. Chem. Soc.* 101(17):5074-5075 (1979).
Teipel et al., "The substrate specificity of fumarase,"*J. Biol. Chem.* 243:5684-5694 (1968).
ter Schure et al., "Pyruvate decarboxylase catalyzes decarboxylation of branched-chain 2-oxo acids but is not essential for fusel alcohol production by *Saccharomyces cerevisiae*,"*Appl. Environ. Microbiol.* 64:1303-1307 (1998).
Teufel et al., "3-hydroxypropionyl-Coenzyme A dehydratase and acryloyl-Coenzyme A reductase, enzymes of the autotrophic 3-hydroxypropionate/4-hydroxybutyrate cycle in the sulfobales,"*J. Bacteriol.* 191:4572-4581 2009).
Thanos and Simon, "Electro-enzymic viologen-mediated stereospecific reduction of 1380. 2-enoates with free and immobilized enoate reductase on cellulose filters or modified carbon electrodes,"*J. Biotechnol.* 6:13-29 (1987).
Thauer, "Microbiology. A Fifth Pathway of Carbon Fixation,"*Science* 318:1732-1733 (2007).
Thomas et al., "Bimetallic nanocatalysts for the conversion of muconic acid to adipic acid."*Chem. Commun.* 21:1126-1127 (2003).
Thornton et al., "Primary structure of the monomer of the 12S subunit of transcarboxylase as deduced from DNA and characterizatio not the product expressed in *Escherichia coli*,"*J. Bacteriol.* 175:5301-5308 (1993).
Thykaer et al., "Metabolic network analysis of an adipoyl-7-ADCA-producing strain of *Penicillium chrysogenum*: elucidation of adipate degradation,"*Metlab. Eng.* 4(2):151-158 (2002).
Tian et al., "Variant tricarboxylic acid cycle in Mycobacterium tuberculosis: identification of a-ketoglutarate decarboxylase,"*Proc. Natl. Acad. Sci. U.S.A.* 102:10670-10675 (2005).
Tischer et al., "Purification and Some Properties of a Hitherto-Unknown Enzyme Reducing the Carbon-Carbon Double Bond of a,β-Unsaturated Carboxylate Anions,"*Eur. J. Biochem.* 97(1):103-112 (1979).
Tobimatsu et al., "Molecular cloning, Sequencing and Characterization of the Genes for Adenosylcobalamin-deptendent Dial Dehydratase of *Klebsiella pneumoniae*,"*Biosci. Biotechnol. Biochem.* 62(9):1744-1777 (1998).
Tobimatsu et al., "Molecular cloning, Sequencing and Expression of the Genes Encoding Adenosylcobalamin-dependent Dial Dehydrase of *Klebsiella oxytoca*,"*J. Biol. Chem.* 270(13):7142-7148 (1995).
Tobin et al., "Localization of Lysine ε-Aminotransferase (lat) and 5-AminoadipyI)-L-Cysteinyl-D-Valine Synthetase (pcbAB) Genes from *Streptomyces clavuligerus* and Production of the Lysine ε-Aminotransferase Activity in *Escherichia coli*,"*J. Bacteriol.* 173(19):6223-6229 (1991).
Tolentino et al., "A pH-regulated promoter for the expression of recombinant proteins in *Escherichia coli*,"*Biotechnol. Lett.* 14:157-162. (1992).
Tomas et al., "Overexpression of groESL in *Clostridium acetobutylicum* Results in Increased Solvent Production and Tolerance, Prolonged Metabolism, and Changes in the Cell's Transcriptional Program,"*Appl. Environ. Microbiol.* 69:4951-4965 (2003).
Toraya et al., "Substrate Specificity of Coenzyme $B_{12}$Dependent Dial Dehydrase: Glycerol as Both a Good Substrate and a Potent Inactivator,"*Biochem. Biophys. Res. Commun.* 69:475-480 (1976).
Toth et al., "The ald Gene, Encoding a Coenzyme A-Acylating Aldehyde Dehydrogenase, Distinguishes *Clostridium beijerinckii* and Two Other Solvent-Producing Clostridia from *Clostridium acetobutylicum*,"*App. Environ. Microbiol.* 65(11):4973-4980 (1999).
Tretter and Adam-Vizi, "Alpha-ketoglutarate dehydrogenase: a target and generator of oxidative stress,"*Philos. Trans. R. Soc. B* 360:2335-2345 (2006).
Trower et al., "Isolation and Characterization of a Cyclohexane-Metabolizing *Xanthobacter* sp.,"*Appl. Environ. Microbiol.* 49(5):1282-1289 (1985).
Truscott et al., "Mechanisms of protein import into mitochondria,"*Curr. Biol.* 13(8):R326-R337 (2003).
Tsao et al., "Production of multifunctional organic acids from renewable resources,"*Adv. Biochem. Eng. Biotechnol.* 65:243-280 (1999).
Tseng et al., "Metabolic Engineering of *Escherichia coli* for Enhanced Production of (R)- and (S)-3-Hydroxybutyrate,"*App. Environ. Microbiol.* 75(10):3137-3145 (2009).
Tseng et al., "Oxygen- and growth rate-dependent regulation of *Escherichia coli* fumarase (FumA, FumB, and BumC) activity,"*J. Bacteriol.* 183(2):461-467 (2001).
Tsujimoto et al., "L-Lysine biosynthetic pathway of *Methylophilus methylotrophus* and construction of an L-Lysine producer,"*J. Biotechnol.* 124:327-337 (2006).
Tucci and Martin, "A novel prokaryotic trans-2-enoyl-CoA reductase from the spirochete Treponema denticola,"*FEBS Lett.* 581(8):1561-1566 (2007).
Tutino et al., "Expression of *Sulfolobus solfataricus* trpE and trpG genes in *E. coli*,"*Biochem. Biophs. Res. Commun.* 230:306-310 (1997).

(56) References Cited

OTHER PUBLICATIONS

Twarog and Wolfe, "Role of butyryl phosphate in the energy metabolism of Clostridium tetanomorphum," J. Bacteriol. 86:112-117 (1963).
Tyurin et al., "Electrotransformation of Clostridum acetobutylicum ATCC 824 using high-voltage radio frequency modulated square pulses," J. Appl. Microbiol. 88(2):220-227 (2000).
Tyurin et al., "Electrotransformation of Clostridium thermocellum," Appl. Environ. Microbiol. 70(2):883-890 (2004).
Tzagoloff and Dieckmann, "PET genes of Saccharomyces cerevisiae," Microbiol. Rev. 54(3):211-225 (1990).
Uchiyama et al., "Identification of the 4-Hydroxycinnamate Decarboxylase (PAD) Gene of Klebsiella oxytoca," Biosci. Biotechnol. Biochem. 72: 116-123 (2008).
Ulaganathan et al., "Structure of Staphylococcus aureus 1,4-dihydroxy-2-naphthoyl-CoA synthase (MenB) in complex with acetoacetyl-CoA," Acta. Crystallodr. Sect. F. Struct. Biol. Cryst. Commun. 63(Pt 11):908-913 (2007).
Umbarger and Brown, "Threonine deamination in Escherichia coli. II. Evidence fro two L -threonine deaminases," J. Bacteriol. 73(1):105-112 (1957).
Underwood et al., "Genetic Changes to Optimize Carbon Partitioning between Ethanol and Biosynthesis in Ethanologenic Escherichia coli," App. Environ. Microbiol. 68(12):6263-6272 (2002).
Urbance et al., "Evaluation of succinic acid continuous and repeat-batch biofilm fermentation by Actinobacillus succinogenes using plastic composite support bioreactors," Appl. Microbiol. Biotechnol. 65(6):664-670 (2004).
Uttaro and Opperdoes, "Purification and characterisation of a novel isopropanol dehydrogenase from Phytomonas sp.," Mol. Biochem. Parasitol. 85:213-219 (1997).
Vadali et al., "Enhanced Isoamyl Acetate Production upon Manipulation of the Acetyl-CoA node in Escherichia coli," Biotech. Prog. 20:692-697 (2004).
Vadali et al., "Production of isoamyl acetate in ackA-pta and/or ldh mutants of E. coli with overexpression of yeast ATF2," Appl. Microbiol. Biotechnol. 63:698-704 (2004).
Vadali et al., "Cofactor engineering of intercellular CoNacetyl-CoA and its effect on metabolic flux redistribution in Escherichia coli," Metab Eng. 6(2): 133-139 (2004).
Valdes-Hevia and Gancedo, "Isolation and characterization of the gene encoding phosphoenolpyruvate carboxykinase from Saccharomyces cerevisiae," FEBS Lett. 258:313-316 (1989).
Valentin et al., "Metabolic pathway for biosynthesis of poly(3-hydroxybutyrate-co-4- hydroxybutyrate) from 4-hydroxybutyrate by Alcaligenes eutrophus," Eur. J.Biochem. 227(1-2):43-60 (1995).
Valentine and Wolfe, "Purification and role of phosphotransbutyrylase," J. Biol.Chem. 235:1948-1952 (1960).
Vamecq et al., "The microsomal dicarboxylyl-CoA synthetase," Biochem. J. 230(3):683-693 (1985).
Van Beilen et al., "Cloning of Baeyer-Villiger monooxygenases from comamonas, Xantherobacter and Rhodococcus using polymerase chain reaction with highly degenerate primers," Environ. Microbiol. 5(3):174-182 (2003).
van der Voorhorst et al., "Genetic and biochemcial characterization of a short-chain alcohol dehydrogenase from the hyperthermophilic archaeon Pyrococcus furiosus," Eur. J. Biochem. 268:3062-3068 (2001).
Van Der Westhuizen, et al., "Autolytic Activity and Butanol tolerance of Clostridium acetobutylicum," Appl. Environ. Microbiol. 44:1277-1281 (1982).
van Grinsven et al., "Acetate:succinate CoA-transferase in the hydrogenosomes of Trichomonas vaginalis: identification and characterization," J. Biol. Chem. 283:1411-1418 (2008).
van Loon and Young, "Intracellular sorting of alcohol dehydregenase isoenzymes in yeast: a cytosolic location oreflects absence of an amino-terminal targeting sequence for the mitochondrion," EMBO J. 5:161-165 (1986).

van Maris et al., "Directed evolution of pyruvate decarboxylase-negative Saccharomyces cerevisiae, yielding a $C_2$ -independent, glucose-tolerant, and pyruvate-hyperproducing yeast," Appl. Environ. Microbiol. 7:159-166 (2004).
Van Mullem et al., "Construction of a set of Saccharomyces cerevisiae vectors designed for recombinational cloning," Yeast 20(8):739-746 (2003).
Vanderwinkel et al., "Growth of Escherichia coli on fatty acids: requirement for Coenzyme A transferase activity," Biochem. Biophys. Res. Commun. 33(6):902-908 (1968).
Vanrolleghem et al., "Validation of a Metabolic Network for Saccharomyces cerevisiae Using Mixed Substrate Studies," Biotechnol. Prog. 12(4):434-448 (1996).
Varadarajan and Miller, "Catalytic Upgrading of Fermentation-Derived Organic Acids," Biotechnol. Prog. 15:845-854 (1999).
Vardar-Schara et al., "Metabolically engineered bacteria for producing hydrogen via fermentation," Microbio. Biotechnol. 1:107-125 (2008).
Varma and Palsson, "Stoichiometric Flux Balance Models Quantitatively Predice Growth and Metabolic By-Product Secretion in Wild-Type Escherichia coli W3110," Appl Env. Microbiol. 60(10):3724-3731 (1994).
Varma and Palsson, "Metabolic Flux Balancing: Basic Concepts, Scientific and Practical Use," Biotechnology 12:994-998 (1994).
Varma et al., "Biochemical Production Capabilities of Escherichia coli," Biotechnol. Bioeng. 42:59-73 (1993).
Varma et al., "Stoichiometric Interpretation of Escherichia coli Glucose Catabolism under Various Oxygenation Rates" Appl. Environ. Microbiol. 59:2465-2473 (1993).
Vazquez et al., "Phosphtransbutyrylase expression in Bacillus megaterium," Curr. Microbiol. 42:345-349 (2001).
Vega et al., "The Biological Production of Ethanol from Synthesis Gas," Appl.. Biochem. Biotechnol. 20/21 :781-797 (1989).
Vellanki et al., "Expression of hepatitis B surface antigen in Saccharomyces cerevisiae utilizing glyceraldehyde-3-phosphate dehydrogenase promoter of Pichia pastoris," Biotechnol. Lett. 29(2):313-318 (2007).
Vemuri et al. "Succinate production in dual-phase Escherichia coli fermentations depends on the time of transition from aerobic to anaerobic conditions," J. Ind. Microbiol. Biotechnol. 28:325-332 (2002).
Vemuri et al., "Effects of growth mode and pyruvate carboxylase on succinic acid production by metabolically engineered strains of Escherichia coli," Appl. Environ. Microbiol. 68(4):1715-1727 (2002).
Venkitasubramanian et al. Biocatalysis in the Pharmaceutical and Biotechnology Industires, ed. R.N. Patel, Chapter 15, pp. 425-440, CRC Press LLC, Boca Raton, FL. 2007.
Venkitasubramanian et al., "Reduction of Carboxylic Acids by Nocardia Aldehyde Oxidoreductase Requires a Phosphopantetheinylated Enzyme," J. Biol. Chem. 282(1):478-485 (2007).
Verhaert et al., "Enzyme kinetics in reversed micelles. 2. Behaviour of enoate reductase," Eur. J. Biochem. 187:73-79 (1990).
Vernal et al., "Cloning and heterologous expression of a broad specificity aminotransferase of Leishmania mexicana promastigotes," FEMS Microbiol. Lett. 229:217-222 (2003).
Vernal et al., "Isolation partial characterization of a broad specificity aminotransferase from leishmania mexicana promastigotes," Mol. Biochem. Parasitol. 96:83-92 (1998).
Vey et al., "Structural basis for glycyl radical formation by pyruvate formate-lyase activating enzyme," Proc. Natl. Acad. Sci. U.S.A. 105:16137-16141 (2008).
Vijay et al., "Diels-Alder reactions between cyclic five-membered dienes and acetylene," J. Mol. Struc. 589-590:291-299 (2002).
Viola, "L-Aspartase: New Tricks From an Old Enzyme," Adv. Enzymol. Relat. Areas. Mol. Biol. 74:295-341 (2000).
Voellmy and Leisinger, "Role of 4-Aminobutyrate Aminotransferase in the Arginine Metabolism of Pseudomonas aeruginosa," J. Bacteriol. 128(3):722-729 (1976).
Voets et al., "Reduced intracellular ionic strength as the initial trigger for activation of endothelial volume-regulated anion channels," Proc. Natl. Acad. Sci. U.S.A. 96:5298-5303 (1999).

(56) References Cited

OTHER PUBLICATIONS

Volkert, et al., "The O(argF-/acZ)205(U169) Deletion Greatly Enhances Resistance to Hydrogen Peroxide in Stationary-Phase *Escherichia coli*,"*J. Bact.* 176(3):1297-1302 (1994).
Volkov et al., "Random chimeragenesis by heteroduplex recombination,"*Methods. Enzymol.* 328:456-463 (2000).
Volkov et al., "Recombination and chimeragenesis by in vitro heteroduplex formation and in vivo repair,"*Nucleic Acids Res.* 27:e18 (1999).
Vrijbloed et al., "Insertional inactivation of methylmalonyl Coenzyme A (CoA) mutase and isobutyryl-CoA mutase genes in *Streptomyces cinnamonensis*: influence on polyketide antibiotic biosynthesis,"*J. Bacteriol.* 181(18):5600-5605 (1999).
Wakil et al., "Studies on the fatty acid oxidizing system of animal tissues. VI. (β- Hydroxyacyl Coenzyme A dehydrogenase,"*J. Biol. Chem.* 207(2):631-638 (1954).
Walker et al., "Yeast pyruvate carboxylase: identification of two genes encoding isoenzymes,"*Biochem. Biophys. Res. Commun.* 176:1210-1217 (2007).
Walter et al., "Molecular characterization of two *Clostridium acetobutylicum* ATCC 824 butanol dehydrogenase isozyme genes,"*J. Bacteriol.* 174(22):7149-7158 (1992).
Walter et al., "Sequence and arrangement of two genes of the butyrate-synthesis pathway of *Clostridium acetobutylicum* ATCC 824,"*Gene* 134(1):107-111 (1993).
Wang and Barker, "Purification and Properties of L -citramalate hydrolase,"*J. Biol. Chem.* 244(10):2516-2526 (1969).
Wang and Seah, "Determination of the metal ion dependence and substrate specificty of a hydratase involve din the degradation pathway of biphenyl/chlorobiphenyl,"*FEBS J.* 272: 966-974 (2005).
Wang et al, "Molecular cloning and functional identification of a novel phenylacetyl-CoA ligase gene from *Penicillium chrysogenum*,"*Biochem. Biopyhs. Res. Commun.* 360(2):453-458 (2007).
Wang et al., "The primary structure of branched-chain a-oxo acid dehydrogenase from *Bacillus subtilis* and its similarity to other a-oxo acid dehydrogenases,"*Eur. J.Biochem.* 213:1091-1099 (1993).
Wang et al., "Bioconversion of fumaric acid to succinic acid by recombinant *E. coli*,"*App. Biochem. Biotechnol.* 70-72:919-928 (1998).
Wang et al., "Cloning, Sequencing, and Expression of the Pyruvate Carboxylase Gene in *Lactococcus lactis* subsp. *lactis* C2,"*App. Environ. Microbiol.* 66(3): 1223-1227 (2000).
Wang et al., "Expression of galactose permease and pyruvate carboxylase in *Escherichia coli* ptsG mutant increases the growth rate and succinate yield under anaerobic conditions,"*Biotechnol. Lett.* 28(2):89-93 (2006).
Wang et al., "Genome-scale in silica aided metabolic analysis and flux comparisons of *Escherichia coli* to improve succinate production,"*App. Microbiol. Biotechnol.* 73(4):887-894 (2006).
Wang et al., "Screening microorganisms for utilization of furfural and possible intermediates in its degradative pathway,"*Biotechnol. Lett.* 16(9):977-982 (1994).
Wang et al., "Site-directed mutagenesis of the phosphorylatable serine (Ser$^8$)in C$_4$ phosphoenolpyruvate carboxylase from sorghum. The effect of negative charge at position 8,"*J. Biol. Chem.* 267:16759-16762. (1992).
Wanner and Tress!, "Purification and characterization of two enone reductases from *Saccharomyces cerevisia*,"*Eur. J. Biochem.* 255(1):271-278 (1998).
Ward et al., "Molecular analysis of the rele of two aromatic aminotransferases and a broad-specificity aminotransferase in the aromatic amino acid metabolism of *Pvococcus furiosus*,"*Archaea* 1:133-141 (2002).
Weaver, "Structure of free fumarase C from *Escherichia coli*," Acta. *Crystallogr. D. Biol. Crystallogr.* 61(Pt 10):1395-1401 (2005).
Weber and Falbe, "Oxo Synthesis Technology,"*Ind. Eng. Chem. Res.* 62:33-37 (1970).

Weidner and Sawers, "Molecular characterization of the Genes Encoding Pyruvate Formate-Lyase and Its Activating enzyme of *clostridium pasteruianum*,"*J. Bacteriol.* 178(8):2440-2444 (1996).
Welch et al., "Purification and Characterization of the NADH-Dependent Butanol Dehydrogenase from *Clostridium acetobutylicum* (ATCC 824),"*Arch. Biochem. Biophys.* 273(2):309-318 (1989).
Wengrovius et al., "Tungsten-Oxo Alkylidene Complexes as Olefin Metathesis Catalysts and the Crystal Structure of W(O)(CHCMe$_3$)(Pet3)C12$^{1}$"*J. Am. Chem. Soc.*
Westin et al., "The identification of a succinyl-CoA thioesterase suggests a novel pathway for succinate production in peroxisomes,"*J. Biol. Chem.* 280(46):38125-38132 (2005).
Wexler et al., "A wide host-range metagenomic library from a waste water treatment plant yields a novel alcohol/aldehyde dehdrogenase,"*Environ. Microbiol.* 7:1917-1926 (2006).
Whalen and Berg, "Analysis of an avtA::Mu d1(Ap lac) Mutant: Metabolic Role of Transaminase C,"*J. Bacteriol.* 150(2):739-746 (1982).
Whalen and Berg, "Gratuitous repression of avtA in *Escherichia coli* and *Salmonella typhimurium*,"*J. Bacteriol.* 158(2):571-574 (1984).
Whelan et al., "Nylon 6 (PA6)," Kunststof en Rubber, Wyt en Zonen Uitgevers. *Rotterdam, NL.* 39(3):38-39 (1986).
Whisstock et al., "Prediction of protein function from protein sequence and structure,"*O. Rev. Biophysics.* 36(3):307-340 (2003).
White et al., "Long-chain alcohol production by yeasts,"*7th Int. Symp. Yeasts* 5465-5470 (1989).
White et al., "The structural biology of type II fatty acid biosynthesis,"*Ann. Rev. Biochem.* 74:791-831 (2005).
Whitehead and Rabinowitz, "Cloning and expression in *Escherichia coli* of the gene for 10-formyltetrahydrofolate synthetase from *Clostridium acidiurici* ("Clostridium acidi-urici"),"*J. Bacteriol.* 167:205-209 (1986).
Whitehead and Rabinowitz, "Nucleotide Sequence of the *Clostridium acidiurici* ("*Clostridium acidi-urici*") Gene for 10-Formyltetrahydrofolate Synthetase Shows Extensive Amino Acid Homology with the Trifunctional Enzyme C$_1$-Tetrahydrofolate Synthase from *Saccharomyces cerevisiae*,"*J. Bacteriol.* 170(7):3255-3261 (1988).
Wiesenborn et al., "Coenzyme A Transferase from *clostridium acetobutylicum* ATCC 824 and Its Role in the Uptake of Acids,"*Appl. Environ. Microbiol.* 55(2):323-329 (1989).
Wiesenborn et al., "Phosphotransbutyrylase from *clostridium acetobutylicum* ATCC 824 and its role in acidogenesis,"*Appl. Environ. Microbiol.* 55:317-322 (1989).
Wilkie and Warren, "Recombinant expression, purification, and characterization of three isoenzymes of aspartate aminotransferase from *Arabidopsis thaliana*,"*Protein. Expr. Purif.* 12:381-389 (1998).
Wilks et al., "A specific, Highly Active Malate Dehydrogenase by Redesign of a Lactate Dehydrogenase Framework,"*Science* 242:1541-1544 (1988).
Wilks et al., "Design of a Specific Phenyllactate Dehydrogenase by Peptide Loop Exchange on the *Bacillus stearothermophilus* Lactate Dehydrogenase Framework,"*Biochemistry* 31:7802-7806 (1992).
Wilks et al., "Designs for a Broad Substrate Specificity Keto Acid Dehydrogenase,"*Biochemistry* 29:8587-8591 (1990).
Willke and Vorlop, "Biotechnological production of itaconic acid,"*Appl. Microbiol. Biotechnol.* 56(3-4):289-295 (2001).
Willke and Vorlop, "Industrial bioconversion of renewable resources as an alternative to conventional chemistry,"*Appl. Microbiol. Biotechnol.* 66(2):131-142 (2004).
Winkler et al., "A new type of a multifunctional β-oxidation enzyme in *euglena*,"*Plant. Physiol.* 131(2):753-762 (2003).
Winzeler et al., "Functional Characterization of S. *cerevisiae* Genome by Gene Deletion and Parallel Analysis,"*Science* 285:901-906 (1999).
Winzer et al., "Differential regulation of two thiolase genes from *Clostridium acetobutylicum* DSM 792"*J. Mol. Microbiol. Biotechnol.* 2(4):531-541 (2000).

(56) References Cited

OTHER PUBLICATIONS

Witkowski et al., "Conversion of β-ketoacyl synthase to a Malonyl Decarboxylase by replacement of the active cysteine with glutamine,"*Biochem istry* 38:11643-11650 (1999).
Wittich and Walter, "Putrescine N-acetyltransferase in *Onchocerca volvulus* and *Ascaris suum* an enzyme which is involved in polyamine degradation and release of N-acetylputrescine,"*Mol. Biochem. Parasitol.* 38:13-17 (1990).
Wolff and Kenealy, "Purification and characterization of the oxygen-sensitive 4-hydroxybutanoate dehydrogenase from *Clostridium kluyveri*,"*Protein Expr. Purif.* 6:206-212 (1995).
Wong et al., "Molecular Properties of Pyruvate Formate-Lyase Activating Enzyme,"*Biochemistry* 32:14102-14110 (1993).
Wong et al., "Sequence saturation mutagenesis (SeSaM): a novel method for directed evolution,"*Nucleic Acids Res* 32:e26 (2004).
Wong et al., "Sequence saturation mutagenesis with tunable mutation frequencies,"*Anal. Biochem.* 341:187-189 (2005).
Wong et al., "Transversion-enriched sequence saturation mutagenesis (SeSaM-Tv+): a random mutagenesis method with consecutive nucleotide exchanges that complements the bias of error-prone PCR,"*Biotechnol. J.* 3:74-82 (2008).
Wood, "Life with CO or $CO_2$ and $H_2$ as a source of carbon and energy,"*Fed. Amer. Societies Experi. Biol. J.* 5:156-163 (1991).
Woods, "Two biochemically distinct classes of fumarase in *Escherichia coli*,"*Biochim. Biophys. Acta* 954(1):14-26 (1988).
Wu and Woodard, "New insights into the evolutionary links relating to the 3-deoxy-D-arabino-heptulosonate 7-phosphate synthase subfamilies,"*J Biol. Chem.* 281:4042-4048 (2006).
Wu et al., "Microbial synthesis of cis-cis-muconic acid by *Sphingobacterium* sp. GcG generated from effluent of a styrene monomer (SM) production plant,"*Enzyme. Microbial Tech.* 35:598-604 (2004).
Wu et al., "Thermotoga maritima 3-deoxy-D-arabino-heptulosonate 7-phosphate (DAHP) synthase: the ancestral eubacterial DAHP synthase?"*J. Biol. Chem.* 278:27525-27531 (2003).
Wu et al., "Life in hot carbon monoxide: the complete genome sequence of *Carboxydothermus hydrogenoformans* Z-2901,"*PLoS Genet.* 1(5):e65 (2005).
Wylie et al., "Nematode.net: a tool for navigating sequences from parasitic and free-living nematodes,"*Nucleic Acids Res.* 32:0423-0426 (2004).
Wynn et al., "Chaperonins GroEL and GroES promote assembly of heterotetramers (α2β2) of mammalian mitochondrial branched-chain α-keto acid decarboxylase in *Escherichia coli*,"*J. Biol. Chem.* 267:12400-12403 (1992).
Wynn et al., "Cloning and expression in *Escherichia coli* of mature E1 β subunit of bovine mitochondrial branched-chain α-keto acid dehydrogenase complex. Mapping of the E1 β-bindina reaion on E2,"*J. Biol. Chem.* 267:1881-1887 (1992).
Yabutani et al., "Analysis of β-ketothiolase and acetoacetyl-CoA reductase genes of a methylotrophic bacterium, *Paracoccus denitrificans*, and their expression in *Escherichia coli*,"*FEMS Microbiol. Lett.* 133:85-90 (1995).
Yagi et al., "Aspartate: 2-oxoglutarate aminotransferase from bakers' yeast: crystallization and characterization ."*J. Biochem.* 92(1):35-43 (1982).
Yagi et al., "Crystallization and properties of aspartate aminotransferase from *Escherichia coli* B,"*FEBS Lett.* 100(1):81-84 (1979).
Yagi et al., "Glutamate-aspartate transaminase from microorganisms,"*Methods. Enzymol.* 113:83-89 (1985).
Yamamoto et al., "Carboxylation reaction catalyzed by 2-oxoglutarate:ferredoxin oxidoreductases from Hydrogenobacter thermophilus,"*Extremophiles* 14:79-85 (2010).
Yamamoto et al., "Purification and Properties of NADP-dependent Formate Dehydrogenase from *Clostridium thermoaceticum*, a tungsten-Selenium-Iron Protein,"*J. Biol. Chem.* 258(3):1826-1832 (1983).

Yamano et al., "Construction of a brewer's yeast having α-acetolactate decarboxylase gene from *acetobacter aceti* ssp. xylinlJm integrated in the genome,"*J. Biotechnol.* 32:173-178 (1994).
Yan and Chen, "Coenzyme A-acylating aldehyde dehydrogenase from *Clostridium beijerinckii* NRRL B592,"*Appl. Environ. Microbiol.* 56:2591-2599 (1990).
Yang et al., "Aspartate Dehydrogenase, a Novel Enzyme Identified from Structural and Functional Studies of TM1643."*J. Biol. Chem.* 278(10):8804-8808 (2003).
Yang et al., "Effect of inactivation of *nuo* and *ackA-pta* on redistribution of metabolic fluxes in *Escherichia coli*,"*Biotechnol Bioeng* 65(3):291-297 (1999).
Yang et al., "Effect of Variation of Klebsiella pneumoniae Acetolactate Synthase Expression on Metabolic Flux Redistribution in *Escherichia coli*,"*Biotechnol. Bioeng.* 69(2)150-159 (2000).
Yang et al., "Metabolic Flux Analysis of *Escherichia coli* Deficient in the Acetate Production Pathway and Expressing the *Bacillus subtilis* Acetolactate Synthase,"*Metab Eng* 1(1):26-34 (1999).
Yang et al., "Nucleotide sequence of the fadA gene. Primary structure of 3-ketoacyl-Coenzyme A thiolase from *Escherichia coli* and the structural organization of the fadAB operon,"*J Biol Chem* 265(18)10424-10429 (1990).
Yang et al., "Nucleotide sequence of the fadA gene. Primary structure of 3-ketoacyl-Coenzyme A thiolase from *Escherichia coli* and the structural organization of the fadAB operon,"*J Biol Chem* 266(24)16255 (1991).
Yang et al., "Nucleotide sequence of the promoter and fadB gene of the fadBA operon and primary structure of the multifunctional fatty acid oxidation protein from *Escherichia coli*,"*Biochem.* 30(27)6788-6795 (1991).
Yang et al., "Redistribution of Metabolic Fluxes in *Escherichia coli* with Fermentative Lactate Dehydrogenase Overexpression and Deletion,"*Metab. Eng.* 1:141-152 (1999).
Yang et al., "The effects of feed and intracellular pyruvate levels on the redistribution of metabolic fluxes in *Escherichia coli*,"*Metab Eng.* 3(2):115-123 (2001).
Yang, "Location of the fadBA operon on the physical map of *Escherichia coli*,"*J. Bacteriol.* 173(23):7405-7406 (1991).
Yanisch-Perron et al., "Improved M13 phage cloning vectors and host strains: nucleotide sequences of the M13mp18 and pUC19 vectors,"*Gene* 33:103-119 (1985).
Yano et al., "Directed evolution of an aspartate aminotransferase with new substrate specificities,"*Proc. Natl. Acad. Sci U.S.A.* 95:5511-5515 (1998).
Yarlett et al., "*Trichomonas vaginalis*: characterization of ornithine decarboxylase,"*Biochem. J.* 293(Pt2):487-493 (1993).
Yeh and Ornston, Evolutionarily Homologous $α_2β_2$ Oligomeric Structures in β-Ketoadipate Succinyl-CoA Transferases from *Acinetobacter calcoaceticus* and *Pseudomonas putida*, *J. Biol. Chem.* 256(4):1565-1569 (1981).
Ylianttila et al., "Crystal Structure of Yeast Peroxisomal Multifunctional Enzyme: Structural Basis for Substrate Specificity of (3R)-hydroxyacyl-CoA Dehydrogenase Units,"*J. Mol. Biol.* 258:1286-1295 (2006).
Ylianttila et al., "Site-directed mutagenesis to enable and improve crystallizability of *candida tropicalis* (3R)-hydroxyacyl-CoA dehydrogenase,"*Biochem. Biophys. Res. Commun.* 324:25-30 (2004).
Yoshida et al., "The Structures of L-Rhamnose Isomerase from *Pseudomonas stutzeri* in Complexes with L-Rhamnose and D-Allose Provide Insights into Broad Substrate Specificity,"*J. Mol. Biol.* 365:1505-1516 (2007).
Yoshimoto, et al., "Isolation and Characterization of the ATF2 Gene Encoding Alcohol Acetyltransferase II in the Bottom Fermenting Yeast *Saccharomyces pastorianus*,"*Yeast* 15:409-417 (1999).
Yoshioka and Hashimoto, "Ester formation by Alcohol Acetyltransferase from Brewers' Yeast,"*Agric. Biol. Chem.* 45:2183-2190 (1981).
Youngleson et al., "Homology between hydroxybutyryl and hydroxyacyl Coenzyme A dehydrogenase enzymes from *Clostridium acetobutylicum* fermentation and vertebrate fatty acid β-oxidation pathways,"*J. Bacteriol.* 171(12):6800-6807 (1989).

(56) References Cited

OTHER PUBLICATIONS

Yun et al., "The genes for anabolic 2-oxoglutarate: ferredoxin oxidoreductse from *hydrogenobacter thermophilus* TK-6,"*Biochem. Biophys. Res. Commun.* 282(2):589-594 (2001).

Yun et al., "ω-Amino acid:pyruvate transaminase from Alcaligenes denitrificans Y2k-2: a new catalyst for kinetic resolution of β-amino acids and amines,"*Appl. Environ. Microbiol.* 70(4):2529-2534 (2004).

Yun et al., "Enhancement of lactate and succinate formation in adhE or pta-ackA mutants of NADH dehydrogenase-deficient *Escherichia coli*,"*J. Appl. Microbiol.* 99(6):1404-1412 (2005).

Zeiher and Randall, "Identification and characterization of Mitochondrial Acetyl-Coenzyme A Hydrolase from *Pisum sativum* L. Seedlings,"*Plant. Physiol.* 94:20-27 (1990).

Zeikus et al., "Biotechnology of succinic acid production and markets for derived industrial products,"*Appl. Microbiol. Biotechnol.* 51: 545-552 (1999).

Zelle et al., "Malic acid production by *Saccharomyces cerevisiae*: engineering of pyruvate carboxylation, oxaloacetate reduction, and malate export,"*Appl. Environ. Microbiol.* 74(9):2766-2777 (2008).

Zerbe-Burkhardt et al., "Cloning, sequencing, expression, and insertional inactivation of the gene for the large subunit of the Coenzyme $B_{12}$-dependent isobutyryl-CoA mutase from *Streptomyces cinnamonensis*,"*J. Biol. Chem.* 273(11):6508-6517 (1998).

Zhang et al., "2-Oxoacid:Ferredoxin Oxidoreductase from the thermoacidophilic Archaeon, *sulfolobus* sp. Strain 7,"*J. Biochem.* 120:587-599 (1996).

Zhang et al., "A new logic for DNA engineering using recombination in *Escherichia coli*,"*Nat. Genet.* 20:123-128 (1998).

Zhang et al., "Directed evolution of a fucosidase from a galactosidase by DNA shuffling and screening,"*Proc. Natl. Acad. Sci. U.S.A.* 94(9):4504-4509 (1997).

Zhang et al., "Functional characterization of the first two actinomycete 4-amino-4-deoxychorismate lyase genes,"*Microbiology* 155:2450-2459 (2009).

Zhang et al., "Genes encoding acyl-CoA dehydrogenase (AcdH) homologues from *Streptomyces coelicolor* and *Streptomyces avermitilis* provide insights into the metabolism of small branched-chain fayy acids and marcrolide antibiotic production,"*Microbiol.* 145 (Pt 9):2323-2334 (1999).

Zhang et al., "Isolation and properties of a levo-lactonase from *Fusarium proliferatum* ECU2002: a robust biocatalyst for production of chiral lactones,"*Appl. Microbiol. Biotechnol.* 75:1087-1094 (2007).

Zhang et al., "Molecular basis for the inhibition of the carboxyltransferase domain of acetyl-Coenzyme-A carboxylase by haloxfop and dicofop," Proc. Natl. Acad. Sci. U.S.A. 101:5910-5915 (2004).

Zhao and Winkler, "A novel α-ketoglutarate reductase activity of the serA-encoded 3-phosphoglycerate dehydrogenase of *Escherichia coli* K-12 and its possible implications for human 2-hydroxyglutaric aciduria,"*J. Bacteriol.* 178(1):232-239 (1996).

Zhao et al., "Molecular evolution by staggered extension process (StEP) in vitro recombination,"*Nat. Biotechnol.* 16:258-261 (1998).

Zhou et al., "Comparison of fumaric acid production by *Rhizopus oryzae* using different neutralizing agents"*Bioproc Biosyst Eng.* 25(3)179-181 (2002).

Zhou et al., "Engineering a native homoethanol pathway in *Escherichia coli* B for ethanol production,"*Biotechnol. Lett.* 30'335-342 (2008).

Zhou et al., "Mycelial pellet formation by *Rhizopus oryzae* ATCC 20344,"*Appl. Biochem. Biotechnol.* 84-86:779-789 (2000).

Zhou et al., "The remarkable structural and functional organization of the eukaryotic pyruvate dehydrogenase complexes,"*Proc. Natl. Acad. Sci. U.S.A.* 98:14802-14807 (2001).

Zhou et al., "Isolation, crystallization and preliminary X-ray analysis of a methanol-induced corrinoid protein from *Moorella thermoacetica*,"*Acta. Crystallogr. Sect. F. Struct. Biol. Cryst. Commun.* 61(Pt 5):537-540 (2005).

Zhu and Sadowski, "Cleavage-dependent ligation by the FLP recombinase. Characterization of a mutant FLP protein with an alteration in a catalytic amino acid,"*J. Biol. Chem.* 270(39):23044-23054 (1995).

Zhuang et al., "The YbgC protein encoded by the ybgC gene of the tol-pal gene cluster of *Haemophilus influenzae* catalyzes acyl-Coenzyme A thioester hydrolysis,"*FEBS Lett.* 516(1-3):161-163 (2002).

Zou et al., "Metabolic engineering for microbial production and applications of copolyesters consisting of 3-hydroxybutyrate and medium-chain-length 3-hydroxyalkanoates,"*Macromol. Biosci.* 7:174-182 (2007).

One page from URL: 1.eee.energy.gov/biomass/information_resources.html (printed Apr. 19, 2010).

One page from URL: expressys.de/ (Printed Dec. 21, 2009).

Two pages from URL: toxnet.nlm.nih.gov/cgi-bin/sis/search/f?./temp/-FwAsma:1 :BASIC (printed Feb. 17, 2010).

Two pages from URL: web.archive.org/web/20080302001450/http://www.verenium.com/PagesTechnology/EnzymeTech/TechEnzyTGR.html (printed Apr. 12, 2010).

Gene Bridges, "Quick & Easy BAC Modification Kit by Red®/ET® Recombination," Technical Protocol, Cat. No. K001, Version 2.6 (2007).

Ferreira-Torres et al., "Microscale process evaluation of recombinant biocatalyst libraries: application to Baeyer-Villiger monooxygenase catalysed lactone synthesis,"*Bioprocess Biosyst. Eng.* 28(2):83-93 (2005).

Locher et al., "Crystal structure of the *Acidaminococcus fermentans* 2-hydroxyglutaryl-CoA dehydratase component A,"*J. Mol. Biol.* 307(1):297-308 (2001).

Niu et al., "Benzene-free synthesis of adipic acid,"*Biotechnol. Prog.* 18:201-211 (2002).

Reed et al., "An expanded genome-scale model of *Escherichia coli* K-12 (iJR904 GSM/GPR),"*Genome. Biol.* 4(9):R54 (2003).

Khajamohiddin et al., A novel meta-cleavage product hydrolase from *Flavobacterium* sp. ATCC27551, Biochemical and Biophysical Research Communications 351 (2006) 675-681 (p. 275, para 1-3).

Chloe et al., "Semi-rational approaches to engineering enzyme activity: combining the benefits of directed evolution and rational design" Current Opin. Biotechnol 16 (4):378-84, 2005.

Skiba et al., "Formation of Protoanemonin from 2-Chloro-cis, cis-Muconate by the Combined Action of Muconate Cycloisomerase and Muconolactone Isomerase" Journal of Bacteriology, Oct. 2002, pp. 5402-5409, vol. 184, No. 19, (p. 5408, right column, last para., p. 5409, left column, first para.).

Seltzer et al., Maleylacetoacetate cis-trans Isomerase: One-Step Double cis-trans Isomerization of Monomethyl Muconate and the Enzyme's Probable Role in Benzene Metabolism, Bioorganic Chemistry 16, 394-407 (1998) (p. 395, para4).

Mars et al., Microbial Degradation of Chloroaromatics: Use of the meta-Cleavage Pathway for Mineralization of Chlorobenzene, Journal of Bacteriology, Jul. 1997, pp. 4530-4537, vol. 179, No. 14 (p. 4535, Fig. 7).

\* cited by examiner

SEMI-SYNTHETIC TEREPHTHALIC ACID VIA MICROORGANISMS THAT PRODUCE MUCONIC ACID

This application is a continuation of U.S. patent application Ser. No. 12/851,478, filed Aug. 5, 2010, which claims the benefit of priority of U.S. Provisional Application No. 61/231,637, filed Aug. 5, 2009, the entire contents of which are incorporated herein by this reference. Also, the entire contents of the ASCII text file entitled "GN00007US2_Sequence Listing.txt" created on Jun. 18, 2014, having a size of 34 kilobytes, is incorporated herein by reference.

BACKGROUND OF THE INVENTION

The present disclosure relates generally to the design of engineered organisms and, more specifically to organisms having selected genotypes for the production of muconic acid.

Terephthalate (also known as terephthalic acid and PTA) is the immediate precursor of polyethylene terephthalate (PET), used to make clothing, resins, plastic bottles and even as a poultry feed additive. Nearly all PTA is produced from para-xylene by the oxidation in air in a process known as the Mid Century Process (Roffia et al., *Ind. Eng. Chem. Prod. Res. Dev.* 23:629-634 (1984)). This oxidation is conducted at high temperature in an acetic acid solvent with a catalyst composed of cobalt and/or manganese salts. Para-xylene is derived from petrochemical sources, and is formed by high severity catalytic reforming of naphtha. Xylene is also obtained from the pyrolysis gasoline stream in a naphtha steam cracker and by toluene disproportion.

PTA, toluene and other aromatic precursors are naturally degraded by some bacteria. However, these degradation pathways typically involve monooxygenases that operate irreversibly in the degradative direction. Hence, biosynthetic pathways for PTA are severely limited by the properties of known enzymes to date.

Muconate (also known as muconic acid, MA) is an unsaturated dicarboxylic acid used as a raw material for resins, pharmaceuticals and agrochemicals. Muconate can be converted to adipic acid, a precursor of Nylon-6,6, via hydrogenation (Draths and Frost, *J. Am. Chem. Soc.* 116; 399-400 (1994)). Alternately, muconate can be hydrogenated using biometallic nanocatalysts (Thomas et al., *Chem. Commun.* 10:1126-1127 (2003)).

Muconate is a common degradation product of diverse aromatic compounds in microbes. Several biocatalytic strategies for making cis,cis-muconate have been developed. Engineered *E. coli* strains producing muconate from glucose via shikimate pathway enzymes have been developed in the Frost lab (U.S. Pat. No. 5,487,987 (1996); Niu et al., *Biotechnol Prog.*, 18:201-211 (2002)). These strains are able to produce 36.8 g/L of cis, cis-muconate after 48 hours of culturing under fed-batch fermenter conditions (22% of the maximum theoretical yield from glucose). Muconate has also been produced biocatalytically from aromatic starting materials such as toluene, benzoic acid and catechol. Strains producing muconate from benzoate achieved titers of 13.5 g/L and productivity of 5.5 g/L/hr (Choi et al., *J. Ferment. Bioeng.* 84:70-76 (1997)). Muconate has also been generated from the effluents of a styrene monomer production plant (Wu et al., *Enzyme and Microbiology Technology* 35:598-604 (2004)).

All biocatalytic pathways identified to date proceed through enzymes in the shikimate pathway, or degradation enzymes from catechol. Consequently, they are limited to producing the cis, cis isomer of muconate, since these pathways involve ring-opening chemistry. The development of pathways for producing trans, trans-muconate and cis, trans-muconate would be useful because these isomers can serve as direct synthetic intermediates for producing renewable PTA via the inverse electron demand Diels-Alder reaction with acetylene. The present invention satisfies this need and provides related advantages as well.

SUMMARY OF INVENTION

The invention provides a non-naturally occurring microbial organism having a muconate pathway having at least one exogenous nucleic acid encoding a muconate pathway enzyme expressed in a sufficient amount to produce muconate. The muconate pathway including an enzyme selected from the group consisting of a beta-ketothiolase, a beta-ketoadipyl-CoA hydrolase, a beta-ketoadipyl-CoA transferase, a beta-ketoadipyl-CoA ligase, a 2-fumarylacetate reductase, a 2-fumarylacetate dehydrogenase, a trans-3-hydroxy-4-hexendioate dehydratase, a 2-fumarylacetate aminotransferase, a 2-fumarylacetate aminating oxidoreductase, a trans-3-amino-4-hexenoate deaminase, a beta-ketoadipate enol-lactone hydrolase, a muconolactone isomerase, a muconate cycloisomerase, a beta-ketoadipyl-CoA dehydrogenase, a 3-hydroxyadipyl-CoA dehydratase, a 2,3-dehydroadipyl-CoA transferase, a 2,3-dehydroadipyl-CoA hydrolase, a 2,3-dehydroadipyl-CoA ligase, a muconate reductase, a 2-maleylacetate reductase, a 2-maleylacetate dehydrogenase, a cis-3-hydroxy-4-hexendioate dehydratase, a 2-maleylacetate aminoatransferase, a 2-maleylacetate aminating oxidoreductase, a cis-3-amino-4-hexendioate deaminase, and a muconate cis/trans isomerase. Other muconate pathway enzymes also are provided. Additionally provided are methods of producing muconate.

BRIEF DESCRIPTION OF THE DRAWINGS

FIG. 6 also shows that several enzymes demonstrated selective condensation of succinyl-CoA and acetyl-CoA to form β-ketoadipyl-CoA as the sole product (right panel).

DETAILED DESCRIPTION OF THE INVENTION

Figure 1:
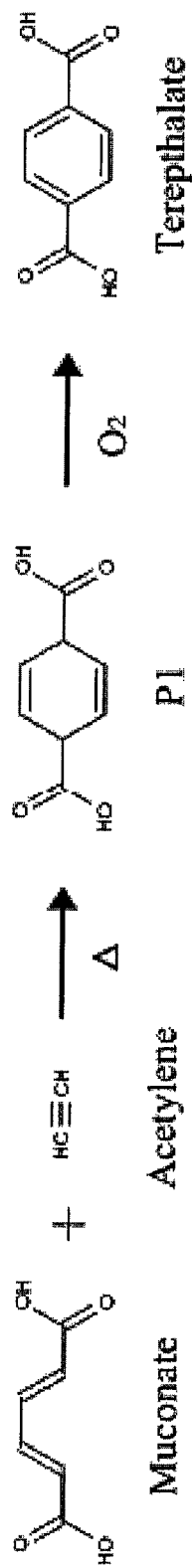
FIG. 1 shows the synthesis of terephthalate from muconate and acetylene via Diels-Alder chemistry. P1 is cyclohexa-2,5-diene-1,4-dicarboxylate.

The present invention is directed, in part, to a biosynthetic pathway for synthesizing muconate from simple carbohydrate feedstocks, which in turn provides a viable synthetic route to PTA. In particular, pathways disclosed herein provide trans,trans-muconate or cis,trans-muconate biocatalytically from simple sugars. The all trans or cis,trans isomer of muconate is then converted to PTA in a two step process via inverse electron demand Diels-Alder reaction with acetylene followed by oxidation in air or oxygen. The Diels-Alder reaction between muconate and acetylene proceeds to form cyclohexa-2,5-diene-1,4-dicarboxylate (P1), as shown in FIG. 1. Subsequent exposure to air or oxygen rapidly converts P1 to PTA.

This invention is also directed, in part, to non-naturally occurring microorganisms that express genes encoding enzymes that catalyze muconate production. Pathways for the production of muconate disclosed herein are derived from central metabolic precursors. Successfully engineering these pathways entails identifying an appropriate set of enzymes with sufficient activity and specificity, cloning their corresponding genes into a production host, optimizing the expression of these genes in the production host, optimizing fermentation conditions, and assaying for product formation following fermentation.

The maximum theoretical yield of muconic acid is 1.09 moles per mole glucose utilized. Achieving this yield involves assimilation of $CO_2$ as shown in equation 1 below:

$$11C_6H_{12}O_6+6CO_2 \rightarrow 12C_6H_6O_4+30H_2O \quad \text{(equation 1)}$$

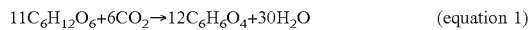

As used herein, the term "muconate" is used interchangeably with muconic acid. Muconate is also used to refer to any of the possible isomeric forms: trans,trans, cis,trans, and cis,cis. However, the present invention provides pathways to the useful trans,trans and cis,trans forms, in particular.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a muconate biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and Drosophila DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having muconate biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiments, the invention provides a non-naturally occurring microbial organism having a muconate pathway that includes at least one exogenous nucleic acid encoding a muconate pathway enzyme expressed in a sufficient amount to produce muconate. The muconate pathway includes an enzyme selected from the group consisting of a beta-ketothiolase, a beta-ketoadipyl-CoA hydrolase, a beta-ketoadipyl-CoA transferase, a beta-ketoadipyl-CoA ligase, a 2-fumarylacetate reductase, a 2-fumarylacetate dehydrogenase, a trans-3-hydroxy-4-hexendioate dehydratase, a 2-fumarylacetate aminotransferase, a 2-fumarylacetate aminating oxidoreductase, a trans-3-amino-4-hexenoate deaminase, a beta-ketoadipate enol-lactone hydrolase, a muconolactone isomerase, a muconate cycloisomerase, a beta-ketoadipyl-CoA dehydrogenase, a 3-hydroxyadipyl-CoA dehydratase, a 2,3-dehydroadipyl-CoA transferase, a 2,3-dehydroadipyl-CoA hydrolase, a 2,3-dehydroadipyl-CoA ligase, a muconate reductase, a 2-maleylacetate reductase, a 2-maleylacetate dehydrogenase, a cis-3-hydroxy-4-hexendioate dehydratase, a 2-maleylacetate aminotransferase, a 2-maleylacetate aminating oxidoreductase, a cis-3-amino-4-hexendioate deaminase, and a muconate cis/trans isomerase.

Figure 2:
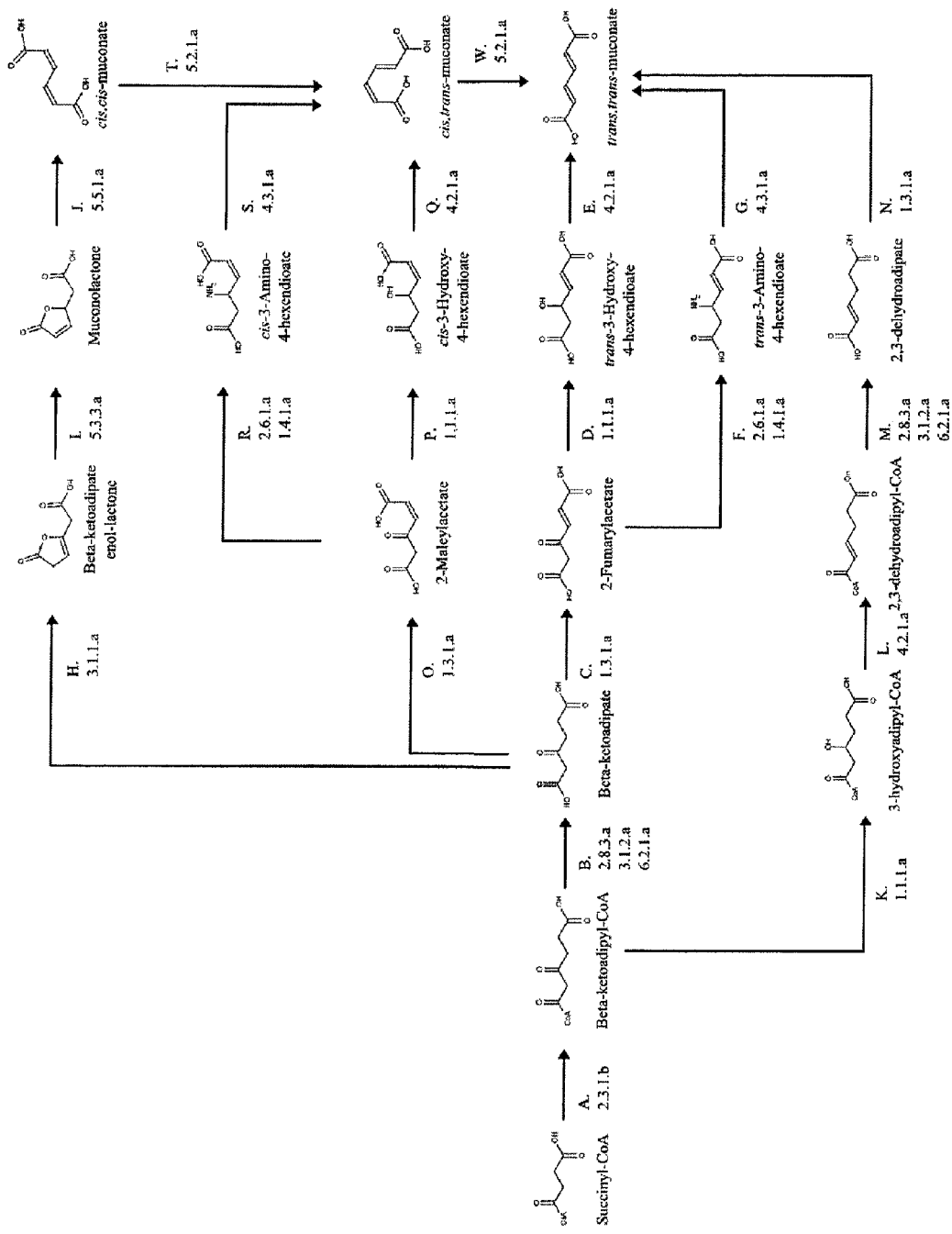
FIG. 2 shows pathways to trans-trans muconate from succinyl CoA. Enzymes are A) beta-ketothiolase, B) beta-ketoadipyl-CoA hydrolase, transferase and/or ligase, C) 2-fumarylacetate reductase, D) 2-fumarylacetate dehydrogenase, E) trans-3-hydroxy-4-hexendioate dehydratase, F) 2-fumarylacetate aminotransferase and/or 2-fumarylacetate aminating oxidoreductase, G) trans-3-amino-4-hexenoate deaminase, H) beta-ketoadipate enol-lactone hydrolase, I) muconolactone isomerase, J) muconate cycloisomerase, K) beta-ketoadipyl-CoA dehydrogenase, L) 3-hydroxyadipyl-CoA dehydratase, M) 2,3-dehydroadipyl-CoA transferase, hydrolase or ligase, N) muconate reductase, O) 2-maleylacetate reductase, P) 2-maleylacetate dehydrogenase, Q) cis-3-hydroxy-4-hexendioate dehydratase, R) 2-maleylacetate aminotransferase and/or 2-maleylacetate aminating oxidoreductase, S) cis-3-amino-4-hexendioate deaminase, T) muconate cis/trans isomerase, W) muconate cis/trans isomerase.

In particular embodiments, the muconate pathway includes a set of muconate pathway enzymes shown in FIG. 2 and selected from the group consisting of:

A) (1) beta-ketothiolase, (2) an enzyme selected from beta-ketoadipyl-CoA hydrolase, beta-ketoadipyl-CoA transferase, and beta-ketoadipyl-CoA ligase, (3) beta-ketoadipate enol-lactone hydrolase, (4) muconolactone isomerase, (5) muconate cycloisomerase, and (6) a muconate cis/trans isomerase;

B) (1) beta-ketothiolase, (2) an enzyme selected from beta-ketoadipyl-CoA hydrolase, beta-ketoadipyl-CoA transferase and beta-ketoadipyl-CoA ligase, (3) 2-maleylacetate reductase, (4) 2-maleylacetate dehydrogenase, (5) cis-3-hydroxy-4-hexendioate dehydratase, and (6) muconate cis/trans isomerase;

C) (1) beta-ketothiolase, (2) an enzyme selected from beta-ketoadipyl-CoA hydrolase, beta-ketoadipyl-CoA transferase and beta-ketoadipyl-CoA ligase, (3) 2-maleylacetate reductase, (4) an enzyme selected from 2-maleylacetate aminotransferase and 2-maleylacetate aminating oxidoreductase, (5) cis-3-amino-4-hexenoate deaminase, and (6) muconate cis/trans isomerase;

D) (1) beta-ketothiolase, (2) beta-ketoadipyl-CoA dehydrogenase, (3) 3-hydroxyadipyl-CoA dehydratase, (4) an enzyme selected from 2,3-dehydroadipyl-CoA transferase, 2,3-dehydroadipyl-CoA hydrolase and 2,3-dehydroadipyl-CoA ligase, and (5) muconate reductase;

E) (1) beta-ketothiolase, (2) an enzyme selected from beta-ketoadipyl-CoA hydrolase, beta-ketoadipyl-CoA transferase and beta-ketoadipyl-CoA ligase, (3) 2-fumarylacetate reductase, (4) 2-fumarylacetate dehydrogenase, and (5) trans-3-hydroxy-4-hexendioate dehydratase;

F) (1) beta-ketothiolase, (2) an enzyme selected from beta-ketoadipyl-CoA hydrolase, beta-ketoadipyl-CoA transferase and beta-ketoadipyl-CoA ligase, (3) 2-fumarylacetate reductase, (4) an enzyme selected from 2-fumarylacetate aminotransferase and 2-fumarylacetate aminating oxidoreductase, and (5) trans-3-amino-4-hexenoate deaminase.

In some embodiments, a microbial organism having a pathway exemplified by those shown in FIG. 2 can include two or more exogenous nucleic acids each encoding a muconate pathway enzyme, including three, four, five, six, that is up to all of the of enzymes in a muconate pathway. The non-naturally occurring microbial organism having at least one exogenous nucleic acid can include a heterologous nucleic acid. A non-naturally occurring microbial organism having a pathway exemplified by those shown in FIG. 2 can be cultured in a substantially anaerobic culture medium.

In some embodiments, the invention provides a non-naturally occurring microbial organism having a muconate pathway that includes at least one exogenous nucleic acid encoding a muconate pathway enzyme expressed in a sufficient amount to produce muconate. The muconate pathway includes an enzyme selected from the group consisting of a 4-hydroxy-2-ketovalerate aldolase, a 2-oxopentenoate hydratase, a 4-oxalocrotonate dehydrogenase, a 2-hydroxy-4-hexenedioate dehydratase, a 4-hydroxy-2-oxohexanedioate oxidoreductase, a 2,4-dihydroxyadipate dehydratase (acting on 2-hydroxy), a 2,4-dihydroxyadipate dehydratase (acting on 4-hydroxyl group) and a 3-hydroxy-4-hexenedioate dehydratase.

Figure 3:
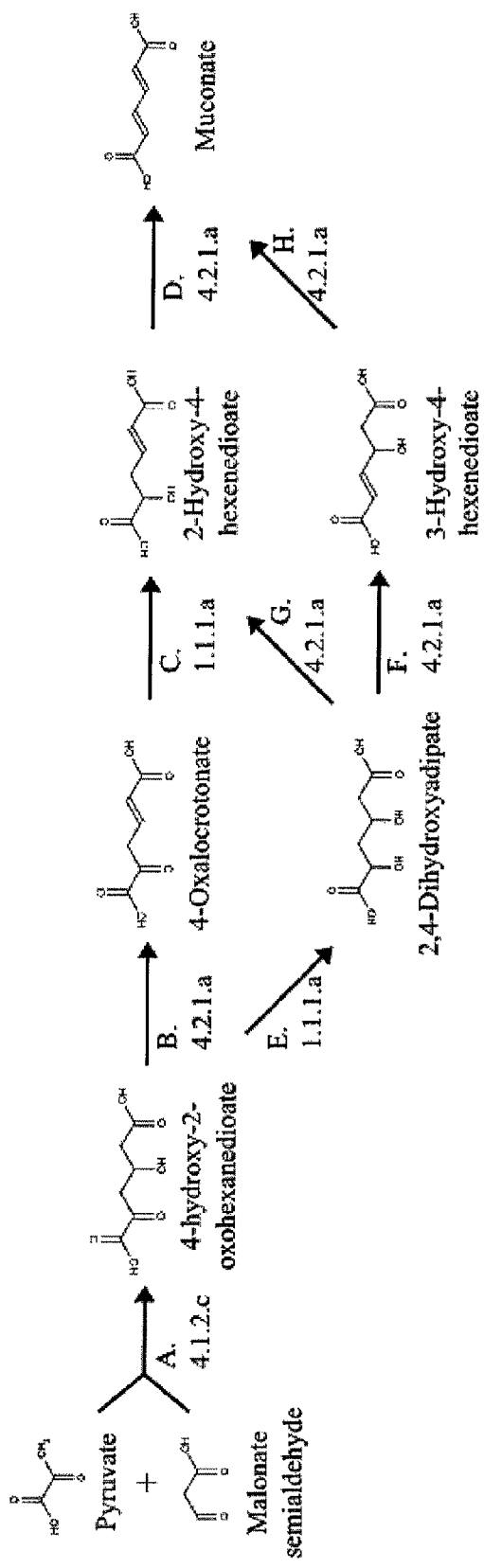
FIG. 3 shows pathways to muconate from pyruvate and malonate semialdehyde. Enzymes are A) 4-hydroxy-2-ketovalerate aldolase, B) 2-oxopentenoate hydratase, C) 4-oxalocrotonate dehydrogenase, D) 2-hydroxy-4-hexenedioate dehydratase, E) 4-hydroxy-2-oxohexanedioate oxidoreductase, F) 2,4-dihydroxyadipate dehydratase (acting on 2-hydroxy), G) 2,4-dihydroxyadipate dehydratase (acting on 4-hydroxyl group) and H) 3-hydroxy-4-hexenedioate dehydratase.

In particular embodiments, the muconate pathway includes a set of muconate pathway enzymes shown in FIG. 3 and selected from the group consisting of:

A) (1) 4-hydroxy-2-ketovalerate aldolase, (2) 2-oxopentenoate hydratase, (3) 4-oxalocrotonate dehydrogenase, (4) 2-hydroxy-4-hexenedioate dehydratase;

B) (1) 4-hydroxy-2-ketovalerate aldolase, (2) 4-hydroxy-2-oxohexanedioate oxidoreductase, (3) 2,4-dihydroxyadipate dehydratase (acting on 2-hydroxy), (4) 3-hydroxy-4-hexenedioate dehydratase; and C) (1) 4-hydroxy-2-ketovalerate aldolase, (2) 4-hydroxy-2-oxohexanedioate oxidoreductase, (3) 2,4-dihydroxyadipate dehydratase (acting on 4-hydroxyl group), (4) 2-hydroxy-4-hexenedioate dehydratase.

In some embodiments, a microbial organism having a pathway exemplified by those shown in FIG. 3 can include two or more exogenous nucleic acids each encoding a muconate pathway enzyme, including three, four, that is up to all of the of enzymes in a muconate pathway. The non-naturally occurring microbial organism having at least one exogenous nucleic acid can include a heterologous nucleic acid. A non-naturally occurring microbial organism having a pathway exemplified by those shown in FIG. 3 can be cultured in a substantially anaerobic culture medium.

In some embodiments, the invention provides a non-naturally occurring microbial organism having a muconate pathway that includes at least one exogenous nucleic acid encoding a muconate pathway enzyme expressed in a sufficient amount to produce muconate. The muconate pathway includes an enzyme selected from the group consisting of an HODH aldolase, an OHED hydratase, an OHED decarboxylase, an HODH formate-lyase, an HODH dehydrogenase, an OHED formate-lyase, an OHED dehydrogenase, a 6-OHE dehydrogenase, a 3-hydroxyadipyl-CoA dehydratase, a 2,3-dehydroadipyl-CoA hydrolase, a 2,3-dehydroadipyl-CoA transferase, a 2,3-dehydroadipyl-CoA ligase, and a muconate reductase.

Figure 4:
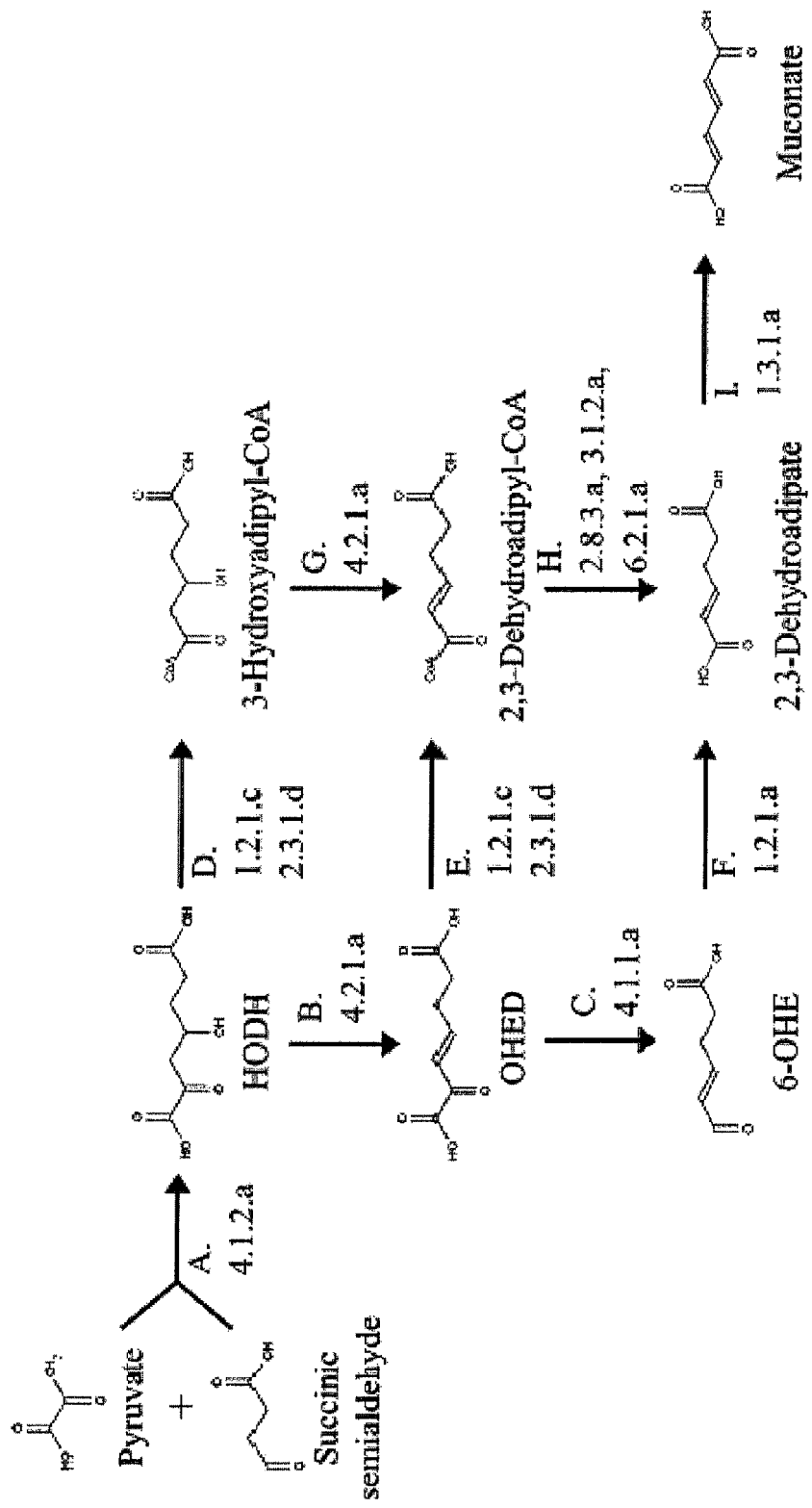
FIG. 4 shows pathways to muconate from pyruvate and succinic semialdehyde. Enzymes are A) HODH aldolase, B) OHED hydratase, C) OHED decarboxylase, D) HODH formate-lyase and/or HODH dehydrogenase, E) OHED formate-lyase and/or OHED dehydrogenase, F) 6-OHE dehydrogenase, G) 3-hydroxyadipyl-CoA dehydratase, H) 2,3-dehydroadipyl-CoA hydrolase, transferase or ligase, I) muconate reductase. Abbreviations are: HODH=4-hydroxy-2-oxoheptane-1,7-dioate, OHED=2-oxohept-4-ene-1,7-dioate, 6-OHE=6-oxo-2,3-dehydrohexanoate.

In particular embodiments, the muconate pathway includes a set of muconate pathway enzymes shown in FIG. 4 and selected from the group consisting of:

A) (1) HODH aldolase, (2) OHED hydratase, (3) OHED decarboxylase, (4) 6-OHE dehydrogenase, and (5) muconate reductase;

B) (1) HODH aldolase, (2) OHED hydratase, (3) an enzyme selected from OHED formate-lyase and OHED dehydrogenase, (4) an enzyme selected from 2,3-dehydroadipyl-CoA hydrolase, 2,3-dehydroadipyl-CoA transferase and 2,3-dehydroadipyl-CoA ligase, and (5) muconate reductase; and C) (1) HODH aldolase, (2) an enzyme selected from HODH formate-lyase and HODH dehydrogenase, (3) 3-hydroxyadipyl-CoA dehydratase, (4) an enzyme selected from 2,3-dehydroadipyl-CoA hydrolase, 2,3-dehydroadipyl-CoA transferase and 2,3-dehydroadipyl-CoA ligase, and (5) muconate reductase In some embodiments, a microbial organism having a pathway exemplified by those shown in FIG. 4 can include two or more exogenous nucleic acids each encoding a muconate pathway enzyme, including three, four, five, that is up to all of the of enzymes in a muconate pathway. The non-naturally occurring microbial organism having at least one exogenous nucleic acid can include a heterologous nucleic acid. A non-naturally occurring microbial organism having a pathway exemplified by those shown in FIG. 4 can be cultured in a substantially anaerobic culture medium.

In some embodiments, the invention provides a non-naturally occurring microbial organism having a muconate pathway that includes at least one exogenous nucleic acid encoding a muconate pathway enzyme expressed in a sufficient amount to produce muconate. The muconate pathway includes an enzyme selected from the group consisting of a lysine aminotransferase, a lysine aminating oxidoreductase, a 2-aminoadipate semialdehyde dehydrogenase, a 2-aminoadipate deaminase, a muconate reductase, a lysine-2,3-aminomutase, a 3,6-diaminohexanoate aminotransferase, a 3,6-diaminohexanoate aminating oxidoreductase, a 3-aminoadipate semialdehyde dehydrogenase, and a 3-aminoadipate deaminase.

Figure 5:
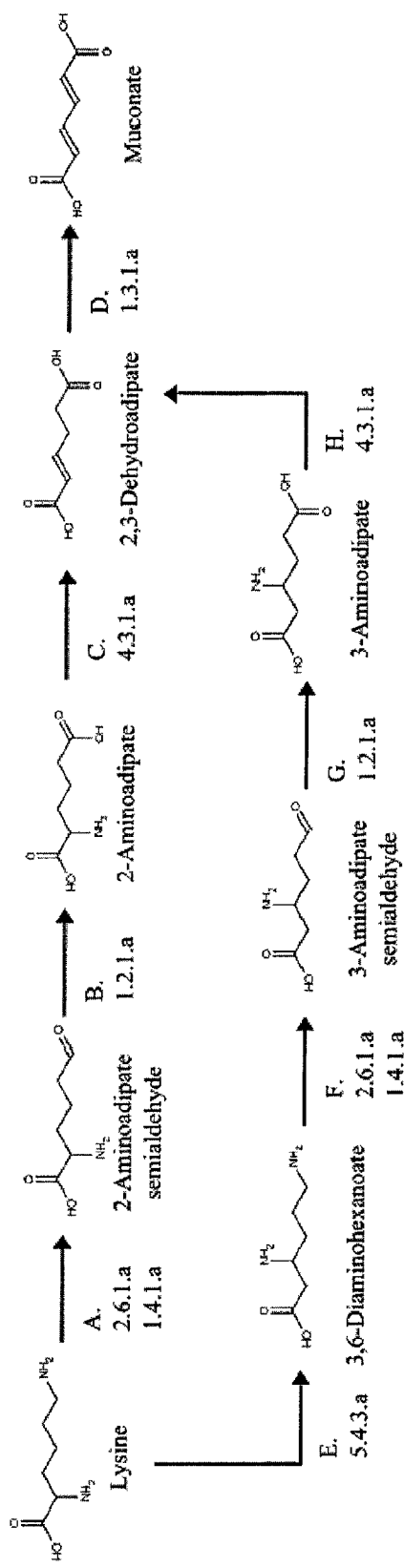
FIG. 5 shows pathways to muconate from lysine. Enzymes are A) lysine aminotransferase and/or aminating oxidoreductase, B) 2-aminoadipate semialdehyde dehydrogenase, C) 2-aminoadipate deaminase, D) muconate reductase, E) lysine-2,3-aminomutase, F) 3,6-diaminohexanoate aminotransferase and/or aminating oxidoreductase, G) 3-aminoadipate semialdehyde dehydrogenase, H) 3-aminoadipate deaminase.

In particular embodiments, the muconate pathway includes a set of muconate pathway enzymes shown in FIG. 5 and selected from the group consisting of:

A) (1) lysine aminotransferase, (2) lysine aminating oxidoreductase, (3) 2-aminoadipate semialdehyde dehydrogenase, (4) 2-aminoadipate deaminase, and (5) muconate reductase B) (1) lysine-2,3-aminomutase, (2) 3,6-diaminohexanoate aminotransferase, (3) 3,6-diaminohexanoate aminating oxidoreductase, (4) 3-aminoadipate semialdehyde dehydrogenase, (5) 3-aminoadipate deaminase, and (6) muconate reductase.

In some embodiments, a microbial organism having a pathway exemplified by those shown in FIG. 5 can include two or more exogenous nucleic acids each encoding a muconate pathway enzyme, including three, four, five, six, that is up to all of the of enzymes in a muconate pathway. The non-naturally occurring microbial organism having at least one exogenous nucleic acid can include a heterologous nucleic acid. A non-naturally occurring microbial organism having a pathway exemplified by those shown in FIG. 2 can be cultured in a substantially anaerobic culture medium.

In an additional embodiment, the invention provides a non-naturally occurring microbial organism having a muconate pathway, wherein the non-naturally occurring microbial organism comprises at least one exogenous nucleic acid encoding an enzyme or protein that converts a substrate to a product selected from the group consisting of succinyl-CoA to beta-ketoadipyl-CoA, beta-ketoadipyl-CoA to 3-hydroxyadipyl-CoA, 3-hydroxyadipyl-CoA to 2,3-dehydroadipyl-CoA, 2,3-dehydroadipyl-CoA to 2,3-dehydroadipate, and 2,3-dehydroadipate to trans,trans-muconate. Alternatively, the non-naturally occurring microbial organism comprises at least one exogenous nucleic acid encoding an enzyme or protein that converts a substrate to a product selected from the group consisting of succinyl-CoA to beta-ketoadipyl-CoA, beta-ketoadipyl-CoA to beta-ketoadipate, beta-ketoadipate to 2-maleylacetate, 2-maleylacetate to cis-3-hydroxy-4-hexendioate, cis-3-hydroxy-4-hexendioate to cis,trans-muconate, and cis,trans-muconate to trans,trans-muconate. Alternatively, the non-naturally occurring microbial organism comprises at least one exogenous nucleic acid encoding an enzyme or protein that converts a substrate to a product selected from the group consisting of succinyl-CoA to beta-ketoadipyl-CoA, beta-ketoadipyl-CoA to beta-ketoadipate, beta-ketoadipate to 2-maleylacetate, 2-maleylacetate to cis-3-amino-4-hexendioate, cis-3-amino-4-hexendioate to cis,trans-muconate, and cis,trans-muconate to trans,trans-muconate. Alternatively, the non-naturally occurring microbial organism comprises at least one exogenous nucleic acid encoding an enzyme or protein that converts a substrate to a product selected from the group consisting of succinyl-CoA to beta-ketoadipyl-CoA, beta-ketoadipyl-CoA to beta-ketoadipate, beta-ketoadipate to 2-fumarylacetate, 2-fumarylacetate to trans-3-hydroxy-4-hexendioate, and trans-3-hydroxy-4-dienoate to trans,trans-muconate. Alternatively, the non-naturally occurring microbial organism comprises at least one exogenous nucleic acid encoding an enzyme or protein that converts a substrate to a product selected from the group consisting of succinyl-CoA to beta-ketoadipyl-CoA, beta-ketoadipyl-CoA to beta-ketoadipate, beta-ketoadipate to 2-fumarylacetate, 2-fumarylacetate to trans-3-amino-4-hexendioate, trans-3-amino-4-hexendioate to trans,trans-muconate. Alternatively, the non-naturally occurring microbial organism comprises at least one exogenous nucleic acid encoding an enzyme or protein that converts a substrate to a product selected from the group consisting of succinyl-CoA to beta-ketoadipyl-CoA, beta-ketoadipyl-CoA to beta-ketoadipate, beta-ketoadipate to beta-ketoadipate enol-lactone, beta-ketoadipate enol-lactone to muconolactone, muconolactone to cis,cis-muconate, cis,cis-muconate to cis,trans-muconate, and cis,trans muconate to trans,trans-muconate. Thus, the invention provides a non-naturally occurring microbial organism containing at least one exogenous nucleic acid encoding an enzyme or protein, where the enzyme or protein converts the substrates and products of a muconate pathway, such as those shown in FIG. 2.

In an additional embodiment, the invention provides a non-naturally occurring microbial organism having a muconate pathway, wherein the non-naturally occurring microbial organism comprises at least one exogenous nucleic acid encoding an enzyme or protein that converts a substrate to a product selected from the group consisting of pyruvate and malonate semialdehyde to 4-hydroxy-2-oxohexandioate, 4-hydroxy-2-oxohexandioate to 4-oxalocrotonate, 4-oxalocrotonate to 2-hydroxy-4-hexendioate, and 2-hydroxy-4-hexendioate to muconate. Alternatively, the non-naturally occurring microbial organism comprises at least one exogenous nucleic acid encoding an enzyme or protein that converts a substrate to a product selected from the group consisting of pyruvate and malonate semialdehyde to 4-hydroxy-2-oxohexandioate, 4-hydroxy-2-oxohexandioate to 2,4-dihydroxyadipate, 2,4-dihydroxyadipate to 2-hydroxy-4-hexendioate, and 2-hydroxy-4-hexendioate to muconate. Alternatively, the non-naturally occurring microbial organism comprises at least one exogenous nucleic acid encoding an enzyme or protein that converts a substrate to a product selected from the group consisting of pyruvate and malonate semialdehyde to 4-hydroxy-2-oxohexandioate, 4-hydroxy-2-oxohexandioate to 2,4-dihydroxyadipate, 2,4-dihydroxyadipate to 3-hydroxy-4-hexendioate, and 3-hydroxy-4-hexendioate to muconate. Thus, the invention provides a non-naturally occurring microbial organism containing at least one exogenous nucleic acid encoding an enzyme or protein, where the enzyme or protein converts the substrates and products of a muconate pathway, such as those shown in FIG. 3.

In an additional embodiment, the invention provides a non-naturally occurring microbial organism having a muconate pathway, wherein the non-naturally occurring microbial organism comprises at least one exogenous nucleic acid encoding an enzyme or protein that converts a substrate to a product selected from the group consisting of pyruvate and succinic semialdehyde to HODH, HODH to 3-hydroxyadipyl-CoA, 3-hydroxy adipyl-CoA to 2,3-dehydroadipyl-CoA, 2,3-dehydroadipyl-CoA to 2,3-dehydroadipate, and 2,3-dehydroadipate to muconate. Alternatively, the non-naturally occurring microbial organism comprises at least one exogenous nucleic acid encoding an enzyme or protein that converts a substrate to a product selected from the group consisting of pyruvate and succinic semialdehyde to HODH, HODH to OHED, OHED to 2,3-dehydroadipyl-CoA, 2,3-dehydroadipyl-CoA to 2,3-dehydroadipate, and 2,3-dehydroadipate to muconate. Alternatively, the non-naturally occurring microbial organism comprises at least one exogenous nucleic acid encoding an enzyme or protein that converts a substrate to a product selected from the group consisting of pyruvate and succinic semialdehyde to HODH, HODH to OHED, OHED to 6-OHE, 6-OHE to 2,3-dehydroadipate, and 2,3-dehydroadipate to muconate. Thus, the invention provides a non-naturally occurring microbial organism containing at least one exogenous nucleic acid encoding an enzyme or protein, where the enzyme or protein converts the substrates and products of a muconate pathway, such as those shown in FIG. 4.

In an additional embodiment, the invention provides a non-naturally occurring microbial organism having a muconate pathway, wherein the non-naturally occurring microbial organism comprises at least one exogenous nucleic acid encoding an enzyme or protein that converts a substrate to a product selected from the group consisting of lysine to 2-aminoadipate semialdehyde, 2-aminoadipate semialdehyde to 2-aminoadipate, 2-aminoadipate to 2,3-dehydroadipate, and 2,3-dehydroadipate to muconate. Alternatively, the non-naturally occurring microbial organism comprises at least one exogenous nucleic acid encoding an enzyme or protein that converts a substrate to a product selected from the group consisting of lysine to 3,6-diaminohexanoate, 3,6-diaminohexanoate to 3-aminoadipate semialdehyde, 3-aminoadipate semialdehyde to 3-aminoadipate, 3-aminoadipate to 2,3-dehydroadipate, and 2,3-dehydroadipate to muconate. Thus, the invention provides a non-naturally occurring microbial organism containing at least one exogenous nucleic acid encoding an enzyme or protein, where the enzyme or protein converts the substrates and products of a muconate pathway, such as those shown in FIG. 5.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

Muconate can be produced from succinyl-CoA via beta-ketoadipate in a minimum of five enzymatic steps, shown in FIG. 2. In the first step of all pathways, succinyl-CoA is joined to acetyl-CoA by a beta-ketothiolase to form beta-ketoadipyl-CoA (Step A). In one embodiment, the beta-keto functional group is reduced and dehydrated to form 2,3-dehydroadipyl-CoA (Steps K and L). The CoA moiety is then removed by a CoA hydrolase, transferase or ligase to form 2,3-dehydroadipate (Step M). Finally, 2,3-dehydroadipate is oxidized to form the conjugated diene muconate by an enoate oxidoreductase (Step N).

In other embodiments, beta-ketoadipyl-CoA is converted to beta-ketoadipate by a CoA hydrolase, transferase or ligase (Step B). Beta-ketoadipate is then converted to 2-maleylacetate by maleylacetate reductase (Step O). The beta-ketone of 2-maleylacetate is then reduced to form cis-3-hydroxy-4-hexenoate (Step P). This product is further dehydrated to cis,trans-muconate in Step Q. Step W provides a muconate cis/trans-isomerase to provide trans,trans-muconate.

A similar route entails the conversion of 2-maleylacetate to cis-3-amino-4-hexenoate by an aminotransferase or aminating oxidoreductase (Step R). Deamination of cis-3-amino-4-hexenoate is subsequently carried out to form cis, trans-muconate (Step S).

Alternatively, beta-ketoadipate can be converted to 2-fumarylacetate by action of a fumarylacetate reductase (Step C). Such a reductase can be engineered by directed evolution, for example, of the corresponding maleylacetate reductase. Reduction of the keto group and dehydration provides trans,trans-muconate (Steps D and E). Alternatively, reductive amination, followed by deamination also affords the trans,trans-muconate product (Steps F and G)

In yet another route, beta-ketoadipate can be cyclized to an enol-lactone by beta-ketoadipyl enol-lactone hydrolase (Step H). The double bond in the lactone ring is then shifted by muconolactone isomerase (Step I). Finally, muconolactone is converted to cis,cis-muconate by muconate cycloisomerase (Step J). Muconate cycloisomerase may selectively form the cis,cis isomer of muconate. Further addition of a cis/trans isomerase converts the cis,cis isomer to the favored trans, trans or trans, cis configurations (Steps T and W, which can be incorporated into a single isomerization step).

The pathways detailed in FIG. 2 can achieve a maximum theoretical yield of 1.09 moles muconate per mole glucose utilized under anaerobic and aerobic conditions. With and without aeration, the maximum ATP yield is 1 mole of ATP per glucose utilized at the maximum muconate yield. The first step of this pathway, the condensation of succinyl-CoA and acetyl-CoA by beta-ketothiolase, has been demonstrated by Applicants is shown below in Example I.

Another pathway for muconate synthesis involves the condensation of pyruvate and malonate semialdehyde, as shown in FIG. 3. Malonate semialdehyde can be formed in the cell by several different pathways. Two example pathways are: 1) decarboxylation of oxaloacetate, and 2) conversion of 2-phosphoglycerate to glycerol which can then be dehydrated to malonate semialdehyde by a diol dehydratase. In one pathway, malonate semialdehyde and pyruvate are condensed to form 4-hydroxy-2-oxohexanedioate (Step A). This product is dehydrated to form 4-oxalocrotonate (Step B). 4-Oxalocrotonate is converted to muconate by reduction and dehydration of the 2-keto group (Steps C and D).

Alternately, the 2-keto group of 4-hydroxy-2-oxohexanedioate is reduced by an alcohol-forming oxidoreductase (Step E). The product, 2,4-dihydroxyadipate is then dehydrated at the 2- or 4-hydroxy position to form 2-hydroxy-4-hexenedioate (Step G) or 3-hydroxy-4-hexenedioate (Step F). Subsequent dehydration yields the diene, muconate (Steps D or H). This pathway is energetically favorable and is useful because it does not require carboxylation steps. Also, the pathway is driven by the stability of the muconate end product.

Several pathways for producing muconate from pyruvate and succinic semialdehyde are detailed in FIG. 4. Such pathways entail aldol condensation of pyruvate with succinic semialdehyde to 4-hydroxy-2-oxoheptane-1,7-dioate (HODH) by HODH aldolase (Step A). In one route, HODH is dehydrated to form 2-oxohept-4-ene-1,7-dioate (OHED) by OHED hydratase (Step B). OHED is then decarboxylated to form 6-oxo-2,3-dehydrohexanoate (6-OHE) (Step C). This product is subsequently oxidized to the diacid and then further oxidized to muconate (Steps F, I).

Alternately, HODH is converted to 3-hydroxyadipyl-CoA by a formate-lyase or an acylating decarboxylating dehydrogenase (Step D). The 3-hydroxy group of 3-hydroxyadipyl-CoA is then dehydrated to form the enoyl-CoA (Step G). The CoA moiety of 2,3-dehydroadipyl-CoA is removed by a CoA hydrolase, ligase or transferase (Step H). Finally, 2,3-dehydroadipate is oxidized to muconate by muconate reductase (Step I).

In yet another route, OHED is converted to 2,3-dehydroadipyl-CoA by a formate-lyase or acylating decarboxylating dehydrogenase (Step E). 2,3-Dehydroadipyl-CoA is then transformed to muconate.

Pathways for producing muconate from lysine are detailed in FIG. 5. In one embodiment, lysine is converted to 2-aminoadipate semialdehyde by an aminotransferase or aminating oxidoreductase (Step A). 2-Aminoadipate semialdehyde is then oxidized to form 2-aminoadipate (Step B). The 2-amino group is then deaminated by a 2-aminoadipate deaminase (Step C). The product, 2,3-dehydroadipate is further oxidized to muconate by muconate reductase (Step D).

In an alternate route, the 2-amino group of lysine is shifted to the 3-position by lysine-2,3-aminomutase (Step E). The product, 3,6-diaminohexanoate, is converted to 3-aminoadipate semialdehyde by an aminotransferase or aminating oxidoreductase (Step F). Oxidation of the aldehyde (Step G) and deamination (Step H) yields 2,3-dehydroadipate, which is then converted to muconate (Step D).

All transformations depicted in FIGS. 2-5 fall into the general categories of transformations shown in Table 1. Below is described a number of biochemically characterized genes in each category. Specifically listed are genes that can be applied to catalyze the appropriate transformations in FIGS. 2-5 when properly cloned and expressed.

Table 1 shows the enzyme types useful to convert common central metabolic intermediates into muconate. The first three digits of each label correspond to the first three Enzyme Commission number digits which denote the general type of transformation independent of substrate specificity.

TABLE 1

| Label | Function |
| --- | --- |
| 1.1.1.a | Oxidoreductase (oxo to alcohol, and reverse) |
| 1.2.1.a | Oxidoreductase (acid to oxo) |
| 1.2.1.c | Oxidoreductase (2-ketoacid to acyl-CoA) |
| 1.3.1.a | Oxidoreductase (alkene to alkane, and reverse) |
| 1.4.1.a | Oxidoreductase (aminating) |
| 2.3.1.b | Acyltransferase (beta-ketothiolase) |
| 2.3.1.d | Acyltransferase (formate C-acyltransferase) |
| 2.6.1.a | Aminotransferase |
| 2.8.3.a | CoA transferase |
| 3.1.1.a | Enol-lactone hydrolase |
| 3.1.2.a | CoA hydrolase |
| 4.1.1.a | Carboxy-lyase |
| 4.1.2.a | Aldehyde-lyase |
| 4.2.1.a | Hydro-lyase |
| 4.3.1.a | Ammonia-lyase |
| 5.2.1.a | Cis/trans isomerase |
| 5.3.3.a | Lactone isomerase |
| 5.4.3.a | Aminomutase |
| 5.5.1.a | Lactone cycloisomerase |
| 6.2.1.a | CoA synthetase |

Several transformations depicted in FIGS. 2-5 require oxidoreductases that convert a ketone functionality to a hydroxyl group. The conversion of beta-ketoadipyl-CoA to 3-hydroxyadipyl-CoA (FIG. 2, Step K) is catalyzed by a 3-oxoacyl-CoA dehydrogenase. The reduction of 2-fumarylacetate to trans-3-hydroxy-4-hexendioate (FIG. 2, Step D) or 2-maleylacetate to cis-3-hydroxy-4-hexendioate (FIG. 2, Step P), is catalyzed by an oxidoreductase that converts a 3-oxoacid to a 3-hydroxyacid. Reduction of the ketone group of 4-oxalocrotonate and 4-hydroxy-2-oxohexanedioate to their corresponding hydroxyl group is also catalyzed by enzymes in this family (FIG. 3, Steps C and E).

Exemplary enzymes for converting beta-ketoadipyl-CoA to 3-hydroxyadipyl-CoA (FIG. 2, Step K) include 3-hydroxyacyl-CoA dehydrogenases. Such enzymes convert 3-oxoacyl-CoA molecules into 3-hydroxyacyl-CoA molecules and are often involved in fatty acid beta-oxidation or phenylacetate catabolism. For example, subunits of two fatty acid oxidation complexes in *E. coli*, encoded by fadB and fadJ, function as 3-hydroxyacyl-CoA dehydrogenases (Binstock and Schultz, *Methods Enzymol.* 71Pt C:403-411 (1981)). Furthermore, the gene products encoded by phaC in *Pseudomonas putida* U (Olivera et al., *Proc. Natl. Acad. Sci. U.S.A.* 95:6419-6424 (1998)) and paaC in *Pseudomonas fluorescens* ST (Di et al., *Arch. Microbiol.* 188:117-125 (2007)) catalyze the reverse reaction of step B in FIG. 10, that is, the oxidation of 3-hydroxyadipyl-CoA to form 3-oxoadipyl-CoA, during the catabolism of phenylacetate or styrene. Note that the reactions catalyzed by such enzymes are reversible. In addition, given the proximity in *E. coli* of paaH to other genes in the phenylacetate degradation operon (Nogales et al., *Microbiology* 153:357-365 (2007)) and the fact that paaH mutants cannot grow on phenylacetate (Ismail et al., *Eur. J. Biochem.* 270:3047-3054 (2003)), it is expected that the *E. coli* paaH gene encodes a 3-hydroxyacyl-CoA dehydrogenase. Genbank information related to these genes is summarized in Table 2 below.

TABLE 2

| Gene | GI # | Accession No. | Organism |
| --- | --- | --- | --- |
| fadB | 119811 | P21177.2 | *Escherichia coli* |
| fadJ | 3334437 | P77399.1 | *Escherichia coli* |
| paaH | 16129356 | NP_415913.1 | *Escherichia coli* |
| phaC | 26990000 | NP_745425.1 | *Pseudomonas putida* |
| paaC | 106636095 | ABF82235.1 | *Pseudomonas fluorescens* |

Additional exemplary oxidoreductases capable of converting 3-oxoacyl-CoA molecules to their corresponding 3-hydroxyacyl-CoA molecules include 3-hydroxybutyryl-CoA dehydrogenases. The enzyme from *Clostridium acetobutylicum*, encoded by hbd, has been cloned and functionally expressed in *E. coli* (Youngleson et al., *J. Bacteriol.* 171:6800-6807 (1989)). Additional genes include Hbd1 (C-terminal domain) and Hbd2 (N-terminal domain) in *Clostridium kluyveri* (Hillmer and Gottschalk, *FEBS Lett.* 21:351-354 (1972)) and HSD17B10 in *Bos taurus* (Wakil et al., *J. Biol. Chem.* 207:631-638 (1954)). Yet other genes demonstrated to reduce acetoacetyl-CoA to 3-hydroxybutyryl-CoA are phbB from *Zoogloea ramigera* (Ploux et al., *Eur. J. Biochem.* 174:177-182 (1988)) and phaB from *Rhodobacter sphaeroides* (Alber et al., *Mol. Microbiol.* 61:297-309 (2006)). The former gene is NADPH-dependent, its nucleotide sequence has been determined (Peoples and Sinskey, *Mol. Microbiol.* 3:349-357 (1989)) and the gene has been expressed in *E. coli*. Substrate specificity studies on the gene led to the conclusion that it could accept 3-oxopropionyl-CoA as an alternate substrate (Ploux et al., *Eur. J. Biochem.* 174:177-182 (1988)). Genbank information related to these genes is summarized in Table 3 below.

TABLE 3

| Gene | GI # | Accession No. | Organism |
| --- | --- | --- | --- |
| hbd | 18266893 | P52041.2 | *Clostridium acetobutylicum* |
| Hbd2 | 146348271 | EDK34807.1 | *Clostridium kluyveri* |
| Hbd1 | 146345976 | EDK32512.1 | *Clostridium kluyveri* |
| HSD17B10 | 3183024 | O02691.3 | *Bos taurus* |
| phaB | | | *Rhodobacter sphaeroides* |
| phbB | | | *Zoogloea ramigera* |

A number of similar enzymes have been found in other species of *Clostridia* and in *Metallosphaera sedula* (Berg et al., *Science* 318:1782-1786 (2007)) as shown in Table 4.

TABLE 4

| Gene | GI # | Accession No. | Organism |
| --- | --- | --- | --- |
| hbd | 15895965 | NP_349314.1 | *Clostridium acetobutylicum* |
| hbd | 20162442 | AAM14586.1 | *Clostridium beijerinckii* |
| Msed_1423 | 146304189 | YP_001191505 | *Metallosphaera sedula* |
| Msed_0399 | 146303184 | YP_001190500 | *Metallosphaera sedula* |
| Msed_0389 | 146303174 | YP_001190490 | *Metallosphaera sedula* |
| Msed_1993 | 146304741 | YP_001192057 | *Metallosphaera sedula* |

There are various alcohol dehydrogenases for converting 2-maleylacetate to cis-3-hydroxy-4-hexenoate (FIG. 2, Step P), 2-fumarylacetate to trans-3-hydroxy-4-hexenoate (FIG. 2, Step D), 4-oxalocrotonate to 5-hydroxyhex-2-enedioate (FIG. 3, Step C) and 4-hydroxy-2-oxohexanedioate to 2,4-dihydroxyadipate (FIG. 3, Step E). Two enzymes capable of converting an oxoacid to a hydroxyacid are encoded by the malate dehydrogenase (mdh) and lactate dehydrogenase (ldhA) genes in *E. coli*. In addition, lactate dehydrogenase from *Ralstonia eutropha* has been shown to demonstrate high activities on substrates of various chain lengths such as lactate, 2-oxobutyrate, 2-oxopentanoate and 2-oxoglutarate (Steinbuchel and Schlegel, *Eur. J. Biochem.* 130:329-334 (1983)). Conversion of alpha-ketoadipate into alpha-hydroxyadipate can be catalyzed by 2-ketoadipate reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977)). An additional gene for these steps is the mitochondrial 3-hydroxybutyrate dehydrogenase (bdh) from the human heart which has been cloned and characterized (Marks et al., *J. Biol. Chem.* 267:15459-15463 (1992)). This enzyme is a dehydrogenase that operates on a 3-hydroxyacid. Another exemplary alcohol dehydrogenase converts acetone to isopropanol as was shown in *C. beijerinckii* (Ismail et al., *Eur. J. Biochem.* 270:3047-3054 (2003)) and *T. brockii* (Lamed and Zeikus, *Biochem. J.* 195:183-190 (1981); Peretz and Burstein, *Biochemistry* 28:6549-6555 (1989)). Genbank information related to these genes is summarized in Table 5 below.

TABLE 5

| Gene | GI # | Accession No. | Organism |
| --- | --- | --- | --- |
| mdh | 1789632 | AAC76268.1 | *Escherichia coli* |
| ldhA | 16129341 | NP_415898.1 | *Escherichia coli* |
| bdh | 177198 | AAA58352.1 | *Homo sapiens* |
| adh | 60592974 | AAA23199.2 | *Clostridium beijerinckii* |
| adh | 113443 | P14941.1 | *Thermoanaerobacter brockii* |

Enzymes in the 1.2.1 family are NAD(P)+-dependent oxidoreductases that convert aldehydes to acids. Reactions catalyzed by enzymes in this family include the oxidation of 6-OHE (FIG. 4, Step F), 2-aminoadipate semialdehyde (FIG. 5, Step B) and 3-aminoadipate semialdehyde (FIG. 5, Step G) to their corresponding acids. An exemplary enzyme is the NAD+-dependent aldehyde dehydrogenases (EC 1.2.1.3). Two aldehyde dehydrogenases found in human liver, ALDH-1 and ALDH-2, have broad substrate ranges for a variety of aliphatic, aromatic and polycyclic aldehydes (Klyosov, A. A., *Biochemistry* 35:4457-4467 (1996)). Active ALDH-2 has been efficiently expressed in *E. coli* using the GroEL proteins as chaperonins (Lee et al., *Biochem. Biophys. Res. Commun.* 298:216-224 (2002)). The rat mitochondrial aldehyde dehydrogenase also has a broad substrate range that includes the enoyl-aldehyde crotonaldehyde (Siew et al., *Arch. Biochem. Biophys.* 176:638-649 (1976)). The *E. coli* gene astD also encodes an NAD+-dependent aldehyde dehydrogenase active on succinic semialdehyde (Kuznetsova et al., *FEMS Microbiol. Rev.* 29:263-279 (2005)). Genbank information related to these genes is summarized in Table 5 below.

TABLE 6

| Gene | GI # | Accession No. | Organism |
|------|------|---------------|----------|
| ALDH-2 | 118504 | P05091.2 | *Homo sapiens* |
| ALDH-2 | 14192933 | NP_115792.1 | *Rattus norvegicus* |
| astD | 3913108 | P76217.1 | *Escherichia coli* |

Two transformations in FIG. 4 require conversion of a 2-ketoacid to an acyl-CoA (FIG. 4, Steps D and E) by an enzyme in the EC class 1.2.1. Such reactions are catalyzed by multi-enzyme complexes that catalyze a series of partial reactions which result in acylating oxidative decarboxylation of 2-keto-acids. Exemplary enzymes that can be used include 1) branched-chain 2-keto-acid dehydrogenase, 2) alpha-ketoglutarate dehydrogenase, and 3) the pyruvate dehydrogenase multienzyme complex (PDHC). Each of the 2-keto-acid dehydrogenase complexes occupies positions in intermediary metabolism, and enzyme activity is typically tightly regulated (Fries et al., *Biochemistry* 42:6996-7002 (2003)). The enzymes share a complex but common structure composed of multiple copies of three catalytic components: alpha-ketoacid decarboxylase (E1), dihydrolipoamide acyltransferase (E2) and dihydrolipoamide dehydrogenase (E3). The E3 component is shared among all 2-keto-acid dehydrogenase complexes in an organism, while the E1 and E2 components are encoded by different genes. The enzyme components are present in numerous copies in the complex and utilize multiple cofactors to catalyze a directed sequence of reactions via substrate channeling. The overall size of these dehydrogenase complexes is very large, with molecular masses between 4 and 10 million Da (i.e., larger than a ribosome).

Activity of enzymes in the 2-keto-acid dehydrogenase family is normally low or limited under anaerobic conditions in *E. coli*. Increased production of NADH (or NADPH) could lead to a redox-imbalance, and NADH itself serves as an inhibitor to enzyme function. Engineering efforts have increased the anaerobic activity of the *E. coli* pyruvate dehydrogenase complex (Kim et al., *Appl. Environ. Microbiol.* 73:1766-1771 (2001); Kim et al., *J. Bacteriol.* 190:3851-3858 (2008); Zhou et al., *Biotechnol. Lett.* 30:335-342 (2008)). For example, the inhibitory effect of NADH can be overcome by engineering an H322Y mutation in the E3 component (Kim et al., *J. Bacteriol.* 190:3851-3858 (2008)). Structural studies of individual components and how they work together in complex provide insight into the catalytic mechanisms and architecture of enzymes in this family (Aevarsson et al., *Nat. Struct. Biol.* 6:785-792 (1999); Zhou et al., *Proc. Natl. Acad. Sci. U.S.A.* 98:14802-14807 (2001)). The substrate specificity of the dehydrogenase complexes varies in different organisms, but generally branched-chain keto-acid dehydrogenases have the broadest substrate range.

Alpha-ketoglutarate dehydrogenase (AKGD) converts alpha-ketoglutarate to succinyl-CoA and is the primary site of control of metabolic flux through the TCA cycle (Hansford, R. G., *Curr. Top. Bioenerg.* 10:217-278 (1980)). Encoded by genes sucA, sucB and lpd in *E. coli*, AKGD gene expression is downregulated under anaerobic conditions and during growth on glucose (Park et al., *Mol. Microbiol.* 15:473-482 (1993)). Although the substrate range of AKGD is narrow, structural studies of the catalytic core of the E2 component pinpoint specific residues responsible for substrate specificity (Knapp et al., *J. Mol. Biol.* 280:655-668 (1998)). The *Bacillus subtilis* AKGD, encoded by odhAB (E1 and E2) and pdhD (E3, shared domain), is regulated at the transcriptional level and is dependent on the carbon source and growth phase of the organism (Resnekov et al., *Mol. Gen. Genet.* 234:285-296 (1992)). In yeast, the LPD1 gene encoding the E3 component is regulated at the transcriptional level by glucose (Roy and Dawes, *J. Gen. Microbiol.* 133:925-933 (1987)). The E1 component, encoded by KGD1, is also regulated by glucose and activated by the products of HAP2 and HAP3 (Repetto and Tzagoloff, *Moll. Cell. Biol.* 9:2695-2705 (1989)). The AKGD enzyme complex, inhibited by products NADH and succinyl-CoA, is known in mammalian systems, as impaired function of has been linked to several neurological diseases (Tretter and dam-Vizi, *Philos. Trans. R. Soc. Lond B Biol. Sci.* 360:2335-2345 (2005)). Genbank information related to these genes is summarized in Table 7 below.

TABLE 7

| Gene | GI # | Accession No. | Organism |
|------|------|---------------|----------|
| sucA | 16128701 | NP_415254.1 | *Escherichia coli* |
| sucB | 16128702 | NP_415255.1 | *Escherichia coli* |
| lpd | 16128109 | NP_414658.1 | *Escherichia coli* |
| odhA | 51704265 | P23129.2 | *Bacillus subtilis* |
| odhB | 129041 | P16263.1 | *Bacillus subtilis* |
| pdhD | 118672 | P21880.1 | *Bacillus subtilis* |
| KGD1 | 6322066 | NP_012141.1 | *Saccharomyces cerevisiae* |
| KGD2 | 6320352 | NP_010432.1 | *Saccharomyces cerevisiae* |
| LPD1 | 14318501 | NP_116635.1 | *Saccharomyces cerevisiae* |

Branched-chain 2-keto-acid dehydrogenase complex (BCKAD), also known as 2-oxoisovalerate dehydrogenase, participates in branched-chain amino acid degradation pathways, converting 2-keto acids derivatives of valine, leucine and isoleucine to their acyl-CoA derivatives and $CO_2$. The complex has been studied in many organisms including *Bacillus subtilis* (Wang et al., *Eur. J. Biochem.* 213:1091-1099 (1993)), *Rattus norvegicus* (Namba et al., *J. Biol. Chem.* 244:4437-4447 (1969)) and *Pseudomonas putida* (Sokatch et al., *J. Bacteriol.* 148:647-652 (1981)). In *Bacillus subtilis* the enzyme is encoded by genes pdhD (E3 component), bfmBB (E2 component), bfmBAA and bfmBAB (E1 component) (Wang et al., *Eur. J. Biochem.* 213:1091-1099 (1993)). In mammals, the complex is regulated by phosphorylation by specific phosphatases and protein kinases. The complex has been studied in rat hepatocytes (Chicco et al., *J. Biol. Chem.* 269:19427-19434 (1994)) and is encoded by genes Bckdha (E1 alpha), Bckdhb (E1 beta), Dbt (E2), and Dld (E3). The E1 and E3 components of the *Pseudomonas putida* BCKAD complex have been crystallized (Aevarsson et al., *Nat. Struct. Biol.* 6:785-792 (1999); Mattevi et al., *Science* 255:1544-1550 (1992)) and the enzyme complex has been studied (Sokatch et al., *J. Bacteriol.* 148:647-652 (1981)). Transcription of the *P. putida* BCKAD genes is activated by the gene product of bkdR (Hesslinger et al., *Mol. Microbiol.* 27:477-492 (1998)). In some organisms including *Rattus norvegicus* (Paxton et al., *Biochem. J.* 234:295-303 (1986)) and *Saccharomyces cerevisiae* (Sinclair et al., *Biochem. Mol. Biol. Int.* 31:911-9122 (1993)), this complex has been shown to have a broad substrate range that includes linear oxo-acids such as 2-oxobutanoate and alpha-ketoglutarate, in addition to the branched-chain amino acid precursors. The active site of the bovine BCKAD was engineered to favor alternate substrate acetyl-CoA (Meng and Chuang, *Biochemistry* 33:12879-12885 (1994)). Genbank information related to these genes is summarized in Table 8 below.

TABLE 8

| Gene | GI # | Accession No. | Organism |
| --- | --- | --- | --- |
| bfmBB | 16079459 | NP_390283.1 | *Bacillus subtilis* |
| bfmBAA | 16079461 | NP_390285.1 | *Bacillus subtilis* |
| bfmBAB | 16079460 | NP_390284.1 | *Bacillus subtilis* |
| pdhD | 118672 | P21880.1 | *Bacillus subtilis* |
| lpdV | 118677 | P09063.1 | *Pseudomonas putida* |
| bkdB | 129044 | P09062.1 | *Pseudomonas putida* |
| bkdA1 | 26991090 | NP_746515.1 | *Pseudomonas putida* |
| bkdA2 | 26991091 | NP_746516.1 | *Pseudomonas putida* |
| Bckdha | 77736548 | NP_036914.1 | *Rattus norvegicus* |
| Bckdhb | 158749538 | NP_062140.1 | *Rattus norvegicus* |
| Dbt | 158749632 | NP_445764.1 | *Rattus norvegicus* |
| Dld | 40786469 | NP_955417.1 | *Rattus norvegicus* |

The pyruvate dehydrogenase complex, catalyzing the conversion of pyruvate to acetyl-CoA, has also been studied. In the *E. coli* enzyme, specific residues in the E1 component are responsible for substrate specificity (Bisswanger, H., *J. Biol. Chem.* 256:815-822 (1981); Bremer, J., *Eur. J. Biochem.* 8:535-540 (1969); Gong et al., *J. Biol. Chem.* 275:13645-13653 (2000)). As mentioned previously, enzyme engineering efforts have improved the *E. coli* PDH enzyme activity under anaerobic conditions (Kim et al., *Appl. Environ. Microbiol.* 73:1766-1771 (2007); Kim et al., *J. Bacteriol.* 190:3851-3858 (2008); Zhou et al., *Biotechnol. Letter.* 30:335-342 (2008)). In contrast to the *E. coli* PDH, the *B. subtilis* complex is active and required for growth under anaerobic conditions (Nakano et al., *J. Bacteriol.* 179:6749-6755 (1997)). The *Klebsiella pneumoniae* PDH, characterized during growth on glycerol, is also active under anaerobic conditions (Menzel et al., *J. Biotechnol.* 56:135-142 (1997)). Crystal structures of the enzyme complex from bovine kidney (Zhou et al., *Proc. Natl. Acad. Sci. U.S.A.* 98:14802-14807 (2001)) and the E2 catalytic domain from *Azotobacter vinelandii* are available (Mattevi et al., *Science* 255:1544-1550 (1992)). Some mammalian PDH enzymes complexes can react on alternate substrates such as 2-oxobutanoate, although comparative kinetics of *Rattus norvegicus* PDH and BCKAD indicate that BCKAD has higher activity on 2-oxobutanoate as a substrate (Paxton et al., *Biochem. J.* 234:295-303 (1986)). Genbank information related to these genes is summarized in Table 9 below.

TABLE 9

| Gene | GI # | Accession No. | Organism |
| --- | --- | --- | --- |
| aceE | 16128107 | NP_414656.1 | *Escherichia coli* |
| aceF | 16128108 | NP_414657.1 | *Escherichia coli* |
| lpd | 16128109 | NP_414658.1 | *Escherichia coli* |
| pdhA | 3123238 | P21881.1 | *Bacillus subtilis* |
| pdhB | 129068 | P21882.1 | *Bacillus subtilis* |
| pdhC | 129054 | P21883.2 | *Bacillus subtilis* |
| pdhD | 118672 | P21880.1 | *Bacillus subtilis* |
| aceE | 152968699 | YP_001333808.1 | *Klebsiella pneumonia* |
| aceF | 152968700 | YP_001333809.1 | *Klebsiella pneumonia* |
| lpdA | 152968701 | YP_001333810.1 | *Klebsiella pneumonia* |
| Pdha1 | 124430510 | NP_001004072.2 | *Rattus norvegicus* |
| Pdha2 | 16758900 | NP_446446.1 | *Rattus norvegicus* |
| Dlat | 78365255 | NP_112287.1 | *Rattus norvegicus* |
| Dld | 40786469 | NP_955417.1 | *Rattus norvegicus* |

As an alternative to the large multienzyme 2-keto-acid dehydrogenase complexes described above, some anaerobic organisms utilize enzymes in the 2-ketoacid oxidoreductase family (OFOR) to catalyze acylating oxidative decarboxylation of 2-keto-acids. Unlike the dehydrogenase complexes, these enzymes contain iron-sulfur clusters, utilize different cofactors, and use ferredoxin or flavodoxin as electron acceptors in lieu of NAD(P)H. While most enzymes in this family are specific to pyruvate as a substrate (POR) some 2-keto-acid:ferredoxin oxidoreductases have been shown to accept a broad range of 2-ketoacids as substrates including alpha-ketoglutarate and 2-oxobutanoate (Fukuda and Wakagi, *Biochim. Biophys. Acta.* 1597_74-80 (2002); Zhang et al., *J. Biochem.* 120:587-599 (1996)). One such enzyme is the OFOR from the thermoacidophilic archaeon *Sulfolobus tokodaii* 7, which contains an alpha and beta subunit encoded by gene ST2300 (Fukuda and Wakagi, supra; Zhang et al., supra). A plasmid-based expression system has been developed for efficiently expressing this protein in *E. coli* (Fukuda et al., *Eur. J. Biochem.* 268:5639-5646 (2001)) and residues involved in substrate specificity were determined (Fukuda and Wakagi, supra). Two OFORs from *Aeropyrum pernix* str. K1 have also been recently cloned into *E. coli*, characterized, and found to react with a broad range of 2-oxoacids (Nishizawa et al., *FEBS Lett.* 579_2319-2322 (2005)). The gene sequences of these OFOR enzymes are available, although they do not have GenBank identifiers assigned to date. There is bioinformatic evidence that similar enzymes are present in all archaea, some anaerobic bacteria and amitochondrial eukarya (Fukuda and Wakagi, supra). This class of enzyme is also interesting from an energetic standpoint, as reduced ferredoxin could be used to generate NADH by ferredoxin-NAD reductase (Petitdemange et al., *Biochim. Biophys. Acta* 421:334-337 (1976)). Also, since most of the enzymes are designed to operate under anaerobic conditions, less enzyme engineering may be required relative to enzymes in the 2-keto-acid dehydrogenase complex family for activity in an anaerobic environment. Genbank information related to these genes is summarized in Table 10 below.

TABLE 10

| Gene | GI # | Accession No. | Organism |
| --- | --- | --- | --- |
| ST2300 | 15922633 | NP_378302.1 | *Sulfolobus tokodaii* 7 |

Three transformations fall into the category of oxidoreductases that reduce an alkene to an alkane (EC 1.3.1.-). The conversion of beta-ketoadipate to 2-maleylacetate (FIG. 2, Step O) is also catalyzed by the 2-enoate oxidoreductase maleylacetate reductase (MAR). A similar enzyme converts beta-ketoadipate to 2-fumarylacetate (FIG. 2, Step C). The oxidization of 2,3-dehydroadipate to muconate (FIG. 2, Step N) is catalyzed by a 2-enoate oxidoreductase with muconate reductase functionality.

2-Enoate oxidoreductase enzymes are known to catalyze the NAD(P)H-dependent reduction and oxidation of a wide variety of α,β-unsaturated carboxylic acids and aldehydes (Rohdich et al., *J. Biol. Chem.* 276:5779-5787 (2001)). In the recently published genome sequence of *C. kluyveri*, 9 coding sequences for enoate reductases were reported, out of which one has been characterized (Seedorf et al., *Proc. Natl. Acad. Sci. U.S.A.* 105:2128-2133 (2008)). The enr genes from both *C. tyrobutyricum* and *M. thermoaceticum* have been cloned and sequenced and show 59% identity to each other. The former gene is also found to have approximately 75% similarity to the characterized gene in *C. kluyveri* (Giesel and Simon, *Arch. Microbiol.* 135:51-57 (1983)). It has been reported based on these sequence results that enr is very similar to the dienoyl CoA reductase in *E. coli* (fadH) (Rohdich et al., *J. Biol. Chem.* 276:5779-5787 (2001)). The *C. thermoaceticum* enr gene has also been expressed in a catalytically active form in *E. coli* (Rohdich et al., supra). Genbank information related to these genes is summarized in Table 11 below.

TABLE 11

| Gene | GI # | Accession No. | Organism |
| --- | --- | --- | --- |
| enr | 169405742 | ACA54153.1 | *Clostridium botulinum* A3 str |
| enr | 2765041 | CAA71086.1 | *Clostridium tyrobutyricum* |
| enr | 3402834 | CAA76083.1 | *Clostridium kluyveri* |
| enr | 83590886 | YP_430895.1 | *Moorella thermoacetica* |
| fadH | 16130976 | NP_417552.1 | *Escherichia coli* |

MAR is a 2-enoate oxidoreductase catalyzing the reversible reduction of 2-maleylacetate (cis-4-oxohex-2-enedioate) to 3-oxoadipate (FIG. 2, Step O). MAR enzymes naturally participate in aromatic degradation pathways (Camara et al., *J. Bacteriol.* 191:4905-4915 (2009); Huang et al., *Appl. Environ. Microbiol.* 72:7238-7245 (2006); Kaschabek and Reineke, J. Bacteriol. 177:320-325 (1995); Kaschabek and Reineke, *J. Bacteriol.* 175:6075-6081 (1993)). The enzyme activity was identified and characterized in *Pseudomonas* sp. strain B13 (Kaschabek and Reineke, (1995) supra; Kaschabek and Reineke, (1993) supra), and the coding gene was cloned and sequenced (Kasberg et al., *J. Bacteriol.* 179:3801-3803 (1997)). Additional MAR genes include clcE gene from *Pseudomonas* sp. strain B13 (Kasberg et al., supra), macA gene from *Rhodococcus opacus* (Seibert et al., *J. Bacteriol.* 175:6745-6754 (1993)), the macA gene from *Ralstonia eutropha* (also known as *Cupriavidus necator*) (Seibert et al., *Microbiology* 150:463-472 (2004)), tfdFII from *Ralstonia eutropha* (Seibert et al., (1993) supra) and NCgl1112 in *Corynebacterium glutamicum* (Huang et al., *Appl. Environ Microbiol.* 72:7238-7245 (2006)). A MAR in *Pseudomonas reinekei* MT1, encoded by ccaD, was recently identified and the nucleotide sequence is available under the DBJ/EMBL GenBank accession number EF159980 (Camara et al., *J. Bacteriol.* 191:4905-4915 (2009). Genbank information related to these genes is summarized in Table 12 below.

TABLE 12

| Gene | GI # | Accession No. | Organism |
| --- | --- | --- | --- |
| clcE | 3913241 | O30847.1 | *Pseudomonas* sp. strain B13 |
| macA | 7387876 | O84992.1 | *Rhodococcus opacus* |
| macA | 5916089 | AAD55886 | *Cupriavidus necator* |
| tfdFII | 1747424 | AC44727.1 | *Ralstonia eutropha* JMP134 |
| NCgl1112 | 19552383 | NP_600385 | *Corynebacterium glutamicum* |
| ccaD | | | *Pseudomonas reinekei* MT1 |

In Step R of FIG. 2, 2-maleylacetate is transaminated to form 3-amino-4-hexanoate. The conversion of 2-fumarylacetate to trans-3-amino-4-hexenedioate is a similar transformation (FIG. 2, Step F). These reactions are performed by aminating oxidoreductases in the EC class 1.4.1. Enzymes in this EC class catalyze the oxidative deamination of alpha-amino acids with NAD+ or NADP+ as acceptor, and the reactions are typically reversible. Exemplary enzymes include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (Korber et al., J. Mol. Biol. 234:1270-1273 (1993); McPherson and Wootton, *Nucleic Acids Res.* 11:5257-5266 (1983)), gdh from *Thermotoga maritime* (Kort et al., *Extremophiles* 1:52-60-1997); Lebbink et al., *J. Mol. Biol.* 280:287-296 (1998); Lebbink et al., *J. Mol. Biol.* 289:357-369 (1999)), and gdhA1 from *Halobacterium salinarum* (Ingoldsby et al., *Gene* 349:237-244 (2005)) catalyze the reversible conversion of glutamate to 2-oxoglutarate and ammonia, while favoring NADP(H), NAD(H), or both, respectively. The ldh gene of *Bacillus cereus* encodes the LeuDH protein that has a wide of range of substrates including leucine, isoleucine, valine, and 2-aminobutanoate (Ansorge and Kula, *Biotechnol. Bioeng.* 68:557-562 (2000); Stoyan et al., *J. Biotechnol.* 54:77-80 (1997)). The nadX gene from *Thermotoga maritima* encoding for the aspartate dehydrogenase is involved in the biosynthesis of NAD (Yang et al., *J. Biol. Chem.* 278:8804-8808 (2003)). Genbank information related to these genes is summarized in Table 13 below.

TABLE 13

| Gene | GI # | Accession No. | Organism |
| --- | --- | --- | --- |
| gdhA | 118547 | P00370 | *Escherichia coli* |
| gdh | 6226595 | P96110.4 | *Thermotoga maritima* |
| gdhA1 | 15789827 | NP_279651.1 | *Halobacterium salinarum* |
| ldh | 61222614 | P0A393 | *Bacillus cereus* |
| nadX | 15644391 | NP_229443.1 | *Thermotoga maritima* |

The conversions of lysine to 2-aminoadipate semialdehyde (FIG. 5, Step A) and 3,6-diaminohexanoate to 3-aminoadipate semialdehyde (FIG. 5, Step F) are catalyzed by aminating oxidoreductases that transform primary amines to their corresponding aldehydes. The lysine 6-dehydrogenase (deaminating), encoded by the lysDH genes, catalyze the oxidative deamination of the 6-amino group of L-lysine to form 2-aminoadipate-6-semialdehyde, which can spontaneously and reversibly cyclize to form $\Delta^1$-piperideine-6-carboxylate (Misono and Nagasaki, *J. Bacteriol.* 150:398-401 (1982)). Exemplary enzymes are found in *Geobacillus stearothermophilus* (Heydari et al., *Appl. Environ. Microbiol.* 70:937-942 (2004)), *Agrobacterium tumefaciens* (Hashimoto et al., *J. Biochem.* 106:76-80 (1989), Misono and Nagasaki, supra), and *Achromobacter denitrificans* (Ruldeekulthamrong et al., BMB. Rep. 41:790-795 (2008)). Such enzymes can convert 3,6-diaminohexanoate to 3-aminoadipate semialdehyde given the structural similarity between 3,6-diaminohexanoate and lysine. Genbank information related to these genes is summarized in Table 14 below.

TABLE 14

| Gene | GI # | Accession No. | Organism |
| --- | --- | --- | --- |
| lysDH | 13429872 | BAB39707 | *Geobacillus stearothermophilus* |
| lysDH | 15888285 | NP_353966 | *Agrobacterium tumefaciens* |
| lysDH | 74026644 | AAZ94428 | *Achromobacter denitrificans* |

FIG. 2, step A uses a 3-oxoadipyl-CoA thiolase, or equivalently, succinyl CoA:acetyl CoA acyl transferase (β-ketothiolase). The gene products encoded by pcaF in *Pseudomonas* strain B13 (Kaschabek et al., *J. Bacteriol.* 184:207-215 (2002)), phaD in *Pseudomonas putida* U (Olivera et al., *Proc. Natl. Acad. Sci. U.S.A.* 95:6419-6424 (1998)), paaE in *Pseudomonas fluorescens* ST (Di et al., *Arch. Micbrobiol.* 188:117-125 (2007)), and paaJ from *E. coli* (Nogales et al., *Microbiology* 153:357-365 (2007)) catalyze the conversion of 3-oxoadipyl-CoA into succinyl-CoA and acetyl-CoA during the degradation of aromatic compounds such as phenylacetate or styrene. Since beta-ketothiolase enzymes catalyze reversible transformations, these enzymes can also be employed for the synthesis of 3-oxoadipyl-CoA. Several beta-ketothiolases were shown to have significant and selective activities in the oxoadipyl-CoA forming direction as shown in Example I below including bkt from *Pseudomonas putida*, pcaF and bkt from *Pseudomonas aeruginosa* PAO1, bkt from *Burkholderia ambifaria* AMMD, paaJ from *E. coli*, and phaD from *P. putida*. Genbank information related to these genes is summarized in Table 15 below.

TABLE 15

| Gene | GI # | Accession No. | Organism |
| --- | --- | --- | --- |
| paaJ | 16129358 | NP_415915.1 | *Escherichia coli* |
| pcaF | 17736947 | AAL02407 | *Pseudomonas knackmussii* (B13) |
| phaD | 3253200 | AAC24332.1 | *Pseudomonas putida* |
| pcaF | 506695 | AAA85138.1 | *Pseudomonas putida* |
| paaE | 106636097 | ABF82237.1 | *Pseudomonas fluorescens* |
| bkt | | | *Burkholderia ambifaria* AMMD |
| bkt | | | *Pseudomonas aeruginosa* PAO1 |
| pcaF | | | *Pseudomonas aeruginosa* PAO1 |

The acylation of ketoacids HODH and OHED to their corresponding CoA derivatives (FIG. 4, Steps D and E) and concurrent release of formate, is catalyzed by formate C-acyltransferase enzymes in the EC class 2.3.1. Enzymes in this class include pyruvate formate-lyase and ketoacid formate-lyase. Pyruvate formate-lyase (PFL, EC 2.3.1.54), encoded by pflB in *E. coli*, converts pyruvate into acetyl-CoA and formate. The active site of PFL contains a catalytically essential glycyl radical that is posttranslationally activated under anaerobic conditions by PFL-activating enzyme (PFL-AE, EC 1.97.1.4) encoded by pflA (Knappe et al., *Proc. Natl. Acad. Sci. U.S.A.* 81:1332-1335 (1984); Wong et al., *Biochemistry* 32:14102-14110 (1993)). A pyruvate formate-lyase from *Archaeglubus fulgidus* encoded by pflD has been cloned, expressed in *E. coli* and characterized (Lehtio and Goldman, *Protein Eng Des Sel* 17:545-552 (2004)). The crystal structures of the *A. fulgidus* and *E. coli* enzymes have been resolved (Lehtio et al., *J. Mol. Biol.* 357:221-235 (2006); Leppanen et al., *Structure* 7:733-744 (1999)). Additional PFL and PFL-AE enzymes are found in *Clostridium pasteurianum* (Weidner and Sawyers, *J. Bacteriol.* 178:2440-2444 (1996)) and the eukaryotic alga *Chlamydomonas reinhardtii* (Hemschemeier et al., *Eukaryot. Cell* 7:518_526 (2008)). Keto-acid formate-lyase (EC 2.3.1.-), also known as 2-ketobutyrate formate-lyase (KFL) and pyruvate formate-lyase 4, is the gene product of tdcE in *E. coli*. This enzyme catalyzes the conversion of 2-ketobutyrate to propionyl-CoA and formate during anaerobic threonine degradation, and can also substitute for pyruvate formate-lyase in anaerobic catabolism (Simanshu et al., *J. Biosci.* 32:1195-1206 (2007)). The enzyme is oxygen-sensitive and, like PflB, requires post-translational modification by PFL-AE to activate a glycyl radical in the active site (Hesslinger et al., *Mol. Microbiol.* 27:477-492 (1998)). Genbank information related to these genes is summarized in Table 16 below.

TABLE 16

| Gene | GI # | Accession No. | Organism |
| --- | --- | --- | --- |
| pflB | 16128870 | NP_415423.1 | *Escherichia coli* |
| pflA | 16128869 | NP_415422.1 | *Escherichia coli* |
| tdcE | 48994926 | AAT48170.1 | *Escherichia coli* |
| pflD | 11499044 | NP_070278.1 | *Archaeglubus fulgidus* |
| pfl | 2500058 | Q46266.1 | *Clostridium pasteurianum* |
| act | 1072362 | CAA63749.1 | *Clostridium pasteurianum* |
| pfl1 | 159462978 | XP_001689719.1 | *Chlamydomonas reinhardtii* |
| pflA1 | 159485246 | XP_001700657.1 | *Chlamydomonas reinhardtii* |

Several reactions in FIGS. 2 and 5 are catalyzed by aminotransferases in the EC class 2.6.1 (FIG. 2, Steps F and R and FIG. 5, Steps A and F). Such enzymes reversibly transfer amino groups from aminated donors to acceptors such as pyruvate and alpha-ketoglutarate. The conversion of lysine to 2-aminoadipate (FIG. 5, Step A) is naturally catalyzed by lysine-6-aminotransferase (EC 2.6.1.36). This enzyme function has been demonstrated in yeast and bacteria. Enzymes from *Candida utilis* (Hammer et al *J. Basic Microbiol.* 32:21-27 (1992)), *Flavobacterium lutescens* (Fuji et al. *J. Biochem.* 128:391-397 (2000)) and *Streptomyces clavuligenus* (Romero et al. *J. Ind. Microbiol. Biotechnol.* 18:241-246 (1997)) have been characterized. A recombinant lysine-6-aminotransferase from *S. clavuligenus* was functionally expressed in *E. coli* (Tobin et al *J. Bacteriol.* 173:6223-6229 (1991)). The *F. lutescens* enzyme is specific to alpha-ketoglutarate as the amino acceptor (Soda et al. *Biochemistry* 7:4110-4119 (1968)). Lysine-6-aminotransferase is also an enzyme that can catalyze the transamination of 3,6-diaminohexanoate (FIG. 5, Step F), as this substrate is structurally similar to lysine. Genbank information related to these genes is summarized in Table 17 below.

TABLE 17

| Gene | GI # | Accession No. | Organism |
| --- | --- | --- | --- |
| lat | 10336502 | BAB13756.1 | *Flavobacterium lutescens* |
| lat | 153343 | AAA26777.1 | *Streptomyces clavuligenus* |

In Steps R and F of FIG. 2 the beta-ketones of 2-maleylacetate and 2-fumarylacetate, respectively, are converted to secondary amines. Beta-alanine/alpha-ketoglutarate aminotransferase (WO08027742) reacts with beta-alanine to form malonic semialdehyde, a 3-oxoacid similar in structure to 2-maleylacetate. The gene product of SkPYD4 in *Saccharomyces kluyveri* was shown to preferentially use beta-alanine as the amino group donor (Andersen and Hansen, *Gene* 124:105-109 (1993)). SkUGA1 encodes a homologue of *Saccharomyces cerevisiae* GABA aminotransferase, UGA1 (Ramos et al., *Eur. J. Biochem.* 149:401-404 (1985)), whereas SkPYD4 encodes an enzyme involved in both -alanine and GABA transamination (Andersen and Hansen, supra). 3-Amino-2-methylpropionate transaminase catalyzes the transformation from methylmalonate semialdehyde to 3-amino-2-methylpropionate. The enzyme has been characterized in *Rattus norvegicus* and *Sus scrofa* and is encoded by Abat (Kakimoto et al., Biochim. Biophys. Acta 156:374-380 (1968); Tamaki et al., *Methods Enzymol.* 324: 376-389 (2000)). Genbank information related to these genes is summarized in Table 18 below.

TABLE 18

| Gene | GI # | Accession No. | Organism |
| --- | --- | --- | --- |
| SkyPYD4 | 98626772 | ABF58893.1 | *Lachancea kluyveri* |
| SkUGA1 | 98626792 | ABF58894.1 | *Lachancea kluyveri* |
| UGA1 | 6321456 | NP_011533.1 | *Saccharomyces cerevisiae* |
| Abat | 122065191 | P50554.3 | *Rattus norvegicus* |
| Abat | 120968 | P80147.2 | *Sus scrofa* |

Another enzyme that can catalyze the aminotransferase reactions in FIGS. 2 and 5 is gamma-aminobutyrate transaminase (GABA transaminase), which naturally interconverts succinic semialdehyde and glutamate to 4-aminobutyrate and alpha-ketoglutarate and is known to have a broad substrate range (Liu et al., *Biochemistry* 43:10896-10905 (2004); Shigeoka and Nakano, *Arch. Biochem. Biophys.* 288:22-28 (1991); Schulz et al., *Appl. Environ. Microbiol.* 56:1-6 (1990)). *E. coli* has two GABA transaminases, encoded by gabT (Bartsch and Schulz, *J. Bacteriol.* 172: 7035-7042 (1990)) and puuE (Kurihara et al., *J. Biol. Chem.* 280:4602-4608 (2005)). GABA transaminases in *Mus musculus*, *Pseudomonas fluorescens*, and *Sus scrofa* have been shown to react with alternate substrates (Cooper, A. J., *Methods Enzymol.* 113:80-82 (1985); Scott and Jakoby, *J. Biol. Chem.* 234:932-936 (19590. Genbank information related to these genes is summarized in Table 19 below.

TABLE 19

| Gene | GI # | Accession No. | Organism |
| --- | --- | --- | --- |
| gabT | 16130576 | NP_417148.1 | *Escherichia coli* |
| puuE | 16129263 | P_415818.1 | *Escherichia coli* |
| aba | 37202121 | NP_766549.2 | *Mus musculus* |
| gabT | 70733692 | YP_257332.1 | *Pseudomonas fluorescens* |
| aba | 47523600 | NP_999428.1 | *Sus scrofa* |

CoA transferases catalyze the reversible transfer of a CoA moiety from one molecule to another. Conversion of beta-ketoadipyl-CoA to beta-ketoadipate (FIG. 2, Step B) is accompanied by the acylation of succinate by beta-ketoadipyl-CoA transferase. The de-acylation of 2,3-dehydroadipyl-CoA (FIG. 2, Step M and FIG. 4, Step H) can also be catalyzed by an enzyme in the 2.8.3 family.

Beta-ketoadipyl-CoA transferase (EC 2.8.3.6), also known as succinyl-CoA:3:oxoacid-CoA transferase, is encoded by pcaI and pcaJ in *Pseudomonas putida* (Kaschabek et al., *J. Bacteriol.* 184:207-215 (2002)). Similar enzymes based on homology exist in *Acinetobacter* sp. ADP1 (Kowalchuk et al., *Gene* 146:23-30 (1994)). Additional exemplary succinyl-CoA:3:oxoacid-CoA transferases are present in *Helicobacter pylori* (Corthesy-Theulaz et al., *J. Biol. Chem.* 272:25659-25667 (1997)) and *Bacillus subtilis* (Stols et al., *Protein Expr. Purif.* 53:396-403 (2007)). Genbank information related to these genes is summarized in Table 20 below.

TABLE 20

| Gene | GI # | Accession No. | Organism |
| --- | --- | --- | --- |
| pcaI | 24985644 | AAN69545.1 | *Pseudomonas putida* |
| pcaJ | 26990657 | NP_746082.1 | *Pseudomonas putida* |
| pcaI | 50084858 | YP_046368.1 | *Acinetobacter* sp. ADP1 |
| pcaJ | 141776 | AAC37147.1 | *Acinetobacter* sp. ADP1 |
| pcaI | 21224997 | NP_630776.1 | *Streptomyces coelicolor* |
| pcaJ | 21224996 | NP_630775.1 | *Streptomyces coelicolor* |
| HPAG1_0676 | 108563101 | YP_627417 | *Helicobacter pylori* |
| HPAG1_0677 | 108563102 | YP_627418 | *Helicobacter pylori* |
| ScoA | 16080950 | NP_391778 | *Bacillus subtilis* |
| ScoB | 16080949 | NP_391777 | *Bacillus subtilis* |

The glutaconyl-CoA-transferase (EC 2.8.3.12) enzyme from anaerobic bacterium *Acidaminococcus fermentans* reacts with glutaconyl-CoA and 3-butenoyl-CoA (Mack et al., *Eur. J. Biochem.* 226:41-51 (1994)), substrates similar in structure to 2,3-dehydroadipyl-CoA. The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., *Eur. J. Biochem.* 118:315-321 (1981)). The enzyme has been cloned and expressed in *E. coli* (Mack, supra). Genbank information related to these genes is summarized in Table 21 below.

TABLE 21

| Gene | GI # | Accession No. | Organism |
| --- | --- | --- | --- |
| gctA | 559392 | CAA57199.1 | *Acidaminococcus fermentans* |
| gctB | 559393 | CAA57200.1 | *Acidaminococcus fermentans* |

Other exemplary CoA transferases are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., *Proc. Natl. Acad. Sci U.S.A.* 105:2128-2133 (2008); Sohling and Gottschalk, *J. Bacteriol.* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). Genbank information related to these genes is summarized in Table 22 below.

TABLE 22

| Gene | GI # | Accession No. | Organism |
| --- | --- | --- | --- |
| cat1 | 729048 | P38946.1 | *Clostridium kluyveri* |
| cat2 | 172046066 | P38942.2 | *Clostridium kluyveri* |
| cat3 | 146349050 | EDK35586.1 | *Clostridium kluyveri* |
| TVAG_395550 | 123975034 | XP_001330176 | *Trichomonas vaginalis* G3 |
| Tb11.02.0290 | 71754875 | XP_828352 | *Trypanosoma brucei* |

A CoA transferase that can utilize acetyl-CoA as the CoA donor is acetoacetyl-CoA transferase, encoded by the *E. coli* atoA (alpha subunit) and atoD (beta subunit) genes (Korolev et al., *Acta Crystallagr. D. Biol. Crystallagr.* 58:2116-2121 (2002); Vanderwinkel et al., *Biochem. Biophys. Res. Commun.* 33:902-908 (1968)). This enzyme has a broad substrate range (Sramek and Frerman, *Arch. Biochem. Biophys.* 171: 14-26 (1975)) and has been shown to transfer the CoA moiety to acetate from a variety of branched and linear acyl-CoA substrates, including isobutyrate (Matthies and Schink, *Appl. Environ. Microbiol.* 58:1435-1439 (1992)), valerate (Vanderwinkel et al, supra) and butanoate (Vanderwinkel et al, supra). This enzyme is induced at the transcriptional level by acetoacetate, so modification of regulatory control may be necessary for engineering this enzyme into a pathway (Pauli and Overath, *Eur. J. Biochem.* 29:553-562 (1972)). Similar enzymes exist in *Corynebacterium glutamicum* ATCC 13032 (Duncan et al., *Appl. Environ. Microbiol.* 68:5186-5190 (2002)), *Clostridium acetobutylicum* (Cary et al., *Appl. Environ. Microbiol.* 56:1576-1583 (1990); Weisenborn et al., *Appl. Environ. Microbiol.* 55:323-329 (1989)), and *Clostridium saccharoperbutylacetonicum* (Kosaka et al., *Biosci. Biotechnol. Biochem.* 71:58-58 (2007)). Genbank information related to these genes is summarized in Table 23 below.

TABLE 23

| Gene | GI # | Accession No. | Organism |
| --- | --- | --- | --- |
| atoA | 2492994 | P76459.1 | *Escherichia coli* |
| atoD | 2492990 | P76458.1 | *Escherichia coli* |
| actA | 62391407 | YP_226809.1 | *Corynebacterium glutamicum* |
| cg0592 | 62389399 | YP_224801.1 | *Corynebacterium glutamicum* |
| ctfA | 15004866 | NP_149326.1 | *Clostridium acetobutylicum* |
| ctfB | 15004867 | NP_149327.1 | *Clostridium acetobutylicum* |
| ctfA | 31075384 | AAP42564.1 | *Clostridium saccharoperbutylacetonicum* |
| ctfB | 31075385 | AAP42565.1 | *Clostridium saccharoperbutylacetonicum* |

In Step H of FIG. 2, the lactonization of beta-ketoadipate to form β-ketoadipate-enol-lactone is be catalyzed by the beta-ketoadipate enol-lactonase (EC-3.1.1.24). Beta-ketoadipate enol-lactonase also participates in the catechol branch of the beta-ketoadipate pathway to degrade aromatic compounds, in the reverse direction of that required in Step H of FIG. 2. This enzyme is encoded by the pcaD gene in *Pseudomonas putida* (Hughes et al., *J. Gen Microbiol.* 134:2877-2887 (1988)), *Rhodococcus opacus* (Eulberg et al., *J. Bacteriol.* 180:1072-1081 (1998)) and *Ralstonia eutropha*. In *Acinetobacter calcoaceticus*, genes encoding two β-ketoadipate enol-lactone hydrolases were identified (Patel et al., *J. Biol. Chem.* 250:6567 (1975)). Genbank information related to these genes is summarized in Table 24 below.

TABLE 24

| Gene | GI # | Accession No. | Organism |
| --- | --- | --- | --- |
| ELH | 6015088 | Q59093 | *Acinetobacter calcoaceticus* |
| ELH2 | 6166146 | P00632 | *Acinetobacter calcoaceticus* |
| pcaD | 24982842 | AAN67003 | *Pseudomonas putida* |
| pcaD | 75426718 | O67982 | *Rhodococcus opacus* |
| pcaD | 75411823 | javascript:Blast2 ('Q9EV41')Q9EV45 | *Ralstonia eutropha* |

The hydrolysis of acyl-CoA molecules to their corresponding acids is carried out by acyl CoA hydrolase enzymes in the 3.1.2 family, also called thioesterases. Several eukaryotic acetyl-CoA hydrolases (EC 3.1.2.1) have broad substrate specificity and thus represent suitable enzymes for hydrolyzing beta-ketoadipyl-CoA and 2,3-dehydroadipyl-CoA (FIG. 2, Steps B and M and FIG. 4, Step H). For example, the enzyme from *Rattus norvegicus* brain (Robinson et al., *Biochem. Biophys. Res. Commun.* 71:959-965 (1976)) can react with butyryl-CoA, hexanoyl-CoA and malonyl-CoA. The enzyme from the mitochondrion of the pea leaf also has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher and Randall, *Plant Physiol.* 94:20-27 (1990)). The acetyl-CoA hydrolase, ACH1, from *S. cerevisiae* represents another hydrolase (Buu et al., *J. Biol. Chem.* 278:17203-17209 (2003)). Genbank information related to these genes is summarized in Table 25 below.

TABLE 25

| Gene | GI # | Accession No. | Organism |
| --- | --- | --- | --- |
| acot12 | 18543355 | NP_570103.1 | *Rattus norvegicus* |
| ACH1 | 6319456 | NP_009538 | *Saccharomyces cerevisiae* |

Another hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., *J. Biol. Chem.* 280:38125-28132 (2005)) and the closest *E. coli* homolog, tesB, which can also hydrolyze a broad range of CoA thioesters (Naggert et al., *J. Biol. Chem.* 266:11044-11050 (1991)). A similar enzyme has also been characterized in the rat liver (Deana, R., *Biochem. Int.* 26:767-773 (1992)). Genbank information related to these genes is summarized in Table 26 below.

TABLE 26

| Gene | GI # | Accession No. | Organism |
| --- | --- | --- | --- |
| tesB | 16128437 | NP_414986 | *Escherichia coli* |
| acot8 | 3191970 | CAA15502 | *Homo sapiens* |
| acot8 | 51036669 | NP_570112 | *Rattus norvegicus* |

Other potential *E. coli* thioester hydrolases include the gene products of tesA (Bonner and Bloch, *J. Biol. Chem.* 247:3123-3133 (1972)), ybgC (Kuznetsova et al., *FEBS Microbiol. Rev.* 29:263-279 (2005); Zhuang et al., *FEBS Lett.* 516:161-163 (2002)), paaI (Song et al., *J. Biol. Chem.* 281:11028-11038 (2006)), and ybdB (Leduc et al., *J. Bacteriol.* 1889:7112-7126 (2007)). Genbank information related to these genes is summarized in Table 27 below.

TABLE 27

| Gene | GI # | Accession No. | Organism |
| --- | --- | --- | --- |
| teas | 16128478 | NP_415027 | *Escherichia coli* |
| ybgC | 16128711 | NP_415264 | *Escherichia coli* |
| paaI | 16129357 | NP_415914 | *Escherichia coli* |
| ybdB | 16128580 | NP_415129 | *Escherichia coli* |

Yet another hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack and Buckel, *FEBS Lett.* 405:209-212 (1997)), compounds similar in structure to 2,3-dehydroadipyl-CoA. This indicates that the enzymes encoding succinyl-CoA:3-ketoacid-CoA transferases and acetoacetyl-CoA:acetyl-CoA transferases can also serve as enzymes for this reaction step but would require certain mutations to change their function. Genbank information related to these genes is summarized in Table 28 below.

TABLE 28

| Gene | GI # | Accession No. | Organism |
| --- | --- | --- | --- |
| gctA | 559392 | CAA57199 | *Acidaminococcus fermentans* |
| gctB | 559393 | CAA57200 | *Acidaminococcus fermentans* |

Step C of FIG. 4 is catalyzed by a 2-ketoacid decarboxylase that generates 6-oxo-2,3-dehydrohexanoate (6-OHE) from 2-oxohept-4-ene-1,7-dioate (OHED). The decarboxylation of keto-acids is catalyzed by a variety of enzymes with varied substrate specificities, including pyruvate decarboxylase (EC 4.1.1.1), benzoylformate decarboxylase (EC 4.1.1.7), alpha-ketoglutarate decarboxylase and branched-chain alpha-ketoacid decarboxylase. Pyruvate decarboxylase (PDC), also termed keto-acid decarboxylase, is a key enzyme in alcoholic fermentation, catalyzing the decarboxylation of pyruvate to acetaldehyde. The enzyme from *Saccharomyces cerevisiae* has a broad substrate range for aliphatic 2-keto acids including 2-ketobutyrate, 2-ketovalerate, 3-hydroxypyruvate and 2-phenylpyruvate (22). This enzyme has been extensively studied, engineered for altered activity, and functionally expressed in *E. coli* (Killenberg-Jabs et al., *Eur. J. Biochem.* 268:1698-1704 (2001); Li and Jordan, *Biochemistry* 38:10004-10012 (1999); ter Schure et al., *Appl. Environ. Microbiol* 64:1303-1307 (1998)). The PDC from *Zymomonas mobilus*, encoded by pdc, also has a broad substrate range and has been a subject of directed engineering studies to alter the affinity for different substrates (Siegert et al., *Protein Eng Des Sel* 18:345-357 (2005)). The crystal structure of this enzyme is available (Killenberg-Jabs, et al., supra). Other well-characterized PDC enzymes include the enzymes from *Acetobacter pasteurians* (Chandra et al., *Arch. Microbiol.* 176:443-451 (2001)) and *Kluyveromyces lactis* (Krieger et al., *Eur. J. Biochem.* 269: 3256-3263 (2002)). Genbank information related to these genes is summarized in Table 29 below.

TABLE 29

| Gene | GI # | Accession No. | Organism |
| --- | --- | --- | --- |
| pdc | 118391 | P06672.1 | *Zymomonas mobilus* |
| pdc1 | 30923172 | P06169 | *Saccharomyces cerevisiae* |
| pdc | 20385191 | AM21208 | *Acetobacter pasteurians* |
| pdc1 | 52788279 | Q12629 | *Kluyveromyces lactis* |

Like PDC, benzoylformate decarboxylase (EC 4.1.1.7) has a broad substrate range and has been the target of enzyme engineering studies. The enzyme from *Pseudomonas putida* has been extensively studied and crystal structures of this enzyme are available (Hasson et al., *Biochemistry* 37:9918-9930 (1998); Polovnikova et al., *Biochemistry* 42:1820-1830 (2003)). Site-directed mutagenesis of two residues in the active site of the *Pseudomonas putida* enzyme altered the affinity (Km) of naturally and non-naturally occurring substrates (Siegert et al., *Protein Eng Des Sel* 18:345-357 (2005)). The properties of this enzyme have been further modified by directed engineering (Lingen et al., *Protein Eng.* 15:585-593 (2002); Lingen et al., *Chembiochem.* 4:721-726 (2003)). The enzyme from *Pseudomonas aeruginosa*, encoded by mdlC, has also been characterized experimentally (Barrowman et al., *FEMS Microbiology Letters* 34:57-60 (1986)). Additional genes from *Pseudomonas stutzeri*, *Pseudomonas fluorescens* and other organisms can be inferred by sequence homology or identified using a growth selection system developed in *Pseudomonas putida* (Henning et al., *Appl. Environ. Microbiol.* 72:7510-7517 (2006)). Genbank information related to these genes is summarized in Table 30 below.

TABLE 30

| Gene | GI # | Accession No. | Organism |
| --- | --- | --- | --- |
| mdlC | 3915757 | P20906.2 | *Pseudomonas putida* |
| mdlC | 81539678 | Q9HUR2.1 | *Pseudomonas aeruginosa* |
| dpgB | 126202187 | ABN80423.1 | *Pseudomonas stutzeri* |
| ilvB-1 | 70730840 | YP_260581.1 | *Pseudomonas fluorescens* |

A third enzyme capable of decarboxylating 2-oxoacids is alpha-ketoglutarate decarboxylase (KGD). The substrate range of this class of enzymes has not been studied to date. The KDC from *Mycobacterium tuberculosis* (Tian et al., *Proc. Natl. Acad. Sci U.S.A.* 102:10670-10675 (2005)) has been cloned and functionally expressed, although it is large (~130 kD) and GC-rich. KDC enzyme activity has been detected in several species of rhizobia including *Bradyrhizobium japonicum* and *Mesorhizobium loti* (Green et al., *J. Bacteriol.* 182:2838-2844 (2000)). Although the KDC-encoding gene(s) have not been isolated in these organisms, the genome sequences are available and several genes in each genome are annotated as putative KDCs. A KDC from *Euglena gracilis* has also been characterized but the gene associated with this activity has not been identified to date (Shigeoka and Nakano, *Arch. Biochem. Biophys.* 288:22-28 (1991)). The first twenty amino acids starting from the N-terminus were sequenced MTYKAPVKDVKFLLDK-VFKV (Shigeoka and Nakano, supra). The gene could be identified by testing genes containing this N-terminal sequence for KDC activity. Genbank information related to these genes is summarized in Table 31 below.

TABLE 31

| Gene | GI # | Accession No. | Organism |
| --- | --- | --- | --- |
| kgd | 160395583 | O50463.4 | *Mycobacterium tuberculosis* |
| kgd | 27375563 | NP_767092.1 | *Bradyrhizobium japonicum* |
| kgd | 13473636 | NP_105204.1 | *Mesorhizobium loti* |

A fourth enzyme for catalyzing this reaction is branched chain alpha-ketoacid decarboxylase (BCKA). This class of enzyme has been shown to act on a variety of compounds varying in chain length from 3 to 6 carbons (Oku and Kaneda, *J. Bio. Chem.* 263:18386-18396 (1988); Smit et al., *App. Environ. Microbiol.* 71:303-311 (2005)). The enzyme in *Lactococcus lactis* has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., supra). The enzyme has been structurally characterized (Berg et al., *Science* 318:1782-1786 (2007)). Sequence alignments between the *Lactococcus lactis* enzyme and the pyruvate decarboxylase of *Zymomonas mobilus* indicate that the catalytic and substrate recognition residues are nearly identical (Siegert et al., *Protein Eng Des Sel* 18:345-357 (2005)), so this enzyme can be subjected to directed engineering. Decarboxylation of alpha-ketoglutarate by a BCKA was detected in *Bacillus subtilis*; however, this activity was low (5%) relative to activity on other branched-chain substrates (Oku and Kaneda, supra) and the gene encoding this enzyme has not been identified to date. Additional BCKA genes can be identified by homology to the *Lactococcus lactis* protein sequence. Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria. Genbank information related to these genes is summarized in Table 32 below.

TABLE 32

| Gene | GI # | Accession No. | Organism |
|---|---|---|---|
| kdcA | 44921617 | AAS49166.1 | Lactococcus lactis |

Recombinant branched chain alpha-keto acid decarboxylase enzymes derived from the E1 subunits of the mitochondrial branched-chain keto acid dehydrogenase complex from Homo sapiens and Bos taurus have been cloned and functionally expressed in E. coli (Davie et al., J. Biol. Chem. 267:16601-16606 (1992); Wynn et al., J. Biol. Chem. 267: 1881-1887 (1992); Wynn et al., J. Biol. Chem. 267:12400-12403 (1992)). It was indicated that co-expression of chaperonins GroEL and GroES enhanced the specific activity of the decarboxylase by 500-fold (Wynn (1992) supra). These enzymes are composed of two alpha and two beta subunits. Genbank information related to these genes is summarized in Table 33 below.

TABLE 33

| Gene | GI # | Accession No. | Organism |
|---|---|---|---|
| BCKDHB | 34101272 | NP_898871.1 | Homo sapiens |
| BCKDHA | 11386135 | NP_000700.1 | Homo sapiens |
| BCKDHB | 115502434 | P21839 | Bos taurus |
| BCKDHA | 129030 | P11178 | Bos taurus |

Aldehyde lyases in EC class 4.1.2 catalyze two key reactions in the disclosed pathways to muconate (FIG. 3, Step A and FIG. 4, Step A). HOHD aldolase, also known as HHED aldolase, catalyzes the conversion of 4-hydroxy-2-oxo-heptane-1,7-dioate (HOHD) into pyruvate and succinic semialdehyde (FIG. 4, Step A). HODH aldolase is a divalent metal ion-dependent class II aldolase, catalyzing the final step of 4-hydroxyphenylacetic acid degradation in E. coli C, E. coli W, and other organisms. In the native context, the enzyme functions in the degradative direction. The reverse (condensation) reaction is thermodynamically unfavorable; however the equilibrium can be shifted through coupling HOHD aldolase with downstream pathway enzymes that work efficiently on reaction products. Such strategies have been effective for shifting the equilibrium of other aldolases in the condensation direction (Nagata et al., Appl. Microbiol. Biotechnol. 44:432-438 (1995); Pollard et al., App. Environ. Microbiol. 64:4093-4094 (1998)). The E. coli C enzyme, encoded by hpcH, has been extensively studied and has recently been crystallized (Rea et al., J. Mol. Biol. 373:866-876 (2007); Stringfellow et al., Gene 166:73-76 (1995)). The E. coli W enzyme is encoded by hpaI (Prieto et al., J. Bacteriol. 178:111-120 (1996)). Genbank information related to these genes is summarized in Table 34 below.

TABLE 34

| Gene | GI # | Accession No. | Organism |
|---|---|---|---|
| hpcH | 633197 | CAA87759.1 | Escherichia coli C |
| hpaI | 38112625 | AAR11360.1 | Escherichia coli W |

In Step A of FIG. 3, pyruvate and malonate semialdehyde are joined by an aldehyde lyase to form 4-hydroxy-2-oxohexanedioate. An enzyme catalyzing this exact reaction has not been characterized to date. A similar reaction is catalyzed by 2-dehydro-3-deoxyglucarate aldolase (DDGA, EC 4.1.2.20), a type II aldolase that participates in the catabolic pathway for D-glucarate/galactarate utilization in E. coli. Tartronate semialdehyde, the natural substrate of DDGA, is similar in size and structure to malonate semialdehyde. This enzyme has a broad substrate specificity and has been shown to reversibly condense a wide range of aldehydes with pyruvate (Fish and Blumenthal, Methods Enzymol. 9:529-534 (1966)). The crystal structure of this enzyme has been determined and a catalytic mechanism indicated (Izard and Blackwell, EMBO J. 19:3849-3856 (2000)). Other DDGA enzymes are found in Leptospira interrogans (Li et al., Acta Crystallogr. Sect. F. Struct. Biol. Cryst. Commun. 62:1269-1270 (2006)) and Sulfolobus solfataricus (Buchanan et al., Biochem. J. 343 Pt 3:563-570 (1999)). The S. solfataricus enzyme is highly thermostable and was cloned and expressed in E. coli (Buchanan et al., supra). Genbank information related to these genes is summarized in Table 35 below.

TABLE 35

| Gene | GI # | Accession No. | Organism |
|---|---|---|---|
| garL | 1176153 | P23522.2 | Escherichia coli |
| LA_1624 | 24195249 | AAN48823.1 | Leptospira interrogans |
| AJ224174.1:1..885 | 2879782 | CAA11866.1 | Sulfolobus solfataricus |

The pathways in FIGS. 2-4 employ numerous enzymes in the dehydratase class of enzymes (EC 4.1.2). Several reactions in FIGS. 2 and 3 undergo dehydration reactions similar to the dehydration of malate to fumarate, catalyzed by fumarate hydratase (EC 4.2.1.2). These transformations include the dehydration of 3-hydroxy-4-hexenedioate (FIG. 2, Steps E and Q and FIG. 3, Step H), 4-hydroxy-2-oxohexanedioate (FIG. 3, Step B), 2-hydroxy-4-hexenedioate (FIG. 3, Step D) and 2,4-dihydroxyadipate (FIG. 3, Steps F and G). Fumarate hydratase enzymes are exemplary enzymes for catalyzing these reactions. The E. coli fumarase encoded by fumC dehydrates a variety of alternate substrates including tartrate and threo-hydroxyaspartate (Teipel et al., J. Biol. Chem. 243:5684-5694 (1968)). A wealth of structural information is available for the E. coli enzyme and researchers have successfully engineered the enzyme to alter activity, inhibition and localization (Weaver, T., Acta Crystallogr. D Biol. Crystallogr. 61:1395-1401 (2005)). Exemplary fumarate hydratase enzymes are found in Escherichia coli (Estevez et al., Protein Sci. 11:1552-1557 (2002); Hong and Lee, Biotechnol. Bioprocess Eng. 9:252-255 (2006); Rose and Weaver, Proc. Natl. Acad. Sci. U.S.A. 101:3393-3397 (2004)); Agnihotri and Liu, Bioorg. Med. Chem. 11:9-20 (2003)), Corynebacterium glutamicum (Genda et al., Biosci. Biotechnol. Biochem. 71:1102-1109 (2006)), Campylobacter jejuni (Smith and Gray, Catalysis Letters 6:195-199 (1990)), Thermus thermophilus (Mizobata et al., Arch. Biochem. Biophys. 355:49-55 (1998)), and Rattus norvegicus (Kobayashi et al., J. Biochem. 89:1923-1931 (1981)). Genbank information related to these genes is summarized in Table 36 below.

TABLE 36

| Gene | GI # | Accession No. | Organism |
|---|---|---|---|
| fumC | 120601 | P05042.1 | Escherichia coli K12 |
| fumC | 39931596 | Q8NRN8.1 | Corynebacterium glutamicum |
| fumC | 9789756 | O69294.1 | Campylobacter jejuni |
| fumC | 75427690 | P84127 | Thermus thermophilus |
| fumH | 120605 | P14408.1 | Rattus norvegicus |

Another enzyme for catalyzing these reactions is citramalate hydrolyase (EC 4.2.1.34), an enzyme that naturally dehydrates 2-methylmalate to mesaconate. This enzyme has been studied in *Methanocaldococcus jannaschii* in the context of the pyruvate pathway to 2-oxobutanoate, where it has been shown to have a broad substrate specificity (Drevland et al., *J. Bacteriol.* 189:4391-4400 (2007)). This enzyme activity was also detected in *Clostridium tetanomorphum, Morganella morganii, Citrobacter amalonaticus* where it is thought to participate in glutamate degradation (Kato and Asano *Arch. Microbiol.* 168:457-463 (1997)). The *M. jannaschii* protein sequence does not bear significant homology to genes in these organisms. Genbank information related to these genes is summarized in Table 37 below.

TABLE 37

| Gene | GI # | Accession No. | Organism |
| --- | --- | --- | --- |
| leuD | 3122345 | Q58673.1 | *Methanocaldococcus jannaschii* |

The enzyme OHED hydratase (FIG. 4, Step B) participates in 4-hydroxyphenylacetic acid degradation, where it converts 2-oxo-hept-4-ene-1,7-dioate (OHED) to 2-oxo-4-hydroxy-hepta-1,7-dioate (HODH) using magnesium as a cofactor (Burks et al., *J. Am. Chem. Soc.* 120 (1998). OHED hydratase enzymes have been identified and characterized in *E. coli* C (Izumi et al., *J. Mol. Biol.* 370:899-911 (2007); Roper et al., *Gene* 156:47-51 (1995)) and *E. coli* W (Prieto et al., *J. Bacteriol.* 178:111-120 (1996)). Sequence comparison reveals homologs in a range of bacteria, plants and animals. Enzymes with highly similar sequences are contained in *Klebsiella pneumonia* (91% identity, evalue=2e-138) and *Salmonella enterica* (91% identity, evalue=4e-138), among others. Genbank information related to these genes is summarized in Table 38 below.

TABLE 38

| Gene | GI # | Accession No. | Organism |
| --- | --- | --- | --- |
| hpcG | 556840 | CAA57202.1 | *Escherichia coli* C |
| hpaH | 757830 | CAA86044.1 | *Escherichia coli* W |
| hpaH | 150958100 | ABR80130.1 | *Klebsiella pneumoniae* |
| Sari_01896 | 160865156 | ABX21779.1 | *Salmonella enterica* |

Dehydration of 3-hydroxyadipyl-CoA to 2,3-dehydroadipyl-CoA (FIG. 2, Step L and FIG. 4, Step G) is catalyzed by an enzyme with enoyl-CoA hydratase activity. 3-Hydroxybutyryl-CoA dehydratase (EC 4.2.1.55), also called crotonase, is an enoyl-CoA hydratase that dehydrates 3-hydroxyisobutyryl-CoA to form crotonyl-CoA (FIG. 3, step 2). Crotonase enzymes are required for n-butanol formation in some organisms, particularly *Clostridial* species, and also comprise one step of the 3-hydroxypropionate/4-hydroxybutyrate cycle in thermoacidophilic Archaea of the genera *Sulfolobus, Acidianus*, and *Metallosphaera*. Exemplary genes encoding crotonase enzymes can be found in *C. acetobutylicum* (Atsumi et al., *Metab. Eng.* 10:305-211 (2008); Boynton et al., *J. Bacteriol.* 178:3015-3024 (1996)), *C. kluyveri* (Hillmer and Gottschalk, *FEBS Lett.* 21:351-354 (1972)), and *Metallosphaera sedula* (Berg et al., *Science* 318:1782-1786 (2007)) though the sequence of the latter gene is not known. Genbank information related to these genes is summarized in Table 39 below.

TABLE 39

| Gene | GI # | Accession No. | Organism |
| --- | --- | --- | --- |
| crt | 15895969 | NP_349318.1 | *Clostridium acetobutylicum* |
| crt1 | 153953091 | YP_001393856.1 | *Clostridium kluyveri* |

Additional enoyl-CoA hydratases (EC 4.2.1.17) catalyze the dehydration of a range of 3-hydroxyacyl-CoA substrates (Agnihotri and Liu, *Bioorg. Med. Chem.* 11:9-20 (2003); Conrad et al., *J. Bacteriol.* 118:103-111 (1974); Roberts et al., *Arch. Microbiol.* 117:99-108 (1978)). The enoyl-CoA hydratase of *Pseudomonas putida*, encoded by ech, catalyzes the conversion of 3-hydroxybutyryl-CoA to crotonyl-CoA (Roberts et al., supra). Additional enoyl-CoA hydratase enzymes are phaA and phaB, of *P. putida*, and paaA and paaB from *P. fluorescens* (Olivera et al., *Proc. Natl. Acad. Sci U.S.A.* 95:6419-6424 (1998)). The gene product of pimF in *Rhodopseudomonas palustris* is predicted to encode an enoyl-CoA hydratase that participates in pimeloyl-CoA degradation (Harrison and Harwood, *Microbiology* 151:727-736 (2005)). Lastly, a number of *Escherichia coli* genes have been shown to demonstrate enoyl-CoA hydratase functionality including maoC (Park and Lee, *Appl. Biochem. Biotechnol.* 113-116:335-346 (2004)), paaF (Ismail et al., *Eur. J. Biochem.* 270:3047-3054 (2003); Park and Lee, supra; Park and Yup, *Biotechnol. Bioeg* 86:681-686 (2004)) and paaG (Ismail et al., *Eur. J. Biochem.* 270:3047-3054 (2003); Park and Lee, supra; Park and Yup, *Biotechnol. Bioeg* 86:681-686 (2004)). Genbank information related to these genes is summarized in Table 40 below.

TABLE 40

| Gene | GI # | Accession No. | Organism |
| --- | --- | --- | --- |
| ech | 26990073 | NP_745498.1 | *Pseudomonas putida* |
| paaA | 26990002 | NP_745427.1 | *Pseudomonas putida* |
| paaB | 26990001 | NP_745426.1 | *Pseudomonas putida* |
| phaA | 106636093 | ABF82233.1 | *Pseudomonas fluorescens* |
| phaB | 106636094 | ABF82234.1 | *Pseudomonas fluorescens* |
| pimF | 39650635 | CAE29158 | *Rhodopseudomonas palustris* |
| maoC | 16129348 | NP_415905.1 | *Escherichia coli* |
| paaF | 16129354 | NP_415911.1 | *Escherichia coli* |
| paaG | 16129355 | NP_415912.1 | *Escherichia coli* |

Alternatively, the *E. coli* gene products of fadA and fadB encode a multienzyme complex involved in fatty acid oxidation that exhibits enoyl-CoA hydratase activity (Nakahigashi and Inokuchi, *Nucleic Acids Res.* 18:4937 (1990); Yang, S. Y. *J. Bacteriol.* 173:7405-7406 (1991); Yang et al., *Biochemistry* 30:6788-6795 (1991)). Knocking out a negative regulator encoded by fadR can be utilized to activate the fadB gene product (Sato et al., *J. Biosci. Bioeng.* 103:38-44 (2007)). The fadI and fadJ genes encode similar functions and are naturally expressed under anaerobic conditions (Campbell et al., *Mol. Microbiol.* 47:793-805 (2003)). Genbank information related to these genes is summarized in Table 41 below.

TABLE 41

| Gene | GI # | Accession No. | Organism |
| --- | --- | --- | --- |
| fadA | 49176430 | YP_026272.1 | *Escherichia coli* |
| fadB | 16131692 | NP_418288.1 | *Escherichia coli* |
| fadI | 16130275 | NP_416844.1 | *Escherichia coli* |
| fadJ | 16130274 | NP_416843.1 | *Escherichia coli* |
| fadR | 16129150 | NP_415705.1 | *Escherichia coli* |

An enzyme in the ammonia-lyase family is required to deaminate 3-amino-4-hexenedioate (FIG. 2, Steps G and S), 2-aminoadipate (FIG. 5, Step C) and 3-aminoadipate (FIG. 5, Step H). Enzymes catalyzing this exact transformation has not been identified. However the three substrates bear structural similarity to aspartate, the native substrate of aspartase (EC 4.3.1.1.). Aspartase is a widespread enzyme in microorganisms, and has been characterized extensively (Wakil et al., *J. Biol. Chem.* 207:631-638 (1954)). The *E. coli* enzyme has been shown to react with a variety of alternate substrates including aspartatephenylmethylester, asparagine, benzylaspartate and malate (Ma et al., *Ann N.Y. Acad Sci.* 672:60-65 (1992)). In addition, directed evolution was been employed on this enzyme to alter substrate specificity (Asano et al., *Biomol. Eng.* 22:95-101 (2005)). The crystal structure of the *E. coli* aspartase, encoded by aspA, has been solved (Shi et al., *Biochemistry* 36:9136-9144 (1997)). Enzymes with aspartase functionality have also been characterized in *Haemophilus influenzae* (Sjostrom et al., *Biochim. Biophys. Acta* 1324:182-190 (1997)), *Pseudomonas fluorescens* (Takagi and Kisumi, *J. Bacteriol.* 161:1-6 (1985)), *Bacillus subtilis* (Sjostrom et al., supra) and *Serratia marcescens* (Takagi and Kisumi supra). Genbank information related to these genes is summarized in Table 42 below.

TABLE 42

| Gene | GI # | Accession No. | Organism |
| --- | --- | --- | --- |
| aspA | 90111690 | NP_418562 | *Escherichia coli* |
| aspA | 1168534 | P44324.1 | *Haemophilus influenzae* |
| aspA | 114273 | P07346.1 | *Pseudomonas fluorescens* |
| ansB | 251757243 | P26899.1 | *Bacillus subtilis* |
| aspA | 416661 | P33109.1 | *Serratia marcescens* |

Another deaminase enzyme is 3-methylaspartase (EC 4.3.1.2). This enzyme, also known as beta-methylaspartase and 3-methylaspartate ammonia-lyase, naturally catalyzes the deamination of threo-3-methylasparatate to mesaconate. The 3-methylaspartase from *Clostridium tetanomorphum* has been cloned, functionally expressed in *E. coli*, and crystallized (Asuncion et al., *Acta Crystallogr. D. Biol Crystallogr.* 57:731-733 (2001); Asuncion et al., *J. Biol. Chem.* 277:8306-8311 (2002); Botting et al. *Biochemistry* 27:2953-2955 (1988); Goda et al., *Biochemistry* 31:10747-10756 (1992)). In *Citrobacter amalonaticus*, this enzyme is encoded by BAA28709 (Kato and Asano, *Arch. Microbiol.* 168:457-463 (1997)). 3-methylaspartase has also been crystallized from *E. coli* YG1002 (Asano and Kato, *FEBS Microbiol. Lett.* 118:255-258 (1994)) although the protein sequence is not listed in public databases such as GenBank. Sequence homology can be used to identify additional genes, including CTC_02563 in *C. tetani* and ECs0761 in *Escherichia coli* O157:H7. Genbank information related to these genes is summarized in Table 43 below.

TABLE 43

| Gene | GI # | Accession No. | Organism |
| --- | --- | --- | --- |
| mal | 259429 | AAB24070.1 | *Clostridium tetanomorphum* |
| BAA28709 | 3184397 | BAA28709.1 | *Citrobacter amalonaticus* |
| CTC_02563 | 28212141 | NP_783085.1 | *Clostridium tetani* |
| ECs0761 | 13360220 | BAB34184.1 | *Escherichia coli* O157:H7 |

In FIG. 2 Step J, muconolactone is converted to muconate by muconate cycloisomerase. However, muconate cycloisomerase usually results in the formation of cis,cis-muconate, which may be difficult for the subsequent Diels-Alder chemistry. The cis, trans- or trans, trans-isomers are preferred. Therefore, the addition of a cis, trans isomerase may help to improve the yield of terephthalic acid. Enzymes for similar isomeric conversions include maleate cis,trans-isomerase (EC 5.2.1.1), maleylacetone cis-trans-isomerase (EC 5.2.1.2), and cis,trans-isomerase of unsaturated fatty acids (Cti).

Maleate cis, trans-isomerase (EC 5.2.1.1) catalyzes the conversion of maleic acid in cis formation to fumarate in trans formation (Scher and Jakoby, *J. Biol. Chem.* 244:1878-1882 (1969)). The *Alcalidgenes faecalis* maiA gene product has been cloned and characterized (Hatakeyeama et al., *Biochem. Biophys. Res. Commun.* 239:74-79 (1997)). Other maleate cis,trans-isomerases are available in *Serratia marcescens* (Hatakeyama et al., *Biosci. Biotechnol. Biochem.* 64:1477-1485 (2000)), *Ralstonia eutropha* and *Geobacillus stearothermophilus*. Genbank information related to these genes is summarized in Table 44 below.

TABLE 44

| Gene | GI # | Accession No. | Organism |
| --- | --- | --- | --- |
| maiA | 2575787 | BAA23002 | *Alcaligenes faecalis* |
| maiA | 113866948 | YP_725437 | *Ralstonia eutropha* H16 |
| maiA | 4760466 | BAA77296 | *Geobacillus stearothermophilus* |
| maiA | 8570038 | BAA96747.1 | *Serratia marcescens* |

Maleylacetone cis,trans-isomerase (EC 5.2.1.2) catalyzes the conversion of 4-maleyl-acetoacetate to 4-fumaryl-acetyacetate, a cis to trans conversion. This enzyme is encoded by maiA in *Pseudomonas aeruginosa* Fernandez-Canon and Penalva, *J. Biol. Chem.* 273:329-337 (1998)) and *Vibrio cholera* (Seltzer, S., *J. Biol. Chem.* 248:215-222 (1973)). A similar enzyme was identified by sequence homology in *E. coli* O157. Genbank information related to these genes is summarized in Table 45 below.

TABLE 45

| Gene | GI # | Accession No. | Organism |
| --- | --- | --- | --- |
| maiA | 15597203 | NP_250697 | *Pseudomonas aeruginosa* |
| maiA | 15641359 | NP_230991 | *Vibrio cholerae* |
| maiA | 189355347 | EDU73766 | *Escherichia coli* O157 |

The cti gene product catalyzes the conversion of cis-unsaturated fatty acids (UFA) to trans-UFA. The enzyme has been characterized in *P. putida* (Junker and Ramos, *J. Bacteriol.* 181:5693-5700 (1999)). Similar enzymes are found in *Shewanella* sp. MR-4 and *Vibrio cholerae*. Genbank information related to these genes is summarized in Table 46 below.

TABLE 46

| Gene | GI # | Accession No. | Organism |
| --- | --- | --- | --- |
| cti | 5257178 | AAD41252 | *Pseudomonas putida* |
| cti | 113968844 | YP_732637 | *Shewanella* sp. MR-4 |
| cti | 229506276 | ZP_04395785 | *Vibrio cholerae* |

The endocyclic migration of the double bond in the structure of β-ketoadipate-enol-lactone to form muconolactone (FIG. 2, Step I) is catalyzed by muconolactone isomerase (EC 5.3.3.4). Muconolactone isomerase also participates in the catechol branch of the β-ketoadipate pathway to degrade aromatic compounds, at the reverse direction of Step G. Muconolactone isomerase is encoded by the catC gene. The *Pseudomonas putida* muconolactone isomerase was purified and partial amino acid sequences of cyanogen bromide fragments were determined (Meagher, R. B., *Biochim. Biophys. Acta* 494:33-47 (1997)). A DNA fragment carrying the catBCDE genes from *Acinetobacter calcoaceticus* was isolated by complementing *P. putida* mutants and the complemented activities were expressed constitutively in the recombinant *P. putida* strains (Shanley et, al., *J. Bacteriol.* 165:557-563 (1986). The *A. calcoaceticus* catBCDE genes were also expressed at high levels in *Escherichia coli* under the control of a lac promoter (Shanley et al., supra). The aniline-assimilating bacterium *Rhodococcus* sp. AN-22 CatC was purified to homogeneity and characterized as a homo-octamer with a molecular mass of 100 kDa (Matsumura et al., *Biochem. J.* 393:219-226 (2006)). The crystal structure of *P. putida* muconolactone isomerase was solved (Kattie et al., *J. Mol. Biol.* 205:557-571 (1989)). Genbank information related to these genes is summarized in Table 47 below.

TABLE 47

| Gene | GI # | Accession No. | Organism |
| --- | --- | --- | --- |
| Q3LHT1 | 122612792 | catC | *Rhodococcus* sp. AN-22 |
| Q43932 | 5915883 | catC | *Acinetobacter calcoaceticus* |
| Q9EV41 | 75464174 | catC | *Ralstonia eutropha* |
| P00948 | 5921199 | catC | *Pseudomonas putida* |
| Q9Z9Y5 | 75475019 | catC | *Frateuria* species ANA-18 |

Lysine 2,3-aminomutase (EC 5.4.3.2) converts lysine to (3S)-3,6-diaminohexanoate (FIG. 5, Step E), shifting an amine group from the 2- to the 3-position. The enzyme is found in bacteria that ferment lysine to acetate and butyrate, including as *Fusobacterium nuleatum* (kamA) (Barker et al., *J. Bacteriol.* 152:201-207 (1982)) and *Clostridium subterminale* (kamA) (Chirpich et al., *J. Biol. Chem.* 245:1778-1789 (1970)). The enzyme from *Clostridium subterminale* has been crystallized (Lepore et al., *Proc. Natl. Acad. Sci U.S.A.* 102:13819-13824 (2005)). An enzyme encoding this function is also encoded by yodO in *Bacillus subtilus* (Chen et al., *Biochem. J.* 348 Pt 3:539-549 (2000)). The enzyme utilizes pyridoxal 5'-phosphate as a cofactor, requires activation by S-Adenosylmethoionine, and is stereoselective, reacting with the only with L-lysine. Genbank information related to these genes is summarized in Table 48 below.

TABLE 48

| Gene | GI # | Accession No. | Organism |
| --- | --- | --- | --- |
| yodO | 4033499 | O34676.1 | *Bacillus subtilus* |
| kamA | 75423266 | Q9XBQ8.1 | *Clostridium subterminale* |
| kamA | 81485301 | Q8RHX4 | *Fusobacterium nuleatum* subsp. *nuleatum* |

In Step H of FIG. 2, the ring opening reaction of muconolactone to form muconate is catalyzed by muconate cycloisomerase (EC 5.5.1.1). Muconate cycloisomerase naturally converts cis,cis-muconate to muconolactone in the catechol branch of the β-ketoadipate pathway to degrade aromatic compounds. This enzyme has not been shown to react with the trans,trans isomer. The muconate cycloisomerase reaction is reversible and is encoded by the catB gene. The *Pseudomonas putida* catB gene was cloned and sequenced (Aldrich et al., *Gene* 52:185-195 (1987)), the catB gene product was studied (Neidhart et al., *Nature* 347:692-694 (1990)) and its crystal structures were resolved (Helin et al., *J. Mol. Biol.* 254:918-941 (1995)). A DNA fragment carrying the catBCDE genes from *Acinetobacter calcoaceticus* was isolated by complementing *P. putida* mutants and the complemented activities were expressed constitutively in the recombinant *P. putida* strains (Shanley et al., *J. Bacteriol.* 165:557-563 (1986)). The *A. calcoaceticus* catBCDE genes were also expressed at high levels in *Escherichia coli* under the control of a lac promoter (Shanley et al., supra). The *Rhodococcus* sp. AN-22 CatB was purified to homogeneity and characterized as a monomer with a molecular mass of 44 kDa. The enzyme was activated by $Mn^{2+}$, $Co^{2+}$ and $Mg^{2+}$ (Matsumura et al., *Biochem. J.* 393:219-226 (2006)). Muconate cycloisomerases from other species, such as *Rhodococcus rhodochrous* N75, *Frateuria* species ANA-18, and *Trichosporon cutaneum* were also purified and studied (Cha and Bruce, FEMS Microbiol. Lett. 224:29-34 2003); Mazur et al., *Biochemistry* 33:1961-1970 (1994); Murakami et al., *Biosci Biotechnol. Biochem.* 62:1129-1133 (1998)). Genbank information related to these genes is summarized in Table 49 below.

TABLE 49

| Gene | GI # | Accession No. | Organism |
| --- | --- | --- | --- |
| catB | P08310 | 115713 | *Pseudomonas putida* |
| catB | Q43931 | 51704317 | *Acinetobacter calcoaceticus* |
| catB | Q3LHT2 | 122612793 | *Rhodococcus* sp. AN-22 |
| catB | Q9Z9Y1 | 75424020 | *Frateuria* species ANA-18 |
| catB | P46057 | 1170967 | *Trichosporon cutaneum* |

The conversion of beta-ketoadipyl-CoA to beta-ketoadipate (FIG. 2, Step B) and 2,3-dehydroadipyl-CoA to 2,3-dehydroadipate (FIG. 2, Step M and FIG. 4, Step H) can be catalyzed by a CoA acid-thiol ligase or CoA synthetase in the 6.2.1 family of enzymes. Enzymes catalyzing these exact transformations have not been characterized to date; however, several enzymes with broad substrate specificities have been described in the literature. ADP-forming acetyl-CoA synthetase (ACD, EC 6.2.1.13) is an enzyme that couples the conversion of acyl-CoA esters to their corresponding acids with the concomitant synthesis of ATP. ACD I from *Archaeoglobus fulgidus*, encoded by AF1211, was shown to operate on a variety of linear and branched-chain substrates including isobutyrate, isopentanoate, and fumarate (Musfeldt and Schonheit, *J. Bacteriol.* 184:636-644 (2002)). A second reversible ACD in *Archaeoglobus fulgidus*, encoded by AF1983, was also shown to have a broad substrate range with high activity on cyclic compounds phenylacetate and indoleacetate (Musfeldt and Shonheit, supra). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen and Schonheit, supra). Directed evolution or engineering can be used to modify this enzyme to operate at the physiological temperature of the host organism. The enzymes from *A. fulgidus*, *H. marismortui* and *P. aerophilum* have all been cloned, functionally expressed, and characterized in *E. coli* (Brasen and Shonheit, supra; Musfeldt and Schonheit, supra). An additional enzyme is encoded by sucCD in *E. coli*, which naturally catalyzes the formation of succinyl-CoA from succinate with the concomitant consumption of one ATP, a reaction which is reversible in vivo (Buck et al., *Biochemistry* 24:6245-6252 (1985)). Genbank information related to these genes is summarized in Table 50 below.

TABLE 50

| Gene | GI # | Accession No. | Organism |
|---|---|---|---|
| AF1211 | 11498810 | NP_070039.1 | *Archaeoglobus fulgidus* DSM 4304 |
| AF1983 | 11499565 | NP_070807.1 | *Archaeoglobus fulgidus* DSM 4304 |
| scs | 55377722 | YP_135572.1 | *Haloarcula marismortui* |
| PAE3250 | 18313937 | NP_560604.1 | *Pyrobaculum aerophilum* str. IM2 |
| sucC | 16128703 | NP_415256.1 | *Escherichia coli* |
| sucD | 1786949 | AAC73823.1 | *Escherichia coli* |

Another enzyme for this step is 6-carboxyhexanoate-CoA ligase, also known as pimeloyl-CoA ligase (EC 6.2.1.14), which naturally activates pimelate to pimeloyl-CoA during biotin biosynthesis in gram-positive bacteria. The enzyme from *Pseudomonas mendocina*, cloned into *E. coli*, was shown to accept the alternate substrates hexanedioate and nonanedioate (Binieda et al, *Biochem. J.* 340 Pt 3:793-801 (1999)). Other enzymes are found in *Bacillus subtilis* (Bower et al., *J. Bacteriol.* 178:4122-4130 (1996)) and *Lysinibacillus sphaericus* (formerly *Bacillus sphaericus*) (Ploux et al., *Biochem. J.* 287 Pt 3:685-690 (1992)). Genbank information related to these genes is summarized in Table 51 below.

TABLE 51

| Gene | GI # | Accession No. | Organism |
|---|---|---|---|
| pauA | 15596214 | NP_249708.1 | *Pseudomonas mendocina* |
| bioW | 50812281 | NP_390902.2 | *Bacillus subtilis* |
| bioW | 115012 | P22822.1 | *Lysinibacillus sphaericus* |

Additional CoA-ligases include the rat dicarboxylate-CoA ligase for which the sequence is yet uncharacterized (Vamecq et al., *Biochem. J.* 230:683-693 (1985)), either of the two characterized phenylacetate-CoA ligases from *P. chrysogenum* (Lamas-Maceiras et al., *Biochem. J.* 395:147-155 (2006); Wang et al., *Biochem. Biophys. Res. Commun.* 360:453-458 (2007)) and the phenylacetate-CoA ligase from *Pseudomonas putida* (Martinez-Blanco et al., *J. Biol. Chem.* 265:7084-7090 (1990)). Acetoacetyl-CoA synthetases from *Mus musculus* (Hasegawa et al., *Biochim. Biophys. Acta* 1779:414-419 (2008)) and *Homo sapiens* (Ohgami et al., *Biochem. Pharmacol.* 65:989-994 (2003)) naturally catalyze the ATP-dependant conversion of acetoacetate into acetoacetyl-CoA. Genbank information related to these genes is summarized in Table 52 below.

TABLE 52

| Gene | GI # | Accession No. | Organism |
|---|---|---|---|
| phl | 77019264 | CAJ15517.1 | *Penicillium chrysogenum* |
| phlB | 152002983 | ABS19624.1 | *Penicillium chrysogenum* |
| paaF | 22711873 | AAC24333.2 | *Pseudomonas putida* |
| AACS | 21313520 | NP_084486.1 | *Mus musculus* |
| AACS | 31982927 | NP_076417.2 | *Homo sapiens* |

In some embodiments, the present invention provides a semi-synthetic method for synthesizing terephthalate (PTA) that includes preparing muconic acid by culturing the above-described organisms, reacting the resultant muconic acid with acetylene to form a cyclohexadiene adduct (P1, FIG. 1), and oxidizing the cyclohexadiene adduct to form PTA. Semi-synthetic methods combine the biosynthetic preparation of advanced intermediates with conventional organic chemical reactions.

While the culturing of muconic acid is discussed further below, the Diels-Alder reaction conditions are detailed here. Diels-Alder reactions are widespread in the chemical industry and are known to those skilled in the art (Carruthers, W., Some Modern Methods of Organic Synthesis, Cambridge University Press (1986); Norton, J., *Chem. Review* 31:319-523 (1942); Sauer, J., *Angewandte Chemie* 6:16-33 (1967)). This class of pericyclic reactions is well-studied for its ability to generate cyclic compounds at low energetic cost. Diels-Alder reactions are thus an attractive and low-cost way of making a variety of pharmaceuticals and natural products.

In a Diels-Alder reaction, a conjugated diene or heterodiene reacts with an alkene, alkyne, or other unsaturated functional group, known as a dienophile, to form a six-membered ring. One aspect of the Diels-Alder reaction is that the two components usually have complementary electronic character, as determined by the energies of the highest occupied molecular orbital (HOMO) and lowest unoccupied molecular orbital (LUMO) of the diene and dienophile (Carruthers, W., Some Modern Methods of Organic Synthesis, Cambridge University Press (1986). In normal mode, the diene is electron-rich and the dienophile is electron-poor, although this is not always the case. The method of the present invention provides the opposite electronic configuration with an electron poor diene and a relatively electron rich dienophile, in what is termed an inverse electron demand Diels-Alder reaction. The main physical constraint for this type of reaction is that the conjugated diene must be able to adopt a cisoid conformation for the reaction to proceed. A wide variety of substituted conjugated dienes and dienophiles are able to undergo this chemistry.

In the disclosed reaction of FIG. 1, muconate is the conjugated diene, and is beneficially in the trans,trans or cis,trans isomeric configuration for the reaction to proceed. The cis, cis isomer of muconate, prevalent in biological systems as a degradation product of catechol, is unlikely to adopt the required cisoid conformation due to steric hindrance of the carboxylic acid groups. The trans,trans isomer of muconate (shown in FIG. 1) is able to react in Diels-Alder reactions with a variety of dienes (Deno, N. C., *J. Am. Chem. Soc.* 72:4057-4059 (1950); Sauer, J., *Angewandte Chemie* 6:16-33 (1967)).

Acetylene serves as the dienophile in the production of PTA. Acetylene and substituted acetylene derivatives are well-known dienophiles ((Carruthers, W., Some Modern Methods of Organic Synthesis, Cambridge University Press (1986); U.S. Pat. No. 3,513,209, Clement, R. A.; Dai et al., *J. Am. Chem. Soc.* 129:645-657 (2007)). The addition of electron-withdrawing substituents increases reactivity in normal mode Diels Alder reactions; likewise, in the inverse electron demand, electron donating groups are employed to increase reactivity. At elevated temperatures, unsubstituted acetylene has been shown to react with butadiene and other substituted linear and cyclic dienes (U.S. Pat. No. 3,513,209, Clement, R. A.; Norton, J., *Chem. Review* 31:319-523 (1942); Vijaya et al., *J. Mol. Struct.* 589-590:291-299 (2002)).

Increased temperature can be used to perform the Diels-Alder reaction in FIG. 1. For example, the Diels-Alder reaction of acetylene with 1,3-butadiene to form 1,4-cyclohexadiene is performed in the range of 80-300° C. (U.S. Pat. No. 3,513,209, Clement, R. A. supra).

Other reaction conditions that have been shown to enhance the rate of Diels-Alder reactions include elevated pressure, the addition of a Lewis acid, and stoichiometric excess of acetylene. Elevated pressure up to 1000 atmospheres was shown to enhance the rate of 1,4-cyclohexadiene formation from butadiene and acetylene (U.S. Pat. No. 3,513,209, Clement, R. A.). Catalytic amounts of Lewis acids can also improve reaction rate (Nicolaou et al., *Angewandte Chemie* 41:1668-1698 (2002)). Some suitable Lewis acids include magnesium halides such as magnesium chloride, magnesium bromide or magnesium iodide or zinc halides such as zinc chloride, zinc bromide or zinc iodide. Stoichiometric excess of acetylene will aid in reducing formation of homopolymerization byproducts.

Oxidation of the Diels-Alder product, cyclohexa-2,5-diene-1,4-dicarboxylate (P1), to PTA can be accomplished in the presence or absence of catalyst under mild reaction conditions. The driving force for P1 oxidation is the formation of the aromatic ring of PTA. Precedence for the conversion of P1 to PTA in the absence of catalyst is the conversion of 1,4-cyclohexadiene to benzene in air (U.S. Pat. No. 3,513,209, Clement, R. A.). 1,4-Cyclohexadiene is also converted to benzene by catalysis, for example using transition metal complexes such as bis(arene)molybdenum (0) and bis(arene)chromium(0) (Fochi, G., *Organometallics* 7:225-2256 (1988)) or electroactive binuclear rhodium complexes (Smith and Gray, *Catalysis Letters* 6:195-199 (1990)).

In some embodiments, the method for synthesizing PTA includes isolating muconic acid from the culture broth prior to reacting with acetylene in the Diels-Alder reaction. This is particularly helpful since the Diels-Alder reaction, is frequently done in the absence of a solvent, especially under thermal conditions. Isolation of muconic acid can involve various filtration and centrifugation techniques. Cells of the culture and other insoluble materials can be filtered via ultrafiltration and certain salts can be removed by nanofiltration. Because muconic acid is a diacid, standard extraction techniques can be employed that involve adjusting the pH. After removal of substantially all solids and salts, the muconic acid can be separated from water by removal of water with heating in vacuo, or by extraction at low pH. For example, following the addition of sulfuric acid or phosphoric acid to the fermentation broth in sufficient amounts (pH 3 or lower), the free carboxylate acid form of muconic acid precipitates out of solution (U.S. Pat. No. 4,608,338). In this form, muconic acid is readily separated from the aqueous solution by filtration or other conventional means.

In some embodiments, the muconic acid need not be isolated. Instead, the Diels-Alder reaction between muconic acid and acetylene can be performed in the culture broth. In such a case, the culture broth can be optionally filtered prior to adding acetylene.

The non-naturally occurring microbial organisms of the invention can be produced by introducing expressible nucleic acids encoding one or more of the enzymes or proteins participating in one or more muconate biosynthetic pathways. Depending on the host microbial organism chosen for biosynthesis, nucleic acids for some or all of a particular muconate biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve muconate biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as muconate.

Depending on the muconate biosynthetic pathway constituents of a selected host microbial organism, the non-naturally occurring microbial organisms of the invention will include at least one exogenously expressed muconate pathway-encoding nucleic acid and up to all encoding nucleic acids for one or more muconate biosynthetic pathways. For example, muconate biosynthesis can be established in a host deficient in a pathway enzyme or protein through exogenous expression of the corresponding encoding nucleic acid. In a host deficient in all enzymes or proteins of a muconate pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of muconate can be included, such as those shown in FIGS. 2-5.

Given the teachings and guidance provided herein, those skilled in the art will understand that the number of encoding nucleic acids to introduce in an expressible form will, at least, parallel the muconate pathway deficiencies of the selected host microbial organism. Therefore, a non-naturally occurring microbial organism of the invention can have one, two, three, four, six, etc. up to all nucleic acids encoding the enzymes or proteins constituting a muconate biosynthetic pathway disclosed herein. In some embodiments, the non-naturally occurring microbial organisms also can include other genetic modifications that facilitate or optimize muconate biosynthesis or that confer other useful functions onto the host microbial organism. One such other functionality can include, for example, augmentation of the synthesis of one or more of the muconate pathway precursors such as succinyl-CoA.

Generally, a host microbial organism is selected such that it produces the precursor of a muconate pathway, either as a naturally produced molecule or as an engineered product that either provides de novo production of a desired precursor or increased production of a precursor naturally produced by the host microbial organism. For example, succinyl-CoA is produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a muconate pathway.

In some embodiments, a non-naturally occurring microbial organism of the invention is generated from a host that contains the enzymatic capability to synthesize muconate. In this specific embodiment it can be useful to increase the synthesis or accumulation of a muconate pathway product to, for example, drive muconate pathway reactions toward muconate production. Increased synthesis or accumulation can be accomplished by, for example, overexpression of nucleic acids encoding one or more of the above-described muconate pathway enzymes or proteins. Overexpression of the enzyme or enzymes and/or protein or proteins of the muconate pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing muconate, through overexpression of one, two, three, four, five, six, that is, up to all nucleic acids encoding muconate biosynthetic pathway enzymes or proteins. In addition, a non-naturally occurring organism can be generated by mutagenesis of an endogenous gene that results in an increase in activity of an enzyme in the muconate biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a muconate biosynthetic pathway onto the microbial organism. Alternatively, encoding nucleic acids can be introduced to produce an intermediate microbial organism having the biosynthetic capability to catalyze some of the required reactions to confer muconate biosynthetic capability. For example, a non-naturally occurring microbial organism having a muconate biosynthetic pathway can comprise at least two exogenous nucleic acids encoding desired enzymes or proteins. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention and so forth, as desired, so long as the combination of enzymes and/or proteins of the desired biosynthetic pathway results in production of the corresponding desired product. Similarly, any combination of four, or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of muconate as described herein, the non-naturally occurring microbial organisms and methods of the invention also can be utilized in various combinations with each other and with other microbial organisms and methods well known in the art to achieve product biosynthesis by other routes. For example, one alternative to produce muconate other than use of the muconate producers is through addition of another microbial organism capable of converting a muconate pathway intermediate to muconate. One such procedure includes, for example, the fermentation of a microbial organism that produces a muconate pathway intermediate. The muconate pathway intermediate can then be used as a substrate for a second microbial organism that converts the muconate pathway intermediate to muconate. The muconate pathway intermediate can be added directly to another culture of the second organism or the original culture of the muconate pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, muconate. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of muconate can be accomplished by constructing a microbial organism that contains biosynthetic pathways for conversion of one pathway intermediate to another pathway intermediate or the product. Alternatively, muconate also can be biosynthetically produced from microbial organisms through co-culture or co-fermentation using two organisms in the same vessel, where the first microbial organism produces a muconate intermediate and the second microbial organism converts the intermediate to muconate.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce muconate.

Sources of encoding nucleic acids for a muconate pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite muconate biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of muconate described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative muconate biosynthetic pathway exists in an unrelated species, muconate biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize muconate.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*. *E. coli* is a particularly useful host organisms since it is a well characterized microbial organism suitable for genetic engineering. Other particularly useful host organisms include yeast such as *Saccharomyces cerevisiae*.

Methods for constructing and testing the expression levels of a non-naturally occurring muconate-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of muconate can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more muconate biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (e.g., $>10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened.

Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-

742 (2007), Patel (ed.), CRC Press; Otten and Quax, *Biomol. Eng* 22:1-9 (2005); and Sen et al., *Appl Biochem. Biotechnol* 143:212-223 (2007)) to be effective at creating diverse variant libraries and these methods have been successfully applied to the improvement of a wide range of properties across many enzyme classes.

Enzyme characteristics that have been improved and/or altered by directed evolution technologies include, for example, selectivity/specificity—for conversion of non-natural substrates; temperature stability—for robust high temperature processing; pH stability—for bioprocessing under lower or higher pH conditions; substrate or product tolerance—so that high product titers can be achieved; binding ($K_m$)—broadens substrate binding to include non-natural substrates; inhibition ($K_i$)—to remove inhibition by products, substrates, or key intermediates; activity (kcat)—increases enzymatic reaction rates to achieve desired flux; expression levels—increases protein yields and overall pathway flux; oxygen stability—for operation of air sensitive enzymes under aerobic conditions; and anaerobic activity—for operation of an aerobic enzyme in the absence of oxygen.

The following exemplary methods have been developed for the mutagenesis and diversification of genes to target desired properties of specific enzymes. Any of these can be used to alter/optimize activity of a decarboxylase enzyme.

EpPCR (Pritchard et al., *J Theor. Biol* 234:497-509 (2005)) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful. A high number of mutants can be generated by EpPCR, so a high-throughput screening assay or a selection method (especially using robotics) is useful to identify those with desirable characteristics.

Error-prone Rolling Circle Amplification (epRCA) (Fujii et al., *Nucleic Acids Res* 32:e145 (2004); and Fujii et al., *Nat. Protoc.* 1:2493-2497 (2006)) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the $Mn^{2+}$ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a kit.

DNA or Family Shuffling (Stemmer, *Proc. Natl. Acad. Sci. U.S.A.* 91:10747-10751 (1994); and Stemmer, *Nature* 370:389-391 (1994)) typically involves digestion of two or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious, random and neutral mutations that might confer antigenicity.

Staggered Extension (StEP) (Zhao et al., *Nat. Biotechnol* 16:258-261 (1998)) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template. (Shao et al., *Nucleic Acids Res* 26:681-683 (1998)) Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair. (Volkov et al, *Nucleic Acids Res* 27:e18 (1999); and Volkov et al., *Methods Enzymol.* 328:456-463 (2000)) The mismatch repair step is at least somewhat mutagenic. Heteroduplexes transform more efficiently than linear homoduplexes. This method is suitable for large genes and whole operons.

Random Chimeragenesis on Transient Templates (RACHITT) (Coco et al., *Nat. Biotechnol* 19:354-359 (2001)) employs Dnase I fragmentation and size fractionation of ssDNA. Homologous fragments are hybridized in the absence of polymerase to a complementary ssDNA scaffold. Any overlapping unhybridized fragment ends are trimmed down by an exonuclease. Gaps between fragments are filled in, and then ligated to give a pool of full-length diverse strands hybridized to the scaffold (that contains U to preclude amplification). The scaffold then is destroyed and is replaced by a new strand complementary to the diverse strand by PCR amplification. The method involves one strand (scaffold) that is from only one parent while the priming fragments derive from other genes; the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates. (Lee et al., *J. Molec. Catalysis* 26:119-129 (2003)) No DNA endonucleases are used. Unidirectional ssDNA is made by DNA polymerase with random primers or serial deletion with exonuclease. Unidirectional ssDNA are only templates and not primers. Random priming and exonucleases don't introduce sequence bias as true of enzymatic cleavage of DNA shuffling/RACHITT. RETT can be easier to optimize than StEP because it uses normal PCR conditions instead of very short extensions. Recombination occurs as a component of the PCR steps—no direct shuffling. This method can also be more random than StEP due to the absence of pauses.

In Degenerate Oligonucleotide Gene Shuffling (DOGS) degenerate primers are used to control recombination between molecules; (Bergquist and Gibbs, *Methods Mol. Biol.* 352:191-204 (2007); Bergquist et al., *Biomol. Eng* 22:63-72 (2005); Gibbs et al., *Gene* 271:13-20 (2001)) this can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest. (Ostermeier et al., *Proc. Natl. Acad. Sci. U.S.A.* 96:3562-3567 (1999); and Ostermeier et al., *Nat. Biotechnol* 17:1205-1209 (1999)) Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is similar to ITCHY except that phosphothioate dNTPs are used to generate truncations. (Lutz et al., *Nucleic Acids Res* 29:E16 (2001)) Relative to ITCHY, THIO-ITCHY can be easier to optimize, provide more reproducibility, and adjustability.

SCRATCHY combines two methods for recombining genes, ITCHY and DNA shuffling. (Lutz et al., *Proc. Natl. Acad. Sci. U.S.A.* 98:11248-11253 (2001)) SCRATCHY combines the best features of ITCHY and DNA shuffling. First, ITCHY is used to create a comprehensive set of fusions between fragments of genes in a DNA homology-independent fashion. This artificial family is then subjected to a DNA-shuffling step to augment the number of crossovers. Computational predictions can be used in optimization. SCRATCHY is more effective than DNA shuffling when sequence identity is below 80%.

In Random Drift Mutagenesis (RNDM) mutations made via epPCR followed by screening/selection for those retaining usable activity. (Bergquist et al., *Biomol. Eng* 22:63-72 (2005)) Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates pool of random length fragments using random incorporation of a phosphothioate nucleotide and cleavage; this pool is used as a template to 2) extend in the presence of "universal" bases such as inosine; 3) replication of a inosine-containing complement gives random base incorporation and, consequently, mutagenesis. (Wong et al., *Biotechnol J.* 3:74-82 (2008); Wong et al., *Nucleic Acids Res* 32:e26 (2004); and Wong et al., *Anal. Biochem.* 341:187-189 (2005)) Using this technique it can be possible to generate a large library of mutants within 2-3 days using simple methods. This technique is non-directed in comparison to the mutational bias of DNA polymerases. Differences in this approach makes this technique complementary (or an alternative) to epPCR.

In Synthetic Shuffling, overlapping oligonucleotides are designed to encode "all genetic diversity in targets" and allow a very high diversity for the shuffled progeny. (Ness et al., *Nat. Biotechnol* 20:1251-1255 (2002)) In this technique, one can design the fragments to be shuffled. This aids in increasing the resulting diversity of the progeny. One can design sequence/codon biases to make more distantly related sequences recombine at rates approaching those observed with more closely related sequences. Additionally, the technique does not require physically possessing the template genes.

Nucleotide Exchange and Excision Technology NexT exploits a combination of dUTP incorporation followed by treatment with uracil DNA glycosylase and then piperidine to perform endpoint DNA fragmentation. (Muller et al., *Nucleic Acids Res* 33:e117 (2005)) The gene is reassembled using internal PCR primer extension with proofreading polymerase. The sizes for shuffling are directly controllable using varying dUPT::dTTP ratios. This is an end point reaction using simple methods for uracil incorporation and cleavage. Other nucleotide analogs, such as 8-oxo-guanine, can be used with this method. Additionally, the technique works well with very short fragments (86 bp) and has a low error rate. The chemical cleavage of DNA used in this technique results in very few unshuffled clones.

In Sequence Homology-Independent Protein Recombination (SHIPREC) a linker is used to facilitate fusion between two distantly/unrelated genes. Nuclease treatment is used to generate a range of chimeras between the two genes. These fusions result in libraries of single-crossover hybrids. (Sieber et al., *Nat. Biotechnol* 19:456-460 (2001)) This produces a limited type of shuffling and a separate process is required for mutagenesis. In addition, since no homology is needed this technique can create a library of chimeras with varying fractions of each of the two unrelated parent genes. SHIPREC was tested with a heme-binding domain of a bacterial CP450 fused to N-terminal regions of a mammalian CP450; this produced mammalian activity in a more soluble enzyme.

In Gene Site Saturation Mutagenesis™ (GSSM™) the starting materials are a supercoiled dsDNA plasmid containing an insert and two primers which are degenerate at the desired site of mutations. (Kretz et al., *Methods Enzymol.* 388:3-11 (2004)) Primers carrying the mutation of interest, anneal to the same sequence on opposite strands of DNA. The mutation is typically in the middle of the primer and flanked on each side by ~20 nucleotides of correct sequence. The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (i.e., one codon). The technique facilitates the generation of all possible replacements at a single-site with no nonsense codons and results in equal to near-equal representation of most possible alleles. This technique does not require prior knowledge of the structure, mechanism, or domains of the target enzyme. If followed by shuffling or Gene Reassembly, this technology creates a diverse library of recombinants containing all possible combinations of single-site up-mutations. The utility of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations. (Reidhaar-Olson et al. Methods Enzymol. 208: 564-586 (1991); and Reidhaar-Olson et al. Science 241:53-57 (1988)) Simultaneous substitutions at two or three sites are possible using this technique. Additionally, the method tests a large multiplicity of possible sequence changes at a limited range of sites. This technique has been used to explore the information content of the lambda repressor DNA-binding domain.

Combinatorial Multiple Cassette Mutagenesis (CMCM) is essentially similar to CCM except it is employed as part of a larger program: 1) Use of epPCR at high mutation rate to 2) ID hot spots and hot regions and then 3) extension by CMCM to cover a defined region of protein sequence space. (Reetz et al., Angew. Chem. Int. Ed Engl. 40:3589-3591 (2001).) As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique conditional is mutator plasmids allow increases of 20- to 4000-X in random and natural mutation frequency during selection and block accumulation of deleterious mutations when selection is not required. (Selifonova et al., Appl Environ Microbiol 67:3645-3649 (2001)) This technology is based on a plasmid-derived mutD5 gene, which encodes a mutant subunit of DNA polymerase III. This subunit binds to endogenous DNA polymerase III and compromises the proofreading ability of polymerase III in any strain that harbors the plasmid. A broad-spectrum of base substitutions and frameshift mutations occur. In order for effective use, the mutator plasmid should be removed once the desired phenotype is achieved; this is accomplished through a temperature sensitive origin of replication, which allows for plasmid curing at 41° C. It should be noted that mutator strains have been explored for quite some time (e.g., see Low et al., J. Mol. Biol. 260:359-3680 (1996)). In this technique very high spontaneous mutation rates are observed. The conditional property minimizes non-desired background mutations. This technology could be combined with adaptive evolution to enhance mutagenesis rates and more rapidly achieve desired phenotypes.

"Look-Through Mutagenesis (LTM) is a multidimensional mutagenesis method that assesses and optimizes combinatorial mutations of selected amino acids." (Rajpal et al., Proc Natl Acad Sci U.S.A. 102:8466-8471 (2005)) Rather than saturating each site with all possible amino acid changes, a set of nine is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This is a rational approach to minimize the number of random combinations and can increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to creating a large library of chimeras (multiple mutations) of a single gene. (Tunable GeneReassembly™ (TGR™) Technology supplied by Verenium Corporation) Typically this technology is used in combination with ultra-high-throughput screening to query the represented sequence space for desired improvements. This technique allows multiple gene recombination independent of homology. The exact number and position of cross-over events can be pre-determined using fragments designed via bioinformatic analysis. This technology leads to a very high level of diversity with virtually no parental gene reformation and a low level of inactive genes. Combined with GSSM™, a large range of mutations can be tested for improved activity. The method allows "blending" and "fine tuning" of DNA shuffling, e.g. codon usage can be optimized.

In Silico Protein Design Automation (PDA) is an optimization algorithm that anchors the structurally defined protein backbone possessing a particular fold, and searches sequence space for amino acid substitutions that can stabilize the fold and overall protein energetics. (Hayes et al., Proc Natl Acad Sci U.S.A. 99:15926-15931 (2002)) This technology uses in silico structure-based entropy predictions in order to search for structural tolerance toward protein amino acid variations. Statistical mechanics is applied to calculate coupling interactions at each position. Structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants ($10^{50}$). The choice of sequence variants to test is related to predictions based on the most favorable thermodynamics. Ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves: 1) use knowledge of structure/function to choose a likely site for enzyme improvement; 2) saturation mutagenesis at chosen site using Stratagene QuikChange (or other suitable means); 3) screen/select for desired properties; and 4) with improved clone(s), start over at another site and continue repeating. (Reetz et al., Nat. Protoc. 2:891-903 (2007); and Reetz et al., Angew. Chem. Int. Ed Engl. 45:7745-7751 (2006)) This is a proven methodology, which assures all possible replacements at a given position are made for screening/selection.

Any of the aforementioned methods for mutagenesis can be used alone or in any combination. Additionally, any one or combination of the directed evolution methods can be used in conjunction with adaptive evolution techniques.

The present invention provides a method for producing muconate that includes culturing a non-naturally occurring microbial organism having a muconate pathway. The pathway includes at least one exogenous nucleic acid encoding a muconate pathway enzyme expressed in a sufficient amount to produce muconate, under conditions and for a sufficient period of time to produce muconate. The muconate pathway includes an enzyme selected from the group consisting of a beta-ketothiolase, a beta-ketoadipyl-CoA hydrolase, a beta-ketoadipyl-CoA transferase, a beta-ketoadipyl-CoA ligase, a 2-fumarylacetate reductase, a 2-fumarylacetate dehydrogenase, a trans-3-hydroxy-4-hexendioate dehydratase, a 2-fumarylacetate aminotransferase, a 2-fumarylacetate aminating oxidoreductase, a trans-3-amino-4-hexenoate deaminase, a beta-ketoadipate enol-lactone hydrolase, a muconolactone isomerase, a muconate cycloisomerase, a beta-ketoadipyl-CoA dehydrogenase, a 3-hydroxyadipyl-CoA dehydratase, a 2,3-dehydroadipyl-CoA transferase, a 2,3-dehydroadipyl-CoA hydrolase, a 2,3-dehydroadipyl-CoA ligase, a muconate reductase, a 2-maleylacetate reductase, a 2-maleylacetate dehydrogenase, a cis-3-hydroxy-4-hexendioate dehydratase, a 2-maleylacetate aminotransferase, a 2-maleylacetate aminating oxidoreductase, a cis-3-amino-4-hexendioate deaminase, and a muconate cis/trans isomerase.

In some embodiments, the muconate pathway includes, a set of muconate pathway enzymes such as those exemplified in FIG. 2; the set of muconate pathway enzymes are selected from the group consisting of:

A) (1) beta-ketothiolase, (2) an enzyme selected from beta-ketoadipyl-CoA hydrolase, beta-ketoadipyl-CoA transferase, and beta-ketoadipyl-CoA ligase, (3) beta-ketoadipate enol-lactone hydrolase, (4) muconolactone isomerase, (5) muconate cycloisomerase, and (6) muconate cis/trans isomerase;

B) (1) beta-ketothiolase, (2) an enzyme selected from beta-ketoadipyl-CoA hydrolase, beta-ketoadipyl-CoA transferase and beta-ketoadipyl-CoA ligase, (3) 2-maleylacetate reductase, (4) 2-maleylacetate dehydrogenase, (5) cis-3-hydroxy-4-hexendioate dehydratase, and (6) muconate cis/trans isomerase;

C) (1) beta-ketothiolase, (2) an enzyme selected from beta-ketoadipyl-CoA hydrolase, beta-ketoadipyl-CoA transferase and beta-ketoadipyl-CoA ligase, (3) 2-maleylacetate reductase, (4) an enzyme selected from 2-maleylacetate aminotransferase and 2-maleylacetate aminating oxidoreductase, (5) cis-3-amino-4-hexenoate deaminase, and (6) muconate cis/trans isomerase;

D) (1) beta-ketothiolase, (2) beta-ketoadipyl-CoA dehydrogenase, (3) 3-hydroxyadipyl-CoA dehydratase, (4) an enzyme selected from 2,3-dehydroadipyl-CoA transferase, 2,3-dehydroadipyl-CoA hydrolase and 2,3-dehydroadipyl-CoA ligase, and (5) muconate reductase;

E) (1) beta-ketothiolase, (2) an enzyme selected from beta-ketoadipyl-CoA hydrolase, beta-ketoadipyl-CoA transferase and beta-ketoadipyl-CoA ligase, (3) 2-fumarylacetate reductase, (4) 2-fumarylacetate dehydrogenase, and (5) trans-3-hydroxy-4-hexendioate dehydratase;

F) (1) beta-ketothiolase, (2) an enzyme selected from beta-ketoadipyl-CoA hydrolase, beta-ketoadipyl-CoA transferase and beta-ketoadipyl-CoA ligase, (3) 2-fumarylacetate reductase, (4) an enzyme selected from 2-fumarylacetate aminotransferase and 2-fumarylacetate aminating oxidoreductase, and (5) trans-3-amino-4-hexenoate deaminase.

In some embodiments, the present invention provides a method for producing muconate that includes culturing a non-naturally occurring microbial organism having a muconate pathway. The pathway comprising at least one exogenous nucleic acid encoding a muconate pathway enzyme expressed in a sufficient amount to produce muconate, under conditions and for a sufficient period of time to produce muconate. The muconate pathway includes a 4-hydroxy-2-ketovalerate aldolase, a 2-oxopentenoate hydratase, a 4-oxalocrotonate dehydrogenase, a 2-hydroxy-4-hexenedioate dehydratase, a 4-hydroxy-2-oxohexanedioate oxidoreductase, a 2,4-dihydroxyadipate dehydratase (acting on 2-hydroxy), a 2,4-dihydroxyadipate dehydratase (acting on 4-hydroxyl group) and a 3-hydroxy-4-hexenedioate dehydratase.

In some embodiments, the muconate pathway includes, a set of muconate pathway enzymes such as those exemplified in FIG. 3; the set of muconate pathway enzymes are selected from the group consisting of:

A) (1) 4-hydroxy-2-ketovalerate aldolase, (2) 2-oxopentenoate hydratase, (3) 4-oxalocrotonate dehydrogenase, (4) 2-hydroxy-4-hexenedioate dehydratase;

B) (1) 4-hydroxy-2-ketovalerate aldolase, (2) 4-hydroxy-2-oxohexanedioate oxidoreductase, (3) 2,4-dihydroxyadipate dehydratase (acting on 2-hydroxy), (4) 3-hydroxy-4-hexenedioate dehydratase; and C) (1) 4-hydroxy-2-ketovalerate aldolase, (2) 4-hydroxy-2-oxohexanedioate oxidoreductase, (3) 2,4-dihydroxyadipate dehydratase (acting on 4-hydroxyl group), (4) 2-hydroxy-4-hexenedioate dehydratase.

In some embodiments, the present invention provides a method for producing muconate that includes culturing a non-naturally occurring microbial organism having a muconate pathway. The pathway includes at least one exogenous nucleic acid encoding a muconate pathway enzyme expressed in a sufficient amount to produce muconate, under conditions and for a sufficient period of time to produce muconate. The muconate pathway includes an enzyme selected from the group consisting of an HODH aldolase, an OHED hydratase, an OHED decarboxylase, an HODH formate-lyase, an HODH dehydrogenase, an OHED formate-lyase, an OHED dehydrogenase, a 6-OHE dehydrogenase, a 3-hydroxyadipyl-CoA dehydratase, a 2,3-dehydroadipyl-CoA hydrolase, a 2,3-dehydroadipyl-CoA transferase, a 2,3-dehydroadipyl-CoA ligase, and a muconate reductase.

In some embodiments, the muconate pathway includes, a set of muconate pathway enzymes such as those exemplified in FIG. 4; the set of muconate pathway enzymes are selected from the group consisting of:

A) (1) HODH aldolase, (2) OHED hydratase, (3) OHED decarboxylase, (4) 6-OHE dehydrogenase, and (5) muconate reductase;

B) (1) HODH aldolase, (2) OHED hydratase, (3) an enzyme selected from OHED formate-lyase and OHED dehydrogenase, (4) an enzyme selected from 2,3-dehydroadipyl-CoA hydrolase, 2,3-dehydroadipyl-CoA transferase and 2,3-dehydroadipyl-CoA ligase, and (5) muconate reductase; and C) (1) HODH aldolase, (2) an enzyme selected from HODH formate-lyase and HODH dehydrogenase, (3) 3-hydroxyadipyl-CoA dehydratase, (4) an enzyme selected from 2,3-dehydroadipyl-CoA hydrolase, 2,3-dehydroadipyl-CoA transferase and 2,3-dehydroadipyl-CoA ligase, and (5) muconate reductase.

In some embodiments, the present invention provides a method for producing muconate that includes culturing a non-naturally occurring microbial organism having a muconate pathway. The pathway includes at least one exogenous nucleic acid encoding a muconate pathway enzyme expressed in a sufficient amount to produce muconate, under conditions and for a sufficient period of time to produce muconate. The muconate pathway includes an enzyme selected from the group consisting of a lysine aminotransferase, a lysine aminating oxidoreductase, a 2-aminoadipate semialdehyde dehydrogenase, a 2-aminoadipate deaminase, a muconate reductase, a lysine-2,3-aminomutase, a 3,6-diaminohexanoate aminotransferase, a 3,6-diaminohexanoate aminating oxidoreductase, a 3-aminoadipate semialdehyde dehydrogenase, and a 3-aminoadipate deaminase.

In some embodiments, the muconate pathway includes, a set of muconate pathway enzymes such as those exemplified in FIG. 5; the set of muconate pathway enzymes are selected from the group consisting of:

A) (1) lysine aminotransferase, (2) lysine aminating oxidoreductase, (3) 2-aminoadipate semialdehyde dehydrogenase, (4) 2-aminoadipate deaminase, and (5) muconate reductase B) (1) lysine-2,3-aminomutase, (2) 3,6-diaminohexanoate aminotransferase, (3) 3,6-diaminohexanoate aminating oxidoreductase, (4) 3-aminoadipate semialdehyde dehydrogenase, (5) 3-aminoadipate deaminase, and (6) muconate reductase.

In some embodiments, the foregoing non-naturally occurring microbial organism can be cultured in a substantially anaerobic culture medium.

Suitable purification and/or assays to test for the production of muconate can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art. For example, a spectrophotometric assay for succinyl-CoA:3-ketoacid-CoA transferase (FIG. 2, Step B) entails measuring the change in the absorbance corresponding to the product CoA molecule (i.e., succinyl-CoA) in the presence of the enzyme extract when supplied with succinate and β-ketoadipyl-CoA (Corthesy-Theulaz et al., *J Biol Chem.*, 272(41) (1997)). Succinyl-CoA can alternatively be measured in the presence of excess hydroxylamine by complexing the succinohydroxamic acid formed to ferric salts as referred to in (Corthesy-Theulaz et al., *J. Biol Chem.* 272(41) (1997)). The specific activity of muconate reductase can be assayed in the reductive direction using a colorimetric assay adapted from the literature (Durre et al., *FEMS Microbiol. Rev.* 17:251-262 (1995); Palosaari et al., *J. Bacteriol.* 170:2971-2976 (1988); Welch et al., *Arch. Biochem. Biophys.* 273:309-318 (1989)). In this assay, the substrates muconate and NADH are added to cell extracts in a buffered solution, and the oxidation of NADH is followed by reading absorbance at 340 nM at regular intervals. The resulting slope of the reduction in absorbance at 340 nM per minute, along with the molar extinction coefficient of NADH at 340 nM (6000) and the protein concentration of the extract, can be used to determine the specific activity of muconate reductase.

The muconate can be separated from other components in the culture using a variety of methods well known in the art, as briefly described above Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the muconate producers can be cultured for the biosynthetic production of muconate.

For the production of muconate, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in U.S. patent application Ser. No. 11/891,602, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time. NOTE—Ideally this process would operate at low pH using an organisms that tolerates pH levels in the range 2-4.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of muconate.

In addition to renewable feedstocks such as those exemplified above, the muconate microbial organisms of the invention also can be modified for growth on syngas as its source of carbon. In this specific embodiment, one or more proteins or enzymes are expressed in the muconate producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

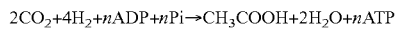

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a muconate pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, muconate and any of the intermediate metabolites in the muconate pathway. All that is required is to engineer in one or more of the required enzyme or protein activities to achieve biosynthesis of the desired compound or intermediate including, for example, inclusion of some or all of the muconate biosynthetic pathways. Accordingly, the invention provides a non-naturally occurring microbial organism that produces and/or secretes muconate when grown on a carbohydrate or other carbon source and produces and/or secretes any of the intermediate metabolites shown in the muconate pathway when grown on a carbohydrate or other carbon source. The muconate producing microbial organisms of the invention can initiate synthesis from an intermediate, such as any of the intermediates shown in FIGS. 2-5.

The non-naturally occurring microbial organisms of the invention are constructed using methods well known in the art as exemplified herein to exogenously express at least one nucleic acid encoding a muconate pathway enzyme or protein in sufficient amounts to produce muconate. It is understood that the microbial organisms of the invention are cultured under conditions sufficient to produce muconate. Following the teachings and guidance provided herein, the non-naturally occurring microbial organisms of the invention can achieve biosynthesis of muconate resulting in intracellular concentrations between about 0.1-200 mM or more. Generally, the intracellular concentration of muconate is between about 3-150 mM, particularly between about 5-200 mM and more particularly between about 8-150 mM, including about 10 mM, 50 mM, 75 mM, 100 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application Ser. No. 11/891,602, filed Aug. 10, 2007. Any of these conditions can be employed with the non-naturally occurring microbial organisms as well as other anaerobic conditions well known in the art. Under such anaerobic conditions, the muconate producers can synthesize muconate at intracellular concentrations of 5-10 mM or more as well as all other concentrations exemplified herein. It is understood that, even though the above description refers to intracellular concentrations, muconate producing microbial organisms can produce muconate intracellularly and/or secrete the product into the culture medium.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of muconate includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of muconate. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of muconate. Generally, and as with non-continuous culture procedures, the continuous and/or near-continuous production of muconate will include culturing a non-naturally occurring muconate producing organism of the invention in sufficient nutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of muconate can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the muconate producers of the invention for continuous production of substantial quantities of muconate, the muconate producers also can be, for example, simultaneously subjected to chemical synthesis procedures to convert the product to other compounds or the product can be separated from the fermentation culture and sequentially subjected to chemical conversion to convert the product to other compounds, if desired.

In addition to the above procedures, growth condition for achieving biosynthesis of muconate can include the addition of an osmoprotectant to the culturing conditions. In certain embodiments, the non-naturally occurring microbial organisms of the invention can be sustained, cultured or fermented as described above in the presence of an osmoprotectant. Briefly, an osmoprotectant means a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of muconate.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

It is understood that modifications which do not substantially affect the activity of the various embodiments of this invention are also provided within the definition of the invention provided herein. Accordingly, the following examples are intended to illustrate but not limit the present invention.

EXAMPLE I

Demonstration of Enzyme Activity for Condensing Succinyl-CoA and Acetyl-CoA to Form β-Ketoadipyl-CoA This Example shows the identification of enzymes for the formation of beta-ketoadipyl-CoA from succinyl-CoA and acetyl-CoA.

Several β-ketothiolase enzymes have been shown to break β-ketoadipyl-CoA into acetyl-CoA and succinyl-CoA. For example, the gene products encoded by pcaF in *Pseudomonas* strain B13 (Kaschabek et al., *J. Bacteriol.* 184(1): 207-15 (2002)), phaD in *Pseudomonas putida* U (Olivera et al., *Proc Natl Acad Sci USA*, 95(11), 6419-24 (1998)), paaE in *Pseudomonas fluorescens* ST (Di Gennaro et al., *Arch Microbiol*, 188(2), 117-25 (2007)), and paaJ from *E. coli* (Nogales et al., *Microbiology* 153(Pt 2), 357-65 (2007)) catalyze the conversion of 3-oxoadipyl-CoA into succinyl-CoA and acetyl-CoA during the degradation of aromatic compounds such as phenylacetate or styrene. To confirm that β-ketothiolase enzymes exhibit condensation activity, several thiolases (Table 53) were cloned into a derivative of pZE13 (Lutz et al., *Nucleic Acids Res*, 29(18), 3873-81 (2001)), which results in the clones having a carboxy-terminal 6×His tag.

TABLE 53

Cloned Thiolases

| Enzyme | Species Template | Gene | Length | 5' PRIMER | 3' PRIMER |
|---|---|---|---|---|---|
| beta-ketothiolase | *Ralstonia eutropha* H16 | bktB | 1185 | ATGACGCGTG AAGTGGTAGT GGTAAG | GATACGCTCGA AGATGGCGG |
| 2-Methylacetoacetyl-CoA Thiolase (branched chain?) | *Mus musculus* | ACAT1 | 1215 | ATGGAAGTAA GATGCCTGGA ACGAAG | CAGCTTCTCAAT CAGCAGGGC |
| 2-Methylacetoacetyl-CoA Thiolase (branched chain?) | *Pseudomonas putida* (KT2440) | fadAx | 1194 | ATGACCCTCG CCAATGACCC | GTACAGGCATTC AACAGCCATGG |
| beta-ketothiolase | *Caenorhabditis elegans* | kat-1 | 1167 | ATGAACAAAC ATGCTTTCATC GTCG | TAATTTCTGGAT AACCATTCCACT TGAGC |
| beta-ketothiolase NP_415915.1 | *Escherichia coli* | paaJ | 1206 | ATGCGTGAAG CCTTTATTTGT GACG | AACACGCTCCA GAATCATGGCG |
| beta-ketothiolase AAN68887.1 | *Pseudomonas putida* (KT2440) | phaD | 1221 | ATGAATGAAC CGACCCACGC C | GAGGCGCTCGA TGATCATGG |
| beta-ketothiolase NP_349476.1 | *Clostridium acetobutylicum* ATCC 824 | thiA | 1179 | ATGAAAGAAG TTGTAATAGCT AGTGCAGTAA GAAC | GCACTTTTCTAG CAATATTGCTGT TCC |
| beta-ketothiolase NP_149242.1 | *Clostridium acetobutylicum* ATCC 824 | thiB | 1179 | ATGAGAGATG TAGTAATAGT AAGTGCTGTA AGAACTG | GTCTCTTTCAAC TACGAGAGCTGT TCCC |

TABLE 53-continued

Cloned Thiolases

| Enzyme | Organism | Gene | Size | Forward | Reverse |
|---|---|---|---|---|---|
| 3-oxoadipyl-CoA thiolase | Candida albicans SC5314 | POT98 | 1182 | ATGTTCAAGAAATCAGCTAATGATATTGTTG | CTCGTTAGCAAACAAGGCAGCG |
| 3-oxoadipyl-CoA thiolase | Candela albicans SC5314 | POT1 | 1227 | ATGGATAGATTAAATCAATTAAGTGGTCAATTAAAACC | TTCCTTAATCAATATGGAGGCAGCAC |
| 3-oxoadipyl-CoA thiolase | Candida albicans SC5314 | POT2 | 1233 | ATGTCATCCAAACAACAATACTTGAAGAAG | TTCTCTAACCAAAACAGAAGCAGCACC |
| beta-ketoadipyl CoA thiolase pcaF | Pseudomonas aeruginosa PAO1 | pcaF | 1206 | ATGAGCCGCGAGGTATTCATCTG | GACCCGCTCGATGGCCAG |
| acyl-CoA thiolase | Pseudomonas aeruginosa PAO1 | bkt | 1206 | ATGCTCGATGCCTATATCTACGCC | TCGGCAGCGCTCGATCAC |
| 3-oxoadipyl-CoA thiolase | Pseudomonas putida (KT2440) | pcaF | 1203 | ATGCACGACGTATTCATCTGTGACG | AACCCGCTCGATGGCCAAC |
| 3-oxoadipyl-CoA thiolase | Burkholderia ambifaria AMMD | bkt | 1203 | ATGACCGACGCCTACATCTGCG | CACGCGTTCGATCGCGATC |
| beta-ketothiolase | Ascaris suum | bkt | 1242 | ATGGCCACCTCAAGACTTGTCTGC | CAATTTCTCGATGACCATTCCACC |

| Enzyme | ORF SEQ |
|---|---|
| beta-ketothiolase | atgacgcgtgaagtggtagtggtaagcggtgtccgtaccgcgatcgggacctttggcg<br>gcagcctgaaggatgtggcaccggcggagctgggcgcactggtggtgcgcgaggc<br>gctggcgcgcgcgcaggtgtcgggcgacgatgtcggccacgtggtattcggcaacgt<br>gatccagaccgagccgcgcgacatgtatctgggccgcgtcgccggccgtcaacggcg<br>gggtgacgatcaacgcccccgcgctgaccgtgaaccgcctgtgcggctcgggcctgc<br>aggccattgtcagcgccgcgcagaccatcctgctgggcgataccgacgtcgccatcg<br>gcggcggcgcggaaagcatgagccgcgcaccgtacctggcgccggcagcgcgctg<br>gggcgcacgcatgggcgacgccggcctggtcgacatgatgctgggtgcgctgcacg<br>atcccttccatcgcatccacatgggcgtgaccgccgagaatgtcgccaaggaatacga<br>catctcgcgcgcgcagcaggacgaggccgcgctggaatcgcaccgccgcgcttcgg<br>cagcgatcaaggccggctacttcaaggaccagatcgtcccggtggtgagcaagggcc<br>gcaagggcgacgtgaccttcgacaccgacgagcacgtgcgccatgacgccaccatc<br>gacgacatgaccaagctcaggccggtcttcgtcaaggaaaacggcacggtcacggcc<br>ggcaatgcctcgggcctgaacgacgccgccgccgcggtggtgatgatggagcgcgc<br>cgaagccgagcgccgcggcctgaagcgctggcccgcctggtgtcgtacggccatg<br>ccggcgtggacccgaaggccatgggcatcggccgccggtgccggcgacgaagatcgc<br>gctggagcgcgccggcctgcaggtgtcggacctggacgtgatcgaagccaacgaag<br>cctttgccgcacaggcgtgcgccgtgaccaaggcgctcggtctggacccggccaagg<br>ttaacccgaacggctcgggcatctcgctgggccacccgatcggcgccaccggtgccc<br>tgatcacggtgaaggcgctgcatgagctgaaccgcgtgcagggccgctacgcgctgg<br>tgacgatgtgcatcggcggcgggcagggcattgccgccatcttcgagcgtatctga |
| 2-Methylacetoacetyl-CoA Thiolase (branched chain?) | atggaagtaagatgcctggaacgaagttatgcatccaaacccactttgaatgaagtggtt<br>atagtaagtgctataagaactcccattggatccttcctgggcagccttgcctctcagccg<br>gccactaaacttggtactgctgcaattcagggagccattgagaaggcagggattccaaa<br>agaagaagtgaaggaagtctacatgggcaatgtcatccaaggggtgaaggacagg<br>cccctaccaggcaagcaacactgggcgcaggtttacctatttccactccatgcaccaca<br>gtaaacaaggtttgtgcttcaggaatgaaagccatcatgatggcctctcaaagtcttatgt<br>gtggacatcaggatgtgatggtggcaggcgggatggagagcatgtccaatgtcccata<br>cgtaatgagcagaggagcaacaccatatggtggggtaaaacttgaagacctgattgta<br>aaagacgggctaactgatgtctacaataaaattcatatgggtaactgtgctgagaatact<br>gcaaagaagatgaatatctcacggcaggaacaggatacgtacgctctcagctcttacac<br>cagaagtaaagaagcgtgggacgcagggaagtttgccagtgagattactcccatcacc<br>atctcagtgaaaggtaaaccagatgtggtggtgaaagaagatgaagaatacaagcgtg<br>ttgactttagtaaagtgccaaagctcaagaccgtgttccagaaagaaaatggcacaata<br>acagctgccaatgccagcacactgaacgatggagcagctgctctggttctcatgactgc<br>agaggcagcccagaggctcaatgttaagccattggcacgaattgcacatttgctgatg<br>ctgccgtagaccccattgattttccacttgcgcctgcatatgccgtacctaaggttcttaaa<br>tatgcaggactgaaaaaagaagacattgccatgtgggaagtaaatgaagcattcagtgt<br>ggttgtgctagccaacattaaaatgctggagattgaccccaaaaagtaaatatccacg<br>gaggagctgtttctctgggccatccaattgggatgtctggagcccggattgttgttcatat |

TABLE 53-continued

Cloned Thiolases

| | |
|---|---|
| | ggctcatgccctgaagccaggagagttcggtctggctagtatttgcaacggaggagga<br>ggtgcttccgccctgctgattgagaagctgtag |
| 2-Methylacetoacetyl-CoA Thiolase (branched chain?) | atgacccccgccaatgaccccatcgttatcgtcagcgccgtgcgcacgcccatgggcg<br>ggttgcagggcgacctcaagagcctgactgcgccgcaactgggcagcgccgccattc<br>gtgctgccgtggaacgggccggcatcgatgccgccggtgtcgagcaggtactgttcg<br>gctgcgtgctgccggccggccagggccaggcaccggcacgccaggccgcgctggg<br>cgccgggctggacaagacacccacctgcaccaccctgaacaagatgtgcggctcgg<br>gtatgcaagccgcgatcatggcccatgacctgctgctggccggcaccgcagacgtgg<br>tagtggcgggtggcatggaaagcatgaccaacgcgccgtacctgctggacaaagccc<br>gtggcggctaccgcatgggccacggcaagatcatcgaccacatgttcatggacggtct<br>cgaagacgcctacgacaaaggccgcctgatgggtaccttgccgaggactgtgccca<br>ggccaatgccttcagccgcgaggcccaggaccagttcgccatcgcctcgctgacccg<br>agcgcaggaagccatcagcagcggccgttttgccgccgagatcgtgccggtggaagt<br>caccgagggcaaggaaaagcgcgtcatcaaggatgacgagcagccgcccaaggcg<br>cgtctggacaagattgcgcagctcaaaccggcgtttcgtgaaggcggcaccgtgacg<br>gcggccaacgccagttcgatttccgacggcgctgcggcgctggtactgatgcgccgct<br>ccgaggccgacaaacgtggcctcaagccattggccgtcatccacggccacgccgcct<br>ttgccgacacccccgcgctgttcccgaccgcccccgatcggcgcgatcgacaaactgat<br>gaaacgcaccggctggaacctggccgaagtcgacctgttcgagatcaacgaggcctt<br>cgccgtggtcaccctggcggccatgaaacacctcgacctgccacacgacaaggtcaa<br>tatccacggcggcgcctgcgccctcggtcacccgatcggcgcttctggcgcacgtatt<br>ctggtcacccctgttgtcggccttgcgccagaacaatctgcgtcggggtgtggcggccat<br>ctgcatcggcggtggcgaggccacggccatggctgttaatgcctgtactga |
| beta-ketothiolase | atgaacaaacatgctttcatcgtcggagccgcccgtacacctattggatcatttcgttcttc<br>tctctcttcggtaactgctccagagctcgcctcggttgccatcaaagcagcattggagcg<br>tggagcagtcaagccgagttcaattcaggaggtgttccttggtcaagtctgtcaagcaa<br>atgctggtcaagctcccgctcgtcaagcagctcttggagccggactcgatcttcggttg<br>ctgttaccaccgtcaataaagtgtgctcttctgggctgaaagcaatcattcttgctgccca<br>gcaaattcaaaccggtcatcaagattttgccattggcggaggaatggagagcatgtcac<br>aagtaccattttatgttcaaagaggagagatcccatatggtggatttcaagtgattgatgg<br>aatcgtcaaagacggactgaccgatgctttatgataaagttcacatgggaaactgcggag<br>agaagacttcaaaagaaatgggaattacacgtaaagaccaagacgaatatgctatcaa<br>cagctacaaaaagtcagctaaagcatgggagaatgaaatatcggaccagaagtggt<br>gccagtgaacgtcaaatcaaagaagggagtcacgattgttgataaagatgaagagttca<br>caaaagtcaatttcgacaagttcacctcgctgagaactgttttccagaaagacggaacta<br>tcactgctgctaatgcttcaacattgaacgacggtgcagctgctgtcattgttgcctcaca<br>ggaagcagtttccgagcaaagcttaaagcctctggcccgaattttggcttatggagatgc<br>cgccacgcaccccactcgatttcgctgtagcaccaactttgatgttcccaaaaattcttgaa<br>agagcaggagtcaagcaatcagatgttgctcaatgggaagttaatgaagccttctcatgt<br>gttccccttgctttcatcaaaaaactaggagtcgatccatcccttgtgaacccacatggag<br>gagctgtttcaattggtcaccccatcggaatgtccggagcccgcctcatcactcatcttgt<br>gcacacactcaaaagtggccaaatcggagttgctgccatttgcaatggaggtggtggct<br>caagtggaatggttatccagaaattataa |
| beta-ketothiolase<br>NP_415915.1 | atgcgtgaagcctttatttgtgacggaattcgtacgccaattggtcgctacggcggggca<br>ttatcaagtgttcggtcgatgatctggctgctatccctttgcgggaactgctggtgcgaa<br>acccgcgtctcgatgcggagtgtatcgatgatgtgatcctcggctgtgctaatcaggca<br>ggagaagataaccgtaacgtagcccggatggcgactttactggcggggctgccgcag<br>agtgtttccggcacaaccattaaccgcttgtgtggttccgggctggacgcactggggttt<br>gccgcacgggcgattaaagcgggcgatggcgatttgctgatcgccggtggcgtggag<br>tcaatgtcacggggcaccgtttgttatgggcaaggcagccagtcatttctcgtcaggct<br>gagatgttcgataccactattggctggcgatttgtgaacccgctcatggctcagcaatttg<br>gaactgacagcatgccggaaacggcagagaatgtagctgaactgttaaaaatctcacg<br>agaagatcaagatagttttgcgctacgcagtcagcaacgtacggcaaaagcgcaatcc<br>tcaggcattctggctgaggagattgttccggttgtgttgaaaaacaagaaaggtgttgta<br>acagaaatacaacatgatgagcatctgcgcccggaaacgacgctggaacagttacgtg<br>ggttaaaagcaccatttcgtgccaatggggtgattaccgcaggcaatgcttccggggtg<br>aatgacggagccgctgcgttgattattgccagtgaacagatggcagcagcgcaagga<br>ctgacaccgcgggcgcgtatcgtagccatggcaaccgcccgggtgggaaccgcgcct<br>gatggggcttggtccggtgcctgcaactcgccgggtgctggaacgcgcagggctgag<br>tattcacgatatggacgtgattgaactgaacgaagcgttcgcggcccaggcgttgggtg<br>tactacgcgaattggggctgcctgatgatgcccacatgttaaccccaacggaggcgct<br>atcgccttaggccatccgttgggaatgagtggtgccgccctggcactggctgccagcc<br>atgagctgcatcggcgtaaccggtcgttacgcattgtgccaccatgtgcatcggtgtcggtc<br>agggcatcgccatgattctggagcgtgtttga |
| beta-ketothiolase<br>AAN68887.1 | atgaatgaaccgacccacgccgatgccttgatcatcgacgccgtgcgcacgccattg<br>gccgctatgccggggccctgagcagcgtgcgcgccgacgacctggcggccatcccg<br>ctcaaaagccttgatccagcgtcacccgaactggactggaaagccattgatgacgttat<br>cttcggctgtgccaaccaggctggcgaagacaaccgcaacgtggcccacatggcga<br>gcctgctggccgggctgccactcgaagtaccagggaccacgatcaaccgcctgtgcg<br>gttccggtctggatgccatcggtaatgcggcacgtgccctgcgctgcggtgaagcggg<br>gctcatgctggccggtggtgtggagtccatgtcgcgtgcaccgtttgtgatgggtaagt<br>cggagcaggcattcgggcgtgcggccgagctgttcgacaccaccatcggctggcgtttt<br>cgtcaacccgctgatgaaggccgcctacggcatcgattcgatgccggaaacggctga<br>aaacgtggccgaacagttcggcatctcgcgcgccgaccaggatgccttttgccctgcgc |

TABLE 53-continued

Cloned Thiolases

| | |
|---|---|
| | agccagcacaaagccgcagcagctcaggcccgcggccgcctggcgcgggaaatcg<br>tgccggtcgaaatcccgcaacgcaaaggcccagccaaagtggtcgagcatgacgag<br>caccgcgcggcgacacgaccctggagcagctggctcggctcgggacgccgtttcgt<br>gaaggcggcagcgtaacggcgggtaatgcctccggcgtgaatgacggcgcttgcgc<br>cctgctgctggccagcagcgccgcggcccgccgccatgggttgaaggcccgcggcc<br>gcatcgtcggcatggcggtggccggggttgagcccaggctgatgggcattggtccgg<br>tgcctgcgacccgcaaggtgctggcgctcaccggcctggcactggctgacctggatgt<br>catcgaactcaatgaggcctttgccgcccaagggctggccgtgttgcgcgagctgggc<br>ctggccgacgacgacccgcgagtcaaccgcaacggcggcgccatcgccctgggcc<br>atcccctgggcatgagcggtgcccggttggtgaccactgccttgcacgagcttgaaga<br>aacggccggccgctacgccctgtgcaccatgtgcatcggcgtaggccaaggcattgc<br>catgatcatcgagcgcctctga |
| beta-<br>ketothiolase<br>NP_349476.1 | atgaaagaagttgtaatagctagtgcagtaagaacagcgattggatcttatggaaagtct<br>cttaaggatgtaccagctagatttaggagctacagctataaaggaagcagttaaaaa<br>agcaggaataaaaccagaggatgttaatgaagtcattttaggaaatgttcttcaagcagg<br>tttaggacagaatccagcaagacaggcatcttttaaagcaggattaccagttgaaattcc<br>agctatgactattaataaggtttgtggttcaggacttagaacagttagcttagcagcacaa<br>attataaaagcaggagatgctgacgtaataatagcaggtggtatggaaaatatgtctaga<br>gctccttacttagcgaataacgctagatggggatatagaatgggaaacgctaaatttgtt<br>gatgaaatgatcactgacggattgtgggatgcatttaatgattaccacatgggaataaca<br>gcagaaaacatagctgagagatggaacatttcaagagaagaacaagatgagtttgctct<br>tgcatcacaaaaaaaagctgaagaagctataaaatcaggtcaatttaaagatgaaatagt<br>tcctgtagtaattaaaggcagaaagggagaaactgtagttgatacagatgagcaccta<br>gatttggatcaactatagaaggacttgcaaaattaaaacctgccttcaaaaaagatggaa<br>cagttacagctggtaatgcatcaggattaaatgactgtgcagcagtacttgtaatcatgag<br>tgcagaaaaagctaaagagcttggagtaaaaccacttgctaagatagtttcttatggttca<br>gcaggagttgacccagcaataatgggatatggaccttttctatgcaacaaaagcagctatt<br>gaaaaagcaggttggacagttgatgaattagatttaatagaatcaaatgaagcttttgcag<br>ctcaaagtttagcagtagcaaaagatttaaaatttgatatgaataaagtaaatgtaaatgg<br>aggagctattgcccttggtcatccaatggagcatcaggtgcaagaatactcgttactctt<br>gtacacgcaatgcaaaaaagagatgcaaaaaaaggcttagcaacttttatgtataggtgg<br>cggacaaggaacagcaatattgctagaaaagtgctag |
| beta-<br>ketothiolase<br>NP_149242.1 | atgagagatgtagtaatagtaagtgctgtaagaactgcaataggagcatatggaaaaac<br>attaaaggatgtacctgcaacagagttaggagctatagtaataaaaggaagctgaagaa<br>gagctaatataaatccaaatgagattaatgaagttattttgaaatgtacttcaagctgga<br>ttaggccaaaacccagcaagacaagcagcagtaaaagcaggattacctttagaaacac<br>ctgcgtttacaatcaataaggtttgtggttcaggtttaagatctataagtttagcagctcaaa<br>ttataaaagctggagatgctgataccattgtagtaggtggtatggaaaatatgtctagatc<br>accatatttgattaacaatcagagatggggtcaaagaatgggagatagtgaattagttga<br>tgaaatgataaaggatggtttgtgggatgcatttaatggatatcatatgggagtaactgca<br>gaaaatattgcagaacaatggaatataacaagagaagagcaagatgaattttcacttatg<br>tcacaacaaaaagctgaaaaagccattaaaaatggagaatttaaggatgaaatagttcct<br>gtattaataaagactaaaaaaggtgaaatagtctttgatcaagatgaatttcctagattcgg<br>aaacactattgaagcattaagaaaaacttaaacctattttcaaggaaaatggtactgttaca<br>gcaggtaatgcatccggattaaatgatggagctgcagcactagtaataatgagcgctga<br>taaagctaacgctctcggaataaaaccacttgctaagattacttcttacggatcatatggg<br>gtagatccatcaataatgggatatggagcttttttatgcaactaaagctgccttagataaaat<br>taatttaaaaacctgaagacttagatttaattgaagctaacgaggcatatgcttctcaaagta<br>tagcagtaactagagatttaaatttagatatgagtaaagttaatgttaatggtggagctata<br>gcacttggacatccaatggtgcatctggtgcacgtattttagtaacattactatacgctat<br>gcaaaaaagagattcaaaaaaaggtcttgctactctatgtattggtggaggtcagggaa<br>cagctctcgtagttgaaagagactaa |
| 3-oxoadipyl-<br>CoA thiolase | atgttcaagaaatcagctaatgatattgttgttattgcagcaaagagaactccaatcacca<br>agtcaattaaaggtgggttgagtagattatttcctgaggaaatattatatcaagtggttaag<br>ggtactgtatcagattcacaagttgatttaaacttgattgatgatgtgttagtcggtacggtc<br>ttgcaaacttagggggacagaaagctagtgccttggccattaaaaagattggattccca<br>attaagaccacggttaatacggtcaatcgtcaatgtgctagttctgctcaagcgattactta<br>tcaagcaggtagtttgcgtagtggggagaatcaattttgctattgctgctggagtagaaag<br>tatgactcatgattattttcctcatcgtgggattcccacaagaatttctgaatcattttttagctg<br>atgcatccgatgaagctaaaaacgtcttgatgccaatggggataaccagtgaaaatgtt<br>gccactaaatatggaatttctcgtaaacaacaagatgagtttgcccttaattctcatttgaa<br>agcagacaaggctacaaaaactgggtcattttgcaaaagaaatcattcctattcaaacaac<br>ggatgaaaacaaccaacacgttcaataaccaaagatgatggtataaggggaagttcaa<br>caattgaaaagttgggtggcttaaaacctgtgttcaaggatgatgggactactactgctg<br>gtaattcctcgcaaatttcagatggagggtctgctgtgattttaactactcgtcaaaatgct<br>gagaaatcgggagtaaagccaatagctagatttattggttcgtcagtagctggtgttcctt<br>cgggacttatgggaattggtccatcggctgctattcctcaattgttgtcgagattaaatgtt<br>gacacgaaagacattgatattttttgaattgaacgaggcatttgcatcccaactgatttattg<br>tattgaaaaattgggtcttgattatgataaagtcaatccatatggtggagctatagccttgg<br>gacatccattaggagccactggcgcaagagttacggcaacgttgcttaatggattaaaa<br>gatcagaataaagagttgggtgtcatctcaatgtgcacatccacaggtcaaggatacgc<br>tgccttgtttgctaacgagtag |
| 3-oxoadipyl-<br>CoA thiolase | atggatagattaaatcaattaagtggtcaattaaaaccaacttcaaaacaatcccttactca<br>aaagaacccagacgatgttgtcatcgttgcagcatacagaactgccatcggtaaaggttt |

TABLE 53-continued

Cloned Thiolases

| | |
|---|---|
| | caaagggtctttcaaatctgtgcaatctgaattcatcttgactgaattcttgaaagaatttatt<br>aaaaagactggagtcgatgcatctttgattgaagatgttgctattggtaacgttttgaacca<br>agctgctggtgccaccgaacacagaggtgctagtttggctgcaggtattccttacactgc<br>agctttccttgccatcaacagattgtgttcctcagggttaatggccatttctgacattgcca<br>acaaaatcaaaaccggtgaaatcgaatgtggtcttgctggtggtattgaatccatgtctaa<br>aaactatggtagtccaaaagttattccaaagattgacccacacttggctgatgacgaaca<br>aatgagtaaatgtttgattccaatgggtatcaccaacgaaaatgttgctaatgaattcaac<br>attccaagagaaaaacaagatgcctttgctgctaaatcttatagtaaagccgaaaaagcc<br>atctcctctggagctttcaaagatgaaatcttaccaatcagatccattatcagatccccag<br>acggttctgaaaagaaatcattgtcgataccgacgaaggtccaagaaagggtgttgac<br>gctgcttccttgagcaaattgaaaccagcatttggtggtactaccactgccggtaacgctt<br>ctcaaatttcagatggtgctgctggtgttttattgatgaagagaagtttggctgaagccaa<br>aggttacccaattgttgctaaatacattgcttgttcaactgttggtgttccgccagaaatcat<br>gggtgttggtccagcttacgccattccagaagtgttgaagagaactggattgactgtgga<br>tgacgttgatgtgtttgaaatcaacgaagcttttgctgctcaatgtctttactcagctgaaca<br>atgtaatgttccagaagaaaaattgaacataaacggtggtgccatcgctttaggtcatcct<br>cttggttgtactggtgccagacaatatgccactatcttgagattgttgaaaccaggtgaaa<br>ttggtttgacttctatgtgtatcggtagtggtatgggtgctgcctccatattgattaaggaat<br>ag |
| 3-oxoadipyl-<br>CoA thiolase | atgtcatccaaacaacaatacttgaagaagaatcctgacgatgtcgttgtcgttgcagcat<br>acagaactgctttaaccaaaggtggaagaggtggattcaaagatgttggatctgatttcc<br>ttttgaaaaaattgactgaagaatttgttaaaaaaaactggtgttgaccctaaaatcattcaa<br>gatgctgccattggtaatgtcttgaacagaagagctggtgatttcgaacatagaggtgca<br>ttattatctgctggattacccttattcagttccatttgttgcccttaacagacaatgttcatctgg<br>gttaatggccatttctcaagtggccaacaagatcaagactggtgaaattgaatgtggttta<br>gctggtggtgttgaaagtatgacaaaaaaactatggtccagaagcattgattgctattgac<br>cctgcttatgaaaaagacccagaatttgttaaaaacggtattccaatgggtattactaatg<br>aaaatgtttgtgccaaattcaatatttcaagagatgttcaagatcaatttgctgctgaatctt<br>atcaaaaagctgaaaaggcacaaaaagaaggtaaatttgatgatgaaattttaccaattg<br>aagttttccaagaagatgaagatgctgaagatgaagacgaagatgaagatgaagatgc<br>tgaaccaaaagaaaaattggttgttattagtaaagatgaaggtattagaccaggtgttact<br>aaagaaaaattggctaaaattaaaccagctttcaaatctgatggtgtatcttcagctggta<br>actcttcacaagtttccgatggtgctgcctggtgttattgatgaaacgttcatttgctgaaa<br>agaatggattcaaaccattggctaaatacatttcttgtggtgttgctggtgtcccaccaga<br>aattatgggtattggtccagctgttgccattccaaaagtttttgaaacaaactggattatcag<br>tcagtgatattgatatttatgaaatcaatgaagcatttgccggtcaatgtttgtactcaattga<br>aagttgtaatattccaagagaaaaagtcaatcttaatgggggtgctattgccttgggtcac<br>cctcttggttgtactggtgctagacaatacgctactattttaagattgttaaaaccaggtga<br>atttggtgtgacttctatgtgtattggtactggtatgggtgctgcttctgttttggttagagaa<br>taa |
| beta-<br>ketoadipyl<br>CoA thiolase<br>pcaF | atgagccgcgaggtattcatctgcgatgccgtgcgcacgccgatcggccgtttcggcg<br>gcagtcttttccgcggtgcgccgaccacctcgcggcggttggcagggccctgg<br>tcgagcgcaaccccggggtcgactggtcggcgttggacgaggtgttcctcggctgcg<br>ccaaccaggccggcgaggacaaccgtaacgtggcgcgcatggcgctgctgctggcc<br>ggtttgccggagagcgtgcccggcgtcacccctcaaccgcctctgcgcctcggggatg<br>gacgccatcggcacggcgttccgcgccatcgcctgcgggcgagatggagctggccatc<br>gccggcggcgtcgagtcgatgtcgcgcgcgccgtacgtgatgggcaaggccgatag<br>cgccttcggtcgcggccagaagatcgaggacaccaccatcggctggcgcttcgtcaat<br>ccgctgatgaaggagcagtacgcatcgacccgatgccgcagaccgccgacaacgt<br>cgccgacgactatcgcgtgtcgcgtgccgaccaggatgccttcgccctgcgcagcca<br>gcagcgccggcagggcgcaggaggccggtttcttcgcgcgaggaaatcgtcccgg<br>tgacgattcgcgggcgcaagggcgacaccctggtcgagcacgacgagcatccgcgt<br>cccgacaccaccctggaggcgctggcccggctcaagccggtcaacgggccggaga<br>agaccgtcaccgccggcaacgcgtccggggtcaacgacggcgccgccgcgctggt<br>cctggcctccgccgaggcagtggagaagcacggcctgactccggcgcgcgggtgc<br>tgggcatggccagcgccggcgtcgccccacggatcatgggcatcggccggtgccg<br>gcggtgcgcaagctgctgcggcgcctggacctggcgatcgacgccttcgacgtgatc<br>gaactcaacgaagccttcgccagccagggcctggcctgcctgcgcgaactgggcgtg<br>gccgacgacagtgagaaggtcaacccgaacggcggtgccatcgccctcggccaccc<br>gctggggatgagccggtcgcggctggtcctcaccgcgctccatcaacttgagaagag<br>cggcgccggcgcggcctggcgaccatgtgcgtaggcgtcggccaaggcctggcg<br>ctggccatcgagcgggtctga |
| acyl-CoA<br>thiolase | atgctcgatgcctatatctacgccggcctgcgtacgcctttcggccggcatgccggtgc<br>actctcgacggtgcgtccggacgacctggccggcctgctgctggcgcgtctcgcgga<br>aacctccgggttcgccgtcgacgacctggaggatgtgatcctcggttgcaccaaccag<br>gccggcaagacagccgcaacctggcgcgcaacggcctgctgctgcagccggcctgc<br>cggcgcggctgcccgggcagacggtcaaccgcttgtgtgccagcggactgtcggcg<br>gtgatcgacgggcgcgcgatcagttgcggtgagggccggctgtacctggccgg<br>cggcgccgaaagcatgtcccgggcgccgttcgtcatgggcaaggcggagagcgcct<br>tcagccgcacgctggaggtcttcgacagcaccatcggtgcgctgccaacccca<br>ggctggtcgagcgctatggcaacgacagcatgccggagaccggcgacaacgtggcc<br>cgcgccttcggcatcgcccgcgaagacgccgaccgtttcgccgcttcttcccaggcgc<br>gctaccaggctgcgctgaggagggcttttcctcggcgagatccttccggtggaggt<br>gcgtgccggacgcaagggcgagacgcggctggtggagcgcgacgagcatccgcg<br>accgcaggccgacctggcggccctggcgcgcttgccggcgttgttcgccggtgggt |

TABLE 53-continued

Cloned Thiolases

| | |
|---|---|
| | agtgaccgccggtaatgcgtctgggatcaacgacggggcggcggtagtgctgctggg<br>cgatcgcgcgatcggcgagcgcgagggcatccggccgttggcgcggatcctcgcca<br>gcgccagcgtcggcgtcgagccccggttgatgggcatcggcccgcagcaggcgatc<br>ctccgcgcgctgcaacgcgccggcatcgacctggacgaggtcggcctgatcgagatc<br>aacgaagccttcgcgccgcaggtcctggcctgcctgaagttgctcggcctggactacg<br>aggacccgcgggtcaatcccatggcggcgccattgccctcggccatccgctcggcg<br>cctccggtgcgcggctggtgctcaccgcgcccgcgggctgcaacgcatcgagcgg<br>cgctacgcggtggtcagcgtctgtgcgtcgggtcggccagggcgtggcgatggtgatc<br>gagcgctgccgatga |
| 3-oxoadipyl-<br>CoA thiolase | atgcacgacgtattcatctgtgacgccatccgtacccccgatcggccgcttcggcggcgc<br>cctggccagcgtgcgggccgacgacctggccgccgtgccgctgaaggcgctgatcg<br>agcgcaaccctggcgtgcagtgggaccaggtagacgaagtgttcttcggctgcgcca<br>accaggccggtgaagacaaccgcaacgtggcccgcatggcactgctgctggccggc<br>ctgccggaaagcatcccgggcgtcaccctgaaccgtctgtgcgcgtcgggcatggat<br>gccgtcggcaccgcgttccgcgccatcgccagcggcgagatggagctggtgattgcc<br>ggtggcgtcgagtcgatgtcgcgcgccccgttcgtcatgggcaaggctgaaagcgcc<br>tattcgcgcaacatgaagctggaagacaccaccattggctggcgtttcatcaacccgct<br>gatgaagagccagtacggtgtggattccatgccggaaaccgccgacaacgtggccga<br>cgactatcaggtttcgcgtgctgatcaggacgctttcgccctgcgcagccagcagaag<br>gctgccgctgcgcaggctgccggcttctttgccgaagaaatcgtgccggtgcgtatcg<br>ctcacaagaagggcgaaatcatcgtcgaacgtgacgaacacctgcgcccgaaacca<br>cgctggaggcgctgaccaagctcaaaccggtcaacggcccggacaagacggtcacc<br>gccggcaacgcctcgggcgtgaacgacggtgctgcggcgatgatcctggcctcggc<br>cgcagcggtgaagaaacacggcctgactccgcgtgcccgcgttctgggcatggccag<br>cggcggcgttgcgccacgtgtcatgggcattggcccggtgccggcggtgcgcaaact<br>gaccgagcgtctgggatagcggtaagtgatttcgacgtgatcgagcttaacgaagcg<br>tttgccagccaaggcctggcggtgctgcgtgagctgggtgtggctgacgatgcgcccc<br>aggtaaaccctaatggcggtgccattgccctgggccaccccctgggcatgagcggtg<br>cacgcctggtactgactgcgttgcaccagctggagaagagtggcggtcgcaagggcc<br>tggcgaccatgtgtgtgggtgtcggccaaggtctggcgttggccatcgagcgggtttg<br>a |
| 3-oxoadipyl-<br>CoA thiolase | atgaccgacgcctacatctgcgatgcgattcgcacacccatcggccgctacggcggc<br>gccctgaaagacgttcgtgccgacgatctcggcgcggtgccgctcaaggcgctgatc<br>gaacgcaaccggaacgtcgactggtcggcgatcgacgacgtgatctatggctgcgcg<br>aaccaggccggcgaagacaaccgcaacgtcgcgcgcatgtccgcgctgctcgcggg<br>cttgccgaccgccgtgccgggcacgacgctgaaccggttatgcggctcgggcatgga<br>cgccgtcggcacggccgcgcgcgatcaaggcgggcgaggcacgcttgatgatc<br>gcgggcggcgtcgaaagcatgacgcgcgcgccgttcgtgatgggcaaggccgca<br>gcgcattcgcgcgccaggctgcgattttcgacacgacgatcggctggcgtttcattaatc<br>cgctgatgaaacagcaatacggcgtcgattcgatgcccgagacggccgagaacgtcg<br>cggtcgactacaacatcagccgcgccgaccaggatctattcgcgctgcgcagccagc<br>agaaggccgcgcgtgcgcagcaggacggccacgctgccgccgaaatcgtccccgtc<br>acgattgcgcagaaaaaaggcgacgcgctcgtcgtatcgctcgacgagcatccgcgc<br>gaaacatcgctcgaagcgctcgcgaagctgaagggcgtcgtgcgtcccgacggctcg<br>gtcacggccggcaacgcgtcaggcgtcaacgacggcgcatgcgcactgctgctcgc<br>caacgcggaagccgcgatcaatatgggctgcgccgccgccgcgtgtcgtcggcat<br>ggcgagcgccggcgtcgagccgcgcgtgatgggtatcggcccggcgccggccacg<br>cagaaactgttgcgccagctcggcatgacgatcgaccagttcgacgtgatcgagctga<br>acgaagcgttcgcgtcgcagggtctcgcggtgctgcgcatgctcggtgtcgccgacg<br>acgatccgcgcgtgaaccccaacggcggtgcgatcgcgctcggccatccgctcggc<br>gcatcgggtgcgcggctcgtgaccacgggcgcttcaccaactcgagcgtacgggcgg<br>ccgctttgcgctctgtacgatgtgcatcggcgtcggccagggcatcgcgatcgcgatc<br>gaacgcgtgtaa |
| beta-<br>ketothiolase | gtgatggccacctcaagacttgtctgcagcaatttaacgaagcaatgctttacgatctcgt<br>cacgtgctgctagccaatttaccgatgtggtattcgtgggtgccgcacgaacaccggtc<br>ggatcgtttcgctcttcgctttccactgttccagccactgtcctcggagctgaggctattaa<br>gggtgcacttaaacatgccaatctaaaaccctcacaagtgcaagaggtgttctttggctg<br>tgtcgttccatccaactgtggacaagttcctgcccgtcaagcgacacttggagctggatg<br>cgatccttcgacaatcgttacaactctcaataaattgtgcgcctcgggaatgaagtcgatt<br>gcttgtgccgcctcacttttgcaacttggtcttcaagaggttaccgttggtggcggtatgg<br>agagcatgagcttagtgccgtactatcttgaacgtggtgaaactacttatggtggaatga<br>agctcatcgacgtatcccaagagatggtccgactgatgcatatagtaatcaacttatgg<br>gtgcatgcgctgataatgtggctaaacgattcaacatcacccgtgaggaacaggataaa<br>ttcgctattgaaagctataaacgatctgctgctgcatgggagagtggagcatgcaaagct<br>gaagtagttcctattgaagtgacaaagggcaagaaaacatacattgtcaacaaggatga<br>ggaatacatcaaagtcaacttcgagaagcttcccaaactgaaacccgccttcttgaaag<br>acggaaccatcacggctggcaatgcttcaacactgaacgatggtgctgcggcagttgt<br>gatgacgactgtcgaaggagcgaaaaaatacggtgtgaaaccattggcccgattgctc<br>tcatatggtgatgcggcaacaaatccagtcgattttgctattgcaccatcaatggttatccc<br>aaaggtacttaaattggctaatctcgagatcaaggatattgatttgtgggaaatcaacgag<br>gctttcgccgttgttccccttcattcaatgaagacactcggtatcgatcactcgaaagtga<br>acattcatggtggtggcgtatctcttggacatcctattggaatgtctggagctcgaattatc<br>gttcatctgattcatgcgttgaaacctggccagaaaggctgcgctgcaatctgcaatggt<br>ggcggtggcgctggtggaatggtcatcgagaaattgtaa |

Figure 6:
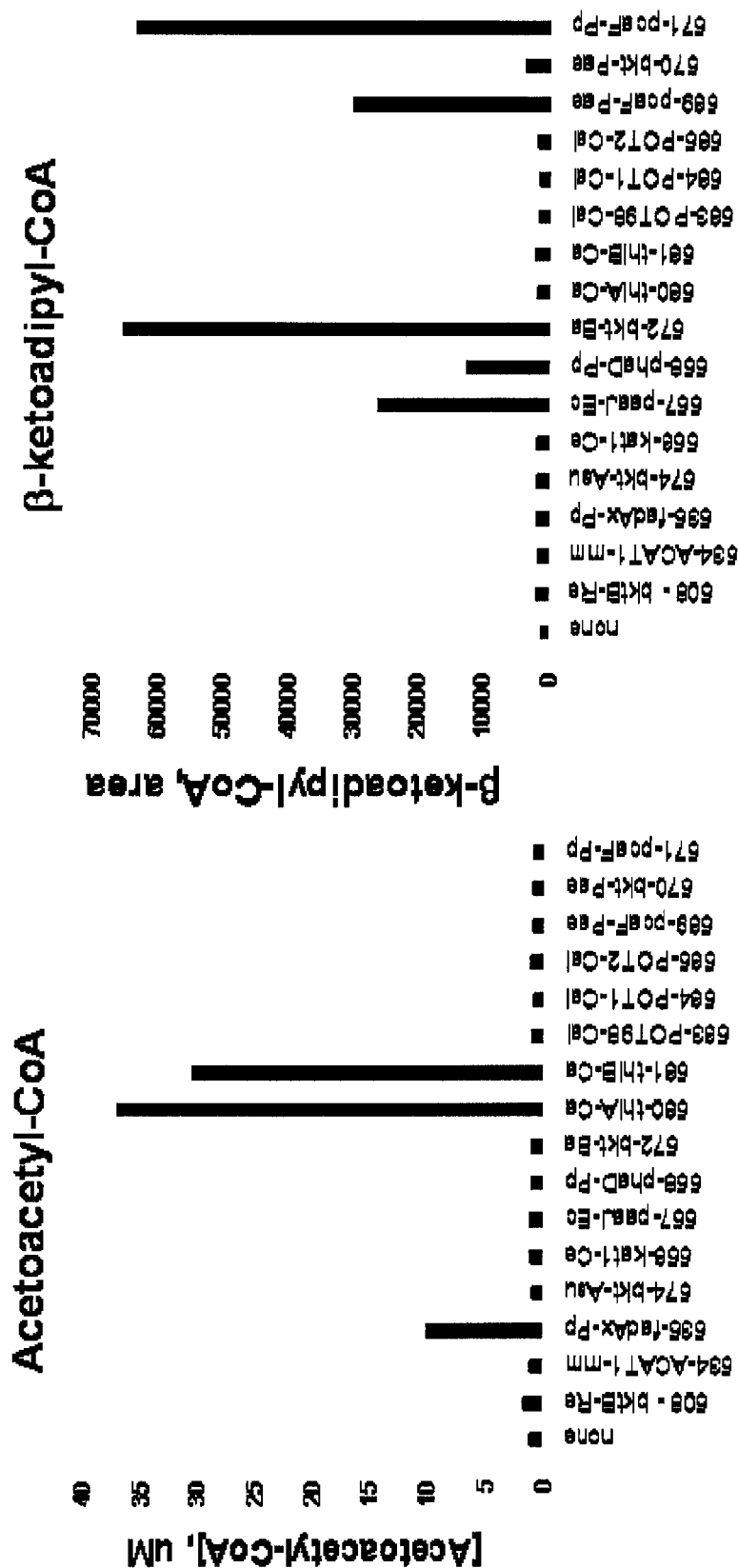
FIG. 6 shows 3 thiolases with demonstrated thiolase activity resulting in acetoacetyl-CoA formation (left panel).

The genes were expressed in *E. coli* and the proteins purified using Ni-NTA spin columns and quantified. To assay enzyme activity in vitro, a 5× CoA:DTNB (Ellman's reagent or 5,5'-dithiobis-(2-nitrobenzoic acid)) mixture was prepared. The mixture consisted of 10 mM succinyl-CoA, 5 mM acetyl-CoA, 30 mM DTNB in 100 mM Tris buffer, pH 7.4. Five µL of the CoA:DTNB mixture was added to 0.5 µM purified thiolase enzyme in 100 mM Tris buffer, pH 7.8 in a final volume of 50 µL. The reaction was incubated at 30° C. for 30 minutes, then quenched with 2.5 µL 10% formic acid and samples frozen at −20° C. until ready for analysis by LC/MS. Because many thiolases can condense two acetyl-CoA molecules into acetoaceytl-CoA, production of acetoacetyl-CoA was examined. FIG. 6 shows that 3 thiolases demonstrated thiolase activity which resulted in acetoacetyl-CoA formation. These were fadAx from *Pseudomonas putida*, thiA from *Clostridium acetobutylicum* and thiB also from *Clostridium acetobutylicum*. When enzyme assays were examined for condensation of succinyl-CoA and acetyl-CoA into β-ketoadipyl-CoA, several enzymes demonstrated the desired activity; paaJ from *Escherichia coli* (Nogales et al., *Microbiol.* 153:357-365 (2007)), phaD from *Pseudomonas putida* (Olivera et al., *Proc. Natl. Acad. Sci. USA* 95:6419-6424 (1998)), bkt from *Burkholderia* ambifaria AMMD, pcaF from *Pseudomonas putida* KT2440 (Harwood et al., *J. Bacteriol.* 176:6479-6488 (1994)), and pcaF from *Pseudomonas aeruginosa* PAO1. There was excellent specificity between the thiolases. Those that generated significant amounts of β-ketoadipyl-CoA did not produce significant amounts of acetoacetyl-CoA and likewise those that made acetoacetyl-CoA did not make detectable amounts of β-ketoadipyl-CoA.

EXAMPLE II

Preparation of Terepthalate from Acetylene and Muconate

This Example provides conditions for the thermal inverse electron demand Diels-Alder reaction for the preparation of PTA from acetylene and muconate.

A lab-scale Parr reactor is flushed with nitrogen gas, evacuated and charged with (1 equivalent) trans, trans-muconic acid and (10 equivalents) acetylene. The reactor is then heated to 200° C. and held at this temperature for 12 hours. An initial pressure of 500 p.s.i.g. is applied. The reactor is then vented, exposed to air and cooled. The contents of the reactor are distilled at room temperature and pressure to yield volatile and nonvolatile fractions. The contents of each fraction are evaluated qualitatively by gas chromatographic analysis (GC-MS).

For quantitative analysis, standards of the starting materials and the expected products, cyclohexa-2,5-diene-1,4-dicarboxylate and terepthalate, are prepared. A known amount of cyclohexane is mixed with a known amount of the volatile fraction and the mixture is subjected to gas chromatography. The cyclohexane and terepthalate components are condensed from the effluent of the chromatogram into a single trap, the contents of which are diluted with carbon tetrachloride or $CDCl_3$ and then examined by NMR spectroscopy. Comparison of the appropriate areas of the NMR spectrum permits calculation of yields.

EXAMPLE III

Preparation of a Muconate Producing Microbial Organism, in which the Muconate is Derived from Succinyl-CoA This example describes the generation of a microbial organism that has been engineered to produce muconate from succinyl-CoA and acetyl-CoA via beta-ketoadipate, as shown in FIG. 2. This example also provides a method for engineering a strain that overproduces muconate.

*Escherichia coli* is used as a target organism to engineer a muconate-producing pathway as shown in FIG. 5. *E. coli* provides a good host for generating a non-naturally occurring microorganism capable of producing muconate. *E. coli* is amenable to genetic manipulation and is known to be capable of producing various products, like ethanol, acetic acid, formic acid, lactic acid, and succinic acid, effectively under anaerobic, microaerobic or aerobic conditions.

First, an *E. coli* strain is engineered to produce muconate from succinyl-CoA via the route outlined in FIG. 2. For the first stage of pathway construction, genes encoding enzymes to transform central metabolites succinyl-CoA and acetyl-CoA to 2-maleylacetate (FIG. 2, Step A) is assembled onto vectors. In particular, the genes pcaF (AAA85138), pcaIJ (AAN69545 and NP_746082) and clcE (O30847) genes encoding beta-ketothiolase, beta-ketoadipyl-CoA transferase and 2-maleylacetate reductase, respectively, are cloned into the pZE13 vector (Expressys, Ruelzheim, Germany), under the control of the PA1/lacO promoter. The genes bdh (AAA58352.1) and fumC (P05042.1), encoding 2-maleylacetate dehydrogenase and 3-hydroxy-4-hexenedioate dehydratase, respectively, are cloned into the pZA33 vector (Expressys, Ruelzheim, Germany) under the PA1/lacO promoter. The two sets of plasmids are transformed into *E. coli* strain MG1655 to express the proteins and enzymes required for muconate synthesis from succinyl-CoA.

The resulting genetically engineered organism is cultured in glucose containing medium following procedures well known in the art (see, for example, Sambrook et al., supra, 2001). The expression of muconate pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered *E. coli* strain to produce muconate through this pathway is confirmed using HPLC, gas chromatography-mass spectrometry (GCMS) or liquid chromatography-mass spectrometry (LCMS).

Microbial strains engineered to have a functional muconate synthesis pathway from succinyl-CoA are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

After successful demonstration of enhanced muconate production via the activities of the exogenous enzymes, the genes encoding these enzymes are inserted into the chromosome of a wild type *E. coli* host using methods known in the art. Such methods include, for example, sequential single crossover (Gay et al., *J. Bacteriol.* 153:1424-1431 (1983)) and Red/ET methods from GeneBridges (Zhang et al., Improved RecT or RecET cloning and subcloning method (WO/2003/010322)). Chromosomal insertion provides several advantages over a plasmid-based system, including greater stability and the ability to co-localize expression of pathway genes.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of muconate. One modeling method is the bilevel optimization approach, OptKnock (Burgard et al., *Biotechnol. Bioengineer.* 84:647-657 (2003)), which is applied to select gene knockouts that collectively result in better production of muconate. Adaptive evolution also can be used to generate better producers of, for example, the 4-acetylbutyrate intermediate or the muconate product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the muconate producer to further increase production.

For large-scale production of muconate, the above muconate pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as $H_2SO_4$. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A transformed *Escherichia coli* having a muconate pathway that produces muconate pathway enzymes, said muconate pathway enzymes comprising a (1) beta-ketothiolase, (2) an enzyme selected from beta-ketoadipyl-CoA hydrolase and beta-ketoadipyl-CoA transferase, (3) beta-ketoadipate enol-lactone hydrolase, (4) muconolactone isomerase, (5) muconate cycloisomerase, and (6) muconate cis/trans isomerase, wherein said *Escherichia coli* comprises at least one exogenous nucleic acid encoding a muconate pathway enzyme obtained from bacteria, yeast, fungi, plant or mammal, and wherein the at least one exogenous nucleic acid is overexpressed resulting in increased synthesis or accumulation of a muconate.

2. The *Escherichia coli* organism of claim 1, wherein said *Escherichia coli* organism comprises two exogenous nucleic acids each encoding a muconate pathway enzyme.

3. The *Escherichia coli* organism of claim 1, wherein said *Escherichia coli* organism comprises three exogenous nucleic acids each encoding a muconate pathway enzyme.

4. The *Escherichia coli* organism of claim 1, wherein said *Escherichia coli* organism comprises four exogenous nucleic acids each encoding a muconate pathway enzyme.

5. The *Escherichia coli* organism of claim 1, wherein said *Escherichia coli* organism comprises five exogenous nucleic acids each encoding a muconate pathway enzyme.

6. The *Escherichia coli* organism of claim 1, wherein said *Escherichia coli* organism comprises six exogenous nucleic acids each encoding a muconate pathway enzyme.

7. The *Escherichia coli* organism of claim 1, wherein said at least one exogenous nucleic acid is a heterologous nucleic acid.

8. The *Escherichia coli* organism of claim 1, wherein said *Escherichia coli* organism is in a substantially anaerobic culture medium.

9. A method for producing muconate, comprising culturing the *Escherichia coli* organism according to any one of claim 1 and claims 2-8.

10. The method of claim 9, further comprising a starting material selected from pyruvate, succinic semialdehyde, and lysine.

11. The *Escherichia coli* organism of claim 1, wherein the at least one exogenous nucleic acid encoding a muconate pathway enzyme has a mitochondrial leader sequence removed.

12. The method of claim 9, wherein the culturing said *Escherichia coli* organism is in a substantially anaerobic culture medium.

13. The method of claim 9, wherein a starting material is selected from pyruvate, succinic semialdehyde, and lysine.

* * * * *

SEQUENCE LISTING

```
<160> NUMBER OF SEQ ID NOS: 50

<210> SEQ ID NO 1
<211> LENGTH: 20
<212> TYPE: PRT
<213> ORGANISM: Euglena gracilis

<400> SEQUENCE: 1

Met Thr Tyr Lys Ala Pro Val Lys Asp Val Lys Phe Leu Leu Asp Lys
1               5                  10                  15

Val Phe Lys Val
            20

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgacgcgtg aagtggtagt ggtaag                                        26

<210> SEQ ID NO 4
<211> LENGTH: 20
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 4
gatacgctcg aagatggcgg                                                20

<210> SEQ ID NO 5
<211> LENGTH: 1185
<212> TYPE: DNA
<213> ORGANISM: Ralstonia eutropha

<400> SEQUENCE: 5
atgacgcgtg aagtggtagt ggtaagcggt gtccgtaccg cgatcgggac ctttggcggc      60
agcctgaagg atgtggcacc ggcggagctg ggcgcactgg tggtgcgcga ggcgctggcg     120
cgcgcgcagg tgtcgggcga cgatgtcggc cacgtggtat tcggcaacgt gatccagacc     180
gagccgcgcg acatgtatct gggccgcgtc gcggccgtca acggcggggt gacgatcaac     240
gcccccgcgc tgaccgtgaa ccgcctgtgc ggctcgggcc tgcaggccat tgtcagcgcc     300
gcgcagacca tcctgctggg cgataccgac gtcgccatcg gcggcggcgc ggaaagcatg     360
agccgcgcac cgtacctggc gccggcagcg cgctggggcg cacgcatggg cgacgccggc     420
ctggtcgaca tgatgctggg tgcgctgcac gatcccttcc atcgcatcca catgggcgtg     480
accgccgaga atgtcgccaa ggaatacgac atctcgcgcg cgcagcagga cgaggccgcg     540
ctggaatcgc accgccgcgc ttcggcagcg atcaaggccg gctacttcaa ggaccagatc     600
gtcccggtgg tgagcaaggg ccgcaagggc gacgtgacct cgacaccga cgagcacgtg     660 cgccatgacg ccaccatcga cgacatgacc aagctcaggc cggtcttcgt caaggaaaac     720
ggcacggtca cggccggcaa tgcctcgggc ctgaacgacg ccgccgccgc ggtggtgatg     780
atggagcgcg ccgaagccga cgcgccgcgg ctgaagccgc tggcccgcct ggtgtcgtac     840
ggccatgccg gcgtggaccc gaaggccatg gcatcggcc cggtgccggc gacgaagatc     900
gcgctggagc gcgccggcct gcaggtgtcg gacctggacg tgatcgaagc caacgaagcc     960
tttgccgcac aggcgtgcgc cgtgaccaag gcgctcggtc tggacccggc caaggttaac    1020
ccgaacggct cgggcatctc gctgggccac ccgatcggcg ccaccggtgc cctgatcacg    1080
gtgaaggcgc tgcatgagct gaaccgcgtg cagggccgct acgcgctggt gacgatgtgc    1140
atcggcggcg ggcagggcat tgccgccatc ttcgagcgta tctga                   1185

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atggaagtaa gatgcctgga acgaag                                         26

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 7
cagcttctca atcagcaggg c                                              21

<210> SEQ ID NO 8
<211> LENGTH: 1215
<212> TYPE: DNA
<213> ORGANISM: Mus musculus

<400> SEQUENCE: 8
atggaagtaa gatgcctgga acgaagttat gcatccaaac ccactttgaa tgaagtggtt      60
atagtaagtg ctataagaac tcccattgga tccttcctgg gcagccttgc ctctcagccg     120
gccactaaac ttggtactgc tgcaattcag ggagccattg agaaggcagg gattccaaaa     180
gaagaagtga aggaagtcta catgggcaat gtcatccaag ggggtgaagg acaggcccct     240
accaggcaag caacactggg cgcaggttta cctatttcca ctccatgcac cacagtaaac     300
aaggtttgtg cttcaggaat gaaagccatc atgatggcct ctcaaagtct tatgtgtgga     360
catcaggatg tgatggtggc aggcgggatg agagcatgt ccaatgtccc atacgtaatg     420
agcagaggag caacaccata tggtggggta aaacttgaag acctgattgt aaaagacggg     480
ctaactgatg tctacaataa aattcatatg ggtaactgtg ctgagaatac tgcaaagaag     540
atgaatatct cacggcagga acaggatacg tacgctctca gctcttacac cagaagtaaa     600
gaagcgtggg acgcagggaa gtttgccagt gagattactc ccatcaccat ctcagtgaaa     660
ggtaaaccag atgtggtggt gaaagaagat gaagaataca agcgtgttga ctttagtaaa     720
gtgccaaagc tcaagaccgt gttccagaaa gaaaatggca caataacagc tgccaatgcc     780
agcacactga acgatggagc agctgctctg gttctcatga ctgcagaggc agcccagagg     840
ctcaatgtta agccattggc acgaattgca gcatttgctg atgctgccgt agaccccatt     900
gattttccac ttgcgcctgc atatgccgta cctaaggttc ttaaatatgc aggactgaaa     960
aaagaagaca ttgccatgtg ggaagtaaat gaagcattca gtgtggttgt gctagccaac    1020
attaaaatgc tggagattga ccccaaaaa gtaaatatcc acggaggagc tgtttctctg    1080
ggccatccaa ttgggatgtc tggagcccgg attgttgttc atatggctca tgccctgaag    1140
ccaggagagt tcggtctggc tagtatttgc aacggaggag gaggtgcttc cgccctgctg    1200
attgagaagc tgtag                                                    1215

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgaccctcg ccaatgaccc                                                20

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtacaggcat tcaacagcca tgg                                            23
```

<210> SEQ ID NO 11
<211> LENGTH: 1194
<212> TYPE: DNA
<213> ORGANISM: Pseudomonas putida

<400> SEQUENCE: 11

```
atgaccctcg ccaatgaccc catcgttatc gtcagcgccg tgcgcacgcc catgggcggg      60
ttgcagggcg acctcaagag cctgactgcg ccgcaactgg gcagcgccgc cattcgtgct     120
gccgtggaac gggccggcat cgatgccgcc ggtgtcgagc aggtactgtt cggctgcgtg     180
ctgccggccg gccagggcca ggcaccggca cgccaggccg cgctgggcgc cgggctggac     240
aagcacacca cctgcaccac cctgaacaag atgtgcggct cgggtatgca agccgcgatc     300
atggcccatg acctgctgct ggccggcacc gcagacgtgg tagtggcggg tggcatggaa     360
agcatgacca acgcgccgta cctgctggac aaagcccgtg gcggctaccg catgggccac     420
ggcaagatca tcgaccacat gttcatggac ggtctcgaag acgcctacga caaaggccgc     480
ctgatgggta ccttttgccga ggactgtgcc caggccaatg ccttcagccg cgaggcccag     540
gaccagttcg ccatcgcctc gctgacccga gcgcaggaag ccatcagcag cggccgttttt     600
gccgccgaga tcgtgccggt ggaagtcacc gagggcaagg aaaagcgcgt catcaaggat     660
gacgagcagc cgcccaaggc gcgtctggac aagattgcgc agctcaaacc ggcgtttcgt     720
gaaggcggca ccgtgacggc ggccaacgcc agttcgattt ccgacggcgc tgcggcgctg     780
gtactgatgc gccgctccga ggccgacaaa cgtggcctca agccattggc cgtcatccac     840
ggccacgccg cctttgccga caccccggcg ctgttcccga ccgccccgat cggcgcgatc     900
gacaaactga tgaaacgcac cggctggaac ctggccgaag tcgacctgtt cgagatcaac     960
gaggccttcg ccgtggtcac cctggcggcc atgaaacacc tcgacctgcc acacgacaag    1020
gtcaatatcc acggcggcgc ctgcgcccct cggtcaccga tcggcgcttc tggcgcacgt    1080
attctggtca ccctgttgtc ggccttgcgc cagaacaatc tgcgtcgggg tgtggcggcc    1140
atctgcatcg gcggtggcga ggccacggcc atggctgttg aatgcctgta ctga          1194
```

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgaacaaac atgctttcat cgtcg                                             25

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
taatttctgg ataaccattc cacttgagc                                         29

<210> SEQ ID NO 14
<211> LENGTH: 1167
<212> TYPE: DNA

<213> ORGANISM: Caenorhabditis elegans

<400> SEQUENCE: 14

```
atgaacaaac atgctttcat cgtcggagcc gcccgtacac ctattggatc atttcgttct      60
tctctctctt cggtaactgc tccagagctc gcctcggttg ccatcaaagc agcattggag     120
cgtggagcag tgaagccgag ttcaattcag gaggtgttcc ttggtcaagt ctgtcaagca     180
aatgctggtc aagctcccgc tcgtcaagca gctcttggag ccggactcga tctttcggtt     240
gctgttacca ccgtcaataa agtgtgctct tctgggctga agcaatcat tcttgctgcc      300
cagcaaattc aaaccggtca tcaagatttt gccattggcg gaggaatgga gagcatgtca     360
caagtaccat tttatgttca agaggagag atcccatatg gtggatttca agtgattgat      420
ggaatcgtca agacggact gaccgatgct tatgataaag ttcacatggg aaactgcgga      480
gagaagactt caaaagaaat gggaattaca cgtaaagacc aagacgaata tgctatcaac     540
agctacaaaa agtcagctaa agcatggag aatggaaata tcggaccaga agtggtgcca      600
gtgaacgtca aatcaaagaa gggagtcacg attgttgata agatgaaga ttcacaaaa       660
gtcaatttcg acaagttcac ctcgctgaga actgttttcc agaaagacgg aactatcact     720
gctgctaatg cttcaacatt gaacgacggt gcagctgctg tcattgttgc ctcacaggaa     780
gcagtttccg agcaaagctt aaagcctctg gcccgaattt tggcttatgg agatgccgcc     840
acgcacccac tcgatttcgc tgtagcacca actttgatgt tcccaaaaat tcttgaaaga     900
gcaggagtga agcaatcaga tgttgctcaa tgggaagtta tgaagccctt ctcatgtgtt     960
ccccttgctt tcatcaaaaa actaggagtc gatccatccc ttgtgaaccc acatggagga    1020
gctgtttcaa ttggtcaccc catcggaatg tccggagccc gcctcatcac tcatcttgtg    1080
cacacactca aaagtggcca aatcggagtt gctgccattt gcaatggagg tggtggctca    1140
agtggaatgg ttatccagaa attataa                                       1167
```

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
atgcgtgaag cctttatttg tgacg                                           25
```

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
aacacgctcc agaatcatgg cg                                              22
```

<210> SEQ ID NO 17
<211> LENGTH: 1206
<212> TYPE: DNA
<213> ORGANISM: Escherichia coli

<400> SEQUENCE: 17

```
atgcgtgaag cctttatttg tgacggaatt cgtacgccaa ttggtcgcta cggcggggca      60
```

```
ttatcaagtg ttcgggctga tgatctggct gctatccctt tgcgggaact gctggtgcga       120
aacccgcgtc tcgatgcgga gtgtatcgat gatgtgatcc tcggctgtgc taatcaggcg       180
ggagaagata accgtaacgt agcccggatg gcgactttac tggcggggct gccgcagagt       240
gtttccggca caaccattaa ccgcttgtgt ggttccgggc tggacgcact ggggtttgcc       300
gcacgggcga ttaaagcggg cgatggcgat ttgctgatcg ccggtggcgt ggagtcaatg       360
tcacgggcac cgtttgttat gggcaaggca gccagtgcat tttctcgtca ggctgagatg       420
ttcgatacca ctattggctg gcgatttgtg aacccgctca tggctcagca atttggaact       480
gacagcatgc cggaaacggc agagaatgta gctgaactgt taaaaatctc acgagaagat       540
caagatagtt ttgcgctacg cagtcagcaa cgtacggcaa aagcgcaatc ctcaggcatt       600
ctggctgagg agattgttcc ggttgtgttg aaaaacaaga aggtgttgt aacagaaata       660 caacatgatg agcatctgcg cccggaaacg acgctggaac agttacgtgg gttaaaagca       720
ccatttcgtg ccaatggggt gattaccgca ggcaatgctt ccggggtgaa tgacggagcc       780
gctgcgttga ttattgccag tgaacagatg gcagcagcgc aaggactgac accgcgggcg       840
cgtatcgtag ccatggcaac cgccggggtg gaaccgcgcc tgatggggct tggtccggtg       900
cctgcaactc gccgggtgct ggaacgcgca gggctgagta ttcacgatat ggacgtgatt       960
gaactgaacg aagcgttcgc ggcccaggcg ttgggtgtac tacgcgaatt ggggctgcct      1020
gatgatgccc cacatgttaa ccccaacgga ggcgctatcg ccttaggcca tccgttggga      1080
atgagtggtg cccgcctggc actggctgcc agccatgagc tgcatcggcg taacggtcgt      1140
tacgcattgt gcaccatgtg catcggtgtc ggtcagggca tcgccatgat tctggagcgt      1200
gtttga                                                                 1206
```

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atgaatgaac cgacccacgc c                                                   21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaggcgctcg atgatcatgg                                                     20

<210> SEQ ID NO 20
<211> LENGTH: 1221
<212> TYPE: DNA
<213> ORGANISM: Pseudomonas putida

<400> SEQUENCE: 20
atgaatgaac cgacccacgc cgatgccttg atcatcgacg ccgtgcgcac gcccattggc        60
cgctatgccg gggccctgag cagcgtgcgc gccgacgacc tggcggccat cccgctcaaa       120

```
gccttgatcc agcgtcaccc cgaactggac tggaaagcca ttgatgacgt tatcttcggc    180
tgtgccaacc aggctggcga agacaaccgc aacgtggccc acatggcgag cctgctggcc    240
gggctgccac tcgaagtacc aggaccacg atcaaccgcc tgtgcggttc cggtctggat    300
gccatcggta atgcggcacg tgccctgcgc tgcggtgaag cggggctcat gctggccggt    360
ggtgtggagt ccatgtcgcg tgcaccgttt gtgatgggta agtcggagca ggcattcggg    420
cgtgcggccg agctgttcga caccaccatc ggctggcgtt tcgtcaaccc gctgatgaag    480
gccgcctacg catcgattc gatgccggaa acggctgaaa acgtggccga acagttcggc    540
atctcgcgcg ccgaccagga tgcctttgcc ctgcgcagcc agcacaaagc cgcagcagct    600
caggcccgcg ccgcctggc gcgggaaatc gtgccggtcg aaatcccgca acgcaaaggc    660
ccagccaaag tggtcgagca tgacgagcac ccgcgcggcg cacgaccct ggagcagctg    720 gctcggctcg ggacgccgtt tcgtgaaggc ggcagcgtaa cggcgggtaa tgcctccggc    780
gtgaatgacg gcgcttgcgc cctgctgctg gccagcagcg ccgcggcccg ccgccatggg    840
ttgaaggccc gcggccgcat cgtcggcatg gcggtggccg gggttgagcc caggctgatg    900
ggcattggtc cggtgcctgc gacccgcaag gtgctggcgc tcaccggcct ggcactggct    960
gacctggatg tcatcgaact caatgaggcc tttgccgccc aagggctggc cgtgttgcgc    1020
gagctgggcc tggccgacga cgacccgcga gtcaaccgca acggcggcgc catcgccctg    1080
ggccatcccc tgggcatgag cggtgcccgg ttggtgacca ctgccttgca cgagcttgaa    1140
gaaacggccg ccgctacgc cctgtgcacc atgtgcatcg gcgtaggcca aggcattgcc    1200
atgatcatcg agcgcctctg a                                             1221
```

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
atgaaagaag ttgtaatagc tagtgcagta agaac                                35

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 22 gcactttct agcaatattg ctgttcc                                          27

<210> SEQ ID NO 23
<211> LENGTH: 1179
<212> TYPE: DNA
<213> ORGANISM: Clostridium acetobutylicum

<400> SEQUENCE: 23

```
atgaaagaag ttgtaatagc tagtgcagta agaacagcga ttggatctta tggaaagtct    60
cttaaggatg taccagcagt agatttagga gctacagcta taaggaagc agttaaaaaa    120 gcaggaataa aaccgagga tgttaatgaa gtcattttag gaaatgttct tcaagcaggt    180
ttaggacaga atccagcaag acaggcatct tttaaagcag gattaccagt tgaaattcca    240
```

```
gctatgacta ttaataaggt ttgtggttca ggacttagaa cagttagctt agcagcacaa      300
attataaaag caggagatgc tgacgtaata atagcaggtg gtatggaaaa tatgtctaga      360
gctccttact tagcgaataa cgctagatgg ggatatagaa tgggaaacgc taaatttgtt      420
gatgaaatga tcactgacgg attgtgggat gcatttaatg attaccacat gggaataaca      480
gcagaaaaca tagctgagag atggaacatt tcaagagaag aacaagatga gtttgctctt      540
gcatcacaaa aaaagctgaa agaagctata aaatcaggtc aatttaaaga tgaaatagtt      600
cctgtagtaa ttaaaggcag aaagggagaa actgtagttg atacagatga gcaccctaga      660
tttggatcaa ctatagaagg acttgcaaaa ttaaaacctg ccttcaaaaa agatggaaca      720
gttacagctg gtaatgcatc aggattaaat gactgtgcag cagtacttgt aatcatgagt      780
gcagaaaaag ctaaagagct tggagtaaaa ccacttgcta agatagtttc ttatggttca      840
gcaggagttg acccagcaat aatgggatat ggaccttttct atgcaacaaa agcagctatt      900
gaaaaagcag gttggacagt tgatgaatta gatttaatag aatcaaatga agcttttgca      960
gctcaaagtt tagcagtagc aaaagattta aaatttgata tgaataaagt aaatgtaaat     1020
ggaggagcta ttgcccttgg tcatccaatt ggagcatcag gtgcaagaat actcgttact     1080
cttgtacacg caatgcaaaa aagagatgca aaaaaaggct tagcaacttt atgtataggt     1140
ggcggacaag gaacagcaat attgctagaa aagtgctag                            1179
```

```
<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atgagagatg tagtaatagt aagtgctgta agaactg                               37

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtctctttca actacgagag ctgttccc                                         28

<210> SEQ ID NO 26
<211> LENGTH: 1179
<212> TYPE: DNA
<213> ORGANISM: Clostridium acetobutylicum

<400> SEQUENCE: 26
atgagagatg tagtaatagt aagtgctgta agaactgcaa taggagcata tggaaaaaca      60
ttaaaggatg tacctgcaac agagttagga gctatagtaa taaggaagc tgtaagaaga     120 gctaatataa atccaaatga gattaatgaa gttattttg gaaatgtact tcaagctgga     180
ttaggccaaa acccagcaag acaagcagca gtaaaagcag gattaccttt agaaacacct     240
gcgtttacaa tcaataaggt ttgtggttca ggtttaagat ctataagttt agcagctcaa     300
attataaaag ctggagatgc tgataccatt gtagtaggtg gtatggaaaa tatgtctaga     360
```

```
tcaccatatt tgattaacaa tcagagatgg ggtcaaagaa tgggagatag tgaattagtt      420
gatgaaatga taaaggatgg tttgtgggat gcatttaatg gatatcatat gggagtaact      480
gcagaaaata ttgcagaaca atggaatata acaagagaag agcaagatga attttcactt      540
atgtcacaac aaaaagctga aaaagccatt aaaaatggag aatttaagga tgaaatagtt      600
cctgtattaa taaagactaa aaaaggtgaa atagtctttg atcaagatga atttcctaga      660
ttcggaaaca ctattgaagc attaagaaaa cttaaaccta ttttcaagga aaatggtact      720
gttacagcag gtaatgcatc cggattaaat gatggagctg cagcactagt aataatgagc      780
gctgataaag ctaacgctct cggaataaaa ccacttgcta agattacttc ttacggatca      840 tatgggtag  atccatcaat aatgggatat ggagcttttt atgcaactaa agctgcctta      900
gataaaatta atttaaaacc tgaagactta gatttaattg aagctaacga ggcatatgct      960
tctcaaagta tagcagtaac tagagattta aatttagata tgagtaaagt taatgttaat     1020
ggtggagcta tagcacttgg acatccaata ggtgcatctg gtgcacgtat tttagtaaca     1080
ttactatacg ctatgcaaaa aagagattca aaaaaaggtc ttgctactct atgtattggt     1140
ggaggtcagg gaacagctct cgtagttgaa agagactaa                            1179
```

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
atgttcaaga aatcagctaa tgatattgtt g                                      31
```

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
ctcgttagca aacaaggcag cg                                                22
```

<210> SEQ ID NO 29
<211> LENGTH: 1182
<212> TYPE: DNA
<213> ORGANISM: Candida albicans

<400> SEQUENCE: 29

```
atgttcaaga aatcagctaa tgatattgtt gttattgcag caaagagaac tccaatcacc       60
aagtcaatta aaggtgggtt gagtagatta tttcctgagg aaatattata tcaagtggtt      120
aagggtactg tatcagattc acaagttgat ttaaacttga ttgatgatgt gttagtcggt      180
acggtcttgc aaactttagg gggacagaaa gctagtgcct tggccattaa aaagattgga      240
ttcccaatta agaccacggt taatacggtc aatcgtcaat gtgctagttc tgctcaagcg      300
attacttatc aagcaggtag tttgcgtagt ggggagaatc aatttgctat tgctgctgga      360
gtagaaagta tgactcatga ttattttcct catcgtggga ttcccacaag aatttctgaa      420
tcatttttag ctgatgcatc cgatgaagct aaaaacgtct tgatgccaat ggggataacc      480
agtgaaaatg ttgccactaa atatggaatt tctcgtaaac aacaagatga gtttgcccctt      540
```

```
aattctcatt tgaaagcaga caaggctaca aaactgggtc attttgcaaa agaaatcatt      600
cctattcaaa caacggatga aaacaaccaa cacgtttcaa taaccaaaga tgatggtata      660
aggggaagtt caacaattga aaagttgggt ggcttaaaac ctgtgttcaa ggatgatggg      720
actactactg ctggtaattc ctcgcaaatt tcagatggag gtctgctgt gattttaact       780 actcgtcaaa atgctgagaa atcgggagta aagccaatag ctagatttat tggttcgtca      840
gtagctggtg ttccttcggg acttatggga attggtccat cggctgctat tcctcaattg      900
ttgtcgagat taaatgttga cacgaaagac attgatattt ttgaattgaa cgaggcattt      960
gcatcccaac tgatttattg tattgaaaaa ttgggtcttg attatgataa agtcaatcca     1020
tatggtggag ctatagcctt gggacatcca ttaggagcca ctggcgcaag agttacggca     1080
acgttgctta atggattaaa agatcagaat aaagagttgg gtgtcatctc aatgtgcaca     1140
tccacaggtc aaggatacgc tgccttgttt gctaacgagt ag                       1182

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atggatagat taaatcaatt aagtggtcaa ttaaaacc                              38

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttccttaatc aatatggagg cagcac                                           26

<210> SEQ ID NO 32
<211> LENGTH: 1227
<212> TYPE: DNA
<213> ORGANISM: Candida albicans

<400> SEQUENCE: 32
atggatagat taaatcaatt aagtggtcaa ttaaaaccaa cttcaaaaca atcccttact       60
caaaagaacc cagacgatgt tgtcatcgtt gcagcataca gaactgccat cggtaaaggt      120
ttcaaagggt ctttcaaatc tgtgcaatct gaattcatct tgactgaatt cttgaaagaa      180
tttattaaaa agactggagt cgatgcatct ttgattgaag atgttgctat tggtaacgtt      240
ttgaaccaag ctgctggtgc caccgaacac agaggtgcta gtttggctgc aggtattcct      300
tacactgcag ctttccttgc catcaacaga ttgtgttcct cagggttaat ggccatttct      360
gacattgcca acaaaatcaa aaccggtgaa atcgaatgtg gtcttgctgg tggtattgaa      420
tccatgtcta aaaactatgg tagtccaaaa gttattccaa agattgaccc acacttggct      480
gatgacgaac aaatgagtaa atgtttgatt ccaatgggta tcaccaacga aaatgttgct      540
aatgaattca acattccaag agaaaaacaa gatgcctttg ctgctaaatc ttatagtaaa      600
gccgaaaaag ccatctcctc tggagctttc aaagatgaaa tcttaccaat cagatccatt      660
```

| atcagatccc cagacggttc tgaaaaagaa atcattgtcg ataccgacga aggtccaaga | 720 |
| aagggtgttg acgctgcttc cttgagcaaa ttgaaaccag catttggtgg tactaccact | 780 |
| gccggtaacg cttctcaaat ttcagatggt gctgctggtg ttttattgat gaagagaagt | 840 |
| ttggctgaag ccaaaggtta cccaattgtt gctaaataca ttgcttgttc aactgttggt | 900 |
| gttccgccag aaatcatggg tgttggtcca gcttacgcca ttccagaagt gttgaagaga | 960 |
| actggattga ctgtgatga cgttgatgtg tttgaaatca cgaagctttt gctgctcaa | 1020 |
| tgtctttact cagctgaaca atgtaatgtt ccagaagaaa aattgaacat aaacggtggt | 1080 |
| gccatcgctt taggtcatcc tcttggttgt actggtgcca gacaatatgc cactatcttg | 1140 |
| agattgttga aaccaggtga aattggtttg acttctatgt gtatcggtag tggtatgggt | 1200 |
| gctgcctcca tattgattaa ggaatag | 1227 |

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
atgtcatcca aacaacaata cttgaagaag                    30

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
ttctctaacc aaaacagaag cagcacc                       27

<210> SEQ ID NO 35
<211> LENGTH: 1233
<212> TYPE: DNA
<213> ORGANISM: Candida albicans

<400> SEQUENCE: 35

| atgtcatcca aacaacaata cttgaagaag aatcctgacg atgtcgttgt cgttgcagca | 60 |
| tacagaactg ctttaaccaa aggtggaaga ggtggattca aagatgttgg atctgatttc | 120 |
| cttttgaaaa aattgactga agaatttgtt aaaaaaactg gtgttgaccc taaaatcatt | 180 |
| caagatgctg ccattggtaa tgtcttgaac agaagagctg gtgatttcga acatagaggt | 240 |
| gcattattat ctgctggatt accttattca gttccatttg ttgcccttaa cagacaatgt | 300 |
| tcatctgggt taatggccat ttctcaagtg gccaacaaga tcaagactgg tgaaattgaa | 360 |
| tgtggtttag ctggtggtgt tgaaagtatg acaaaaaact atggtccaga agcattgatt | 420 |
| gctattgacc ctgcttatga aaaagaccca gaatttgtta aaaacggtat tccaatgggt | 480 |
| attactaatg aaaatgtttg tgccaaattc aatatttcaa gagatgttca agatcaatttt | 540 |
| gctgctgaat cttatcaaaa agctgaaaag gcacaaaaag aaggtaaatt tgatgatgaa | 600 |
| attttaccaa ttgaagtttt ccaagaagat gaagatgctg aagatgaaga cgaagatgaa | 660 |
| gatgaagatg ctgaaccaaa agaaaaattg gttgttatta gtaaagatga aggtattaga | 720 |
| ccaggtgtta ctaaagaaaa attggctaaa attaaaccag ctttcaaatc tgatggtgta | 780 |

```
tcttcagctg gtaactcttc acaagtttcc gatggtgctg ccttggtgtt attgatgaaa        840
cgttcatttg ctgaaaagaa tggattcaaa ccattggcta aatacatttc ttgtggtgtt        900
gctggtgtcc caccagaaat tatgggtatt ggtccagctg ttgccattcc aaaagttttg        960
aaacaaactg gattatcagt cagtgatatt gatatttatg aaatcaatga agcatttgcc       1020
ggtcaatgtt tgtactcaat tgaaagttgt aatattccaa gagaaaaagt caatcttaat       1080
gggggtgcta ttgccttggg tcaccctctt ggttgtactg gtgctagaca atacgctact       1140
attttaagat tgttaaaacc aggtgaattt ggtgtgactt ctatgtgtat tggtactggt       1200
atgggtgctg cttctgtttt ggttagagaa taa                                    1233

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atgagccgcg aggtattcat ctg                                                 23

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gacccgctcg atggccag                                                       18

<210> SEQ ID NO 38
<211> LENGTH: 1206
<212> TYPE: DNA
<213> ORGANISM: Pseudomonas aeruginosa

<400> SEQUENCE: 38
atgagccgcg aggtattcat ctgcgatgcc gtgcgcacgc cgatcggccg tttcggcggc         60
agtctttccg cggtgcgcgc cgacgacctc gcggcggtgc cgctgaaggc cctggtcgag        120
cgcaacccgg gggtcgactg gtcggcgttg gacgaggtgt tcctcggctg cgccaaccag        180
gccggcgagg acaaccgtaa cgtggcgcgc atggcgctgc tgctggccgg tttgccggag        240
agcgtgcccg cgtcacccct caaccgcctc tgcgcctcgg ggatggacgc catcggcacg        300
gcgttccgcg ccatcgcctg cggcgagatg gagctggcca tcgccggcgg cgtcgagtcg        360
atgtcgcgcg cgccgtacgt gatgggcaag gccgatagcg ccttcggtcg cggccagaag        420
atcgaggaca ccaccatcgg ctggcgcttc gtcaatccgc tgatgaagga gcagtacggc        480
atcgacccga tgccgcagac cgccgacaac gtcgccgacg actatcgcgt gtcgcgtgcc        540
gaccaggatg ccttcgccct gcgcagccag cagcgcgccg gcagggcgca ggaggccggt        600
ttcttcgccg aggaaatcgt cccggtgacg attcgcgggc gcaagggcga caccctggtc        660
gagcacgacg agcatccgcg tcccgacacc accctggagg cgctggcccg gctcaagccg        720
gtcaacgggc cggagaagac cgtcaccgcc ggcaacgcgt ccggggtcaa cgacggcgcc        780
gccgcgctgg tcctggcctc cgccgaggca gtggagaagc acggcctgac tccgcgcgcg        840
```

```
cgggtgctgg gcatggccag cgccggcgtc gccccacgga tcatgggcat cggcccggtg      900
ccggcggtgc gcaagctgct gcggcgcctg gacctggcga tcgacgcctt cgacgtgatc      960
gaactcaacg aagccttcgc cagccagggc ctggcctgcc tgcgcgaact gggcgtggcc     1020
gacgacagtg agaaggtcaa cccgaacggc ggtgccatcg ccctcggcca cccgctgggg     1080
atgagcggtg cgcggctggt cctcaccgcg ctccatcaac ttgagaagag cggcggccgg     1140
cgcggcctgg cgaccatgtg cgtaggcgtc ggccaaggcc tggcgctggc catcgagcgg     1200
gtctga                                                                1206
```

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
atgctcgatg cctatatcta cgcc                                              24
```

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
tcggcagcgc tcgatcac                                                     18
```

<210> SEQ ID NO 41
<211> LENGTH: 1206
<212> TYPE: DNA
<213> ORGANISM: Pseudomonas aeruginosa

<400> SEQUENCE: 41

```
atgctcgatg cctatatcta cgccggcctg cgtacgcctt cggccggca tgccggtgca       60 ctctcgacgg tgcgtccgga cgacctggcc ggcctgctgc tggcgcgtct cgcggaaacc     120
tccgggttcg ccgtcgacga cctggaggat gtgatcctcg gttgcaccaa ccaggccggc     180
gaagacagcc gcaacctggc gcgcaacgcg ctgctcgcag ccggcctgcc ggcgcggctg     240
cccgggcaga cggtcaaccg cttgtgtgcc agcggactgt cggcggtgat cgacgcggcg     300
cgcgcgatca gttgcggtga gggccggctg tacctggccg gcggcgccga aagcatgtcc     360
cgggcgccgt tcgtcatggg caaggcgag agcgccttca gccgcacgct ggaggtcttc     420
gacagcacca tcggcgcgcg cttcgccaac cccaggctgg tcgagcgcta tggcaacgac     480
agcatgccgg agaccggcga caacgtggcc cgcgccttcg gcatcgcccg cgaagacgcc     540
gaccgtttcg ccgcttcttc ccaggcgcgc taccaggctg cgctggagga gggctttttc     600
ctcggcgaga tccttccggt ggaggtgcgt gccggacgca agggcgagac gcggctggtg     660
gagcgcgacg agcatccgcg accgcaggcc gacctggcgg ccctggcgcg cttgccggcg     720
ttgttcgccg gtggggtagt gaccgccggt aatgcgtctg ggatcaacga cggggcggcg     780
gtagtgctgc tggcgatcg cgcgatcggc gagcgcgagg gcatccgcc gttggcgcgg     840 atcctcgcca gcgccagcgt cggcgtcgag ccccggttga tgggcatcgg cccgcagcag     900
gcgatcctcc gcgcgctgca acgcgccggc atcgacctgg acgaggtcgg cctgatcgag     960
```

```
atcaacgaag ccttcgcgcc gcaggtcctg gcctgcctga agttgctcgg cctggactac    1020
gaggacccgc gggtcaatcc ccatggcggc gccattgccc tcggccatcc gctcggcgcc    1080
tccggtgcgc gcctggtgct caccgccgcc cgcgggctgc aacgcatcga gcggcgctac    1140
gcggtggtca gcctgtgcgt cgggctcggc cagggcgtgg cgatggtgat cgagcgctgc    1200
cgatga                                                               1206
```

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
atgcacgacg tattcatctg tgacg                                            25
```

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
aacccgctcg atggccaac                                                   19
```

<210> SEQ ID NO 44
<211> LENGTH: 1203
<212> TYPE: DNA
<213> ORGANISM: Pseudomonas putida

<400> SEQUENCE: 44

```
atgcacgacg tattcatctg tgacgccatc cgtaccccga tcggccgctt cggcggcgcc     60
ctggccagcg tgcgggccga cgacctggcc gccgtgccgc tgaaggcgct gatcgagcgc    120
aaccctggcg tgcagtggga ccaggtagac gaagtgttct tcggctgcgc caaccaggcc    180
ggtgaagaca accgcaacgt ggcccgcatg gcactgctgc tggccggcct gccggaaagc    240
atcccgggcg tcaccctgaa ccgtctgtgc gcgtcgggca tggatgccgt cggcaccgcg    300
ttccgcgcca tcgccagcgg cgagatggag ctggtgattg ccggtggcgt cgagtcgatg    360
tcgcgcgccc cgttcgtcat gggcaaggct gaaagcgcct attcgcgcaa catgaagctg    420
gaagacacca ccattggctg gcgtttcatc aacccgctga tgaagagcca gtacggtgtg    480
gattccatgc cggaaaccgc cgacaacgtg gccgacgact atcaggtttc gcgtgctgat    540
caggacgctt tcgccctgcg cagccagcag aaggctgccg ctgcgcaggc tgccggcttc    600
tttgccgaag aaatcgtgcc ggtgcgtatc gctcacaaga agggcgaaat catcgtcgaa    660
cgtgacgaac acctgcgccc ggaaaccacg ctggaggcgc tgaccaagct caaaccggtc    720
aacggcccgg acaagacggt caccgccggc aacgcctcgg cgtgaacga cggtgctgcg    780 gcgatgatcc tggcctcggc cgcagcggtg aagaaacacg gcctgactcc gcgtgcccgc    840
gttctgggca tggccagcgg cggcgttgcg ccacgtgtca tgggcattgg cccggtgccg    900
gcggtgcgca aactgaccga gcgtctgggg atagcggtaa gtgatttcga cgtgatcgag    960
cttaacgaag cgtttgccag ccaaggcctg gcggtgctgc gtgagctggg tgtggctgac   1020
```

```
gatgcgcccc aggtaaaccc taatggcggt gccattgccc tgggccaccc cctgggcatg    1080
agcggtgcac gcctggtact gactgcgttg caccagctgg agaagagtgg cggtcgcaag    1140
ggcctggcga ccatgtgtgt gggtgtcggc caaggtctgg cgttggccat cgagcgggtt    1200
tga                                                                  1203

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
atgaccgacg cctacatctg cg                                              22

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cacgcgttcg atcgcgatc                                                  19

<210> SEQ ID NO 47
<211> LENGTH: 1203
<212> TYPE: DNA
<213> ORGANISM: Burkholderia ambifaria

<400> SEQUENCE: 47
atgaccgacg cctacatctg cgatgcgatt cgcacaccca tcggccgcta cggcggcgcc     60
ctgaaagacg ttcgtgccga cgatctcggc gcggtgccgc tcaaggcgct gatcgaacgc    120
aaccggaacg tcgactggtc ggcgatcgac gacgtgatct atggctgcgc gaaccaggcc    180
ggcgaagaca accgcaacgt cgcgcgcatg tccgcgctgc tcgcgggctt gccgaccgcc    240
gtgccgggca cgacgctgaa ccggttatgc ggctcgggca tggacgccgt cggcacggcc    300
gcgcgcgcga tcaaggcggg cgaggcacgc ttgatgatcg cgggcggcgt cgaaagcatg    360
acgcgcgcgc cgttcgtgat gggcaaggcc gccagcgcat cgcgcgccca ggctgcgatt    420
ttcgacacga cgatcggctg gcgtttcatt aatccgctga tgaaacagca atacggcgtc    480
gattcgatgc ccgagacggc cgagaacgtc gcggtcgact acaacatcag ccgcgccgac    540
caggatctat tcgcgctgcg cagccagcag aaggccgcgc gtgcgcagca ggacggcacg    600
ctcgccgccg aaatcgtccc cgtcacgatt gcgcagaaaa aaggcgacgc gctcgtcgta    660
tcgctcgacg agcatccgcg cgaaacatcg ctcgaagcgc tcgcgaagct gaagggcgtc    720
gtgcgtcccg acggctcggt cacggccggc aacgcgtcag gcgtcaacga cggcgcatgc    780
gcactgctgc tcgccaacgc ggaagccgcc gatcaatatg ggctgcgccg ccgcgcgcgt    840
gtcgtcggca tggcgagcgc cggcgtcgag ccgcgcgtga tgggtatcgg cccggcgccg    900
gccacgcaga aactgttgcg ccagctcggc atgacgatcg accagttcga cgtgatcgag    960
ctgaacgaag cgttcgcgtc gcagggtctc gcggtgctgc gcatgctcgg tgtcgccgac   1020
gacgatccgc gcgtgaaccc caacggcggt gcgatcgcgc tcggccatcc gctcggcgca   1080
tcgggtgcgc ggctcgtgac cacggcgctt caccaactcg agcgtacggg cggccgcttt   1140
```

```
gcgctctgta cgatgtgcat cggcgtcggc cagggcatcg cgatcgcgat cgaacgcgtg    1200
taa                                                                 1203

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
atggccacct caagacttgt ctgc                                            24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
caatttctcg atgaccattc cacc                                            24

<210> SEQ ID NO 50
<211> LENGTH: 1242
<212> TYPE: DNA
<213> ORGANISM: Ascaris suum

<400> SEQUENCE: 50
gtgatggcca cctcaagact tgtctgcagc aatttaacga agcaatgctt tacgatctcg     60
tcacgtgctg ctagccaatt taccgatgtg gtattcgtgg gtgccgcacg aacaccggtc    120
ggatcgtttc gctcttcgct ttccactgtt ccagccactg tcctcggagc tgaggctatt    180
aagggtgcac ttaaacatgc caatctaaaa ccctcacaag tgcaagaggt gttctttggc    240
tgtgtcgttc catccaactg tggacaagtt cctgcccgtc aagcgacact ggagctgga    300 tgcgatcctt cgacaatcgt tacaactctc aataaattgt gcgcctcggg aatgaagtcg    360
attgcttgtg ccgcctcact tttgcaactt ggtcttcaag aggttaccgt tggtggcggt    420
atggagagca tgagcttagt gccgtactat cttgaacgtg gtgaaactac ttatggtgga    480
atgaagctca tcgacggtat cccaagagat ggtccgactg atgcatatag taatcaactt    540
atgggtgcat cgctgataa tgtggctaaa cgattcaaca tcacccgtga ggaacaggat    600
aaattcgcta ttgaaagcta taacgatct gctgctgcat gggagagtgg agcatgcaaa    660
gctgaagtag ttcctattga agtgacaaag ggcaagaaaa catacattgt caacaaggat    720
gaggaataca tcaaagtcaa cttcgagaag ctttcccaaac tgaaacccgc cttcttgaaa    780
gacggaacca tcacggctgg caatgcttca acactgaacg atggtgctgc ggcagttgtg    840
atgacgactg tcgaaggagc gaaaaaatac ggtgtgaaac cattggcccg attgctctca    900
tatggtgatg cggcaacaaa tccagtcgat tttgctattg caccatcaat ggttatccca    960
aaggtactta aattggctaa tctcgagatc aaggatattg atttgtggga aatcaacgag   1020
gctttcgccg ttgttcccct tcattcaatg aagacactcg gtatcgatca ctcgaaagtg   1080
aacattcatg gtggtggcgt atctcttgga catcctattg gaatgtctgg agctcgaatt   1140
```

```
atcgttcatc tgattcatgc gttgaaacct ggccagaaag gctgcgctgc aatctgcaat    1200
ggtggcggtg gcgctggtgg aatggtcatc gagaaattgt aa                       1242
```